US007786354B2

(12) United States Patent
Huang et al.

(10) Patent No.: US 7,786,354 B2
(45) Date of Patent: Aug. 31, 2010

(54) COMPOSITIONS AND METHODS OF INCREASING STRESS TOLERANCE IN PLANTS

(75) Inventors: Yafan Huang, Kingston (CA); Maryse Chalifoux, Kingston (CA); Yang Wang, Kingston (CA); Monika Maria Kuzma, Glenburnie (CA); Angela Patricia Gilley, Inverary (CA)

(73) Assignee: Performance Plants, Inc., Kingston, Ontario (CA)

( * ) Notice: Subject to any disclaimer, the term of this patent is extended or adjusted under 35 U.S.C. 154(b) by 686 days.

(21) Appl. No.: 11/560,666

(22) Filed: Nov. 16, 2006

(65) Prior Publication Data

US 2009/0172839 A1 Jul. 2, 2009

Related U.S. Application Data

(63) Continuation of application No. 10/160,764, filed on May 31, 2002, now Pat. No. 7,172,881.

(60) Provisional application No. 60/294,766, filed on May 31, 2001, provisional application No. 60/348,909, filed on Oct. 22, 2001.

(51) Int. Cl.

| | |
|---|---|
| ***C12N 15/09*** | (2006.01) |
| ***C12N 15/82*** | (2006.01) |
| ***A01H 5/00*** | (2006.01) |
| ***A01H 5/10*** | (2006.01) |

(52) U.S. Cl. ....................... 800/289; 800/278; 800/298; 800/295; 435/468; 435/430

(58) Field of Classification Search ....................... None
See application file for complete search history.

(56) References Cited

U.S. PATENT DOCUMENTS

| | | | | |
|---|---|---|---|---|
| 5,097,025 | A | 3/1992 | Benfley et al. | |
| 5,107,065 | A | 4/1992 | Shewmaker et al. | |
| 5,349,124 | A | 9/1994 | Fischhoff et al. | |
| 5,683,439 | A | 11/1997 | Jensen | |
| 7,172,881 | B2 | 2/2007 | Huang et al. | |
| 7,262,338 | B2 * | 8/2007 | McCourt et al. | 800/289 |
| 2001/0026941 | A1 | 10/2001 | Held et al. | |
| 2001/0044938 | A1 | 11/2001 | McCourt et al. | |
| 2003/0061636 | A1 | 3/2003 | McCourt et al. | |
| 2003/0204865 | A1 | 10/2003 | Wan et al. | |
| 2005/0172361 | A1 | 8/2005 | Huang et al. | |
| 2006/0021092 | A1 | 1/2006 | McCourt et al. | |
| 2006/0031966 | A1 | 2/2006 | McCourt et al. | |
| 2006/0037108 | A1 | 2/2006 | McCourt et al. | |

FOREIGN PATENT DOCUMENTS

| | | |
|---|---|---|
| EP | 1033405 | 9/2000 |
| WO | WO 96/30530 | 10/1996 |
| WO | WO 98/05786 | 2/1998 |
| WO | WO 00/18880 | 4/2000 |
| WO | WO 02/16625 | 2/2002 |
| WO | WO 02/097097 | 12/2002 |

OTHER PUBLICATIONS

Zhou et al. The Plant Journal (1997) 12(4), pp. 921-930.*

Bird et al., *Biology and Genetic Review*, 9:220-221 (1991).

Napoli et al., *The Plant Cell*, 2:279-289 (1990).

Sandler et al., *Plant Molecular Biology*, 11:301-310 (1988).

Stam et al., *Annals of Botany*, 79:3-12 (1997).

Pei et al., Science, 282:287-90 (1998).

Partial International Search Report for PCT/IB02/03033. Mailed on Jul. 1, 2003.

An et al., "Functional Analysis of the 3' Control Region of the Potato Wound-Inducible Proteinase Inhibitor II Gene", *Plant Cell*, 1:115-122 (1989).

Andres et al., "Mutational analysis of α-subunit of protein farnesyltransferase", *J. Bio. Chem*., 268(2):1383-1390, 1993.

Atanassova et al., "A 126 bp fragment of a plant histone gene promoter confers preferential expression in meristems of transgenic *Arabidopsis", Plant J*., 2(3):291-300 (1992).

Bartels et al., "Approaches to Improve Stress Tolerance Using Molecular Genetics", *Plant Cell Env*., 17:659-667 (1994).

Bevan et al., "Structure and transcription of the nopaline synthase gene region of T-DNA", *Nucl. Acids Res*., 11(2):369-385 (1983).

Bevan et al., "The structure and transcription start site of a major potato tuber protein gene", *Nucl. Acids Res*., 14(11):4625-4636 (1986).

Bevan, "Binary *Agrobacterium* vectors for plant transformation", *Nucl. Acids Res*., 12(22):8711-8721 (1984).

Bidney et al., "Microprojectile bombardment of plant tissues increases transformation frequency by *Agrobacterium tumefaciens", Plant Mol. Biol*., 18:301-331 (1992).

Bohnert et al., "Strategies for Engineering Water-Stress Tolerance in Plants", *Trends Biotech*., 14(3):89-97 (1996).

Bracha et al., '*Arabidopsis thaliana* CaaX processing zinc-metallic endoprotease (STE24)' retrieved from EBI, Accession No. AF353722 Database accession No. AF353722.

Broun et al., "Catalytic plasticity of fatty acid modification enzymes underlying chemical diversity of plant lipids" *Sci*., 282(5392):1315-1317 (1998).

Chen et al., "cDNA cloning and expression of the peptide-binding beta subunit of rat p21 ras farnesyltransferas, the counterpart of yeast DPR1/RAM1", *Cell*, 66(2):327-334 (1991).

(Continued)

*Primary Examiner*—Medina A Ibrahim
(74) *Attorney, Agent, or Firm*—Mintz Levin Cohn Ferris Glovsky and Popeo, P.C.; Ivor R. Elrifi; Cynthia A. Kozakiewicz

(57) ABSTRACT

The present invention provides novel isolated FT polynucleotides and polypeptides encoded by the FT polynucleotides. Also provided are the antibodies that immunospecifically bind to a FT polypeptide or any derivative, variant, mutant or fragment of the FT polypeptide, polynucleotide or antibody. The invention additionally provides methods of constructing transgenic plants that have altered levels of FT polynucleotides and polypeptides.

4 Claims, 15 Drawing Sheets

OTHER PUBLICATIONS

Christensen et al., "Maize polyubiquitin genes: structure, thermal perturbation of expression and transcript splicing, and promoter activity following transfer to protoplasts by electroporation", *Plant Mol. Biol.*, 18:675-689 (1992).

Christensen et al., "Sequence analysis and transcriptional regulation by heat shock of polyubiquitin transcripts from maize", *Plant Mol. Biol.*, 12:619-632 (1989).

Cutler et al., "A protein farnesyltranferase involved in abscisic acid signal transduction in *Arabidopsis", Sci.*, 273:1239-1241 (1996).

Cutler et al., EMBL Sequence Data Library, XP002090869, Heidelberg, Germany, Accession No. U46574 (1996).

Cutler et al., EMBL Sequence Data Library, XP002090870, Heidelberg, Germany, Accession No. Q38920 (1996).

De Loose et al., "The extension signal peptide allows secretion of a heterologous protein from protoplasts", *Gene*, 99:95-100 (1991).

Delauney et al., "A stable bifunctional antisense transcript inhibiting gene expression in transgenic plants", *PNAS*, 85:4300-4304 (1988).

Deshayes et al., "Liposome-mediated transformation of tobacco mesophyll protoplasts by an *Escherichia coli* plasmid", *EMBO J.*, 4:2731-2737 (1985).

Doerks et al., "Protein annotation: Detective work for function prediction", *Trends Genet.* 14(6):248-250 (1998).

Dratewka-Kos et al., "Polypeptide Structure of Germin as Deduced from cDNA Sequencing", *J. Biol. Chem.*, 264:4896-4900 (1989).

Goldberg, "Regulation of plant gene expression", *Phil. Trans. R. Soc. London*, B314:343-353 (1986).

Goodman et al., "Structure and expression of yeast DPR1, a gene essential for the processing and intracellular localization of ras proteins", *Yeast*, 4:271 (1988).

Guo et al., "Protein tolerance to random amino acid change", *PNAS*, 101:9205-9210 (2004).

Hain et al., "Uptake, integration, expression and genetic transmission of a selectable chimaeric gene by plant protoplasts", *Mol. Gen. Genet.*, 199:161-168 (1985).

Hill et al., Functional analysis of conserved histidines in ADP-glucose pyrophosphorylase from *Escherichia coli', Biochem. Biophys. Res. Comm.*, 244:573-577 (1998).

Horsch et al., "A simple and General Method for Transferring Genes into plants", *Sci.*, 227:1229-1231 (1985).

Kado, "Molecular Mechanisms of Crown Gall Turmorigenesis", *Crit. Rev. Plant Sci.*, 10:1-32 (1991).

Kawabata et al., "Interaction of the transforming growth factor-β type I receptor with farnesyl-protein transferase-α", *J. Bio. Chem.*, 270(50):29628-29631 (1995).

Keil et al., "Primary structure of a proteinase inhibitor II gene from potato (*Solanum tuberosum*)", *Nucl. Acids Res.*, 14:5641-5650 (1986).

Koornneef et al., "The isolation and characterization of abscisic acid-insensitive mutants of *Arabidopsis thaliana", Plant Physiol.*, 61:377-383 (1984).

Last et al., "pEmu: an improved promoter for gene expression in cereal cells", *Theor. Appl. Genet.*, 81:581-588 (1991).

Laursen et al., "Production of fertile transgenic maize by electroporation of suspension culture cells", *Plant Mol. Biol.*, 24:51-61 (1994).

Lazar et al., "Transforming growth factor alpha: mutation of aspartic acid 47 and leucine 48 results in different biological activites", *Mol. Cell. Biol.*, 8:1247-1252 (1988).

Lepetit et al., "A plant histone gene promoter can direct both replication-dependent and -independent gene expression in transgenic plants", *Mol. Gen. Genet.*, 231:276-285 (1992).

Lund et al., "A plant signal sequence enhances the secretion of bacterial ChiA in transgenic tobacco", *Plant Mol. Biol.*, 18:47-53 (1992).

Matsuoka et al., "Propeptide of a precursor to plant vacuolar protein required for vacuolar targeting", *Proc. Nat'l. Acad. Sci. U.S.A.*, 88:834-838 (1991).

McElroy et al., "Isolation of an Efficient Actin Promoter for Use in Rice Transformation", *The Plant Cell*, 2:163-171 (1990).

Merlot et al., "Genetic analysis of abscisic acid signal transduction", *Plant Physiol.*, 114:751-757 (1997).

Mizukami et al., "Separation of AG function in floral meristem determinacy from that in reproductive organ identity by expressing antisense AG mRNA", *Plant Molec. Biol.*, 28(5):767-784 (1995).

Mogen et al., "Upstream Sequences Other than AAUAAA Are Required for Efficient Messenger RNA 3' -End Formation in Plants", *Plant Cell*, 2:1261-1272 (1990).

Moloney et al., "High Efficiency transformation of *Brassica napus* using *Agrobacterium* vectors", *Plant Cell Reports*, 8:238-242 (1989).

Odell et al., "Identification of DNA sequences required for activity of the cauliflower mosaic virus 35S promoter", *Nature*, 313:810-812 (1985).

Pei et al., "Type II CAAX prenyl endopeptidases belong to a novel superfamily of putative membrane-bound metalloproteases", *Trends Biochem. Sci.*, 26(5):275-277 (2001).

Pusch et al., "Nucleotide sequence homology requirements of HIV-1-specific short hairpin RNA", *Nuc. Acids. Res.*, 31(22):6444-6449 (2003).

Qian et al., "Protein farnesyltransferase in plants: Molecular characterization and involvement in cell cycle control", *Plant Cell*, 8:2381-2394 (1996).

Sanford et al., "Delivery of substances into cells and tissues using a particle bombardment process", *Part. Sci. Technol.*, 5:27-37 (1987).

Schafer et al., "Protein prenylation: genes, enzymes, targets and functions", *Ann. Rev. Genet.*, 30:209-237 (1992).

Smith et al., "Antisense RNA inhibition of polygalacturonase gene expression in transgenic tomatoes", *Nature*, 334:724-726 (1988).

Tamura et al., "Osmotic stress tolerance of transgenic tobacco expressing a gene encoding a membrane-located receptor-like protein from tobacco plants", *Plant Physiol.*, 131(2):454-462 (2003).

Temple et al., "Down-regulation of specific members of the glutamine synthetase gene family in alfalfa by antisense RNA technology", *Plant Mol. Biol.*, 37(3):535-547 (1998).

van der Krol, "Inhibition of flower pigmentation by antisense CHS genes: promoter and minimal sequence requirements for the antisense effect", *Plant Mol. Biol.*, 14(4):457-466 (1990).

Velten et al., "Isolation of a dual plant promoter fragment from the Ti plasmid of *Agrobacterium tumefaciens", EMBO J.*, 3(12):2723-2730 (1984).

Verwoert et al., "Developmental specific expression and organelle targeting of the *Escherichia coli fabD* gene, encoding malonyl coenzyme A-acyl carrier protein transacylase in transgenic rape and tobacco seeds", *Plant Mol. Biol.*, 26:189-202 (1994).

Visser et al., "Expression of a chimaeric granule-bound starch synthase-GUS gene in transgenic potato plants", *Plant Mol. Bio.*, 17:691-699 (1991).

Wang et al., "Molecular tailoring of farnesylation for plant drought tolerance and yield protection", *Plant J.*, 43(3):413-424 (2005).

Waterhouse et al., "Virus resistance and gene silencing: Killing the messenger", *Trends Plant Sci.*, 4(11):452-457, (1999).

Wilkins et al., "Role of Propeptide Glycan in Post-Translational Processing and Transport of Barley Lectin to Vacuoles in Transgenic Tobacco", *Plant Cell*, 2:301-313 (1990).

Xu et al., "Effects of Epibrassinolide and Abscisic Acid on *Sorghum* Plants Growing under Soil Water Deficit", *Jpn. J. Crop. Sci.*, 63(4):671-675 (1994).

Yang et al., "Protein farnesyltransferase in plants. Molecular cloning and expression of a homolog of the beta subunit from garden pea", *Plant Physiol.*, 101:667-674 (1993).

Ziegelhoffer et al., "Cloning of the *Arabidopsis* WIGGUM gene identifies a role for farnesylation in meristem development", *PNAS*, 97(13)7633-7638 (2000).

Database EMBL [Online] May 21, 1998, "*Arabidopsis thaliana* protein farnesyltransferase subunit A (FTA) mRNA, complete cds", XP002544993, EMBL: AF064542.

Shafer and Rines, "Protein Prenylation: Genes, Enzymes, Targets, and Functions", Annual Review of Genetics, (1992) 26: 209-237 (1992).

Ziegelhoffer et al., "Cloning of the *Arabidopsis* WIGGUM gene identifies a role for farnesylation in meristem development", PNAS 97:(13) 7633-7668 (2000).

Zhang F.L., and Casey P.J., "Protein Prenylation: Molecular Mechanisms and Functional Consequences", Annual Review of Biochemistry 65:241-269 (1996).

Hightower, et al., "Lysine(164)alpha of protein farnesyltransferase is important for both CaaX substrate binding and catalysis", Biochem. J. 360: 625-631 (2001).

* cited by examiner

NO ABA

WT era 1 9 21

1 μM ABA

WT era 1 9 21

| **DNA** | Brassica napus | Arabidopsis thaliana | PPI Glycine max | Zea mays | Rice | Soy 1 | Soy 2 | Triticum | Tomato | Pea |
|---|---|---|---|---|---|---|---|---|---|---|
| Brassica napus | X | | | | | | | | | |
| Arabidopsis thaliana | 89 | X | | | | | | | | |
| PPI Glycine max | 61 | 55 | X | | | | | | | |
| Zea mays | 57 | 45 | 52 | X | | | | | | |
| Rice | 55 | 46 | 54 | 63 | X | | | | | |
| Soy 1 | 61 | 50 | 98 | 43 | 47 | X | | | | |
| Soy 2 | 61 | 50 | 99 | 41 | 46 | 99 | X | | | |
| Triticum | 58 | 45 | 52 | 56 | 66 | 43 | 41 | X | | |
| Tomato | 65 | 53 | 63 | 44 | 51 | 52 | 49 | 41 | X | |
| Pea | 66 | 55 | 78 | 46 | 50 | 70 | 69 | 44 | 49 | X |
| | | | | | | | | | | |
| **PROTEIN** | Brassica napus | Arabidopsis thaliana | PPI Glycine max | Pea | Tomato | Rice | Zea mays | Soy 1 | Soy 2 | Triticum |
| Brassica napus | X | | | | | | | | | |
| Arabidopsis thaliana | 89 | X | | | | | | | | |
| PPI Glycine max | 65 | 63 | X | | | | | | | |
| Pea | 61 | 61 | 77 | X | | | | | | |
| Tomato | 60 | 59 | 57 | 58 | X | | | | | |
| Rice | 64 | 63 | 56 | 58 | 58 | X | | | | |
| Zea mays | 61 | 56 | 58 | 57 | 56 | 75 | X | | | |
| Soy 1 | 66 | 64 | 98 | 77 | 58 | 57 | 58 | X | | |
| Soy 2 | 66 | 64 | 98 | 78 | 58 | 57 | 58 | 99 | X | |
| Triticum | 61 | 60 | 57 | 59 | 60 | 80 | 73 | 58 | 58 | X |

Fig. 8

| DNA | Brassica napus | Arabidopsis thaliana | Wiggun | PPI Glycine max | Glycine max | PPI Zea maize | Zea maize | Pea | Tomato | Tobacco |
|---|---|---|---|---|---|---|---|---|---|---|
| Brassica napus | X | | | | | | | | | |
| Arabidopsis thaliana | 88 | X | | | | | | | | |
| Wiggum | 88 | 99 | X | | | | | | | |
| PPI Glycine max | 60 | 64 | 65 | X | | | | | | |
| Glycine max | 60 | 64 | 65 | 99 | X | | | | | |
| PPI Zea maize | 38 | 54 | 59 | 63 | 63 | X | | | | |
| Zea maize | 54 | 54 | 59 | 62 | 62 | 99 | X | | | |
| Pea | 65 | 57 | 45 | 78 | 77 | 56 | 56 | X | | |
| Tomato | 68 | 62 | 52 | 70 | 70 | 64 | 64 | 51 | X | |
| Tobacco | 68 | 64 | 60 | 71 | 71 | 65 | 65 | 55 | 83 | X |
| | | | | | | | | | | |
| **PROTEIN** | Brassica napus | Arabidopsis thaliana | Wiggun | PPI Glycine max | Glycine max | PPI Zea maize | Zea maize | Pea | Tomato | Tobacco |
| Brassica napus | X | | | | | | | | | |
| Arabidopsis thaliana | 84 | X | | | | | | | | |
| Wiggum | 84 | 99 | X | | | | | | | |
| PPI Glycine max | 54 | 58 | 59 | X | | | | | | |
| Glycine max | 53 | 58 | 58 | 99 | X | | | | | |
| PPI Zea maize | 52 | 50 | 52 | 58 | 58 | X | | | | |
| Zea maize | 51 | 50 | 52 | 58 | 58 | 99 | X | | | |
| Pea | 58 | 56 | 57 | 78 | 78 | 56 | 56 | X | | |
| Tomato | 60 | 62 | 55 | 63 | 63 | 58 | 58 | 62 | X | |
| Tobacco | 62 | 63 | 59 | 64 | 63 | 58 | 58 | 64 | 83 | X |

Fig. 9

SEQUENCE LISTING

<160> NUMBER OF SEQ ID NOS: 90

<210> SEQ ID NO 1
<211> LENGTH: 999
<212> TYPE: DNA
<213> ORGANISM: Arabidopsis thaliana

<400> SEQUENCE: 1
aaacccggga tgaatttcga cgagaccgtg ccactgagcc aacgattgga gtggtcagac 60
gtggtcccat tgactcagga cgatggtccg aatccagtgg tgccaattgc ctacaaggaa 120
gagttccgcg agactatgga ttacttccgt gcgatttact tttccgacga gcgatctcct 180
cgcgcactac gactcacgga agaaaccctc ctcttaaact ccggcaacta cacagtgtgg 240
catttcaggc gcctagtact cgaggccctt aatcacgact tgtttgaaga actcgagttc 300
atcgaacgca ttgctgagga taactctaag aactaccaac tgtggcatca tcggcgatgg 360
gttgcagaga aactgggtcc tgatgttgca gggagagaac ttgaatttac ccgtagagta 420
ctttcacttg atgccaaaca ttatcatgct tggtcacata ggcagtggac actacgggca 480
ttaggaggat gggaagatga gctcgattac tgtcacgagc tccttgaagc tgacgtcttt 540
aacaattccg cctggaatca gaggtattat gtcatcaccc aatctccttt gttgggaggc 600
ctagaagcca tgagagaatc tgaagtaagc tacacaatca aagccatttt aaccaatcct 660
gcaaacgaga gctcatggcg atacctaaaa gcgctttaca aagacgacaa agaatcctgg 720
attagtgatc caagtgtttc ctcagtctgt ttgaatgttc tatcccgcac agattgcttc 780
catggattcg ctctgagcac ccttttggat cttctatgtg atggactgag accaaccaac 840
gagcataaag actcagtgag agctctagct aatgaagaac cagagactaa cttggccaat 900
ttggtgtgta ctattcttgg tcgtgtagat cctataagag ctaactattg ggcatggagg 960
aagagcaaga ttacagtggc agcaatttga ggatcctttt 999

<210> SEQ ID NO 2
<211> LENGTH: 999
<212> TYPE: DNA
<213> ORGANISM: Artificial Sequence
<220> FEATURE:
<223> OTHER INFORMATION: Description of Artificial Sequence: Complement to SEQ ID:1

<400> SEQUENCE: 2
aaaggatcct caaattgctg ccactgtaat cttgctcttc ctccatgccc aatagttagc 60
tcttatagga tctacacgac caagaatagt acacaccaaa ttggccaagt tagtctctgg 120
ttcttcatta gctagagctc tcactgagtc tttatgctcg ttggttggtc tcagtccatc 180
acatagaaga tccaaaaggg tgctcagagc gaatccatgg aagcaatctg tgcgggatag 240
aacattcaaa cagactgagg aaacacttgg atcactaatc caggattctt tgtcgtcttt 300
gtaaagcgct tttaggtatc gccatgagct ctcgtttgca ggattggtta aaatggcttt 360
gattgtgtag cttacttcag attctctcat ggcttctagg cctcccaaca aaggagattg 420
ggtgatgaca taatacctct gattccaggc ggaattgtta aagacgtcag cttcaaggag 480
ctcgtgacag taatcgagct catcttccca tcctcctaat gcccgtagtg tccactgcct 540
atgtgaccaa gcatgataat gtttggcatc aagtgaaagt actctacggg taaattcaag 600
ttctctccct gcaacatcag gacccagttt ctctgcaacc catcgccgat gatgccacag 660

-continued

```
ttggtagttc ttagagttat cctcagcaat gcgttcgatg aactcgagtt cttcaaacaa    720

gtcgtgatta agggcctcga gtactaggcg cctgaaatgc cacactgtgt agttgccgga    780

gtttaagagg agggtttctt ccgtgagtcg tagtgcgcga ggagatcgct cgtcggaaaa    840

gtaaatcgca cggaagtaat ccatagtctc gcggaactct tccttgtagg caattggcac    900

cactggattc ggaccatcgt cctgagtcaa tgggaccacg tctgaccact ccaatcgttg    960

gctcagtggc acggtctcgt cgaaattcat cccgggttt                            999
```

```
<210> SEQ ID NO 3
<211> LENGTH: 989
<212> TYPE: DNA
<213> ORGANISM: Artificial Sequence
<220> FEATURE:
<223> OTHER INFORMATION: Description of Artificial Sequence:  Sequence
      of SEQ ID NO:1 ligated

<400> SEQUENCE: 3

gatcctcaaa ttgctgccac tgtaatcttg ctcttcctcc atgcccaata gttagctctt     60

ataggatcta cacgaccaag aatagtacac accaaattgg ccaagttagt ctctggttct    120

tcattagcta gagctctcac tgagtcttta tgctcgttgg ttggtctcag tccatcacat    180

agaagatcca aaagggtgct cagagcgaat ccatggaagc aatctgtgcg ggatagaaca    240

ttcaaacaga ctgaggaaac acttggatca ctaatccagg attctttgtc gtctttgtaa    300

agcgctttta ggtatcgcca tgagctctcg tttgcaggat tggttaaaat ggctttgatt    360

gtgtagctta cttcagattc tctcatggct tctaggcctc ccaacaaagg agattgggtg    420

atgacataat acctctgatt ccaggcggaa ttgttaaaga cgtcagcttc aaggagctcg    480

tgacagtaat cgagctcatc ttcccatcct cctaatgccc gtagtgtcca ctgcctatgt    540

gaccaagcat gataatgttt ggcatcaagt gaaagtactc tacgggtaaa ttcaagttct    600

ctccctgcaa catcaggacc cagtttctct gcaacccatc gccgatgatg ccacagttgg    660

tagttcttag agttatcctc agcaatgcgt tcgatgaact cgagttcttc aaacaagtcg    720

tgattaaggg cctcgagtac taggcgcctg aaatgccaca ctgtgtagtt gccggagttt    780

aagaggaggg tttcttccgt gagtcgtagt gcgcgaggag atcgctcgtc ggaaaagtaa    840

atcgcacgga agtaatccat agtctcgcgg aactcttcct tgtaggcaat tggcaccact    900

ggattcggac catcgtcctg agtcaatggg accacgtctg accactccaa tcgttggctc    960

agtggcacgg tctcgtcgaa attcatccc                                       989
```

```
<210> SEQ ID NO 4
<211> LENGTH: 5250
<212> TYPE: DNA
<213> ORGANISM: Artificial Sequence
<220> FEATURE:
<223> OTHER INFORMATION: Description of Artificial Sequence: Plasmid
      pBI121-35S-anti-AtFTA sequence

<400> SEQUENCE: 4

gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360
```

-continued

```
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttctttttgt caagaccgac    540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
```

-continued

```
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tcctcaaatt gctgccactg taatcttgct   3360
cttcctccat gcccaatagt tagctcttat aggatctaca cgaccaagaa tagtacacac   3420
caaattggcc aagttagtct ctggttcttc attagctaga gctctcactg agtctttatg   3480
ctcgttggtt ggtctcagtc catcacatag aagatccaaa agggtgctca gagcgaatcc   3540
atggaagcaa tctgtgcggg atagaacatt caaacagact gaggaaacac ttggatcact   3600
aatccaggat tctttgtcgt ctttgtaaag cgcttttagg tatcgccatg agctctcgtt   3660
tgcaggattg gttaaaatgg ctttgattgt gtagcttact tcagattctc tcatggcttc   3720
taggcctccc aacaaaggag attgggtgat gacataatac ctctgattcc aggcggaatt   3780
gttaaagacg tcagcttcaa ggagctcgtg acagtaatcg agctcatctt cccatcctcc   3840
taatgcccgt agtgtccact gcctatgtga ccaagcatga taatgtttgg catcaagtga   3900
aagtactcta cgggtaaatt caagttctct ccctgcaaca tcaggaccca gtttctctgc   3960
aacccatcgc cgatgatgcc acagttggta gttcttagag ttatcctcag caatgcgttc   4020
gatgaactcg agttcttcaa acaagtcgtg attaagggcc tcgagtacta ggcgcctgaa   4080
atgccacact gtgtagttgc cggagtttaa gaggagggtt tcttccgtga gtcgtagtgc   4140
gcgaggagat cgctcgtcgg aaaagtaaat cgcacggaag taatccatag tctcgcggaa   4200
ctcttccttg taggcaattg gcaccactgg attcggacca tcgtcctgag tcaatgggac   4260
cacgtctgac cactccaatc gttggctcag tggcacggtc tcgtcgaaat tcatcccctc   4320
gaatttcccc gatcgttcaa acatttggca ataaagtttc ttaagattga atcctgttgc   4380
cggtcttgcg atgattatca tataatttct gttgaattac gttaagcatg taataattaa   4440
catgtaatgc atgacgttat ttatgagatg ggtttttatg attagagtcc cgcaattata   4500
catttaatac gcgatagaaa acaaaatata gcgcgcaaac taggataaat tatcgcgcgc   4560
ggtgtcatct atgttactag atcgggaatt cactggccgt cgttttacaa cgtcgtgact   4620
gggaaaaccc tggcgttacc caacttaatc gccttgcagc acatccccct ttcgccagct   4680
ggcgtaatag cgaagaggcc cgcaccgatc gcccttccca acagttgcgc agcctgaatg   4740
gcgcccgctc ctttcgcttt cttcccttcc tttctcgcca cgttcgccgg ctttccccgt   4800
caagctctaa atcgggggct ccctttaggg ttccgattta gtgctttacg gcacctcgac   4860
cccaaaaaac ttgatttggg tgatggttca cgtagtgggc catcgccctg atagacggtt   4920
tttcgccctt tgacgttgga gtccacgttc tttaatagtg gactcttgtt ccaaactgga   4980
acaacactca accctatctc gggctattct tttgatttat aagggatttt gccgatttcg   5040
gaaccaccat caaacaggat tttcgcctgc tggggcaaac cagcgtggac cgcttgctgc   5100
```

-continued

```
aactctctca gggccaggcg gtgaagggca atcagctgtt gcccgtctca ctggtgaaaa   5160

gaaaaaccac cccagtacat taaaaacgtc cgcaatgtgt tattaagttg tctaagcgtc   5220

aatttgttta caccacaata tatcctgcca                                    5250


<210> SEQ ID NO 5
<211> LENGTH: 326
<212> TYPE: PRT
<213> ORGANISM: Arabidopsis thaliana

<400> SEQUENCE: 5

Met Asn Phe Asp Glu Thr Val Pro Leu Ser Gln Arg Leu Glu Trp Ser
 1               5                  10                  15

Asp Val Val Pro Leu Thr Gln Asp Asp Gly Pro Asn Pro Val Val Pro
            20                  25                  30

Ile Ala Tyr Lys Glu Glu Phe Arg Glu Thr Met Asp Tyr Phe Arg Ala
        35                  40                  45

Ile Tyr Phe Ser Asp Glu Arg Ser Pro Arg Ala Leu Arg Leu Thr Glu
    50                  55                  60

Glu Thr Leu Leu Leu Asn Ser Gly Asn Tyr Thr Val Trp His Phe Arg
65                  70                  75                  80

Arg Leu Val Leu Glu Ala Leu Asn His Asp Leu Phe Glu Glu Leu Glu
                85                  90                  95

Phe Ile Glu Arg Ile Ala Glu Asp Asn Ser Lys Asn Tyr Gln Leu Trp
            100                 105                 110

His His Arg Arg Trp Val Ala Glu Lys Leu Gly Pro Asp Val Ala Gly
        115                 120                 125

Arg Glu Leu Glu Phe Thr Arg Arg Val Leu Ser Leu Asp Ala Lys His
    130                 135                 140

Tyr His Ala Trp Ser His Arg Gln Trp Thr Leu Arg Ala Leu Gly Gly
145                 150                 155                 160

Trp Glu Asp Glu Leu Asp Tyr Cys His Glu Leu Leu Glu Ala Asp Val
                165                 170                 175

Phe Asn Asn Ser Ala Trp Asn Gln Arg Tyr Tyr Val Ile Thr Gln Ser
            180                 185                 190

Pro Leu Leu Gly Gly Leu Glu Ala Met Arg Glu Ser Glu Val Ser Tyr
        195                 200                 205

Thr Ile Lys Ala Ile Leu Thr Asn Pro Ala Asn Glu Ser Ser Trp Arg
    210                 215                 220

Tyr Leu Lys Ala Leu Tyr Lys Asp Asp Lys Glu Ser Trp Ile Ser Asp
225                 230                 235                 240

Pro Ser Val Ser Ser Val Cys Leu Asn Val Leu Ser Arg Thr Asp Cys
                245                 250                 255

Phe His Gly Phe Ala Leu Ser Thr Leu Leu Asp Leu Leu Cys Asp Gly
            260                 265                 270

Leu Arg Pro Thr Asn Glu His Lys Asp Ser Val Arg Ala Leu Ala Asn
        275                 280                 285

Glu Glu Pro Glu Thr Asn Leu Ala Asn Leu Val Cys Thr Ile Leu Gly
    290                 295                 300

Arg Val Asp Pro Ile Arg Ala Asn Tyr Trp Ala Trp Arg Lys Ser Lys
305                 310                 315                 320

Ile Thr Val Ala Ala Ile
                325
```

-continued

<210> SEQ ID NO 6
<211> LENGTH: 822
<212> TYPE: DNA
<213> ORGANISM: Brassica napus

<400> SEQUENCE: 6

```
atggattact tccgtgcgat ttacttctcc gacgagcgtt ctgctcgcgc gctgcgactc     60

acggaagaag ctctccgctt aaactcgggc aactacaccg tgtggcactt cgggcgctta    120

gtactcgagg agcttaataa cgacttgtat gaagagctca agttcatcga aagcattgct    180

gaggataact ctaagaacta ccagttgtgg catcatcgac gatgggtcgc agagaaactg    240

ggtcctgatg ttgcaggaaa ggaacttgag tttactcgga gggtactatc acttgatgcc    300

aagcattatc atgcttggtc acataggcag tgggcgctac aagcattagg aggatgggaa    360

aatgagctta actactgcca cgagctcctt gaagctgacg tctttaacaa ctctgcatgg    420

aatcagaggt attacgttat aactagatca ccttcgttgg gaggcctaga agccatgaga    480

gaatctgaag taagctacac agtcaaagcc attttagcaa atcccgggaa cgagagctct    540

tggaggtacc tgaaagccct ttacaaagac gacacagagt cttggattag tgatccaagt    600

gtttcctcag tctgtttgaa agttctctca cgcgcggact gcttccatgg attcgctctg    660

agcacccttt tggatcttct gtgcgatggg ttgagaccaa ccaacgagca tagagactcg    720

gtgaaagctc tagctaatga agaaccagag actaacttgg ccaatttggt gtgtaccatt    780

ctgtgtcgtg ttgatccaat aagagctaac tattgggcat gg                       822
```

<210> SEQ ID NO 7
<211> LENGTH: 276
<212> TYPE: PRT
<213> ORGANISM: Brassica napus

<400> SEQUENCE: 7

```
Met Asp Tyr Phe Arg Ala Ile Tyr Phe Ser Asp Glu Arg Ser Ala Arg
 1               5                  10                  15

Ala Leu Arg Leu Thr Glu Glu Ala Leu Arg Leu Asn Ser Gly Asn Tyr
            20                  25                  30

Thr Val Trp His Phe Gly Arg Leu Val Leu Glu Glu Leu Asn Asn Asp
        35                  40                  45

Leu Tyr Glu Glu Leu Lys Phe Ile Glu Ser Ile Ala Glu Asp Asn Ser
    50                  55                  60

Lys Asn Tyr Gln Leu Trp His His Arg Arg Trp Val Ala Glu Lys Leu
65                  70                  75                  80

Gly Pro Asp Val Ala Gly Leu Glu Lys Glu Phe Thr Arg Arg Val Leu
                85                  90                  95

Ser Leu Asp Ala Lys His Tyr His Ala Trp Ser His Arg Gln Trp Ala
            100                 105                 110

Leu Gln Ala Leu Gly Gly Trp Glu Asn Glu Leu Asn Tyr Cys His Glu
        115                 120                 125

Leu Leu Glu Ala Asp Val Phe Asn Asn Ser Ala Trp Asn Gln Arg Tyr
    130                 135                 140

Tyr Val Ile Thr Arg Ser Pro Ser Leu Gly Gly Leu Glu Ala Met Arg
145                 150                 155                 160

Glu Ser Glu Val Ser Tyr Thr Val Lys Ala Ile Leu Ala Asn Pro Gly
                165                 170                 175

Asn Glu Ser Ser Trp Arg Tyr Leu Lys Ala Leu Tyr Lys Asp Asp Thr
            180                 185                 190
```

-continued

```
Glu Ser Trp Ile Ser Asp Pro Ser Val Ser Ser Val Cys Leu Lys Val
        195                 200                 205

Leu Ser Arg Ala Asp Cys Phe His Gly Phe Ala Leu Ser Thr Leu Leu
    210                 215                 220

Asp Leu Leu Cys Asp Gly Leu Arg Pro Thr Asn Glu His Arg Asp Ser
225                 230                 235                 240

Val Lys Ala Leu Ala Asn Glu Glu Pro Glu Thr Asn Leu Ala Asn Leu
                245                 250                 255

Val Cys Thr Ile Leu Cys Arg Val Asp Pro Ile Arg Ala Asn Tyr Trp
            260                 265                 270

Ala Trp Lys Leu
        275


<210> SEQ ID NO 8
<211> LENGTH: 1110
<212> TYPE: DNA
<213> ORGANISM: Brassica napus

<400> SEQUENCE: 8

tggctttgtt actggattct tcattcaatt gctttgcttg gggagtctgt ggatgatgac      60

ttagaaaaca atgcaatcga ttttcttgga cgttgccagg gttctgatgg tggatatggt     120

ggtggtcctg gccaacttcc acatcttgca acaagttatg ctgcagtgaa tacacttgtt     180

actttaggag gtgagaaagc cttctcttca attaacagag aacaaatggc ttgtttctta     240

agacgaatga aggatacaaa tggaggtttc aggatgcata atatgggaga aatagatgtg     300

cgagcgtgct acactgcgat tttgattgca agcatcctga acattgtgga tgatgaactc     360

acccgcggct taggagatta cattttgagt tgccaaactt atgaaggtgg cattggaggg     420

gaacctggct ccgaagctca tggtgggtac acgtactgtg ggttggctac tatgatttta     480

atcaatgaag tcgaccgctt gaatttggat tcgttaatga attgggttgt acatcgacaa     540

ggagtagaaa tgggattcca aggtaggacg aacaaattgg tcgacggttg ctacacgttt     600

tggcaggcag ccccctgtgt tctactacag cgattttttt catcccagga tatggcacct     660

catggatcat catcacatat gtcacaaggg acagatgaag atcacgagga acatggtcat     720

gatgaagatg atcctgaaga cagtgatgaa gatgattctg atgaggatag cgatgaagat     780

tcagggaatg gtcaccaagt tcatcatacg tctacctaca ttgacaggag aattcaacct     840

gtttttgata gcctcggctt gcaaagatat gtgctcttgt gctctcaggt tgctgatggt     900

ggattcagag acaagctgag gaaaccccgt gacttctacc acacatgtta ctgcctaagc     960

ggtctttccg tggctcaaca cgcttggtca aaagacgagg acactcctcc tttgactcgt    1020

gacattttgg gtggctacgc aaaccacctt gaacctgttc acctcctcca caacattgtc    1080

ttggatcggt attatgaagc ttctagattt                                     1110


<210> SEQ ID NO 9
<211> LENGTH: 370
<212> TYPE: PRT
<213> ORGANISM: Brassica napus

<400> SEQUENCE: 9

Trp Leu Cys Tyr Trp Ile Leu His Ser Ile Ala Leu Leu Gly Glu Ser
 1               5                  10                  15

Val Asp Asp Asp Leu Glu Asn Asn Ala Ile Asp Phe Leu Gly Arg Cys
            20                  25                  30

Gln Gly Ser Asp Gly Gly Tyr Gly Gly Gly Pro Gly Gln Leu Pro His
```

-continued

```
        35                  40                  45

Leu Ala Thr Ser Tyr Ala Ala Val Asn Thr Leu Val Thr Leu Gly Gly
    50                  55                  60

Glu Lys Ala Phe Ser Ser Ile Asn Arg Glu Gln Met Ala Cys Phe Leu
65                  70                  75                  80

Arg Arg Met Lys Asp Thr Asn Gly Gly Phe Arg Met His Asn Met Gly
                85                  90                  95

Glu Ile Asp Val Arg Ala Cys Tyr Thr Ala Ile Leu Ile Ala Ser Ile
            100                 105                 110

Leu Asn Ile Val Asp Asp Glu Leu Thr Arg Gly Leu Gly Asp Tyr Ile
        115                 120                 125

Leu Ser Cys Gln Thr Tyr Glu Gly Gly Ile Gly Gly Glu Pro Gly Ser
    130                 135                 140

Glu Ala His Gly Gly Tyr Thr Tyr Cys Gly Leu Ala Thr Met Ile Leu
145                 150                 155                 160

Ile Asn Glu Val Asp Arg Leu Asn Leu Asp Ser Leu Met Asn Trp Val
                165                 170                 175

Val His Arg Gln Gly Val Glu Met Gly Phe Gln Gly Arg Thr Asn Lys
            180                 185                 190

Leu Val Asp Gly Cys Tyr Thr Phe Trp Gln Ala Ala Pro Cys Val Leu
        195                 200                 205

Leu Gln Arg Phe Phe Ser Ser Gln Asp Met Ala Pro His Gly Ser Ser
    210                 215                 220

Ser His Met Ser Gln Gly Thr Asp Glu Asp His Glu Glu His Gly His
225                 230                 235                 240

Asp Glu Asp Asp Pro Glu Asp Ser Asp Glu Asp Asp Ser Asp Glu Asp
                245                 250                 255

Ser Asp Glu Asp Ser Gly Asn Gly His Gln Val His His Thr Ser Thr
            260                 265                 270

Tyr Ile Asp Arg Arg Ile Gln Pro Val Phe Asp Ser Leu Gly Leu Gln
        275                 280                 285

Arg Tyr Val Leu Leu Cys Ser Gln Val Ala Asp Gly Gly Phe Arg Asp
    290                 295                 300

Lys Leu Arg Lys Pro Arg Asp Phe Tyr His Thr Cys Tyr Cys Leu Ser
305                 310                 315                 320

Gly Leu Ser Val Ala Gln His Ala Trp Ser Lys Asp Glu Asp Thr Pro
                325                 330                 335

Pro Leu Thr Arg Asp Ile Leu Gly Gly Tyr Ala Asn His Leu Glu Pro
            340                 345                 350

Val His Leu Leu His Asn Ile Leu Val Asp Arg Tyr Tyr Glu Ala Ser
        355                 360                 365

Arg Phe
    370
```

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: PCR Primer

<400> SEQUENCE: 10
gccgacagtg gtcccaaaga tgg 23

<210> SEQ ID NO 11

-continued

<211> LENGTH: 30
<212> TYPE: DNA
<213> ORGANISM: Artificial Sequence
<220> FEATURE:
<223> OTHER INFORMATION: Description of Artificial Sequence: PCR Primer

<400> SEQUENCE: 11
aaaggatcct caaattgctg ccactgtaat 30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: PCR Primer

<400> SEQUENCE: 12
aaacccggga tgaatttcga cgagaacgtg 30

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 13
gcaagaccgg caacagga 18

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: PCR Primer

<400> SEQUENCE: 14
tttaagcttg acagaaacag tcagcgagac 30

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 15
gctcttcctc catgccca 18

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: PCR Primer

<400> SEQUENCE: 16
tttaagcttg gagccataga tgcaattcaa 30

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 17

-continued cgggcattag gaggatggga a 21

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 18
gtccggaatt cccgggtc 18

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: PCR Primer

<400> SEQUENCE: 19
ggatccatgg attacttccg tgcgatttac ttctcc 36

<210> SEQ ID NO 20
<211> LENGTH: 39
<212> TYPE: DNA
<213> ORGANISM: Artificial Sequence
<220> FEATURE:
<223> OTHER INFORMATION: Description of Artificial Sequence: PCR Primer

<400> SEQUENCE: 20
aaaaagcttc catgcccaat agttagctct tattggatc 39

<210> SEQ ID NO 21
<211> LENGTH: 38
<212> TYPE: DNA
<213> ORGANISM: Artificial Sequence
<220> FEATURE:
<223> OTHER INFORMATION: Description of Artificial Sequence: PCR Primer

<400> SEQUENCE: 21
aaaaagcttt ggctttgtta ctggattctt cattcaat 38

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence: PCR Primer

<400> SEQUENCE: 22
aaatctagaa gcttcataat accgatccaa gacaatgtt 39

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: PCR Primer

<400> SEQUENCE: 23
aaaggatcca tggaatctgg gtctagcga 29

<210> SEQ ID NO 24
<211> LENGTH: 28
<212> TYPE: DNA

-continued

<213> ORGANISM: Artificial Sequence
<220> FEATURE:
<223> OTHER INFORMATION: Description of Artificial Sequence: PCR Primer

<400> SEQUENCE: 24
aaatctagaa ggaagtctgc tcttgcgc 28

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: PCR Primer

<400> SEQUENCE: 25
aaatctagag ccaccattcc tcgcaacg 28

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: PCR Primer

<400> SEQUENCE: 26
aaagagctcg tggtggagaa tctgggtgc 29

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 27
ggcggatccc gacctaccga gg 22

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: PCR Primer

<400> SEQUENCE: 28
aaagagctcg tggatggatt ggctccagc 29

<210> SEQ ID NO 29
<211> LENGTH: 822
<212> TYPE: DNA
<213> ORGANISM: Artificial Sequence
<220> FEATURE:
<223> OTHER INFORMATION: Description of Artificial Sequence: Complement of SEQ ID NO:6

<400> SEQUENCE: 29
ccatgcccaa tagttagctc ttattggatc aacacgacac agaatggtac acaccaaatt 60
ggccaagtta gtctctggtt cttcattagc tagagctttc accgagtctc tatgctcgtt 120
ggttggtctc aacccatcgc acagaagatc caaaagggtg ctcagagcga atccatggaa 180
gcagtccgcg cgtgagagaa ctttcaaaca gactgaggaa acacttggat cactaatcca 240
agactctgtg tcgtctttgt aaagggcttt caggtacctc caagagctct cgttcccggg 300
atttgctaaa atggctttga ctgtgtagct tacttcagat tctctcatgg cttctaggcc 360

-continued

```
tcccaacgaa ggtgatctag ttataacgta atacctctga ttccatgcag agttgttaaa    420

gacgtcagct tcaaggagct cgtggcagta gttaagctca ttttcccatc ctcctaatgc    480

ttgtagcgcc cactgcctat gtgaccaagc atgataatgc ttggcatcaa gtgatagtac    540

cctccgagta aactcaagtt cctttcctgc aacatcagga cccagtttct ctgcgaccca    600

tcgtcgatga tgccacaact ggtagttctt agagttatcc tcagcaatgc tttcgatgaa    660

cttgagctct tcatacaagt cgttattaag ctcctcgagt actaagcgcc cgaagtgcca    720

cacggtgtag ttgcccgagt ttaagcggag agcttcttcc gtgagtcgca gcgcgcgagc    780

agaacgctcg tcggagaagt aaatcgcacg gaagtaatcc at                       822
```

<210> SEQ ID NO 30
<211> LENGTH: 1110
<212> TYPE: DNA
<213> ORGANISM: Artificial Sequence
<220> FEATURE:
<223> OTHER INFORMATION: Description of Artificial Sequence: Complement
      to Seq Id No:8

<400> SEQUENCE: 30

```
aaatctagaa gcttcataat accgatccaa gacaatgttg tggaggaggt gaacaggttc     60

aaggtggttt gcgtagccac ccaaaatgtc acgagtcaaa ggaggagtgt cctcgtcttt    120

tgaccaagcg tgttgagcca cggaaagacc gcttaggcag taacatgtgt ggtagaagtc    180

acggggtttc ctcagcttgt ctctgaatcc accatcagca acctgagagc acaagagcac    240

atatctttgc aagccgaggc tatcaaaaac aggttgaatt ctcctgtcaa tgtaggtaga    300

cgtatgatga acttggtgac cattccctga atcttcatcg ctatcctcat cagaatcatc    360

ttcatcactg tcttcaggat catcttcatc atgaccatgt tcctcgtgat cttcatctgt    420

cccttgtgac atatgtgatg atgatccatg aggtgccata tcctgggatg aaaaaaatcg    480

ctgtagtaga acacaggggg ctgcctgcca aaacgtgtag caaccgtcga ccaatttgtt    540

cgtcctacct tggaatccca tttctactcc ttgtcgatgt acaacccaat tcattaacga    600

atccaaattc aagcggtcga cttcattgat taaaatcata gtagccaacc cacagtacgt    660

gtacccacca tgagcttcgg agccaggttc ccctccaatg ccaccttcat aagtttggca    720

actcaaaatg taatctccta agccgcgggt gagttcatca tccacaatgt tcaggatgct    780

tgcaatcaaa atcgcagtgt agcacgctcg cacatctatt tctcccatat tatgcatcct    840

gaaacctcca tttgtatcct tcattcgtct taagaaacaa gccatttgtt ctctgttaat    900

tgaagagaag gctttctcac ctcctaaagt aacaagtgta ttcactgcag cataacttgt    960

tgcaagatgt ggaagttggc caggaccacc accatatcca ccatcagaac cctggcaacg   1020

tccaagaaaa tcgattgcat tgttttctaa gtcatcatcc acagactccc caagcaaagc   1080

aattgaatga agaatccagt aacaaagcca                                    1110
```

<210> SEQ ID NO 31
<211> LENGTH: 1041
<212> TYPE: DNA
<213> ORGANISM: Glycine max
<220> FEATURE:
<221> NAME/KEY: misc_feature
<222> LOCATION: (360)...(360)
<223> OTHER INFORMATION: Wherein “n” is A, T, C or G

<400> SEQUENCE: 31

```
atggaatctg ggtctagcga aggagaagag gtgcagcaac gcgtgccgtt gagggagaga     60
```

-continued

```
gtggagtggt cagatgttac tccggttcct caaaacgacg gccctaaccc tgtcgttccg    120

atccagtaca ctgaagagtt ttccgaagtt atggattact ttcgcgccgt ttacctcacc    180

gatgaacgct cccctcgcgc cctcgctctc acagccgaag ccgttcaatt caactccggc    240

aactacactg tgtggcattt ccgacggttg ttacttgagt cgctaaaagt cgacttgaac    300

gatgaactgg agtttgtgga gcgtatggcc gctggaaatt ctaaaaatta tcagatgtgn    360

atgttctgta ggcatcctag acgatgggtt gccgagaagt taggtcctga agctagaaac    420

aatgagctcg agttcaccaa aaagatactg tccgttgatg ccaaacatta tcatgcatgg    480

tctcatagac agtgggctct tcaaacacta ggaggatggg aagatgaact taattattgc    540

acagaactac ttaaagaaga catttttaac aattctgctt ggaatcagag atattttgtc    600

ataacaaggt ctcctttctt ggggggccta aaagctatga gagagtctga agtgctttac    660

accatcgaag ccattatagc ctaccctgaa aatgaaagct cgtggagata tctacgagga    720

ctttataaag gtgaaactac ttcatgggta aatgatcctc aagtttcttc agtatgctta    780

aagattttga gaactaagag caactacgtg tttgctctta gcactatttt agatcttata    840

tgctttggtt atcaaccaaa tgaagacatt agagatgcca ttgacgcctt aaagaccgca    900

gatatggata aacaagattt agatgatgat gagaaagggg aacaacaaaa tttaaatata    960

gcacgaaata tttgttctat cctaaaacaa gttgatccaa ttagaaccaa ctattggatt   1020

tggcgcaaga gcagacttcc t                                             1041
```

<210> SEQ ID NO 32
<211> LENGTH: 1041
<212> TYPE: DNA
<213> ORGANISM: Artificial Sequence
<220> FEATURE:
<223> OTHER INFORMATION: Description of Artificial Sequence: Complement to Seq Id No:31
<220> FEATURE:
<221> NAME/KEY: misc_feature
<222> LOCATION: (682)..(682)
<223> OTHER INFORMATION: Wherein “n” is A, T, C or G

<400> SEQUENCE: 32

```
aggaagtctg ctcttgcgcc aaatccaata gttggttcta attggatcaa cttgttttag     60

gatagaacaa atatttcgtg ctatatttaa attttgttgt tcccctttct catcatcatc    120

taaatcttgt ttatccatat ctgcggtctt taaggcgtca atggcatctc taatgtcttc    180

atttggttga taaccaaagc atataagatc taaaatagtg ctaagagcaa acacgtagtt    240

gctcttagtt ctcaaaatct ttaagcatac tgaagaaact tgaggatcat ttacccatga    300

agtagtttca cctttataaa gtcctcgtag atatctccac gagctttcat tttcagggta    360

ggctataatg gcttcgatgg tgtaaagcac ttcagactct ctcatagctt ttaggccccc    420

caagaaagga gaccttgtta tgacaaaata tctctgattc caagcagaat tgttaaaaat    480

gtcttcttta agtagttctg tgcaataatt aagttcatct tcccatcctc ctagtgtttg    540

aagagcccac tgtctatgag accatgcatg ataatgtttg gcatcaacgg acagtatctt    600

tttggtgaac tcgagctcat tgtttctagc ttcaggacct aacttctcgg caacccatcg    660

tctaggatgc ctacagaaca tncacatctg ataattttta gaatttccag cggccatacg    720

ctccacaaac tccagttcat cgttcaagtc gacttttagc gactcaagta acaaccgtcg    780

gaaatgccac acagtgtagt tgccggagtt gaattgaacg gcttcggctg tgagagcgag    840

ggcgcgaggg gagcgttcat cggtgaggta aacggcgcga aagtaatcca taacttcgga    900
```

-continued

```
aaactcttca gtgtactgga tcggaacgac agggttaggg ccgtcgtttt gaggaaccgg    960

agtaacatct gaccactcca ctctctccct caacggcacg cgttgctgca cctcttctcc   1020

ttcgctagac ccagattcca t                                             1041


<210> SEQ ID NO 33
<211> LENGTH: 347
<212> TYPE: PRT
<213> ORGANISM: Glycine max
<220> FEATURE:
<221> NAME/KEY: VARIANT
<222> LOCATION: (120)...(120)
<223> OTHER INFORMATION: Wherein “Xaa” is any amino acid

<400> SEQUENCE: 33

Met Glu Ser Gly Ser Ser Glu Gly Glu Glu Val Gln Gln Arg Val Pro
 1               5                  10                  15

Leu Arg Glu Arg Val Glu Trp Ser Asp Val Thr Pro Val Pro Gln Asn
            20                  25                  30

Asp Gly Pro Asn Pro Val Val Pro Ile Gln Tyr Thr Glu Glu Phe Ser
        35                  40                  45

Glu Val Met Asp Tyr Phe Arg Ala Val Tyr Leu Thr Asp Glu Arg Ser
    50                  55                  60

Pro Arg Ala Leu Ala Leu Thr Ala Glu Ala Val Gln Phe Asn Ser Gly
65                  70                  75                  80

Asn Tyr Thr Val Trp His Phe Arg Arg Leu Leu Leu Glu Ser Leu Lys
                85                  90                  95

Val Asp Leu Asn Asp Glu Leu Glu Phe Val Glu Arg Met Ala Ala Gly
            100                 105                 110

Asn Ser Lys Asn Tyr Gln Met Xaa Met Phe Cys Arg His Pro Arg Arg
        115                 120                 125

Trp Val Ala Glu Lys Leu Gly Pro Glu Ala Arg Asn Asn Glu Leu Glu
    130                 135                 140

Phe Thr Lys Lys Ile Leu Ser Val Asp Ala Lys His Tyr His Ala Trp
145                 150                 155                 160

Ser His Arg Gln Trp Ala Leu Gln Thr Leu Gly Gly Trp Glu Asp Glu
                165                 170                 175

Leu Asn Tyr Cys Thr Glu Leu Leu Lys Glu Asp Ile Phe Asn Asn Ser
            180                 185                 190

Ala Trp Asn Gln Arg Tyr Phe Val Ile Thr Arg Ser Pro Phe Leu Gly
        195                 200                 205

Gly Leu Lys Ala Met Arg Glu Ser Glu Val Leu Tyr Thr Ile Glu Ala
    210                 215                 220

Ile Ile Ala Tyr Pro Glu Asn Glu Ser Ser Trp Arg Tyr Leu Arg Gly
225                 230                 235                 240

Leu Tyr Lys Gly Glu Thr Thr Ser Trp Val Asn Asp Pro Gln Val Ser
                245                 250                 255

Ser Val Cys Leu Lys Ile Leu Arg Thr Lys Ser Asn Tyr Val Phe Ala
            260                 265                 270

Leu Ser Thr Ile Leu Asp Leu Ile Cys Phe Gly Tyr Gln Pro Asn Glu
        275                 280                 285

Asp Ile Arg Asp Ala Ile Asp Ala Leu Lys Thr Ala Asp Met Asp Lys
    290                 295                 300

Gln Asp Leu Asp Asp Asp Glu Lys Gly Glu Gln Gln Asn Leu Asn Ile
305                 310                 315                 320

Ala Arg Asn Ile Cys Ser Ile Leu Lys Gln Val Asp Pro Ile Arg Thr
```

-continued

```
            325                 330                 335

Asn Tyr Trp Ile Trp Arg Lys Ser Arg Leu Pro
        340                 345
```

<210> SEQ ID NO 34
<211> LENGTH: 1135
<212> TYPE: DNA
<213> ORGANISM: Glycine max

<400> SEQUENCE: 34

```
gccaccattc ctcgcaacgc ccaaaccctc atgttggagc ttcaacgcga taatcacatg     60

cagtatgtct ccaaaggcct tcgccatctc agttccgcat tttccgtttt ggacgctaat    120

cgaccctggc tctgctactg gatcttccac tccattgctt tgttgggaga atccgtcgat    180

gatgaactcg aagataacgc tatcgatttt cttaaccgtt gccaggatcc gaatggtgga    240

tatgccgggg gaccaggcca gatgcctcat attgccacaa cttatgctgc tgttaattca    300

cttattactt tgggtggtga gaaatccctg gcatcaatta atagagataa actgtatggg    360

tttctgcggc ggatgaagca accaaatggt ggattcagga tgcatgatga aggtgaaatt    420

gatgttcgag cttgctacac tgccatttct gttgcaagtg ttttgaacat tttggatgat    480

gagctgatcc agaatgttgg agactacatt ataagctgtc aaacatatga gggtggcatt    540

gctggtgagc ctggttctga ggctcatggt gggtacacct tttgtggatt agctacaatg    600

attctgattg gtgaggttaa tcacttggat ctgcctcgat tagttgactg ggtggtattc    660

cgacaaggta aggaatgtgg attccagggg agaacaaata aactggtgga tggatgctat    720

tccttttggc agggaggtgc tgttgctcta ttgcaaagat tatcttctat tatcaacaaa    780

cagatggaag agacatcaca gatttttgcg gtatcttatg tatctgaagc aaaagaaagt    840

ttggatggaa cctctagtca tgcaacatgc cgtggtgagc atgaaggcac cagtgaatcc    900

agttcatctg attttaaaaa tattgcctat aaatttatta atgagtggag agcacaagaa    960

ccactttttc acagtattgc tttacagcaa tatattctct tatgtgcaca ggagcaagag   1020

ggtggactga gagacaaacc gggtaaacgt agagatcatt atcacacatg ttactgttta   1080

agtggactct cattgtgcca gtatagttgg tcaaagcacc cagattctcc accac        1135
```

<210> SEQ ID NO 35
<211> LENGTH: 1135
<212> TYPE: DNA
<213> ORGANISM: Artificial Sequence
<220> FEATURE:
<223> OTHER INFORMATION: Description of Artificial Sequence: Complement
      to Seq Id No:34

<400> SEQUENCE: 35

```
gtggtggaga atctgggtgc tttgaccaac tatactggca caatgagagt ccacttaaac     60

agtaacatgt gtgataatga tctctacgtt tacccggttt gtctctcagt ccaccctctt    120

gctcctgtgc acataagaga atatattgct gtaaagcaat actgtgaaaa agtggttctt    180

gtgctctcca ctcattaata aatttatagg caatattttt aaaatcagat gaactggatt    240

cactggtgcc ttcatgctca ccacggcatg ttgcatgact agaggttcca tccaaacttt    300

cttttgcttc agatacataa gataccgcaa aaatctgtga tgtctcttcc atctgtttgt    360

tgataataga agataatctt tgcaatagag caacagcacc tccctgccaa aaggaatagc    420

atccatccac cagtttattt gttctcccct ggaatccaca ttccttacct tgtcggaata    480

ccacccagtc aactaatcga ggcagatcca agtgattaac ctcaccaatc agaatcattg    540
```

-continued

```
tagctaatcc acaaaaggtg tacccaccat gagcctcaga accaggctca ccagcaatgc    600

caccctcata tgtttgacag cttataatgt agtctccaac attctggatc agctcatcat    660

ccaaaatgtt caaaacactt gcaacagaaa tggcagtgta gcaagctcga acatcaattt    720

caccttcatc atgcatcctg aatccaccat ttggttgctt catccgccgc agaaacccat    780

acagtttatc tctattaatt gatgccaggg atttctcacc acccaaagta ataagtgaat    840

taacagcagc ataagttgtg gcaatatgag gcatctggcc tggtcccccg gcatatccac    900

cattcggatc ctggcaacgg ttaagaaaat cgatagcgtt atcttcgagt tcatcatcga    960

cggattctcc caacaaagca atggagtgga agatccagta gcagagccag ggtcgattag   1020

cgtccaaaac ggaaaatgcg gaactgagat ggcgaaggcc tttggagaca tactgcatgt   1080

gattatcgcg ttgaagctcc aacatgaggg tttgggcgtt gcgaggaatg gtggc        1135
```

```
<210> SEQ ID NO 36
<211> LENGTH: 378
<212> TYPE: PRT
<213> ORGANISM: Glycine max

<400> SEQUENCE: 36

Ala Thr Ile Pro Arg Asn Ala Gln Thr Leu Met Leu Glu Leu Gln Arg
 1               5                  10                  15

Asp Asn His Met Gln Tyr Val Ser Lys Gly Leu Arg His Leu Ser Ser
            20                  25                  30

Ala Phe Ser Val Leu Asp Ala Asn Arg Pro Trp Leu Cys Tyr Trp Ile
        35                  40                  45

Phe His Ser Ile Ala Leu Leu Gly Glu Ser Val Asp Asp Glu Leu Glu
    50                  55                  60

Asp Asn Ala Ile Asp Phe Leu Asn Arg Cys Gln Asp Pro Asn Gly Gly
65                  70                  75                  80

Tyr Ala Gly Gly Pro Gly Gln Met Pro His Ile Ala Thr Thr Tyr Ala
                85                  90                  95

Ala Val Asn Ser Leu Ile Thr Leu Gly Gly Glu Lys Ser Leu Ala Ser
            100                 105                 110

Ile Asn Arg Asp Lys Leu Tyr Gly Phe Leu Arg Arg Met Lys Gln Pro
        115                 120                 125

Asn Gly Gly Phe Arg Met His Asp Glu Gly Glu Ile Asp Val Arg Ala
    130                 135                 140

Cys Tyr Thr Ala Ile Ser Val Ala Ser Val Leu Asn Ile Leu Asp Asp
145                 150                 155                 160

Glu Leu Ile Gln Asn Val Gly Asp Tyr Ile Ile Ser Cys Gln Thr Tyr
                165                 170                 175

Glu Gly Gly Ile Ala Gly Glu Pro Gly Ser Glu Ala His Gly Gly Tyr
            180                 185                 190

Thr Phe Cys Gly Leu Ala Thr Met Ile Leu Ile Gly Glu Val Asn His
        195                 200                 205

Leu Asp Leu Pro Arg Leu Val Asp Trp Val Val Phe Arg Gln Gly Lys
    210                 215                 220

Glu Cys Gly Phe Gln Gly Arg Thr Asn Lys Leu Val Asp Gly Cys Tyr
225                 230                 235                 240

Ser Phe Trp Gln Gly Gly Ala Val Ala Leu Leu Gln Arg Leu Ser Ser
                245                 250                 255

Ile Ile Asn Lys Gln Met Glu Glu Thr Ser Gln Ile Phe Ala Val Ser
            260                 265                 270
```

-continued

```
Tyr Val Ser Glu Ala Lys Glu Ser Leu Asp Gly Thr Ser Ser His Ala
        275                 280                 285

Thr Cys Arg Gly Glu His Glu Gly Thr Ser Glu Ser Ser Ser Ser Asp
    290                 295                 300

Phe Lys Asn Ile Ala Tyr Lys Phe Ile Asn Glu Trp Arg Ala Gln Glu
305                 310                 315                 320

Pro Leu Phe His Ser Ile Ala Leu Gln Gln Tyr Ile Leu Leu Cys Ala
                325                 330                 335

Gln Glu Gln Glu Gly Gly Leu Arg Asp Lys Pro Gly Lys Arg Arg Asp
            340                 345                 350

His Tyr His Thr Cys Tyr Cys Leu Ser Gly Leu Ser Leu Cys Gln Tyr
        355                 360                 365

Ser Trp Ser Lys His Pro Asp Ser Pro Pro
    370                 375
```

<210> SEQ ID NO 37
<211> LENGTH: 1245
<212> TYPE: DNA
<213> ORGANISM: Zea mays

<400> SEQUENCE: 37

```
ggcggatccc gacctaccga ggctcacggt gacgcaggtg gagcagatga aggtggaggc     60

cagggttggc gacatctacc gctccctctt cggggccgcg cccaacacga aatccatcat    120

gctagagctg tggcgtgatc agcatatcga gtatctgacg cctgggctga ggcatatggg    180

accagccttt catgttctag atgccaatcg cccttggcta tgctactgga tggttcatcc    240

acttgctttg ctggatgaag cacttgatga tgatcttgag aatgatatca tagacttctt    300

agctcgatgt caggataaag atggtggata tagtggtgga cctggacagt tgcctcacct    360

agctacgact tatgctgctg taaatacact tgtgacaata gggagcgaaa gagcattgtc    420

atcaatcaat aggggcaacc tgtacaattt tatgctgcag atgaaagatg tatcaggtgc    480

tttcagaatg catgatggtg gcgaaattga tgtccgtgct tcctacaccg ctatatcggt    540

tgccagcctt gtgaatattc ttgattttaa actggcaaaa ggtgtaggcg actacatagc    600

aagatgtcaa acttatgaag gtggtattgc tggggagcct tatgctgaag cacatggtgg    660

gtatacattc tgtggattgg ctgctttgat cctgcttaat gaggcagaga aagttgactt    720

gcctagtttg attggctggg tggcttttcg tcaaggagtg gaatgcggat ttcaaggacg    780

aactaataaa ttggttgatg gttgctactc cttttggcag ggagctgcca ttgctttcac    840

acaaaagtta attacgattg ttgataagca attgaggtcc tcgtattcct gcaaaaggcc    900

atcaggagag gatgcctgca gcaccagttc atatgggtgc accgcgaata agtcttcctc    960

tgctgtggac tatgcgaagt ttggatttga ttttatacaa cagagcaacc aaattggccc   1020

actcttccat aacattgccc tgcaacaata catcctactt tgttctcagg tactagaggg   1080

aggcttgagg gataagcctg gaaagaacag agatcactat cattcatgct actgcctcag   1140

tggcctcgca gttagccagt acagtgccat gactgatact ggttcgtgcc cattacctca   1200

gcatgtgctt ggaccgtact ctaatttgct ggagccaatc catcc                    1245
```

<210> SEQ ID NO 38
<211> LENGTH: 1245
<212> TYPE: DNA
<213> ORGANISM: Artificial Sequence
<220> FEATURE:
<223> OTHER INFORMATION: Description of Artificial Sequence: Complement -continued to Seq Id No:37

<400> SEQUENCE: 38

```
ggatggattg gctccagcaa attagagtac ggtccaagca catgctgagg taatgggcac     60

gaaccagtat cagtcatggc actgtactgg ctaactgcga ggccactgag gcagtagcat    120

gaatgatagt gatctctgtt ctttccaggc ttatccctca agcctccctc tagtacctga    180

gaacaaagta ggatgtattg ttgcagggca atgttatgga agagtgggcc aatttggttg    240

ctctgttgta taaaatcaaa tccaaacttc gcatagtcca cagcagagga agacttattc    300

gcggtgcacc catatgaact ggtgctgcag gcatcctctc ctgatggcct tttgcaggaa    360

tacgaggacc tcaattgctt atcaacaatc gtaattaact tttgtgtgaa agcaatggca    420

gctccctgcc aaaaggagta gcaaccatca accaatttat tagttcgtcc ttgaaatccg    480

cattccactc cttgacgaaa agccacccag ccaatcaaac taggcaagtc aactttctct    540

gcctcattaa gcaggatcaa agcagccaat ccacagaatg tatacccacc atgtgcttca    600

gcataaggct ccccagcaat accaccttca taagtttgac atcttgctat gtagtcgcct    660

acaccttttg ccagtttaaa atcaagaata ttcacaaggc tggcaaccga tatagcggtg    720

taggaagcac ggacatcaat ttcgccacca tcatgcattc tgaaagcacc tgatacatct    780

ttcatctgca gcataaaatt gtacaggttg cccctattga ttgatgacaa tgctctttcg    840

ctccctattg tcacaagtgt atttacagca gcataagtcg tagctaggtg aggcaactgt    900

ccaggtccac cactatatcc accatcttta tcctgacatc gagctaagaa gtctatgata    960

tcattctcaa gatcatcatc aagtgcttca tccagcaaag caagtggatg aaccatccag   1020

tagcatagcc aagggcgatt ggcatctaga acatgaaagg ctggtcccat atgcctcagc   1080

ccaggcgtca gatactcgat atgctgatca cgccacagct ctagcatgat ggatttcgtg   1140

ttgggcgcgg ccccgaagag ggagcggtag atgtcgccaa ccctggcctc caccttcatc   1200

tgctccacct gcgtcaccgt gagcctcggt aggtcgggat ccgcc                    1245
```

<210> SEQ ID NO 39
<211> LENGTH: 414
<212> TYPE: PRT
<213> ORGANISM: Zea mays

<400> SEQUENCE: 39

```
Ala Asp Pro Asp Leu Pro Arg Leu Thr Val Thr Gln Val Glu Gln Met
 1               5                  10                  15

Lys Val Glu Ala Arg Val Gly Asp Ile Tyr Arg Ser Leu Phe Gly Ala
            20                  25                  30

Ala Pro Asn Thr Lys Ser Ile Met Leu Glu Leu Trp Arg Asp Gln His
        35                  40                  45

Ile Glu Tyr Leu Thr Pro Gly Leu Arg His Met Gly Pro Ala Phe His
    50                  55                  60

Val Leu Asp Ala Asn Arg Pro Trp Leu Cys Tyr Trp Met Val His Pro
65                  70                  75                  80

Leu Ala Leu Leu Asp Glu Ala Leu Asp Asp Asp Leu Glu Asn Asp Ile
                85                  90                  95

Ile Asp Phe Leu Ala Arg Cys Gln Asp Lys Asp Gly Gly Tyr Ser Gly
            100                 105                 110

Gly Pro Gly Gln Leu Pro His Leu Ala Thr Thr Tyr Ala Ala Val Asn
        115                 120                 125

Thr Leu Val Thr Ile Gly Ser Glu Arg Ala Leu Ser Ser Ile Asn Arg
```

-continued

```
    130                 135                 140

Gly Asn Leu Tyr Asn Phe Met Leu Gln Met Lys Asp Val Ser Gly Ala
145                 150                 155                 160

Phe Arg Met His Asp Gly Gly Glu Ile Asp Val Arg Ala Ser Tyr Thr
                165                 170                 175

Ala Ile Ser Val Ala Ser Leu Val Asn Ile Leu Asp Phe Lys Leu Ala
            180                 185                 190

Lys Gly Val Gly Asp Tyr Ile Ala Arg Cys Gln Thr Tyr Glu Gly Gly
        195                 200                 205

Ile Ala Gly Glu Pro Tyr Ala Glu Ala His Gly Gly Tyr Thr Phe Cys
    210                 215                 220

Gly Leu Ala Ala Leu Ile Leu Leu Asn Glu Ala Glu Lys Val Asp Leu
225                 230                 235                 240

Pro Ser Leu Ile Gly Trp Val Ala Phe Arg Gln Gly Val Glu Cys Gly
                245                 250                 255

Phe Gln Gly Arg Thr Asn Lys Leu Val Asp Gly Cys Tyr Ser Phe Trp
            260                 265                 270

Gln Gly Ala Ala Ile Ala Phe Thr Gln Lys Leu Ile Thr Ile Val Asp
        275                 280                 285

Lys Gln Leu Arg Ser Ser Tyr Ser Cys Lys Arg Pro Ser Gly Glu Asp
    290                 295                 300

Ala Cys Ser Thr Ser Ser Tyr Gly Cys Thr Ala Asn Lys Ser Ser Ser
305                 310                 315                 320

Ala Val Asp Tyr Ala Lys Phe Gly Phe Asp Phe Ile Gln Gln Ser Asn
                325                 330                 335

Gln Ile Gly Pro Leu Phe His Asn Ile Ala Leu Gln Gln Tyr Ile Leu
            340                 345                 350

Leu Cys Ser Gln Val Leu Glu Gly Gly Leu Arg Asp Lys Pro Gly Lys
        355                 360                 365

Asn Arg Asp His Tyr His Ser Cys Tyr Cys Leu Ser Gly Leu Ala Val
    370                 375                 380

Ser Gln Tyr Ser Ala Met Thr Asp Thr Gly Ser Cys Pro Leu Pro Gln
385                 390                 395                 400

His Val Leu Gly Pro Tyr Ser Asn Leu Leu Glu Pro Ile His
                405                 410


<210> SEQ ID NO 40
<211> LENGTH: 5247
<212> TYPE: DNA
<213> ORGANISM: Artificial Sequence
<220> FEATURE:
<223> OTHER INFORMATION: Description of Artificial Sequence: Plasmid
      pBI121-35S-AtFTA

<400> SEQUENCE: 40

gtttacccgc caatatatcc tgtcaaacac tgatagttta aactgaaggc gggaaacgac      60

aatctgatca tgagcggaga attaagggag tcacgttatg acccccgccg atgacgcggg     120

acaagccgtt ttacgtttgg aactgacaga accgcaacgt tgaaggagcc actcagccgc     180

gggtttctgg agtttaatga gctaagcaca tacgtcagaa accattattg cgcgttcaaa     240

agtcgcctaa ggtcactatc agctagcaaa tatttcttgt caaaaatgct ccactgacgt     300

tccataaatt cccctcggta tccaattaga gtctcatatt cactctcaat ccaaataatc     360

tgcaccggat ctggatcgtt tcgcatgatt gaacaagatg gattgcacgc aggttctccg     420

gccgcttggg tggagaggct attcggctat gactgggcac aacagacaat cggctgctct     480
```

-continued

```
gatgccgccg tgttccggct gtcagcgcag gggcgcccgg ttctttttgt caagaccgac    540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
```

-continued

```
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tccatgaatt tcgacgagac cgtgccactg   3360
agccaacgat tggagtggtc agacgtggtc ccattgactc aggacgatgg tccgaatcca   3420
gtggtgccaa ttgcctacaa ggaagagttc cgcgagacta tggattactt ccgtgcgatt   3480
tacttttccg acgagcgatc tcctcgcgca ctacgactca cggaagaaac cctcctctta   3540
aactccggca actacacagt gtggcatttc aggcgcctag tactcgaggc ccttaatcac   3600
gacttgtttg aagaactcga gttcatcgaa cgcattgctg aggataactc taagaactac   3660
caactgtggc atcatcggcg atgggttgca gagaaactgg gtcctgatgt tgcagggaga   3720
gaacttgaat ttacccgtag agtactttca cttgatgcca aacattatca tgcttggtca   3780
cataggcagt ggacactacg ggcattagga ggatgggaag atgagctcga ttactgtcac   3840
gagctccttg aagctgacgt ctttaacaat tccgcctgga atcagaggta ttatgtcatc   3900
acccaatctc ctttgttggg aggcctagaa gccatgagag aatctgaagt aagctacaca   3960
atcaaagcca ttttaaccaa tcctgcaaac gagagctcat ggcgatacct aaaagctctt   4020
tacaaagacg acaaagaatc ctggattagt gatccaagtg tttcctcagt ctgtttgaat   4080
gttctatccc gcacagattg cttccatgga ttcgctctga gcaccctttt ggatcttcta   4140
tgtgatggac tgagaccaac caacgagcat aaagactcag tgagagctct agctaatgaa   4200
gaaccagaga ctaacttggc caatttggtg tgtactattc ttggtcgtgt agatcctgta   4260
agagctaact attgggcatg gaggaagagc aagattacag tggcagcaat ttgactcgaa   4320
tttccccgat cgttcaaaca tttggcaata aagtttctta agattgaatc ctgttgccgg   4380
tcttgcgatg attatcatat aatttctgtt gaattacgtt aagcatgtaa taattaacat   4440
gtaatgcatg acgttattta tgagatgggt ttttatgatt agagtcccgc aattatacat   4500
ttaatacgcg atagaaaaca aaatatagcg cgcaaactag gataaattat cgcgcgcggt   4560
gtcatctatg ttactagatc gggaattcac tggccgtcgt tttacaacgt cgtgactggg   4620
aaaaccctgg cgttacccaa cttaatcgcc ttgcagcaca tccccctttc gccagctggc   4680
gtaatagcga agaggcccgc accgatcgcc cttcccaaca gttgcgcagc ctgaatggcg   4740
cccgctcctt tcgctttctt cccttccttt ctcgccacgt tcgccggctt tccccgtcaa   4800
gctctaaatc gggggctccc tttagggttc cgatttagtg ctttacggca cctcgacccc   4860
aaaaaacttg atttgggtga tggttcacgt agtgggccat cgccctgata gacggttttt   4920
cgccctttga cgttggagtc cacgttcttt aatagtggac tcttgttcca aactggaaca   4980
acactcaacc ctatctcggg ctattctttt gatttataag ggattttgcc gatttcggaa   5040
ccaccatcaa acaggatttt cgcctgctgg ggcaaaccag cgtggaccgc ttgctgcaac   5100
tctctcaggg ccaggcggtg aagggcaatc agctgttgcc cgtctcactg gtgaaaagaa   5160
aaaccacccc agtacattaa aaacgtccgc aatgtgttat taagttgtct aagcgtcaat   5220
```

-continued ttgtttacac cacaatatat cctgcca 5247

<210> SEQ ID NO 41
<211> LENGTH: 5373
<212> TYPE: DNA
<213> ORGANISM: Artificial Sequence
<220> FEATURE:
<223> OTHER INFORMATION: Description of Artificial Sequence: Plasmid
pBI121-rd29A-anti-AtFTA sequence

<400> SEQUENCE: 41
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900
aggctcaagg cgcgcatgcc cgacggcgat gatctcgtcg tgacccatgg cgatgcctgc 960
ttgccgaata tcatggtgga aaatggccgc ttttctggat tcatcgactg tggccggctg 1020
ggtgtggcgg accgctatca ggacatagcg ttggctaccc gtgatattgc tgaagagctt 1080
ggcggcgaat gggctgaccg cttcctcgtg ctttacggta tcgccgctcc cgattcgcag 1140
cgcatcgcct tctatcgcct tcttgacgag ttcttctgag cgggactctg gggttcgaaa 1200
tgaccgacca agcgacgccc aacctgccat cacgagattt cgattccacc gccgccttct 1260
atgaaaggtt gggcttcgga atcgttttcc gggacgccgg ctggatgatc ctccagcgcg 1320
gggatctcat gctggagttc ttcgcccacg ggatctctgc ggaacaggcg gtcgaaggtg 1380
ccgatatcat tacgacagca acggccgaca agcacaacgc cacgatcctg agcgacaata 1440
tgatcgggcc cggcgtccac atcaacggcg tcggcggcga ctgcccaggc aagaccgaga 1500
tgcaccgcga tatcttgctg cgttcggata ttttcgtgga gttcccgcca cagacccgga 1560
tgatccccga tcgttcaaac atttggcaat aaagtttctt aagattgaat cctgttgccg 1620
gtcttgcgat gattatcata taatttctgt tgaattacgt taagcatgta ataattaaca 1680
tgtaatgcat gacgttattt atgagatggg tttttatgat tagagtcccg caattataca 1740
tttaatacgc gatagaaaac aaaatatagc gcgcaaacta ggataaatta tcgcgcgcgg 1800
tgtcatctat gttactagat cgggcctcct gtcaatgctg gcggcggctc tggtggtggt 1860
tctggtggcg gctctgaggg tggtggctct gagggtggcg gttctgaggg tggcggctct 1920
gagggaggcg gttccggtgg tggctctggt tccggtgatt ttgattatga aaagatggca 1980

-continued

```
aacgctaata aggggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180
ggaaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
accctcctct gttttactca caaatatgca aactagaaaa caatcatcag gaataaaggg   3420
tttgattact tctattggaa agactctaga ggatcctcaa attgctgcca ctgtaatctt   3480
gctcttcctc catgcccaat agttagctct tataggatct acacgaccaa gaatagtaca   3540
caccaaattg gccaagttag tctctggttc ttcattagct agagctctca ctgagtcttt   3600
atgctcgttg gttggtctca gtccatcaca tagaagatcc aaaagggtgc tcagagcgaa   3660
tccatggaag caatctgtgc gggatagaac attcaaacag actgaggaaa cacttggatc   3720
actaatccag gattctttgt cgtctttgta aagcgctttt aggtatcgcc atgagctctc   3780
gtttgcagga ttggttaaaa tggctttgat tgtgtagctt acttcagatt ctctcatggc   3840
ttctaggcct cccaacaaag gagattgggt gatgacataa tacctctgat tccaggcgga   3900
attgttaaag acgtcagctt caaggagctc gtgacagtaa tcgagctcat cttcccatcc   3960
tcctaatgcc cgtagtgtcc actgcctatg tgaccaagca tgataatgtt tggcatcaag   4020
tgaaagtact ctacgggtaa attcaagttc tctccctgca acatcaggac ccagtttctc   4080
tgcaacccat cgccgatgat gccacagttg gtagttctta gagttatcct cagcaatgcg   4140
ttcgatgaac tcgagttctt caaacaagtc gtgattaagg gcctcgagta ctaggcgcct   4200
gaaatgccac actgtgtagt tgccggagtt taagaggagg gtttcttccg tgagtcgtag   4260
tgcgcgagga gatcgctcgt cggaaaagta aatcgcacgg aagtaatcca tagtctcgcg   4320
```

-continued gaactcttcc ttgtaggcaa ttggcaccac tggattcgga ccatcgtcct gagtcaatgg 4380
gaccacgtct gaccactcca atcgttggct cagtggcacg gtctcgtcga aattcatccc 4440
ctcgaatttc cccgatcgtt caaacatttg gcaataaagt ttcttaagat tgaatcctgt 4500
tgccggtctt gcgatgatta tcatataatt tctgttgaat tacgttaagc atgtaataat 4560
taacatgtaa tgcatgacgt tatttatgag atgggttttt atgattagag tcccgcaatt 4620
atacatttaa tacgcgatag aaaacaaaat atagcgcgca aactaggata aattatcgcg 4680
cgcggtgtca tctatgttac tagatcggga attcactggc cgtcgtttta caacgtcgtg 4740
actgggaaaa ccctggcgtt acccaactta atcgccttgc agcacatccc cctttcgcca 4800
gctggcgtaa tagcgaagag gcccgcaccg atcgcccttc ccaacagttg cgcagcctga 4860
atggcgcccg ctcctttcgc tttcttccct tcctttctcg ccacgttcgc cggctttccc 4920
cgtcaagctc taaatcgggg gctcccttta gggttccgat ttagtgcttt acggcacctc 4980
gaccccaaaa aacttgattt gggtgatggt tcacgtagtg ggccatcgcc ctgatagacg 5040
gtttttcgcc ctttgacgtt ggagtccacg ttctttaata gtggactctt gttccaaact 5100
ggaacaacac tcaaccctat ctcgggctat tcttttgatt tataagggat tttgccgatt 5160
tcggaaccac catcaaacag gattttcgcc tgctggggca aaccagcgtg gaccgcttgc 5220
tgcaactctc tcagggccag gcggtgaagg gcaatcagct gttgcccgtc tcactggtga 5280
aaagaaaaac caccccagta cattaaaaac gtccgcaatg tgttattaag ttgtctaagc 5340
gtcaatttgt ttacaccaca atatatcctg cca 5373

<210> SEQ ID NO 42
<211> LENGTH: 6285
<212> TYPE: DNA
<213> ORGANISM: Artificial Sequence
<220> FEATURE:
<223> OTHER INFORMATION: Description of Artificial Sequence: Plasmid
pBI121-35S-DA-AtFTA

<400> SEQUENCE: 42
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900
aggctcaagg cgcgcatgcc cgacggcgat gatctcgtcg tgacccatgg cgatgcctgc 960

-continued

```
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tcctcgctct tcctccatgc ccaatagtta   3360
```

-continued

```
gctcttacag gatctacacg accaagaata gtacacacca aattggccaa gttagtctct   3420
ggttcttcat tagctagagc tctcactgag tctttatgct cgttggttgg tctcagtcca   3480
tcacatagaa gatccaaaag ggtgctcaga gcgaatccat ggaagcaatc tgtgcgggat   3540
agaacattca aacagactga ggaaacactt ggatcactaa tccaggattc tttgtcgtct   3600
ttgtaaagag cttttaggta tcgccatgag ctctcgtttg caggattggt taaaatggct   3660
ttgattgtgt agcttacttc agattctctc atggcttcta ggcctcccaa caaaggagat   3720
tgggtgatga cataatacct ctgattccag gcggaattgt taaagacgtc agcttcaagg   3780
agctcgtgac agtaatcgag ctcatcttcc catcctccta atgcccggag gatccccatc   3840
tacccgcttc gcgtcggcat ccggtcagtg gcagtgaagg gcgaacagtt cctgattaac   3900
cacaaaccgt tctactttac tggctttggt cgtcatgaag atgcggactt gcgtggcaaa   3960
ggattcgata acgtgctgat ggtgcacgac cacgcattaa tggactggat tggggccaac   4020
tcctaccgta cctcgcatta cccttacgct gaagagatgc tcgactgggc agatgaacat   4080
ggcatcgtgg tgattgatga aactgctgct gtcggcttttt cgctctcttt aggcattggt   4140
ttcgaagcgg gcaacaagcc gaaagaactg tacagcgaag aggcagtcaa cggggaaact   4200
cagcaagcgc acttacaggc gattaaagag ctgatagcgc gtgacaaaaa ccacccaagc   4260
gtggtgatgt ggagtattgc caacgaaccg gatacccgtc cgcaaggtgc acgggaatat   4320
ttcgcgccac tggcggaagc aacgcgtaaa ctcgacccga cgcgtccgat cacctgcgtc   4380
aatgtaatgt tctgcgacgc tcacaccgat accatcagcg atctctttga tgtgctgtgc   4440
ctgaaccgtt attacggatg gtatgtccaa agcggcgatt tggaaacggc agagaaggta   4500
ctggaaaaag aacttctggc ctggcaggag aaactgtaca ccgacatgtg gagtgaagag   4560
tatcagtgtg catggctgga tatgtatcac cgcgtctttg atcgcgtcag cgccgtcgtc   4620
ggtgaacagg tatggaattt cgccgatttt gcgacctcgc aaggcatatt gcgcgttggc   4680
ggtaacaaga aagggatctt cactcgcgac cgcaaaccga agtcggcggc ttttctgctg   4740
caaaaacgct ggactggcat gaacttcggt gaaaaaccgc agcagggagg caaacaatga   4800
atcaacaact ctcctggcgc accatcgtcg gctacagcct cgggaattgc taccgagctc   4860
gctcttcctc catgcccaat agttagctct tacaggatct acacgaccaa gaatagtaca   4920
caccaaattg gccaagttag tctctggttc ttcattagct agagctctca ctgagtcttt   4980
atgctcgttg gttggtctca gtccatcaca tagaagatcc aaaagggtgc tcagagcgaa   5040
tccatggaag caatctgtgc gggatagaac attcaaacag actgaggaaa cacttggatc   5100
actaatccag gattctttgt cgtctttgta aagagctttt aggtatcgcc atgagctctc   5160
gtttgcagga ttggttaaaa tggctttgat tgtgtagctt acttcagatt ctctcatggc   5220
ttctaggcct cccaacaaag gagattgggt gatgacataa tacctctgat tccaggcgga   5280
attgttaaag acgtcagctt caaggagctc gtgacagtaa tcgagctcat cttcccatcc   5340
tcctaatgcc cgctcgaatt tccccgatcg ttcaaacatt tggcaataaa gtttcttaag   5400
attgaatcct gttgccggtc ttgcgatgat tatcatataa tttctgttga attacgttaa   5460
gcatgtaata attaacatgt aatgcatgac gttatttatg agatgggttt ttatgattag   5520
agtcccgcaa ttatacattt aatacgcgat agaaaacaaa atatagcgcg caaactagga   5580
taaattatcg cgcgcggtgt catctatgtt actagatcgg gaattcactg gccgtcgttt   5640
tacaacgtcg tgactgggaa aaccctggcg ttacccaact taatcgcctt gcagcacatc   5700
```

-continued

```
ccccttttcgc cagctggcgt aatagcgaag aggcccgcac cgatcgccct tcccaacagt   5760

tgcgcagcct gaatggcgcc cgctcctttc gctttcttcc cttcctttct cgccacgttc   5820

gccggctttc cccgtcaagc tctaaatcgg gggctccctt tagggttccg atttagtgct   5880

ttacggcacc tcgaccccaa aaaacttgat ttgggtgatg gttcacgtag tgggccatcg   5940

ccctgataga cggtttttcg ccctttgacg ttggagtcca cgttctttaa tagtggactc   6000

ttgttccaaa ctggaacaac actcaaccct atctcgggct attcttttga tttataaggg   6060

attttgccga tttcggaacc accatcaaac aggattttcg cctgctgggg caaaccagcg   6120

tggaccgctt gctgcaactc tctcagggcc aggcggtgaa gggcaatcag ctgttgcccg   6180

tctcactggt gaaaagaaaa accaccccag tacattaaaa acgtccgcaa tgtgttatta   6240

agttgtctaa gcgtcaattt gtttacacca caatatatcc tgcca                    6285
```

<210> SEQ ID NO 43
<211> LENGTH: 6409
<212> TYPE: DNA
<213> ORGANISM: Artificial Sequence
<220> FEATURE:
<223> OTHER INFORMATION: Description of Artificial Sequence: Plasmid
pBI121-RD29A-DA-AtFTA

<400> SEQUENCE: 43

```
gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420

gccgcttggg tggagaggct attcggctat gactgggcac aacagacaat cggctgctct    480

gatgccgccg tgttccggct gtcagcgcag gggcgcccgg ttctttttgt caagaccgac    540

ctgtccggtg ccctgaatga actgcaggac gaggcagcgc ggctatcgtg gctggccacg    600

acgggcgttc cttgcgcagc tgtgctcgac gttgtcactg aagcgggaag ggactggctg    660

ctattgggcg aagtgccggg gcaggatctc ctgtcatctc accttgctcc tgccgagaaa    720

gtatccatca tggctgatgc aatgcggcgg ctgcatacgc ttgatccggc tacctgccca    780

ttcgaccacc aagcgaaaca tcgcatcgag cgagcacgta ctcggatgga agccggtctt    840

gtcgatcagg atgatctgga cgaagagcat caggggctcg cgccagccga actgttcgcc    900

aggctcaagg cgcgcatgcc cgacggcgat gatctcgtcg tgacccatgg cgatgcctgc    960

ttgccgaata tcatggtgga aaatggccgc ttttctggat tcatcgactg tggccggctg   1020

ggtgtggcgg accgctatca ggacatagcg ttggctaccc gtgatattgc tgaagagctt   1080

ggcggcgaat gggctgaccg cttcctcgtg ctttacggta tcgccgctcc cgattcgcag   1140

cgcatcgcct tctatcgcct tcttgacgag ttcttctgag cgggactctg gggttcgaaa   1200

tgaccgacca agcgacgccc aacctgccat cacgagattt cgattccacc gccgccttct   1260

atgaaaggtt gggcttcgga atcgttttcc gggacgccgg ctggatgatc ctccagcgcg   1320

gggatctcat gctggagttc ttcgcccacg ggatctctgc ggaacaggcg gtcgaaggtg   1380

ccgatatcat tacgacagca acggccgaca agcacaacgc cacgatcctg agcgacaata   1440
```

-continued

```
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180
ggaaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
accctcctct gttttactca caaatatgca aactagaaaa caatcatcag gaataaaggg   3420
tttgattact tctattggaa aggactctag aggatcctcg ctcttcctcc atgcccaata   3480
gttagctctt acaggatcta cacgaccaag aatagtacac accaaattgg ccaagttagt   3540
ctctggttct tcattagcta gagctctcac tgagtcttta tgctcgttgg ttggtctcag   3600
tccatcacat agaagatcca aaagggtgct cagagcgaat ccatggaagc aatctgtgcg   3660
ggatagaaca ttcaaacaga ctgaggaaac acttggatca ctaatccagg attctttgtc   3720
gtctttgtaa agagctttta ggtatcgcca tgagctctcg tttgcaggat tggttaaaat   3780
ggctttgatt gtgtagctta cttcagattc tctcatggct tctaggcctc ccaacaaagg   3840
```

-continued agattgggtg atgacataat acctctgatt ccaggcggaa ttgttaaaga cgtcagcttc 3900
aaggagctcg tgacagtaat cgagctcatc ttcccatcct cctaatgccc ggaggatccc 3960
catctacccg cttcgcgtcg gcatccggtc agtggcagtg aagggcgaac agttcctgat 4020
taaccacaaa ccgttctact ttactggctt tggtcgtcat gaagatgcgg acttgcgtgg 4080
caaaggattc gataacgtgc tgatggtgca cgaccacgca ttaatggact ggattggggc 4140
caactcctac cgtacctcgc attaccctta cgctgaagag atgctcgact gggcagatga 4200
acatggcatc gtggtgattg atgaaactgc tgctgtcggc ttttcgctct ctttaggcat 4260
tggtttcgaa gcgggcaaca agccgaaaga actgtacagc gaagaggcag tcaacgggga 4320
aactcagcaa gcgcacttac aggcgattaa agagctgata gcgcgtgaca aaaaccaccc 4380
aagcgtggtg atgtggagta ttgccaacga accggatacc cgtccgcaag gtgcacggga 4440
atatttcgcg ccactggcgg aagcaacgcg taaactcgac ccgacgcgtc cgatcacctg 4500
cgtcaatgta atgttctgcg acgctcacac cgataccatc agcgatctct ttgatgtgct 4560
gtgcctgaac cgttattacg gatggtatgt ccaaagcggc gatttggaaa cggcagagaa 4620
ggtactggaa aaagaacttc tggcctggca ggagaaactg tacaccgaca tgtggagtga 4680
agagtatcag tgtgcatggc tggatatgta tcaccgcgtc tttgatcgcg tcagcgccgt 4740
cgtcggtgaa caggtatgga atttcgccga ttttgcgacc tcgcaaggca tattgcgcgt 4800
tggcggtaac aagaaaggga tcttcactcg cgaccgcaaa ccgaagtcgg cggcttttct 4860
gctgcaaaaa cgctggactg gcatgaactt cggtgaaaaa ccgcagcagg gaggcaaaca 4920
atgaatcaac aactctcctg gcgcaccatc gtcggctaca gcctcgggaa ttgctaccga 4980
gctcgctctt cctccatgcc caatagttag ctcttacagg atctacacga ccaagaatag 5040
tacacaccaa attggccaag ttagtctctg gttcttcatt agctagagct ctcactgagt 5100
ctttatgctc gttggttggt ctcagtccat cacatagaag atccaaaagg gtgctcagag 5160
cgaatccatg gaagcaatct gtgcgggata gaacattcaa acagactgag gaaacacttg 5220
gatcactaat ccaggattct ttgtcgtctt tgtaaagagc ttttaggtat cgccatgagc 5280
tctcgtttgc aggattggtt aaaatggctt tgattgtgta gcttacttca gattctctca 5340
tggcttctag gcctcccaac aaaggagatt gggtgatgac ataatacctc tgattccagg 5400
cggaattgtt aaagacgtca gcttcaagga gctcgtgaca gtaatcgagc tcatcttccc 5460
atcctcctaa tgcccgctcg aatttccccg atcgttcaaa catttggcaa taaagtttct 5520
taagattgaa tcctgttgcc ggtcttgcga tgattatcat ataatttctg ttgaattacg 5580
ttaagcatgt aataattaac atgtaatgca tgacgttatt tatgagatgg gtttttatga 5640
ttagagtccc gcaattatac atttaatacg cgatagaaaa caaaatatag cgcgcaaact 5700
aggataaatt atcgcgcgcg gtgtcatcta tgttactaga tcgggaattc actggccgtc 5760
gttttacaac gtcgtgactg ggaaaaccct ggcgttaccc aacttaatcg ccttgcagca 5820
catccccctt tcgccagctg gcgtaatagc gaagaggccc gcaccgatcg cccttcccaa 5880
cagttgcgca gcctgaatgg cgcccgctcc tttcgctttc ttcccttcct ttctcgccac 5940
gttcgccggc tttccccgtc aagctctaaa tcgggggctc cctttagggt tccgatttag 6000
tgctttacgg cacctcgacc ccaaaaaact tgatttgggt gatggttcac gtagtgggcc 6060
atcgccctga tagacggttt ttcgcccttt gacgttggag tccacgttct ttaatagtgg 6120
actcttgttc caaactggaa caacactcaa ccctatctcg ggctattctt ttgatttata 6180

-continued

```
agggattttg ccgatttcgg aaccaccatc aaacaggatt ttcgcctgct ggggcaaacc   6240

agcgtggacc gcttgctgca actctctcag ggccaggcgg tgaagggcaa tcagctgttg   6300

cccgtctcac tggtgaaaag aaaaaccacc ccagtacatt aaaaacgtcc gcaatgtgtt   6360

attaagttgt ctaagcgtca atttgtttac accacaatat atcctgcca               6409
```

<210> SEQ ID NO 44
<211> LENGTH: 1254
<212> TYPE: DNA
<213> ORGANISM: Artificial Sequence
<220> FEATURE:
<223> OTHER INFORMATION: Description of Artificial Sequence: Plasmid MuA-anti-GmFTA

<400> SEQUENCE: 44

```
gaattcaaat ttttcgccag ttctaaatat ccggaaacct cttgggatgc cattgcccat     60

ctatctgtaa tttattgacg aaatagacga aaaggaaggt ggctcctata aagcacatca    120

ttgcgataac agaaaggcca ttgttgaaga tacctctgct gacattggtc cccaagtgga    180

agcaccaccc catgaggagc accgtggagt aagaagacgt tcgagccacg tcgaaaaagc    240

aagtgtgttg atgtagtatc tccattgacg taagggatga cgcacaatcc aactatccat    300

cgcaagacca ttgctctata taagaaagtt aatatcattt cgagtggcca cgctgagctc    360

aggaagtctg ctcttgcgcc aaatccaata gttggttcta attggatcaa cttgttttag    420

gatagaacaa atatttcgtg ctatatttaa attttgttgt tcccctttct catcatcatc    480

taaatcttgt ttatccatat ctgcggtctt taaggcgtca atggcatctc taatgtcttc    540

atttggttga taaccaaagc atataagatc taaaatagtg ctaagagcaa acacgtagtt    600

gctcttagtt ctcaaaatct ttaagcatac tgaagaaact tgaggatcat ttacccatga    660

agtagtttca cctttataaa gtcctcgtag atatctccac gagctttcat tttcagggta    720

ggctataatg gcttcgatgg tgtaaagcac ttcagactct ctcatagctt ttaggccccc    780

caagaaagga gaccttgtta tgacaaaata tctctgattc caagcagaat tgttaaaaat    840

gtcttcttta agtagttctg tgcaataatt aagttcatct tcccatcctc ctagtgtttg    900

aagagcccac tgtctatgag accatgcatg ataatgtttg gcatcaacgg acagtatctt    960

tttggtgaac tcgagctgag ctcgaatttc cccgatcgtt caaacatttg gcaataaagt   1020

ttcttaagat tgaatcctgt tgccggtctt gcgatgatta tcatataatt tctgttgaat   1080

tacgttaagc atgtaataat taacatgtaa tgcatgacgt tatttatgag atgggttttt   1140

atgattagag tcccgcaatt atacatttaa tacgcgatag aaaacaaaat atagcgcgca   1200

aactaggata aattatcgcg cgcggtgtca tctatgttac tagatcggga attc         1254
```

<210> SEQ ID NO 45
<211> LENGTH: 1822
<212> TYPE: DNA
<213> ORGANISM: Artificial Sequence
<220> FEATURE:
<223> OTHER INFORMATION: Description of Artificial Sequence: Plasmid RD29A-anti-GmFTA

<400> SEQUENCE: 45

```
ggagccatag atgcaattca atcaaactga aatttctgca agaatctcaa acacggagat     60

ctcaaagttt gaaagaaaat ttatttcttc gactcaaaac aaacttacga aatttaggta    120

gaacttatat acattatatt gtaatttttt gtaacaaaat gtttttatta ttattataga    180

attttactgg ttaaattaaa aatgaataga aaaggtgaat taagaggaga gaggaggtaa    240
```

-continued

```
acattttctt ctatttttc atattttcag gataaattat tgtaaaagtt tacaagattt    300

ccatttgact agtgtaaatg aggaatattc tctagtaaga tcattatttc atctacttct    360

tttatcttct accagtagag gaataaacaa tatttagctc ctttgtaaat acaaattaat    420

tttccttctt gacatcattc aattttaatt ttacgtataa aataaaagat catacctatt    480

agaacgatta aggagaaata caattcgaat gagaaggatg tgccgtttgt tataataaac    540

agccacacga cgtaaacgta aaatgaccac atgatgggcc aatagacatg gaccgactac    600

taataatagt aagttacatt ttaggatgga ataaatatca taccgacatc agttttgaaa    660

gaaaagggaa aaaaagaaaa aataaataaa agatatacta ccgacatgag ttccaaaaag    720

caaaaaaaaa gatcaagccg acacagacac gcgtagagag caaaatgact ttgacgtcac    780

accacgaaaa cagacgcttc atacgtgtcc ctttatctct ctcagtctct ctataaactt    840

agtgagaccc tcctctgttt tactcacaaa tatgcaaact agaaaacaat catcaggaat    900

aaagggtttg attacttcta ttggaaagag gaagtctgct cttgcgccaa atccaatagt    960

tggttctaat tggatcaact tgttttagga tagaacaaat atttcgtgct atatttaaat   1020

tttgttgttc ccctttctca tcatcatcta aatcttgttt atccatatct gcggtcttta   1080

aggcgtcaat ggcatctcta atgtcttcat ttggttgata accaaagcat ataagatcta   1140

aaatagtgct aagagcaaac acgtagttgc tcttagttct caaaatcttt aagcatactg   1200

aagaaacttg aggatcattt acccatgaag tagtttcacc tttataaagt cctcgtagat   1260

atctccacga gctttcattt tcagggtagg ctataatggc ttcgatggtg taaagcactt   1320

cagactctct catagctttt aggcccccca agaaaggaga ccttgttatg acaaaatatc   1380

tctgattcca agcagaattg ttaaaaatgt cttctttaag tagttctgtg caataattaa   1440

gttcatcttc ccatcctcct agtgtttgaa gagcccactg tctatgagac catgcatgat   1500

aatgtttggc atcaacggac agtatctttt tggtgaactc gagctgagct cgaatttccc   1560

cgatcgttca aacatttggc aataaagttt cttaagattg aatcctgttg ccggtcttgc   1620

gatgattatc atataatttc tgttgaatta cgttaagcat gtaataatta acatgtaatg   1680

catgacgtta tttatgagat gggtttttat gattagagtc ccgcaattat acatttaata   1740

cgcgatagaa aacaaaatat agcgcgcaaa ctaggataaa ttatcgcgcg cggtgtcatc   1800

tatgttacta gatcgggaat tc                                            1822
```

<210> SEQ ID NO 46
<211> LENGTH: 1570
<212> TYPE: DNA
<213> ORGANISM: Artificial Sequence
<220> FEATURE:
<223> OTHER INFORMATION: Description of Artificial Sequence: Plasmid
MuA-HP-GmFTA-Nos-Term

<400> SEQUENCE: 46

```
gaattcaaat ttttcgccag ttctaaatat ccggaaacct cttgggatgc cattgcccat     60

ctatctgtaa tttattgacg aaatagacga aaaggaaggt ggctcctata aagcacatca    120

ttgcgataac agaaaggcca ttgttgaaga tacctctgct gacattggtc cccaagtgga    180

agcaccaccc catgaggagc accgtggagt aagaagacgt tcgagccacg tcgaaaaagc    240

aagtgtgttg atgtagtatc tccattgacg taagggatga cgcacaatcc aactatccat    300

cgcaagacca ttgctctata taagaaagtt aatatcattt cgagtggcca cgctgagctc    360

aggaagtctg ctcttgcgcc aaatccaata gttggttcta attggatcaa cttgttttag    420
```

-continued

```
gatagaacaa atatttcgtg ctatatttaa attttgttgt tccccttct catcatcatc    480

taaatcttgt ttatccatat ctgcggtctt taaggcgtca atggcatctc taatgtcttc    540

atttggttga taaccaaagc atataagatc taaaatagtg ctaagagcaa acacgtagtt    600

gctcttagtt ctcaaaatct ttaagcatac tgaagaaact tgaggatcat ttacccatga    660

agtagtttca cctttataaa gtcctcgtag atatctccac gagctttcat tttcagggta    720

ggctataatg gcttcgatgg tgtaaagcac ttcagactct ctcatagctt ttaggccccc    780

caagaaagga gaccttgtta tgacaaaata tctctgattc caagcagaat tgttaaaaat    840

gtcttcttta agtagttctg tgcaataatt aagttcatct tcccatcctc ctagtgtttg    900

aagagcccac tgtctatgag accatgcatg ataatgtttg gcatcaacgg acagtatctt    960

tttggtgaac tcgagcttaa aggtgaaact acttcatggg taaatgatcc tcaagtttct   1020

tcagtatgct taaagatttt gagaactaag agcaactacg tgtttgctct tagcactatt   1080

ttagatctta tatgctttgg ttatcaacca aatgaagaca ttagagatgc cattgacgcc   1140

ttaaagaccg cagatatgga taaacaagat ttagatgatg atgagaaagg ggaacaacaa   1200

aatttaaata tagcacgaaa tatttgttct atcctaaaac aagttgatcc aattagaacc   1260

aactattgga tttggcgcaa gagcagactt cctgagctcg aatttccccg atcgttcaaa   1320

catttggcaa taaagtttct taagattgaa tcctgttgcc ggtcttgcga tgattatcat   1380

ataatttctg ttgaattacg ttaagcatgt aataattaac atgtaatgca tgacgttatt   1440

tatgagatgg gtttttatga ttagagtccc gcaattatac atttaatacg cgatagaaaa   1500

caaaatatag cgcgcaaact aggataaatt atcgcgcgcg gtgtcatcta tgttactaga   1560

tcgggaattc                                                          1570
```

<210> SEQ ID NO 47
<211> LENGTH: 2138
<212> TYPE: DNA
<213> ORGANISM: Artificial Sequence
<220> FEATURE:
<223> OTHER INFORMATION: Description of Artificial Sequence: Plasmid RD29AP-HP-GmFTA-Nos-Term

<400> SEQUENCE: 47

```
ggagccatag atgcaattca atcaaactga aatttctgca agaatctcaa acacggagat     60

ctcaaagttt gaaagaaaat ttatttcttc gactcaaaac aaacttacga aatttaggta    120

gaacttatat acattatatt gtaatttttt gtaacaaaat gtttttatta ttattataga    180

attttactgg ttaaattaaa aatgaataga aaaggtgaat taagaggaga gaggaggtaa    240

acattttctt ctattttttc atattttcag gataaattat tgtaaaagtt tacaagattt    300

ccatttgact agtgtaaatg aggaatattc tctagtaaga tcattatttc atctacttct    360

tttatcttct accagtagag gaataaacaa tatttagctc ctttgtaaat acaaattaat    420

tttccttctt gacatcattc aattttaatt ttacgtataa aataaaagat catacctatt    480

agaacgatta aggagaaata caattcgaat gagaaggatg tgccgtttgt tataataaac    540

agccacacga cgtaaacgta aaatgaccac atgatgggcc aatagacatg gaccgactac    600

taataatagt aagttacatt ttaggatgga ataaatatca taccgacatc agttttgaaa    660

gaaaagggaa aaaaagaaaa aataaataaa agatatacta ccgacatgag ttccaaaaag    720

caaaaaaaaa gatcaagccg acacagacac gcgtagagag caaaatgact ttgacgtcac    780

accacgaaaa cagacgcttc atacgtgtcc ctttatctct ctcagtctct ctataaactt    840
```

-continued

```
agtgagaccc tcctctgttt tactcacaaa tatgcaaact agaaaacaat catcaggaat    900

aaagggtttg attacttcta ttggaaagag gaagtctgct cttgcgccaa atccaatagt    960

tggttctaat tggatcaact tgttttagga tagaacaaat atttcgtgct atatttaaat   1020

tttgttgttc ccctttctca tcatcatcta aatcttgttt atccatatct gcggtcttta   1080

aggcgtcaat ggcatctcta atgtcttcat ttggttgata accaaagcat ataagatcta   1140

aaatagtgct aagagcaaac acgtagttgc tcttagttct caaaatcttt aagcatactg   1200

aagaaacttg aggatcattt acccatgaag tagtttcacc tttataaagt cctcgtagat   1260

atctccacga gctttcattt tcagggtagg ctataatggc ttcgatggtg taaagcactt   1320

cagactctct catagctttt aggcccccca agaaaggaga ccttgttatg acaaaatatc   1380

tctgattcca agcagaattg ttaaaaatgt cttctttaag tagttctgtg caataattaa   1440

gttcatcttc ccatcctcct agtgtttgaa gagcccactg tctatgagac catgcatgat   1500

aatgtttggc atcaacggac agtatctttt tggtgaactc gagcttaaag gtgaaactac   1560

ttcatgggta aatgatcctc aagtttcttc agtatgctta aagattttga gaactaagag   1620

caactacgtg tttgctctta gcactatttt agatcttata tgctttggtt atcaaccaaa   1680

tgaagacatt agagatgcca ttgacgcctt aaagaccgca gatatggata aacaagattt   1740

agatgatgat gagaaagggg aacaacaaaa tttaaatata gcacgaaata tttgttctat   1800

cctaaaacaa gttgatccaa ttagaaccaa ctattggatt tggcgcaaga gcagacttcc   1860

tgagctcgaa tttccccgat cgttcaaaca tttggcaata aagtttctta agattgaatc   1920

ctgttgccgg tcttgcgatg attatcatat aatttctgtt gaattacgtt aagcatgtaa   1980

taattaacat gtaatgcatg acgttattta tgagatgggt ttttatgatt agagtcccgc   2040

aattatacat ttaatacgcg atagaaaaca aaatatagcg cgcaaactag gataaattat   2100

cgcgcgcggt gtcatctatg ttactagatc gggaattc                          2138
```

<210> SEQ ID NO 48
<211> LENGTH: 5511
<212> TYPE: DNA
<213> ORGANISM: Artificial Sequence
<220> FEATURE:
<223> OTHER INFORMATION: Description of Artificial Sequence: Plasmid pBI121-35S-Anti-AtFTB

<400> SEQUENCE: 48

```
gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420

gccgcttggg tggagaggct attcggctat gactgggcac aacagacaat cggctgctct    480

gatgccgccg tgttccggct gtcagcgcag gggcgcccgg ttctttttgt caagaccgac    540

ctgtccggtg ccctgaatga actgcaggac gaggcagcgc ggctatcgtg gctggccacg    600

acgggcgttc cttgcgcagc tgtgctcgac gttgtcactg aagcgggaag ggactggctg    660

ctattgggcg aagtgccggg gcaggatctc ctgtcatctc accttgctcc tgccgagaaa    720
```

-continued

```
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
```

-continued

```
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tccgtccgga attcccgggt cgacccacgc   3360
gtccgggaga ttcagcgaga taagcaattg gattatctga tgaaaggctt aaggcagctt   3420
ggtccgcagt tttcttcctt agatgctaat cgaccttggc tttgttactg gattcttcat   3480
tcaatagctt tgcttgggga gactgtggat gatgaattag aaagcaatgc cattgacttc   3540
cttggacgct gccagggctc tgaaggtgga tacggtggtg gtcctggcca acttccacat   3600
cttgcaacta cttatgctgc agtgaatgca cttgttactt taggaggtga caaagccctt   3660
tcttcaatta atagagaaaa aatgtcttgt tttttaagac ggatgaagga tacaagtgga   3720
ggtttcagga tgcatgatat gggagaaatg gatgttcgtg catgctacac tgcaatttcg   3780
gttgcaagca tcctaaatat tatggatgat gaactcaccc agggcctagg agattacatc   3840
ttgagttgcc aaacttatga aggtggcatt ggaggggaac ctggctccga agctcacggt   3900
gggtatacct actgtggttt ggctgctatg attttaatca atgaggtcga ccgtttgaat   3960
ttggattcat taatgaattg ggctgtacat cgacaaggag tagaaatggg atttcaaggt   4020
aggacgaaca aattggtcga tggttgctac acattttggc aggcagcccc ttgtgttcta   4080
ctacaaagat tatattcaac caatgatcat gacgttcatg gatcatcaca tatatcagaa   4140
gggacaaatg aagaacatca tgctcatgat gaagatgacc ttgaagacag tgatgatgat   4200
gatgattctg atgaggacaa cgatgaagat tcagtgaatg gtcacagaat ccatcataca   4260
tccacctaca ttaacaggag aatgcaactg gtttttgata gcctcggctt gcagagatat   4320
gtactcttgt gctctaagat ccctgacggt ggattcagag acaagccgag gaaaccccgt   4380
gacttctacc acacatgtta ctgcctgagc ggcttgtctg tggctcagca cgcttggtta   4440
aaagacgagg acactcctcc tttgactcgc gacattatgg gtggctactc gaatctcctt   4500
gaacctgttc aacttcttca caacattgtc atggatcagt ataatgaagc tatcgagttc   4560
ttctttaaag cagcatgact cgaatttccc cgatcgttca aacatttggc aataaagttt   4620
cttaagattg aatcctgttg ccggtcttgc gatgattatc atataatttc tgttgaatta   4680
cgttaagcat gtaataatta acatgtaatg catgacgtta tttatgagat gggtttttat   4740
gattagagtc ccgcaattat acatttaata cgcgatagaa aacaaaatat agcgcgcaaa   4800
ctaggataaa ttatcgcgcg cggtgtcatc tatgttacta gatcgggaat tcactggccg   4860
tcgttttaca acgtcgtgac tgggaaaacc ctggcgttac ccaacttaat cgccttgcag   4920
cacatccccc tttcgccagc tggcgtaata gcgaagaggc ccgcaccgat cgcccttccc   4980
aacagttgcg cagcctgaat ggcgcccgct cctttcgctt tcttcccttc ctttctcgcc   5040
acgttcgccg gctttccccg tcaagctcta aatcgggggc tccctttagg gttccgattt   5100
agtgctttac ggcacctcga ccccaaaaaa cttgatttgg gtgatggttc acgtagtggg   5160
ccatcgccct gatagacggt ttttcgccct ttgacgttgg agtccacgtt ctttaatagt   5220
ggactcttgt tccaaactgg aacaacactc aaccctatct cgggctattc ttttgattta   5280
taagggattt tgccgatttc ggaaccacca tcaaacagga ttttcgcctg ctggggcaaa   5340
ccagcgtgga ccgcttgctg caactctctc agggccaggc ggtgaagggc aatcagctgt   5400
tgcccgtctc actggtgaaa agaaaaacca ccccagtaca ttaaaaacgt ccgcaatgtg   5460
```

ttattaagtt gtctaagcgt caatttgttt acaccacaat atatcctgcc a 5511

<210> SEQ ID NO 49
<211> LENGTH: 5635
<212> TYPE: DNA
<213> ORGANISM: Artificial Sequence
<220> FEATURE:
<223> OTHER INFORMATION: Description of Artificial Sequence: Plasmid pBI121-RD29AP-Anti-AtFTB

<400> SEQUENCE: 49
gtttacccgc caatatatcc tgtcaaacac tgatagttta aactgaaggc gggaaacgac 60
aatctgatca tgagcggaga attaagggag tcacgttatg acccccgccg atgacgcggg 120
acaagccgtt ttacgtttgg aactgacaga accgcaacgt tgaaggagcc actcagccgc 180
gggtttctgg agtttaatga gctaagcaca tacgtcagaa accattattg cgcgttcaaa 240
agtcgcctaa ggtcactatc agctagcaaa tatttcttgt caaaaatgct ccactgacgt 300
tccataaatt cccctcggta tccaattaga gtctcatatt cactctcaat ccaaataatc 360
tgcaccggat ctggatcgtt tcgcatgatt gaacaagatg gattgcacgc aggttctccg 420
gccgcttggg tggagaggct attcggctat gactgggcac aacagacaat cggctgctct 480
gatgccgccg tgttccggct gtcagcgcag gggcgcccgg ttctttttgt caagaccgac 540
ctgtccggtg ccctgaatga actgcaggac gaggcagcgc ggctatcgtg gctggccacg 600
acgggcgttc cttgcgcagc tgtgctcgac gttgtcactg aagcgggaag ggactggctg 660
ctattgggcg aagtgccggg gcaggatctc ctgtcatctc accttgctcc tgccgagaaa 720
gtatccatca tggctgatgc aatgcggcgg ctgcatacgc ttgatccggc tacctgccca 780
ttcgaccacc aagcgaaaca tcgcatcgag cgagcacgta ctcggatgga agccggtctt 840
gtcgatcagg atgatctgga cgaagagcat caggggctcg cgccagccga actgttcgcc 900
aggctcaagg cgcgcatgcc cgacggcgat gatctcgtcg tgacccatgg cgatgcctgc 960
ttgccgaata tcatggtgga aaatggccgc ttttctggat tcatcgactg tggccggctg 1020
ggtgtggcgg accgctatca ggacatagcg ttggctaccc gtgatattgc tgaagagctt 1080
ggcggcgaat gggctgaccg cttcctcgtg ctttacggta tcgccgctcc cgattcgcag 1140
cgcatcgcct tctatcgcct tcttgacgag ttcttctgag cgggactctg gggttcgaaa 1200
tgaccgacca agcgacgccc aacctgccat cacgagattt cgattccacc gccgccttct 1260
atgaaaggtt gggcttcgga atcgttttcc gggacgccgg ctggatgatc ctccagcgcg 1320
gggatctcat gctggagttc ttcgcccacg ggatctctgc ggaacaggcg gtcgaaggtg 1380
ccgatatcat tacgacagca acggccgaca agcacaacgc cacgatcctg agcgacaata 1440
tgatcgggcc cggcgtccac atcaacggcg tcggcggcga ctgcccaggc aagaccgaga 1500
tgcaccgcga tatcttgctg cgttcggata ttttcgtgga gttcccgcca cagacccgga 1560
tgatccccga tcgttcaaac atttggcaat aaagtttctt aagattgaat cctgttgccg 1620
gtcttgcgat gattatcata taatttctgt tgaattacgt taagcatgta ataattaaca 1680
tgtaatgcat gacgttattt atgagatggg tttttatgat tagagtcccg caattataca 1740
tttaatacgc gatagaaaac aaaatatagc gcgcaaacta ggataaatta tcgcgcgcgg 1800
tgtcatctat gttactagat cgggcctcct gtcaatgctg gcggcggctc tggtggtggt 1860
tctggtggcg gctctgaggg tggtggctct gagggtggcg gttctgaggg tggcggctct 1920
gagggaggcg gttccggtgg tggctctggt tccggtgatt ttgattatga aaagatggca 1980

-continued

```
aacgctaata aggggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180
ggaaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
accctcctct gttttactca caaatatgca aactagaaaa caatcatcag gaataaaggg   3420
tttgattact tctattggaa aggactctag aggatccgtc cggaattccc gggtcgaccc   3480
acgcgtccgg gagattcagc gagataagca attggattat ctgatgaaag gcttaaggca   3540
gcttggtccg cagttttctt ccttagatgc taatcgacct tggctttgtt actggattct   3600
tcattcaata gctttgcttg gggagactgt ggatgatgaa ttagaaagca atgccattga   3660
cttccttgga cgctgccagg gctctgaagg tggatacggt ggtggtcctg gccaacttcc   3720
acatcttgca actacttatg ctgcagtgaa tgcacttgtt actttaggag gtgacaaagc   3780
cctttcttca attaatagag aaaaaatgtc ttgtttttta agacggatga aggatacaag   3840
tggaggtttc aggatgcatg atatgggaga aatggatgtt cgtgcatgct acactgcaat   3900
ttcggttgca agcatcctaa atattatgga tgatgaactc acccagggcc taggagatta   3960
catcttgagt tgccaaactt atgaaggtgg cattggaggg gaacctggct ccgaagctca   4020
cggtgggtat acctactgtg gtttggctgc tatgatttta atcaatgagg tcgaccgttt   4080
gaatttggat tcattaatga attgggctgt acatcgacaa ggagtagaaa tgggatttca   4140
aggtaggacg aacaaattgg tcgatggttg ctacacattt tggcaggcag ccccttgtgt   4200
tctactacaa agattatatt caaccaatga tcatgacgtt catggatcat cacatatatc   4260
agaaggggaca aatgaagaac atcatgctca tgatgaagat gaccttgaag acagtgatga   4320
```

-continued

```
tgatgatgat tctgatgagg acaacgatga agattcagtg aatggtcaca gaatccatca   4380

tacatccacc tacattaaca ggagaatgca actggttttt gatagcctcg gcttgcagag   4440

atatgtactc ttgtgctcta agatccctga cggtggattc agagacaagc cgaggaaacc   4500

ccgtgacttc taccacacat gttactgcct gagcggcttg tctgtggctc agcacgcttg   4560

gttaaaagac gaggacactc ctcctttgac tcgcgacatt atgggtggct actcgaatct   4620

ccttgaacct gttcaacttc ttcacaacat tgtcatggat cagtataatg aagctatcga   4680

gttcttcttt aaagcagcat gactcgaatt tccccgatcg ttcaaacatt tggcaataaa   4740

gtttcttaag attgaatcct gttgccggtc ttgcgatgat tatcatataa tttctgttga   4800

attacgttaa gcatgtaata attaacatgt aatgcatgac gttatttatg agatgggttt   4860

ttatgattag agtcccgcaa ttatacattt aatacgcgat agaaaacaaa atatagcgcg   4920

caaactagga taaattatcg cgcgcggtgt catctatgtt actagatcgg gaattcactg   4980

gccgtcgttt tacaacgtcg tgactgggaa aaccctggcg ttacccaact taatcgcctt   5040

gcagcacatc ccccttttcgc cagctggcgt aatagcgaag aggcccgcac cgatcgccct   5100

tcccaacagt tgcgcagcct gaatggcgcc cgctcctttc gctttcttcc cttcctttct   5160

cgccacgttc gccggctttc cccgtcaagc tctaaatcgg gggctccctt tagggttccg   5220

atttagtgct ttacggcacc tcgaccccaa aaaacttgat ttgggtgatg gttcacgtag   5280

tgggccatcg ccctgataga cggtttttcg ccctttgacg ttggagtcca cgttctttaa   5340

tagtggactc ttgttccaaa ctggaacaac actcaaccct atctcgggct attcttttga   5400

tttataaggg attttgccga tttcggaacc accatcaaac aggattttcg cctgctgggg   5460

caaaccagcg tggaccgctt gctgcaactc tctcagggcc aggcggtgaa gggcaatcag   5520

ctgttgcccg tctcactggt gaaaagaaaa accaccccag tacattaaaa acgtccgcaa   5580

tgtgttatta agttgtctaa gcgtcaattt gtttacacca caatatatcc tgcca        5635
```

<210> SEQ ID NO 50
<211> LENGTH: 6299
<212> TYPE: DNA
<213> ORGANISM: Artificial Sequence
<220> FEATURE:
<223> OTHER INFORMATION: Description of Artificial Sequence: Plasmid
pBI121-35S-HP-AtFTB

<400> SEQUENCE: 50

```
gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420

gccgcttggg tggagaggct attcggctat gactgggcac aacagacaat cggctgctct    480

gatgccgccg tgttccggct gtcagcgcag gggcgcccgg ttctttttgt caagaccgac    540

ctgtccggtg ccctgaatga actgcaggac gaggcagcgc ggctatcgtg gctggccacg    600

acgggcgttc cttgcgcagc tgtgctcgac gttgtcactg aagcgggaag ggactggctg    660

ctattgggcg aagtgccggg gcaggatctc ctgtcatctc accttgctcc tgccgagaaa    720
```

-continued

```
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
```

-continued

```
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tcctcctcct aggccctggg tgagttcatc   3360
atccataata tttaggatgc ttgcaaccga aattgcagtg tagcatgcac gaacatccat   3420
ttctcccata tcatgcatcc tgaaacctcc acttgtatcc ttcatccgtc ttaaaaaaca   3480
agacattttt tctctattaa ttgaagaaag ggctttgtca cctcctaaag taacaagtgc   3540
attcactgca gcataagtag ttgcaagatg tggaagttgg ccaggaccac caccgtatcc   3600
accttcagag ccctggcagc gtccaaggaa gtcaatggca ttgctttcta attcatcatc   3660
cacagtctcc ccaagcaaag ctattgaatg aagaatccag taacaaagcc aaggtcgatt   3720
agcatctaag gaagaaaact gcggaccaag ctgccttaag cctttcatca gataatccaa   3780
ttgcttatct cgctgaatct cccggacgcg tgggtcgacc cgggaattcc ggacgaggat   3840
ccccatctac ccgcttcgcg tcggcatccg gtcagtggca gtgaagggcg aacagttcct   3900
gattaaccac aaaccgttct actttactgg ctttggtcgt catgaagatg cggacttgcg   3960
tggcaaagga ttcgataacg tgctgatggt gcacgaccac gcattaatgg actggattgg   4020
ggccaactcc taccgtacct cgcattaccc ttacgctgaa gagatgctcg actgggcaga   4080
tgaacatggc atcgtggtga ttgatgaaac tgctgctgtc ggcttttcgc tctctttagg   4140
cattggtttc gaagcgggca acaagccgaa agaactgtac agcgaagagg cagtcaacgg   4200
ggaaactcag caagcgcact tacaggcgat taaagagctg atagcgcgtg acaaaaacca   4260
cccaagcgtg gtgatgtgga gtattgccaa cgaaccggat acccgtccgc aaggtgcacg   4320
ggaatatttc gcgccactgg cggaagcaac gcgtaaactc gacccgacgc gtccgatcac   4380
ctgcgtcaat gtaatgttct gcgacgctca caccgatacc atcagcgatc tctttgatgt   4440
gctgtgcctg aaccgttatt acggatggta tgtccaaagc ggcgatttgg aaacggcaga   4500
gaaggtactg gaaaaagaac ttctggcctg gcaggagaaa ctgtacaccg acatgtggag   4560
tgaagagtat cagtgtgcat ggctggatat gtatcaccgc gtctttgatc gcgtcagcgc   4620
cgtcgtcggt gaacaggtat ggaatttcgc cgattttgcg acctcgcaag gcatattgcg   4680
cgttggcggt aacaagaaag ggatcttcac tcgcgaccgc aaaccgaagt cggcggcttt   4740
tctgctgcaa aaacgctgga ctggcatgaa cttcggtgaa aaaccgcagc agggaggcaa   4800
acaatgaatc aacaactctc ctggcgcacc atcgtcggct acagcctcgg gaattgctac   4860
cgagctcgtc cggaattccc gggtcgaccc acgcgtccgg gagattcagc gagataagca   4920
attggattat ctgatgaaag gcttaaggca gcttggtccg cagttttctt ccttagatgc   4980
taatcgacct tggctttgtt actggattct tcattcaata gctttgcttg gggagactgt   5040
ggatgatgaa ttagaaagca atgccattga cttccttgga cgctgccagg gctctgaagg   5100
tggatacggt ggtggtcctg gccaacttcc acatcttgca actacttatg ctgcagtgaa   5160
tgcacttgtt actttaggag gtgacaaagc cctttcttca attaatagag aaaaaatgtc   5220
ttgtttttta agacggatga aggatacaag tggaggtttc aggatgcatg atatgggaga   5280
aatggatgtt cgtgcatgct acactgcaat ttcggttgca agcatcctaa atattatgga   5340
tgatgaactc acccagggcc taggagctcg aatttccccg atcgttcaaa catttggcaa   5400
taaagtttct taagattgaa tcctgttgcc ggtcttgcga tgattatcat ataatttctg   5460
```

-continued

```
ttgaattacg ttaagcatgt aataattaac atgtaatgca tgacgttatt tatgagatgg   5520

gtttttatga ttagagtccc gcaattatac atttaatacg cgatagaaaa caaaatatag   5580

cgcgcaaact aggataaatt atcgcgcgcg gtgtcatcta tgttactaga tcgggaattc   5640

actggccgtc gttttacaac gtcgtgactg ggaaaaccct ggcgttaccc aacttaatcg   5700

ccttgcagca catccccctt tcgccagctg gcgtaatagc gaagaggccc gcaccgatcg   5760

cccttcccaa cagttgcgca gcctgaatgg cgcccgctcc tttcgctttc ttcccttcct   5820

ttctcgccac gttcgccggc tttccccgtc aagctctaaa tcgggggctc cctttagggt   5880

tccgatttag tgctttacgg cacctcgacc ccaaaaaact tgatttgggt gatggttcac   5940

gtagtgggcc atcgccctga tagacggttt ttcgcccttt gacgttggag tccacgttct   6000

ttaatagtgg actcttgttc caaactggaa caacactcaa ccctatctcg ggctattctt   6060

ttgatttata agggattttg ccgatttcgg aaccaccatc aaacaggatt ttcgcctgct   6120

ggggcaaacc agcgtggacc gcttgctgca actctctcag ggccaggcgg tgaagggcaa   6180

tcagctgttg cccgtctcac tggtgaaaag aaaaaccacc ccagtacatt aaaaacgtcc   6240

gcaatgtgtt attaagttgt ctaagcgtca atttgtttac accacaatat atcctgcca    6299
```

```
<210> SEQ ID NO 51
<211> LENGTH: 6423
<212> TYPE: DNA
<213> ORGANISM: Artificial Sequence
<220> FEATURE:
<223> OTHER INFORMATION: Description of Artificial Sequence: Plasmid
      pBI121-RD29AP-HP-AtFTB

<400> SEQUENCE: 51
```

```
gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420

gccgcttggg tggagaggct attcggctat gactgggcac aacagacaat cggctgctct    480

gatgccgccg tgttccggct gtcagcgcag gggcgcccgg ttctttttgt caagaccgac    540

ctgtccggtg ccctgaatga actgcaggac gaggcagcgc ggctatcgtg gctggccacg    600

acgggcgttc cttgcgcagc tgtgctcgac gttgtcactg aagcgggaag ggactggctg    660

ctattgggcg aagtgccggg gcaggatctc ctgtcatctc accttgctcc tgccgagaaa    720

gtatccatca tggctgatgc aatgcggcgg ctgcatacgc ttgatccggc tacctgccca    780

ttcgaccacc aagcgaaaca tcgcatcgag cgagcacgta ctcggatgga agccggtctt    840

gtcgatcagg atgatctgga cgaagagcat caggggctcg cgccagccga actgttcgcc    900

aggctcaagg cgcgcatgcc cgacggcgat gatctcgtcg tgacccatgg cgatgcctgc    960

ttgccgaata tcatggtgga aaatggccgc ttttctggat tcatcgactg tggccggctg   1020

ggtgtggcgg accgctatca ggacatagcg ttggctaccc gtgatattgc tgaagagctt   1080

ggcggcgaat gggctgaccg cttcctcgtg ctttacggta tcgccgctcc cgattcgcag   1140

cgcatcgcct tctatcgcct tcttgacgag ttcttctgag cgggactctg gggttcgaaa   1200
```

-continued

```
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg ggatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagggagcc   2520
atagatgcaa ttcaatcaaa ctgaaatttc tgcaagaatc tcaaacacgg agatctcaaa   2580
gtttgaaaga aaatttattt cttcgactca aaacaaactt acgaaattta ggtagaactt   2640
atatacatta tattgtaatt ttttgtaaca aaatgttttt attattatta tagaatttta   2700
ctggttaaat taaaaatgaa tagaaaaggt gaattaagag gagagaggag gtaaacattt   2760
tcttctattt tttcatattt tcaggataaa ttattgtaaa agtttacaag atttccattt   2820
gactagtgta aatgaggaat attctctagt aagatcatta tttcatctac ttcttttatc   2880
ttctaccagt agaggaataa acaatattta gctcctttgt aaatacaaat taattttcct   2940
tcttgacatc attcaatttt aattttacgt ataaaataaa agatcatacc tattagaacg   3000
attaaggaga aatacaattc gaatgagaag gatgtgccgt ttgttataat aaacagccac   3060
acgacgtaaa cgtaaaatga ccacatgatg ggccaataga catggaccga ctactaataa   3120
tagtaagtta cattttagga tggaataaat atcataccga catcagtttt gaaagaaaag   3180
ggaaaaaaag aaaaaataaa taaaagatat actaccgaca tgagttccaa aaagcaaaaa   3240
aaaagatcaa gccgacacag acacgcgtag agagcaaaat gactttgacg tcacaccacg   3300
aaaacagacg cttcatacgt gtccctttat ctctctcagt ctctctataa acttagtgag   3360
accctcctct gttttactca caaatatgca aactagaaaa caatcatcag gaataaaggg   3420
tttgattact tctattggaa aggactctag aggatcctcc tcctaggccc tgggtgagtt   3480
catcatccat aatatttagg atgcttgcaa ccgaaattgc agtgtagcat gcacgaacat   3540
ccatttctcc catatcatgc atcctgaaac ctccacttgt atccttcatc cgtcttaaaa   3600
```

-continued

```
aacaagacat tttttctcta ttaattgaag aaagggcttt gtcacctcct aaagtaacaa   3660
gtgcattcac tgcagcataa gtagttgcaa gatgtggaag ttggccagga ccaccaccgt   3720
atccaccttc agagccctgg cagcgtccaa ggaagtcaat ggcattgctt tctaattcat   3780
catccacagt ctccccaagc aaagctattg aatgaagaat ccagtaacaa agccaaggtc   3840
gattagcatc taaggaagaa aactgcggac caagctgcct taagcctttc atcagataat   3900
ccaattgctt atctcgctga atctcccgga cgcgtgggtc gacccgggaa ttccggacga   3960
ggatccccat ctacccgctt cgcgtcggca tccggtcagt ggcagtgaag ggcgaacagt   4020
tcctgattaa ccacaaaccg ttctacttta ctggctttgg tcgtcatgaa gatgcggact   4080
tgcgtggcaa aggattcgat aacgtgctga tggtgcacga ccacgcatta atggactgga   4140
ttggggccaa ctcctaccgt acctcgcatt acccttacgc tgaagagatg ctcgactggg   4200
cagatgaaca tggcatcgtg gtgattgatg aaactgctgc tgtcggcttt tcgctctctt   4260
taggcattgg tttcgaagcg ggcaacaagc cgaaagaact gtacagcgaa gaggcagtca   4320
acggggaaac tcagcaagcg cacttacagg cgattaaaga gctgatagcg cgtgacaaaa   4380
accacccaag cgtggtgatg tggagtattg ccaacgaacc ggatacccgt ccgcaaggtg   4440
cacgggaata tttcgcgcca ctggcggaag caacgcgtaa actcgacccg acgcgtccga   4500
tcacctgcgt caatgtaatg ttctgcgacg ctcacaccga taccatcagc gatctctttg   4560
atgtgctgtg cctgaaccgt tattacggat ggtatgtcca aagcggcgat ttggaaacgg   4620
cagagaaggt actggaaaaa gaacttctgg cctggcagga gaaactgtac accgacatgt   4680
ggagtgaaga gtatcagtgt gcatggctgg atatgtatca ccgcgtcttt gatcgcgtca   4740
gcgccgtcgt cggtgaacag gtatggaatt tcgccgattt tgcgacctcg caaggcatat   4800
tgcgcgttgg cggtaacaag aaagggatct tcactcgcga ccgcaaaccg aagtcggcgg   4860
cttttctgct gcaaaaacgc tggactggca tgaacttcgg tgaaaaaccg cagcagggag   4920
gcaaacaatg aatcaacaac tctcctggcg caccatcgtc ggctacagcc tcgggaattg   4980
ctaccgagct cgtccggaat tcccgggtcg acccacgcgt ccgggagatt cagcgagata   5040
agcaattgga ttatctgatg aaaggcttaa ggcagcttgg tccgcagttt tcttccttag   5100
atgctaatcg accttggctt tgttactgga ttcttcattc aatagctttg cttggggaga   5160
ctgtggatga tgaattagaa agcaatgcca ttgacttcct tggacgctgc cagggctctg   5220
aaggtggata cggtggtggt cctggccaac ttccacatct tgcaactact tatgctgcag   5280
tgaatgcact tgttacttta ggaggtgaca aagccctttc ttcaattaat agagaaaaaa   5340
tgtcttgttt tttaagacgg atgaaggata caagtggagg tttcaggatg catgatatgg   5400
gagaaatgga tgttcgtgca tgctacactg caatttcggt tgcaagcatc ctaaatatta   5460
tggatgatga actcacccag ggcctaggag ctcgaatttc cccgatcgtt caaacatttg   5520
gcaataaagt ttcttaagat tgaatcctgt tgccggtctt gcgatgatta tcatataatt   5580
tctgttgaat tacgttaagc atgtaataat taacatgtaa tgcatgacgt tatttatgag   5640
atgggttttt atgattagag tcccgcaatt atacatttaa tacgcgatag aaaacaaaat   5700
atagcgcgca aactaggata aattatcgcg cgcggtgtca tctatgttac tagatcggga   5760
attcactggc cgtcgtttta caacgtcgtg actgggaaaa ccctggcgtt acccaactta   5820
atcgccttgc agcacatccc cctttcgcca gctggcgtaa tagcgaagag gcccgcaccg   5880
atcgcccttc ccaacagttg cgcagcctga atggcgcccg ctcctttcgc tttcttccct   5940
```

-continued

```
tcctttctcg ccacgttcgc cggctttccc cgtcaagctc taaatcgggg gctcccttta   6000

gggttccgat ttagtgcttt acggcacctc gaccccaaaa aacttgattt gggtgatggt   6060

tcacgtagtg ggccatcgcc ctgatagacg gtttttcgcc ctttgacgtt ggagtccacg   6120

ttctttaata gtggactctt gttccaaact ggaacaacac tcaaccctat ctcgggctat   6180

tcttttgatt tataagggat tttgccgatt tcggaaccac catcaaacag gattttcgcc   6240

tgctggggca aaccagcgtg gaccgcttgc tgcaactctc tcagggccag gcggtgaagg   6300

gcaatcagct gttgcccgtc tcactggtga aaagaaaaac caccccagta cattaaaaac   6360

gtccgcaatg tgttattaag ttgtctaagc gtcaatttgt ttacaccaca atatatcctg   6420

cca                                                                 6423
```

<210> SEQ ID NO 52
<211> LENGTH: 5715
<212> TYPE: DNA
<213> ORGANISM: Artificial Sequence
<220> FEATURE:
<223> OTHER INFORMATION: Description of Artificial Sequence: Plasmid pBI121-35S-AtFTB

<400> SEQUENCE: 52

```
gtttacccgc caatatatcc tgtcaaacac tgatagttta aactgaaggc gggaaacgac     60

aatctgatca tgagcggaga attaagggag tcacgttatg acccccgccg atgacgcggg    120

acaagccgtt ttacgtttgg aactgacaga accgcaacgt tgaaggagcc actcagccgc    180

gggtttctgg agtttaatga gctaagcaca tacgtcagaa accattattg cgcgttcaaa    240

agtcgcctaa ggtcactatc agctagcaaa tatttcttgt caaaaatgct ccactgacgt    300

tccataaatt cccctcggta tccaattaga gtctcatatt cactctcaat ccaaataatc    360

tgcaccggat ctggatcgtt tcgcatgatt gaacaagatg gattgcacgc aggttctccg    420

gccgcttggg tggagaggct attcggctat gactgggcac aacagacaat cggctgctct    480

gatgccgccg tgttccggct gtcagcgcag gggcgcccgg ttctttttgt caagaccgac    540

ctgtccggtg ccctgaatga actgcaggac gaggcagcgc ggctatcgtg gctggccacg    600

acgggcgttc cttgcgcagc tgtgctcgac gttgtcactg aagcgggaag ggactggctg    660

ctattgggcg aagtgccggg gcaggatctc ctgtcatctc accttgctcc tgccgagaaa    720

gtatccatca tggctgatgc aatgcggcgg ctgcatacgc ttgatccggc tacctgccca    780

ttcgaccacc aagcgaaaca tcgcatcgag cgagcacgta ctcggatgga agccggtctt    840

gtcgatcagg atgatctgga cgaagagcat caggggctcg cgccagccga actgttcgcc    900

aggctcaagg cgcgcatgcc cgacggcgat gatctcgtcg tgacccatgg cgatgcctgc    960

ttgccgaata tcatggtgga aaatggccgc ttttctggat tcatcgactg tggccggctg   1020

ggtgtggcgg accgctatca ggacatagcg ttggctaccc gtgatattgc tgaagagctt   1080

ggcggcgaat gggctgaccg cttcctcgtg ctttacggta tcgccgctcc cgattcgcag   1140

cgcatcgcct tctatcgcct tcttgacgag ttcttctgag cgggactctg gggttcgaaa   1200

tgaccgacca agcgacgccc aacctgccat cacgagattt cgattccacc gccgccttct   1260

atgaaaggtt gggcttcgga atcgttttcc gggacgccgg ctggatgatc ctccagcgcg   1320

gggatctcat gctggagttc ttcgcccacg ggatctctgc ggaacaggcg gtcgaaggtg   1380

ccgatatcat tacgacagca acggccgaca agcacaacgc cacgatcctg agcgacaata   1440

tgatcgggcc cggcgtccac atcaacggcg tcggcggcga ctgcccaggc aagaccgaga   1500
```

-continued

```
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg tttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aaagatggca   1980
aacgctaata agggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc ccaagaaggt taaagatgca gtcaaaagat tcaggactaa   2640
ctgcatcaag aacacagaga aagatatatt tctcaagatc agaagtacta ttccagtatg   2700
gacgattcaa ggcttgcttc acaaaccaag gcaagtaata gagattggag tctctaaaaa   2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga gacttttcaa caaagggtaa tatccggaaa   3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga acacggggga ctctagagga tccatgccag tagtaacccg cttgattcgt   3360
ttgaagtgtg tagggctcag acttgaccgg agtggactca atcggcgaat ctgtcacgga   3420
ggacacgggg aatcaacgcg gcggagagtg atggaagagc tttcaagcct aaccgtgagt   3480
cagcgcgagc aatttctggt ggagaacgat gtgttcggga tctataatta cttcgacgcc   3540
agcgacgttt ctactcaaaa atacatgatg gagattcagc gagataagca attggattat   3600
ctgatgaaag gcttaaggca gcttggtccg cagttttctt ccttagatgc taatcgacct   3660
tggctttgtt actggattct tcattcaata gctttgcttg gggagactgt ggatgatgaa   3720
ttagaaagca atgccattga cttccttgga cgctgccagg gctctgaagg tggatacggt   3780
ggtggtcctg gccaacttcc acatcttgca actacttatg ctgcagtgaa tgcacttgtt   3840
actttaggag gtgacaaagc cctttcttca attaatagag aaaaaatgtc ttgtttttta   3900
```

-continued

```
agacggatga aggatacaag tggaggtttc aggatgcatg atatgggaga aatggatgtt   3960

cgtgcatgct acactgcaat ttcggttgca agcatcctaa atattatgga tgatgaactc   4020

acccagggcc taggagatta catcttgagt tgccaaactt atgaaggtgg cattggaggg   4080

gaacctggct ccgaagctca cggtgggtat acctactgtg gtttggctgc tatgatttta   4140

atcaatgagg tcgaccgttt gaatttggat tcattaatga attgggctgt acatcgacaa   4200

ggagtagaaa tgggatttca aggtaggacg aacaaattgg tcgatggttg ctacacattt   4260

tggcaggcag ccccttgtgt tctactacaa agattatatt caaccaatga tcatgacgtt   4320

catggatcat cacatatatc agaagggaca aatgaagaac atcatgctca tgatgaagat   4380

gaccttgaag acagtgatga tgatgatgat tctgatgagg acaacgatga agattcagtg   4440

aatggtcaca gaatccatca tacatccacc tacattaaca ggagaatgca actggttttt   4500

gatagcctcg gcttgcagag atatgtactc ttgtgctcta agatccctga cggtggattc   4560

agagacaagc cgaggaaacc ccgtgacttc taccacacat gttactgcct gagcggcttg   4620

tctgtggctc agcacgcttg gttaaaagac gaggacactc ctcctttgac tcgcgacatt   4680

atgggtggct actcgaatct ccttgaacct gttcaacttc ttcacaacat tgtcatggat   4740

cagtataatg aagctatcga gttcttcttt aaagcagcat gactcgaatt tccccgatcg   4800

ttcaaacatt tggcaataaa gtttcttaag attgaatcct gttgccggtc ttgcgatgat   4860

tatcatataa tttctgttga attacgttaa gcatgtaata attaacatgt aatgcatgac   4920

gttatttatg agatgggttt ttatgattag agtcccgcaa ttatacattt aatacgcgat   4980

agaaaacaaa atatagcgcg caaactagga taaattatcg cgcgcggtgt catctatgtt   5040

actagatcgg gaattcactg gccgtcgttt tacaacgtcg tgactgggaa aaccctggcg   5100

ttacccaact taatcgcctt gcagcacatc ccccttttcgc cagctggcgt aatagcgaag   5160

aggcccgcac cgatcgccct tcccaacagt tgcgcagcct gaatggcgcc cgctcctttc   5220

gctttcttcc cttcctttct cgccacgttc gccggctttc cccgtcaagc tctaaatcgg   5280

gggctccctt tagggttccg atttagtgct ttacggcacc tcgaccccaa aaaacttgat   5340

ttgggtgatg gttcacgtag tgggccatcg ccctgataga cggtttttcg ccctttgacg   5400

ttggagtcca cgttctttaa tagtggactc ttgttccaaa ctggaacaac actcaaccct   5460

atctcgggct attcttttga tttataaggg attttgccga tttcggaacc accatcaaac   5520

aggattttcg cctgctgggg caaaccagcg tggaccgctt gctgcaactc tctcagggcc   5580

aggcggtgaa gggcaatcag ctgttgcccg tctcactggt gaaaagaaaa accaccccag   5640

tacattaaaa acgtccgcaa tgtgttatta agttgtctaa gcgtcaattt gtttacacca   5700

caatatatcc tgcca                                                    5715
```

```
<210> SEQ ID NO 53
<211> LENGTH: 1772
<212> TYPE: DNA
<213> ORGANISM: Artificial Sequence
<220> FEATURE:
<223> OTHER INFORMATION: Description of Artificial Sequence: Plasmid
      MuA-anti-GmFTB-Nos-Term

<400> SEQUENCE: 53

gaattcaaat ttttcgccag ttctaaatat ccggaaacct cttgggatgc cattgcccat     60

ctatctgtaa tttattgacg aaatagacga aaaggaaggt ggctcctata aagcacatca    120

ttgcgataac agaaaggcca ttgttgaaga tacctctgct gacattggtc cccaagtgga    180
```

-continued

```
agcaccaccc catgaggagc accgtggagt aagaagacgt tcgagccacg tcgaaaaagc    240
aagtgtgttg atgtagtatc tccattgacg taagggatga cgcacaatcc aactatccat    300
cgcaagacca ttgctctata taagaaagtt aatatcattt cgagtggcca cgctgagctc    360
gtggtggaga atctgggtgc tttgaccaac tatactggca caatgagagt ccacttaaac    420
agtaacatgt gtgataatga tctctacgtt tacccggttt gtctctcagt ccaccctctt    480
gctcctgtgc acataagaga atatattgct gtaaagcaat actgtgaaaa agtggttctt    540
gtgctctcca ctcattaata aatttatagg caatattttt aaaatcagat gaactggatt    600
cactggtgcc ttcatgctca ccacggcatg ttgcatgact agaggttcca tccaaacttt    660
cttttgcttc agatacataa gataccgcaa aaatctgtga tgtctcttcc atctgtttgt    720
tgataataga agataatctt tgcaatagag caacagcacc tccctgccaa aaggaatagc    780
atccatccac cagtttattt gttctcccct ggaatccaca ttccttacct tgtcggaata    840
ccacccagtc aactaatcga ggcagatcca agtgattaac ctcaccaatc agaatcattg    900
tagctaatcc acaaaaggtg tacccaccat gagcctcaga accaggctca ccagcaatgc    960
caccctcata tgtttgacag cttataatgt agtctccaac attctggatc agctcatcat   1020
ccaaaatgtt caaaacactt gcaacagaaa tggcagtgta gcaagctcga acatcaattt   1080
caccttcatc atgcatcctg aatccaccat ttggttgctt catccgccgc agaaacccat   1140
acagtttatc tctattaatt gatgccaggg atttctcacc acccaaagta ataagtgaat   1200
taacagcagc ataagttgtg gcaatatgag gcatctggcc tggtcccccg gcatatccac   1260
cattcggatc ctggcaacgg ttaagaaaat cgatagcgtt atcttcgagt tcatcatcga   1320
cggattctcc caacaaagca atggagtgga agatccagta gcagagccag ggtcgattag   1380
cgtccaaaac ggaaaatgcg gaactgagat ggcgaaggcc tttggagaca tactgcatgt   1440
gattatcgcg ttgaagctcc aacatgaggg tttgggcgtt gcgaggaatg gtggcgagct   1500
cgaatttccc cgatcgttca aacatttggc aataaagttt cttaagattg aatcctgttg   1560
ccggtcttgc gatgattatc atataatttc tgttgaatta cgttaagcat gtaataatta   1620
acatgtaatg catgacgtta tttatgagat gggtttttat gattagagtc ccgcaattat   1680
acatttaata cgcgatagaa aacaaaatat agcgcgcaaa ctaggataaa ttatcgcgcg   1740
cggtgtcatc tatgttacta gatcgggaat tc                                 1772
```

<210> SEQ ID NO 54
<211> LENGTH: 2340
<212> TYPE: DNA
<213> ORGANISM: Artificial Sequence
<220> FEATURE:
<223> OTHER INFORMATION: Description of Artificial Sequence: Plasmid
RD29AP-anti-GmFTB-Nos-Term

<400> SEQUENCE: 54

```
ggagccatag atgcaattca atcaaactga aatttctgca agaatctcaa acacggagat     60
ctcaaagttt gaaagaaaat ttatttcttc gactcaaaac aaacttacga aatttaggta    120
gaacttatat acattatatt gtaatttttt gtaacaaaat gtttttatta ttattataga    180
attttactgg ttaaattaaa aatgaataga aaaggtgaat taagaggaga gaggaggtaa    240
acattttctt ctattttttc atattttcag gataaattat tgtaaaagtt tacaagattt    300
ccatttgact agtgtaaatg aggaatattc tctagtaaga tcattatttc atctacttct    360
tttatcttct accagtagag gaataaacaa tatttagctc ctttgtaaat acaaattaat    420
```

-continued

```
tttccttctt gacatcattc aattttaatt ttacgtataa aataaaagat catacctatt    480

agaacgatta aggagaaata caattcgaat gagaaggatg tgccgtttgt tataataaac    540

agccacacga cgtaaacgta aaatgaccac atgatgggcc aatagacatg gaccgactac    600

taataatagt aagttacatt ttaggatgga ataaatatca taccgacatc agttttgaaa    660

gaaaagggaa aaaaagaaaa aataaataaa agatatacta ccgacatgag ttccaaaaag    720

caaaaaaaaa gatcaagccg acacagacac gcgtagagag caaaatgact ttgacgtcac    780

accacgaaaa cagacgcttc atacgtgtcc ctttatctct ctcagtctct ctataaactt    840

agtgagaccc tcctctgttt tactcacaaa tatgcaaact agaaaacaat catcaggaat    900

aaagggtttg attacttcta ttggaaaggt ggtggagaat ctgggtgctt tgaccaacta    960

tactggcaca atgagagtcc acttaaacag taacatgtgt gataatgatc tctacgttta   1020

cccggtttgt ctctcagtcc accctcttgc tcctgtgcac ataagagaat atattgctgt   1080

aaagcaatac tgtgaaaaag tggttcttgt gctctccact cattaataaa tttataggca   1140

atatttttaa aatcagatga actggattca ctggtgcctt catgctcacc acggcatgtt   1200

gcatgactag aggttccatc caaactttct tttgcttcag atacataaga taccgcaaaa   1260

atctgtgatg tctcttccat ctgtttgttg ataatagaag ataatctttg caatagagca   1320

acagcacctc cctgccaaaa ggaatagcat ccatccacca gtttatttgt tctcccctgg   1380

aatccacatt ccttaccttg tcggaatacc acccagtcaa ctaatcgagg cagatccaag   1440

tgattaacct caccaatcag aatcattgta gctaatccac aaaaggtgta cccaccatga   1500

gcctcagaac caggctcacc agcaatgcca ccctcatatg tttgacagct tataatgtag   1560

tctccaacat tctggatcag ctcatcatcc aaaatgttca aaacacttgc aacagaaatg   1620

gcagtgtagc aagctcgaac atcaatttca ccttcatcat gcatcctgaa tccaccattt   1680

ggttgcttca tccgccgcag aaacccatac agtttatctc tattaattga tgccagggat   1740

ttctcaccac ccaaagtaat aagtgaatta acagcagcat aagttgtggc aatatgaggc   1800

atctggcctg gtcccccggc atatccacca ttcggatcct ggcaacggtt aagaaaatcg   1860

atagcgttat cttcgagttc atcatcgacg gattctccca acaaagcaat ggagtggaag   1920

atccagtagc agagccaggg tcgattagcg tccaaaacgg aaaatgcgga actgagatgg   1980

cgaaggcctt tggagacata ctgcatgtga ttatcgcgtt gaagctccaa catgagggtt   2040

tgggcgttgc gaggaatggt ggcgagctcg aatttccccg atcgttcaaa catttggcaa   2100

taaagtttct taagattgaa tcctgttgcc ggtcttgcga tgattatcat ataatttctg   2160

ttgaattacg ttaagcatgt aataattaac atgtaatgca tgacgttatt tatgagatgg   2220

gtttttatga ttagagtccc gcaattatac atttaatacg cgatagaaaa caaaatatag   2280

cgcgcaaact aggataaatt atcgcgcgcg gtgtcatcta tgttactaga tcgggaattc   2340
```

<210> SEQ ID NO 55
<211> LENGTH: 2298
<212> TYPE: DNA
<213> ORGANISM: Artificial Sequence
<220> FEATURE:
<223> OTHER INFORMATION: Description of Artificial Sequence: Plasmid
      MuA-HP-GmFTB-Nos-Term

<400> SEQUENCE: 55

```
gaattcaaat ttttcgccag ttctaaatat ccggaaacct cttgggatgc cattgcccat     60

ctatctgtaa tttattgacg aaatagacga aaaggaaggt ggctcctata aagcacatca    120
```

-continued

```
ttgcgataac agaaaggcca ttgttgaaga tacctctgct gacattggtc cccaagtgga    180
agcaccaccc catgaggagc accgtggagt aagaagacgt tcgagccacg tcgaaaaagc    240
aagtgtgttg atgtagtatc tccattgacg taagggatga cgcacaatcc aactatccat    300
cgcaagacca ttgctctata taagaaagtt aatatcattt cgagtggcca cgctgagctc    360
gtggtggaga atctgggtgc tttgaccaac tatactggca caatgagagt ccacttaaac    420
agtaacatgt gtgataatga tctctacgtt tacccggttt gtctctcagt ccacccctctt    480
gctcctgtgc acataagaga atatattgct gtaaagcaat actgtgaaaa agtggttctt    540
gtgctctcca ctcattaata aatttatagg caatattttt aaaatcagat gaactggatt    600
cactggtgcc ttcatgctca ccacggcatg ttgcatgact agaggttcca tccaaacttt    660
cttttgcttc agatacataa gataccgcaa aaatctgtga tgtctcttcc atctgtttgt    720
tgataataga agataatctt tgcaatagag caacagcacc tccctgccaa aaggaatagc    780
atccatccac cagtttattt gttctcccct ggaatccaca ttccttacct tgtcggaata    840
ccacccagtc aactaatcga ggcagatcca agtgattaac ctcaccaatc agaatcattg    900
tagctaatcc acaaaaggtg tacccaccat gagcctcaga accaggctca ccagcaatgc    960
caccctcata tgtttgacag cttataatgt agtctccaac attctggatc agctcatcat   1020
ccaaaatgtt caaaacactt gcaacagaaa tggcagtgta gcaagctcga acatcaattt   1080
caccttcatc atgcatcctg aatccaccat ttggttgctt catccgccgc agaaacccat   1140
acagtttatc tctattaatt gatgccaggg atttctcacc acccaaagta ataagtgaat   1200
taacagcagc ataagttgtg gcaatatgag gcatctggcc tggtccccccg gcatatccac   1260
cattcggatc ctggcaacgg ttaagaaaat cgatagcgtt atcttcgagt tcatcatcga   1320
cggattctcc caacaaagca atggagtgga agatccagta gcagagccag ggtcgattag   1380
cgtccaaaac ggaaaatgcg gaactgagat ggcgaaggcc tttggagaca tactgcatgt   1440
gattatcgcg ttgaagctcc aacatgaggg tttgggcgtt gcgaggaatg gtggcggtga   1500
ggttaatcac ttggatctgc ctcgattagt tgactgggtg gtattccgac aaggtaagga   1560
atgtggattc caggggagaa caaataaact ggtggatgga tgctattcct tttggcaggg   1620
aggtgctgtt gctctattgc aaagattatc ttctattatc aacaaacaga tggaagagac   1680
atcacagatt tttgcggtat cttatgtatc tgaagcaaaa gaaagtttgg atggaacctc   1740
tagtcatgca acatgccgtg gtgagcatga aggcaccagt gaatccagtt catctgattt   1800
taaaaatatt gcctataaat ttattaatga gtggagagca caagaaccac tttttcacag   1860
tattgcttta cagcaatata ttctcttatg tgcacaggag caagagggtg gactgagaga   1920
caaaccgggt aaacgtagag atcattatca cacatgttac tgtttaagtg gactctcatt   1980
gtgccagtat agttggtcaa agcacccaga ttctccacca cgagctcgaa tttccccgat   2040
cgttcaaaca tttggcaata aagtttctta agattgaatc ctgttgccgg tcttgcgatg   2100
attatcatat aatttctgtt gaattacgtt aagcatgtaa taattaacat gtaatgcatg   2160
acgttattta tgagatgggt ttttatgatt agagtcccgc aattatacat ttaatacgcg   2220
atagaaaaca aaatatagcg cgcaaactag gataaattat cgcgcgcggt gtcatctatg   2280
ttactagatc gggaattc                                                   2298
```

<210> SEQ ID NO 56
<211> LENGTH: 2866
<212> TYPE: DNA

-continued

<213> ORGANISM: Artificial Sequence
<220> FEATURE:
<223> OTHER INFORMATION: Description of Artificial Sequence: Plasmid
RD29AP-HP-GmFTB-Nos-Term

<400> SEQUENCE: 56

```
ggagccatag atgcaattca atcaaactga aatttctgca agaatctcaa acacggagat     60
ctcaaagttt gaaagaaaat ttatttcttc gactcaaaac aaacttacga aatttaggta    120
gaacttatat acattatatt gtaatttttt gtaacaaaat gtttttatta ttattataga    180
attttactgg ttaaattaaa aatgaataga aaaggtgaat taagaggaga gaggaggtaa    240
acattttctt ctattttttc atattttcag gataaattat tgtaaaagtt tacaagattt    300
ccatttgact agtgtaaatg aggaatattc tctagtaaga tcattatttc atctacttct    360
tttatcttct accagtagag gaataaacaa tatttagctc ctttgtaaat acaaattaat    420
tttccttctt gacatcattc aattttaatt ttacgtataa aataaaagat catacctatt    480
agaacgatta aggagaaata caattcgaat gagaaggatg tgccgtttgt tataataaac    540
agccacacga cgtaaacgta aaatgaccac atgatgggcc aatagacatg gaccgactac    600
taataatagt aagttacatt ttaggatgga ataaatatca taccgacatc agttttgaaa    660
gaaaagggaa aaaaagaaaa aataaataaa agatatacta ccgacatgag ttccaaaaag    720
caaaaaaaaa gatcaagccg acacagacac gcgtagagag caaaatgact ttgacgtcac    780
accacgaaaa cagacgcttc atacgtgtcc ctttatctct ctcagtctct ctataaactt    840
agtgagaccc tcctctgttt tactcacaaa tatgcaaact agaaaacaat catcaggaat    900
aaagggtttg attacttcta ttggaaaggt ggtggagaat ctgggtgctt tgaccaacta    960
tactggcaca atgagagtcc acttaaacag taacatgtgt gataatgatc tctacgttta   1020
cccggtttgt ctctcagtcc accctcttgc tcctgtgcac ataagagaat atattgctgt   1080
aaagcaatac tgtgaaaaag tggttcttgt gctctccact cattaataaa tttataggca   1140
atatttttaa aatcagatga actggattca ctggtgcctt catgctcacc acggcatgtt   1200
gcatgactag aggttccatc caaactttct tttgcttcag atacataaga taccgcaaaa   1260
atctgtgatg tctcttccat ctgtttgttg ataatagaag ataatctttg caatagagca   1320
acagcacctc cctgccaaaa ggaatagcat ccatccacca gtttatttgt tctcccctgg   1380
aatccacatt ccttaccttg tcggaatacc acccagtcaa ctaatcgagg cagatccaag   1440
tgattaacct caccaatcag aatcattgta gctaatccac aaaaggtgta cccaccatga   1500
gcctcagaac caggctcacc agcaatgcca ccctcatatg tttgacagct tataatgtag   1560
tctccaacat tctggatcag ctcatcatcc aaaatgttca aaacacttgc aacagaaatg   1620
gcagtgtagc aagctcgaac atcaatttca ccttcatcat gcatcctgaa tccaccattt   1680
ggttgcttca tccgccgcag aaacccatac agtttatctc tattaattga tgccagggat   1740
ttctcaccac ccaaagtaat aagtgaatta acagcagcat aagttgtggc aatatgaggc   1800
atctggcctg gtcccccggc atatccacca ttcggatcct ggcaacggtt aagaaaatcg   1860
atagcgttat cttcgagttc atcatcgacg gattctccca acaaagcaat ggagtggaag   1920
atccagtagc agagccaggg tcgattagcg tccaaaacgg aaaatgcgga actgagatgg   1980
cgaaggcctt tggagacata ctgcatgtga ttatcgcgtt gaagctccaa catgagggtt   2040
tgggcgttgc gaggaatggt ggcggtgagg ttaatcactt ggatctgcct cgattagttg   2100
actgggtggt attccgacaa ggtaaggaat gtggattcca ggggagaaca aataaactgg   2160
```

-continued

```
tggatggatg ctattccttt tggcagggag gtgctgttgc tctattgcaa agattatctt   2220

ctattatcaa caaacagatg gaagagacat cacagatttt tgcggtatct tatgtatctg   2280

aagcaaaaga aagtttggat ggaacctcta gtcatgcaac atgccgtggt gagcatgaag   2340

gcaccagtga atccagttca tctgatttta aaaatattgc ctataaattt attaatgagt   2400

ggagagcaca agaaccactt tttcacagta ttgctttaca gcaatatatt ctcttatgtg   2460

cacaggagca agagggtgga ctgagagaca aaccgggtaa acgtagagat cattatcaca   2520

catgttactg tttaagtgga ctctcattgt gccagtatag ttggtcaaag cacccagatt   2580

ctccaccacg agctcgaatt tccccgatcg ttcaaacatt tggcaataaa gtttcttaag   2640

attgaatcct gttgccggtc ttgcgatgat tatcatataa tttctgttga attacgttaa   2700

gcatgtaata attaacatgt aatgcatgac gttatttatg agatgggttt ttatgattag   2760

agtcccgcaa ttatacattt aatacgcgat agaaaacaaa atatagcgcg caaactagga   2820

taaattatcg cgcgcggtgt catctatgtt actagatcgg gaattc                  2866
```

```
<210> SEQ ID NO 57
<211> LENGTH: 1882
<212> TYPE: DNA
<213> ORGANISM: Artificial Sequence
<220> FEATURE:
<223> OTHER INFORMATION: Description of Artificial Sequence: Plasmid
      MuA-anti-Zea mays FTB-Nos-Term

<400> SEQUENCE: 57

gaattcaaat ttttcgccag ttctaaatat ccggaaacct cttgggatgc cattgcccat     60

ctatctgtaa tttattgacg aaatagacga aaaggaaggt ggctcctata aagcacatca    120

ttgcgataac agaaaggcca ttgttgaaga tacctctgct gacattggtc cccaagtgga    180

agcaccaccc catgaggagc accgtggagt aagaagacgt tcgagccacg tcgaaaaagc    240

aagtgtgttg atgtagtatc tccattgacg taagggatga cgcacaatcc aactatccat    300

cgcaagacca ttgctctata taagaaagtt aatatcattt cgagtggcca cgctgagctc    360

ggatggattg gctccagcaa attagagtac ggtccaagca catgctgagg taatgggcac    420

gaaccagtat cagtcatggc actgtactgg ctaactgcga ggccactgag gcagtagcat    480

gaatgatagt gatctctgtt ctttccaggc ttatccctca agcctccctc tagtacctga    540

gaacaaagta ggatgtattg ttgcagggca atgttatgga agagtgggcc aatttggttg    600

ctctgttgta taaaatcaaa tccaaacttc gcatagtcca cagcagagga agacttattc    660

gcggtgcacc catatgaact ggtgctgcag gcatcctctc ctgatggcct tttgcaggaa    720

tacgaggacc tcaattgctt atcaacaatc gtaattaact tttgtgtgaa agcaatggca    780

gctccctgcc aaaaggagta gcaaccatca accaatttat tagttcgtcc ttgaaatccg    840

cattccactc cttgacgaaa agccacccag ccaatcaaac taggcaagtc aactttctct    900

gcctcattaa gcaggatcaa agcagccaat ccacagaatg tatacccacc atgtgcttca    960

gcataaggct ccccagcaat accaccttca taagtttgac atcttgctat gtagtcgcct   1020

acaccttttg ccagtttaaa atcaagaata ttcacaaggc tggcaaccga tatagcggtg   1080

taggaagcac ggacatcaat ttcgccacca tcatgcattc tgaaagcacc tgatacatct   1140

ttcatctgca gcataaaatt gtacaggttg cccctattga ttgatgacaa tgctctttcg   1200

ctccctattg tcacaagtgt atttacagca gcataagtcg tagctaggtg aggcaactgt   1260

ccaggtccac cactatatcc accatcttta tcctgacatc gagctaagaa gtctatgata   1320
```

-continued

```
tcattctcaa gatcatcatc aagtgcttca tccagcaaag caagtggatg aaccatccag   1380

tagcatagcc aagggcgatt ggcatctaga acatgaaagg ctggtcccat atgcctcagc   1440

ccaggcgtca gatactcgat atgctgatca cgccacagct ctagcatgat ggatttcgtg   1500

ttgggcgcgg ccccgaagag ggagcggtag atgtcgccaa ccctggcctc caccttcatc   1560

tgctccacct gcgtcaccgt gagcctcggt aggtcgggat ccgccgagct cgaatttccc   1620

cgatcgttca aacatttggc aataaagttt cttaagattg aatcctgttg ccggtcttgc   1680

gatgattatc atataatttc tgttgaatta cgttaagcat gtaataatta acatgtaatg   1740

catgacgtta tttatgagat gggtttttat gattagagtc ccgcaattat acatttaata   1800

cgcgatagaa aacaaaatat agcgcgcaaa ctaggataaa ttatcgcgcg cggtgtcatc   1860

tatgttacta gatcgggaat tc                                            1882
```

<210> SEQ ID NO 58
<211> LENGTH: 2505
<212> TYPE: DNA
<213> ORGANISM: Artificial Sequence
<220> FEATURE:
<223> OTHER INFORMATION: Description of Artificial Sequence: Plasmid MuA-HP-Zea mays FTB-Nos-Term

<400> SEQUENCE: 58

```
gaattcaaat tttcgccag ttctaaatat ccggaaacct cttgggatgc cattgcccat     60

ctatctgtaa tttattgacg aaatagacga aaaggaaggt ggctcctata aagcacatca    120

ttgcgataac agaaaggcca ttgttgaaga tacctctgct gacattggtc cccaagtgga    180

agcaccaccc catgaggagc accgtggagt aagaagacgt tcgagccacg tcgaaaaagc    240

aagtgtgttg atgtagtatc tccattgacg taagggatga cgcacaatcc aactatccat    300

cgcaagacca ttgctctata taagaaagtt aatatcattt cgagtggcca cgctgagctc    360

ggatggattg gctccagcaa attagagtac ggtccaagca catgctgagg taatgggcac    420

gaaccagtat cagtcatggc actgtactgg ctaactgcga ggccactgag gcagtagcat    480

gaatgatagt gatctctgtt ctttccaggc ttatccctca agcctccctc tagtacctga    540

gaacaaagta ggatgtattg ttgcagggca atgttatgga agagtgggcc aatttggttg    600

ctctgttgta taaaatcaaa tccaaacttc gcatagtcca cagcagagga agacttattc    660

gcggtgcacc catatgaact ggtgctgcag gcatcctctc ctgatggcct tttgcaggaa    720

tacgaggacc tcaattgctt atcaacaatc gtaattaact tttgtgtgaa agcaatggca    780

gctccctgcc aaaaggagta gcaaccatca accaatttat tagttcgtcc ttgaaatccg    840

cattccactc cttgacgaaa agccacccag ccaatcaaac taggcaagtc aactttctct    900

gcctcattaa gcaggatcaa agcagccaat ccacagaatg tatacccacc atgtgcttca    960

gcataaggct ccccagcaat accaccttca taagtttgac atcttgctat gtagtcgcct   1020

acaccttttg ccagtttaaa atcaagaata ttcacaaggc tggcaaccga tatagcggtg   1080

taggaagcac ggacatcaat ttcgccacca tcatgcattc tgaaagcacc tgatacatct   1140

ttcatctgca gcataaaatt gtacaggttg cccctattga ttgatgacaa tgctctttcg   1200

ctccctattg tcacaagtgt atttacagca gcataagtcg tagctaggtg aggcaactgt   1260

ccaggtccac cactatatcc accatcttta tcctgacatc gagctaagaa gtctatgata   1320

tcattctcaa gatcatcatc aagtgcttca tccagcaaag caagtggatg aaccatccag   1380

tagcatagcc aagggcgatt ggcatctaga acatgaaagg ctggtcccat atgcctcagc   1440
```

-continued

```
ccaggcgtca gatactcgat atgctgatca cgccacagct ctagcatgat ggatttcgtg   1500

ttgggcgcgg ccccgaagag ggagcggtag atgtcgccaa ccctggcctc caccttcatc   1560

tgctccacct gcgtcaccgt gagcctcggt aggtcgggat ccgccggatc cgctggggag   1620

ccttatgctg aagcacatgg tgggtataca ttctgtggat tggctgcttt gatcctgctt   1680

aatgaggcag agaaagttga cttgcctagt ttgattggct gggtggcttt tcgtcaagga   1740

gtggaatgcg gatttcaagg acgaactaat aaattggttg atggttgcta ctccttttgg   1800

cagggagctg ccattgcttt cacacaaaag ttaattacga ttgttgataa gcaattgagg   1860

tcctcgtatt cctgcaaaag gccatcagga gaggatgcct gcagcaccag ttcatatggg   1920

tgcaccgcga ataagtcttc ctctgctgtg gactatgcga agtttggatt tgattttata   1980

caacagagca accaaattgg cccactcttc cataacattg ccctgcaaca atacatccta   2040

ctttgttctc aggtactaga gggaggcttg agggataagc ctggaaagaa cagagatcac   2100

tatcattcat gctactgcct cagtggcctc gcagttagcc agtacagtgc catgactgat   2160

actggttcgt gcccattacc tcagcatgtg cttggaccgt actctaattt gctggagcca   2220

atccatccaa gcttgaattt ccccgatcgt tcaaacattt ggcaataaag tttcttaaga   2280

ttgaatcctg ttgccggtct tgcgatgatt atcatataat ttctgttgaa ttacgttaag   2340

catgtaataa ttaacatgta atgcatgacg ttatttatga gatgggtttt tatgattaga   2400

gtcccgcaat tatacattta atacgcgata gaaaacaaaa tatagcgcgc aaactaggat   2460

aaattatcgc gcgcggtgtc atctatgtta ctagatcgga agctt                   2505
```

<210> SEQ ID NO 59
<211> LENGTH: 1323
<212> TYPE: DNA
<213> ORGANISM: Pisum sativum

<400> SEQUENCE: 59

```
caacacctac ctagtgcttc tagttctggt tctaggactg agagtaaaca gaagtgaaga     60

agaatccaga acatggccgg gaatatcgaa gttgaagaag acgatcgtgt gccgctaaga    120

ttacgacctg agtggtcaga tgttactccg atcccacaag acgatggccc tagtcccgtc    180

gtgccgatca actactccga agagttttca gaagttatgg attactttcg tgctgtttac    240

ttcgccaaag aactttcctc tcgcgctctt gctctcaccg ccgaagctat cggtttaaac    300

gccggaaact acactgtgtg gcatttccgg cggttattac ttgagtcact gaaagttgac    360

ctacatgttg aacgggaatt cgtggagcgt gttgccagtg gcaattcaaa aaattatcag    420

atttggcatc atagacgatg ggttgctgag aaattaggac ctgaagctag aaacagtgaa    480

cttgagttca ccaaaaagat tctgtctgtt gacgccaaac actatcatgc atggtctcat    540

aggcagtggg ttcttcaaaa tctaggagga tgggaagatg aactcagtta ttgtagtgaa    600

ctgcttgcag aagacatatt taacaattct gcttggaatc agagatactt cgtcataaca    660

aggtctcccg tcttgggagg gctaaaagcc atgagagagt ctgaagtgct tttcaccgtt    720

gaagccatta tttcttaccc agaaaatgaa agctcatgga gatatcttcg aggacttttc    780

aaagatgaat ccacgttata tgtaaatgat gcccaagtat cttcattatg tttaaagatt    840

ttgaaaacta agagcaacta tttgtttgct ctaagtactc tgctggatct atctgcctcg    900

gttattcaac caaatgaaga tttcagagat gccattgagg ctttaagact tcagattttg    960

ataaaacaag attcagatat agcaataact atttgttcta ttttagaaca agttgatcca   1020

attagagtca actattgggt ctggcggaag agtagacttc ctcaggcagc gtaaaggaca   1080
```

-continued

```
aacttatgtc atatgtgtaa tttttagtct attggaattt gacgtcatgg ataacagggt   1140

ggttgttttt gttatgatat gttttccaga tgtatttcta tatttaacag caaagttgat   1200

ttaacattgg tgttaacaaa ccaatgatct ccaaaaaatc aatgttttat ttctcttcat   1260

ttgtctgatt ttgtggcata acattcttga tgattttgtg gtaaaaaaaa aaaaaaaaaa   1320

aaa                                                                 1323
```

<210> SEQ ID NO 60
<211> LENGTH: 1505
<212> TYPE: DNA
<213> ORGANISM: Lycopersicon esculentum

<400> SEQUENCE: 60

```
taccccgaag gcaattccag tattgaacta ccgccggcag ttttccgatc ggatcccgga     60

gccgagtatc aaatggacag ttgtgaggtg acgaaaacgc gaattccttt caaggaaagg    120

cccgactggg ccgatgtgaa gcccgttccg caagacgacg ggccctgccc ggttgttccc    180

atagcctaca cagaagactt ctctgaaacc atggactact tccgggcaat ttacgtagcc    240

gatgagcgat ctacacgcgc cctccagctt actggtgaag ctattcagct aaaccctgga    300

aattacactg tatggcaatt taggcgtgtt gtgctggagg cattgggtgt tgatttacgt    360

gaagaattga agtttgttga tcgcattgct ggggagaata ccaaaaaatta tcaaatatgg    420

catcatagac ggtggcttgc tgagaagctg ggagctgatg ctgtgacaaa tgagctagaa    480

ttcaccaaga aaatattttc tcaggatgca aaaaattatc atgcttggtc ccatcggcag    540

tgggtccttc aagcacttgg aggatgggaa gatgagcttg cttattgtca acaactcctt    600

gaagatgata tttacaacaa ttctgcttgg aatcagagat actttgtcgt aacacgatca    660

cctctactag gggcctagt ggcaatgagg gaattggaag tgaattacac agttcaagcc    720

atcagagcta gtccagagaa tgaaagtcct tggaggtatc ttcgtggtct ttacaagaat    780

gatacacaat ctctagttca ggattctcaa gtagcatcag tactttggga cgtcttaacc    840

tcccaaaata gtcatgtgca cgctctgagg ttcttgttgg atcttctttg tcatgatttg    900

gaaccgagcc aagaattgaa aagtgctgta gatgttctta ctccccagtc atgctcacca    960

gatttagcac tgacaaagaa aatttgttcc atcttggaac atgctgatcc aatgagagta   1020

aaatattgga attggcgcaa gagcatggtt cgggttcaat tacttcagag tcagaatgca   1080

gagaggttgg ctaatttgag tgttcaagaa tgacttgtga gaatattgta ctgtgtttac   1140

gaaatacata cttgcatcta aggtgatcct tcgggcacat gtgctgggaa gtgactgaat   1200

atcacgaaga actaaaaaaa ctgtgattgg caacattgta ctactccaaa taggtcactt   1260

tcgatgactt tttgtactgc cttgagtttt ggctctgcta tgttttgtaa gttttggata   1320

tggatgcata gcttattgat acttttggtg acttaaaata ctctggaagg caggtagcat   1380

gtgtataatt cactgttact tcccatgtcg agttagatgc ttgaaaattt tagtaggtgt   1440

tcttttatga agcacacatt aatgtggaaa aaaaaaaaaa aaaaaaaaaa aaaaaaaaaa   1500

aaaaa                                                               1505
```

<210> SEQ ID NO 61
<211> LENGTH: 1218
<212> TYPE: DNA
<213> ORGANISM: Oryza sp.

<400> SEQUENCE: 61

-continued

```
gcacgaggtt ctaacgccgc cgccgccgcc gccgtctccg cagaatctga tcgatggcgc     60

cgtcgtcgac gtcgtcggag ggtgcctccg acgagtggtt gccacccagc cggcggccgg    120

agctggcgga cgtggtcccc gtgacgcagg acgacgggcc ccaccccgtg gtggccatcg    180

cctaccggga cgagttccgc gaggtcatgg actacttccg cgccctctac ttcgccggcg    240

agcgcagcgt ccgcgccctc cacctcaccg ccgaggtcat cgaccttaat cccggcaact    300

acacggtgtg gcattttagg cgtcttgttc tagaggcact ggatgctgat ctgcgtgagg    360

aaatggattt tgtggaccga attgtcgaat gtaacccaaa aaattatcaa atctggcatc    420

acaagagatg gcttgcggag aaattaggac cagatattgc aaataaagag cacgaattta    480

caaggaagat actttctatg gatgctaaaa attaccatgc ttggtctcat aggcagtggg    540

ttcttcaagc actgggtgga tgggagactg aactacagta ttgcaaccag ctgcttgagg    600

aagacgtctt caataattca gcttggaatc agagatacct tgtaataaca agttcaccac    660

ttcttggagg ccttgcagca atgcgtgact cggaagtgga ttacacagtt ggggctattc    720

tggctaaccc tcagaatgaa agcccctgga gatacctcaa aggcctgtac aagggtgaaa    780

ataacttgct gatggctgat gagcgcatct ctgatgtttg tctcaaggtc ctgaaacatg    840

attcgacctg cgtatttgct ttgagcttgc tgctcgatct tcttcaaatt ggtttacaac    900

cttcagatga actcaaagga actatcgaag caataaagaa ctctgatcct gaagcagatg    960

aagcagtaga tgctgatctt gcgactgcaa tctgctcaat attgcagaga tgtgatcccc   1020

tgcggataaa ttactggtcc tggtacagga ccactatttc ttctcaaacc tgaagcatgc   1080

agtggcctcc atgaggtcat aatggagata tcttctatct tcgtgtgatt ctgggcgttg   1140

aggtgcctag ctacatttgt tatgaacttt ccttgggcat aactgatcac tgatattact   1200

ccaatattgt gttctaaa                                                 1218
```

<210> SEQ ID NO 62
<211> LENGTH: 1426
<212> TYPE: DNA
<213> ORGANISM: Zea mays

<400> SEQUENCE: 62

```
gcacgagaca gcgcaattac ttaagctatt tgtattcgga tctgatccaa ccctggtggt     60

cagctggact catcgcccat ggagcacact aagtcaggcc ccagcagttg gccagaactg    120

gccgacgtgg tgccggtgcc gcaggacgat gggcctagcc ctgtggtgtc catcgcctat    180

cgagatgact ttcgtgaggt catggattac ttccgcgccc tctacctcac cggtgagcga    240

agccctcgcg ctctccgcct caccgccgag gccatcgagc tcaaccccgg caactacact    300

gtctggcatt tccggcgcct tattctggag tcactagatt ttgatttact agaggagatg    360

aaatttgtcg aaaaaattgc tgaatgcaat ccaaaaaatt accaaatctg gcaccataag    420

agatggcttg ctgagaaatt aggacctggt attgcaaaca aagagcatga attcacaatg    480

aagatacttg ctattgatgc aaaaaattat catgcttggt ctcataggca gtgggttctt    540

caagcgttgg ggggatggga gactgaatta gaatactgtg accacttact taaggaagac    600

gtcttcaata attcagcttg gaatcagaga tactttgtta taacaagatc accatttctt    660

ggtggccttg cggcaatgcg tgattcagaa gtagactaca caattgaagc tattctagca    720

aacgctcaga atgaaagccc ctggaggtac ctcaagggtc tatacaaggg tgagaataac    780

ctgctagtag aggacgagcg catctctgct gtttgtttca aggtcctgaa gaatgattgg    840

acttgtgtat ttgctttgag tttgctgctc gatcttctct gcactggttt gcagccttca    900
```

-continued

```
gatgaactta ggtccactct tgaaacaata aggagctccc atcctgaaac cgcggatgat     960
gatcctgcag ccgctgtttg ctgtatcctg cagaaatgtg atcccctgcg ggtaaattat    1020
tggtcttggt tcaaggacac tctttctcag atctcatgac ttcacatggg ttcacccctt    1080
gtccgcgctg gtccgggctc tgtgagatag acatgtttta gatagtttca ttggacaccc    1140
aaacagagcg gacagagtgt atggctgcta ccttctccgt gactgaaagc agtgcttgta    1200
acgattttgt ttagtaaaat ttgtgagtgt tactgctcca aacaacacct tatgcaacca    1260
tatttgaata tttcacatgt aagcttgaat ccaggtgtgt ttgttaatgt attacacttg    1320
ccatgggagc ctaaatgaga cccataatca cttccactag agtcggaaga ccgtgtcgag    1380
cagttcactc atatggtcac ttaaagcaaa aaaaaaaaaa aaaaaa                   1426
```

```
<210> SEQ ID NO 63
<211> LENGTH: 1261
<212> TYPE: DNA
<213> ORGANISM: Glycine max

<400> SEQUENCE: 63
```

```
gcacgaggat taacgaagga tggaatctgg gtctagcgaa ggagaagagg tgcagcaacg      60
cgtgccgttg agggagagag tggagtggtc agatgttact ccggttcctc aaaacgacgg     120
ccctaaccct gtcgttccga tccagtacac tgaagagttt tccgaagtta tggattactt     180
tcgcgccgtt tacctcaccg atgaacgctc ccctcgcgcc ctcgctctca cagccgaagc     240
cgttcaattc aactccggca actacactgt gtggcatttc cgacggttgt tacttgagtc     300
gctaaaagtc gacttgaacg atgaactgga ttttgtggag cgtatggccg ctggaaattc     360
taaaaattat cagatgtggc atcatagacg atgggttgcc gagaagttag gtcctgaagc     420
tagaaacaat gagctcgagt tcaccaaaaa gatactgtcc gttgatgcca aacattatca     480
tgcatggtct catagacagt gggctcttca aacactagga ggatgggaag atgaacttaa     540
ttattgcaca gaactactta aagaagacat tttaacaat tctgcttgga atcagagata      600
ttttgtcata acaaggtctc ctttcttggg gggcctaaaa gctatgagag agtctgaagt     660
gctttacacc attgaagcca ttatagccta ccctgaaaat gaaagctcgt ggagatatct     720
acgaggactt tataaaggtg aaactacttc atgggtaaat gatcctcaag tttcttcagt     780
atgcttaaag attttgagaa ctaagagcaa ctacgtgttt gctcttagca ctattttaga     840
tcttatatgc tttggttatc aaccaaatga agacattaga gatgccattg acgccttaaa     900
gaccgcagat atggataaac aagatttaga tgatgatgag aaaggggaac aacaaaattt     960
aaatatagca cgaaatattt gttctatcct aaaacaagtt gatccaatta gaaccaacta    1020
ttggatttgg cgcaagagca gacttcctct atcagcttag taaccaaagt aattaaaggg    1080
caactctgtg ttatgtgtaa cctagtttat tgaaactgga tttttattta ttattatttt    1140
ttatgttgtc atgtatctgt ttgtgcaaat ttatcttttt gtcatgccat tactggcatt    1200
tgagtgtaag gattgaaagc catgcagaat aagaaattta agtttttttt tccgttgaaa    1260
a                                                                    1261
```

```
<210> SEQ ID NO 64
<211> LENGTH: 1333
<212> TYPE: DNA
<213> ORGANISM: Glycine max

<400> SEQUENCE: 64
```

-continued

```
gcacgagctt gcgtgtggag tgaagaagat taacgaagga tggaatctgg gtctagcgaa     60
ggagaagagg tgcagcaacg cgtgccgttg agggagagag tggagtggtc agatgttact    120
ccggttcctc aaaacgacgg ccctaaccct gtcgttccga tccagtacac tgaagagttt    180
tccgaagtta tggattactt tcgcgccgtt tacctcaccg atgaacgctc ccctcgcgcc    240
ctcgctctca cagccgaagc cgttcaattc aactccggca actacactgt gtggcatttc    300
cgacggttgt tacttgagtc gctaaaagtc gacttgaacg atgaactgga gtttgtggag    360
cgtatggccg ctggaaattc taaaaattat cagatgtggt gtgatgctct gctctgctct    420
ttcttccata ctttgcatca tagacgatgg gttgccgaga agttaggtcc tgaagctaga    480
aacaatgagc tcgagttcac caaaaagata ctgtccgttg atgccaaaca ttatcatgca    540
tggtctcata gacagtgggc tcttcaaaca ctaggaggat gggaagatga acttaattat    600
tgcacagaac tacttaaaga agacattttt aacaattctg cttggaatca gagatatttt    660
gtcataacaa ggtctccttt cttgggggc ctaaaagcta tgagagagtc tgaagtgctt     720
tacaccattg aagccattat agcctaccct gaaaatgaaa gctcgtggag atatctacga    780
ggactttata aaggtgaaac tacttcatgg gtaaatgatc ctcaagtttc ttcagtatgc    840
ttaaagattt tgagaactaa gagcaactac gtgtttgctc ttagcactat tttagatctt    900
atatgctttg gttatcaacc aaatgaagac attagagatg ccattgacgc cttaaagacc    960
gcagatatgg ataaacaaga tttagatgat gatgagaaag gggaacaaca aaatttaaat   1020
atagcacgaa atatttgttc tatcctaaaa caagttgatc caattagaac caactattgg   1080
atttggcgca agagcagact tcctctatca gcttagtaac caaagtaatt aaagggcaac   1140
tctgtgttat gtgtaaccta gtttattgaa actggatgtt tatttattat tattttttat   1200
gttgtcatgt atctgtttgt gcaaatttat ctttttgtca tgccattact ggcatttgag   1260
tgtaaggatt gaaagccatg cagaataaga aatttaagtt tttttttccg ttgaaaaaaa   1320
aaaaaaaaaa aaa                                                      1333
```

<210> SEQ ID NO 65
<211> LENGTH: 1339
<212> TYPE: DNA
<213> ORGANISM: Triticum sp.

<400> SEQUENCE: 65

```
cggacgtggc gccgctgccg caggccgacg ggccctgccc cgtcgtctcc atcgcttacc     60
gcggcgactt ccgcgaggtc atggactact tccgcgccct ctacgccgcc ggcgagcgca    120
gcccccgcgc cctccgcctc accgccgacg ccatccacct caaccccggc aactacactg    180
tatggcattt caggcgcgtt gttctagagg cactggatgc tgatttattg ctagaaatgc    240
attttgtgga ccaaattgct gaatctaatc caaaaaatta ccaagtctgg catcacaaga    300
gatggcttgc tgagaaaata ggaccagatg ctgcaaatag tgaacatgac ttcacaagga    360
agatacttgc tatggatgct aaaaactacc atgcttggtc ccataggcag tgggttcttc    420
aagcattggg tggatgggag agtgaactgc agtactgcaa ccagcttctt gaggaagatg    480
tcttcaataa ctcagcttgg aatcagagat accttgtggt aacacgatca ccaattcttg    540
ggggccttgc ggcaatgcgc gactcagaag tagattacac agttgaggcc attatggtga    600
accctcagaa tgaaagcccc tggagatacc tcagaggttt atataaggat gataacaatt    660
tgctggtggc tgataatcgc atttctgatg cttgcctcaa ggtcctgaat aaggattgga    720
catgcgtatt tgctttgagc ttcctgcttg atcttcttcg catgggtttg cagccttcga    780
```

-continued

```
atgaacttaa aggaaccatc gaagcaatgg agaactctga tcctgaaacg ggacatgctg    840

atattgcagt agctgtctgc tcaatcctgc agaaatgtga tcccctgcgg ataaactact    900

ggtcatggta ccagaccact ctttcttctt agacatctga aaattcagct gaagacagtt    960

ttagcagcat gatgtaaact caatcgaagg ggttgacgca gtgtatgaaa aacctttcct   1020

gtgatcttgg tgcggagcaa tttgtactga ttttactggg aaaaatcaat caatgacagc   1080

atgcccaaca atgtcttgtg tgaatatgtt actgcctgat attcacatgt tagcagaatg   1140

agaataacca atcaaactcc aacgagcaga ttgttacagt aacggccact ggtggtgtga   1200

aaatcctgaa atctgcttca gtcactttgc cttgtttaca gttgagtctg ttgttgtgat   1260

ctgtacctaa tgcatgtaca caatcatcaa attattagtt tttgtaccaa tgagtattcg   1320

atgaaaaaaa aaaaaaaaa                                                  1339
```

<210> SEQ ID NO 66
<211> LENGTH: 333
<212> TYPE: PRT
<213> ORGANISM: Pisum sativum

<400> SEQUENCE: 66

```
Met Ala Gly Asn Ile Glu Val Glu Glu Asp Asp Arg Val Pro Leu Arg
 1               5                  10                  15

Leu Arg Pro Glu Trp Ser Asp Val Thr Pro Ile Pro Gln Asp Asp Gly
            20                  25                  30

Pro Ser Pro Val Val Pro Ile Asn Tyr Ser Glu Glu Phe Ser Glu Val
        35                  40                  45

Met Asp Tyr Phe Arg Ala Val Tyr Phe Ala Lys Glu Leu Ser Ser Arg
    50                  55                  60

Ala Leu Ala Leu Thr Ala Glu Ala Ile Gly Leu Asn Ala Gly Asn Tyr
65                  70                  75                  80

Thr Val Trp His Phe Arg Arg Leu Leu Leu Glu Ser Leu Lys Val Asp
                85                  90                  95

Leu His Val Glu Arg Glu Phe Val Glu Arg Val Ala Ser Gly Asn Ser
            100                 105                 110

Lys Asn Tyr Gln Ile Trp His His Arg Arg Trp Val Ala Glu Lys Leu
        115                 120                 125

Gly Pro Glu Ala Arg Asn Ser Glu Leu Glu Phe Thr Lys Lys Ile Leu
    130                 135                 140

Ser Val Asp Ala Lys His Tyr His Ala Trp Ser His Arg Gln Trp Val
145                 150                 155                 160

Leu Gln Asn Leu Gly Gly Trp Glu Asp Glu Leu Ser Tyr Cys Ser Glu
                165                 170                 175

Leu Leu Ala Glu Asp Ile Phe Asn Asn Ser Ala Trp Asn Gln Arg Tyr
            180                 185                 190

Phe Val Ile Thr Arg Ser Pro Val Leu Gly Gly Leu Lys Ala Met Arg
        195                 200                 205

Glu Ser Glu Val Leu Phe Thr Val Glu Ala Ile Ile Ser Tyr Pro Glu
    210                 215                 220

Asn Glu Ser Ser Trp Arg Tyr Leu Arg Gly Leu Phe Lys Asp Glu Ser
225                 230                 235                 240

Thr Leu Tyr Val Asn Asp Ala Gln Val Ser Ser Leu Cys Leu Lys Ile
                245                 250                 255

Leu Lys Thr Lys Ser Asn Tyr Leu Phe Ala Leu Ser Thr Leu Leu Asp
            260                 265                 270
```

```
Leu Ser Ala Ser Val Ile Gln Pro Asn Glu Asp Phe Arg Asp Ala Ile
        275                 280                 285

Glu Ala Leu Arg Leu Gln Ile Leu Ile Lys Gln Asp Ser Asp Ile Ala
    290                 295                 300

Ile Thr Ile Cys Ser Ile Leu Glu Gln Val Asp Pro Ile Arg Val Asn
305                 310                 315                 320

Tyr Trp Val Trp Arg Lys Ser Arg Leu Pro Gln Ala Ala
                325                 330


<210> SEQ ID NO 67
<211> LENGTH: 346
<212> TYPE: PRT
<213> ORGANISM: Lycopersicon esculentum

<400> SEQUENCE: 67

Met Asp Ser Cys Glu Val Thr Lys Thr Arg Ile Pro Phe Lys Glu Arg
 1               5                  10                  15

Pro Asp Trp Ala Asp Val Lys Pro Val Pro Gln Asp Asp Gly Pro Cys
            20                  25                  30

Pro Val Val Pro Ile Ala Tyr Thr Glu Asp Phe Ser Glu Thr Met Asp
        35                  40                  45

Tyr Phe Arg Ala Ile Tyr Val Ala Asp Glu Arg Ser Thr Arg Ala Leu
    50                  55                  60

Gln Leu Thr Gly Glu Ala Ile Gln Leu Asn Pro Gly Asn Tyr Thr Val
65                  70                  75                  80

Trp Gln Phe Arg Arg Val Val Leu Glu Ala Leu Gly Val Asp Leu Arg
                85                  90                  95

Glu Glu Leu Lys Phe Val Asp Arg Ile Ala Gly Glu Asn Thr Lys Asn
            100                 105                 110

Tyr Gln Ile Trp His His Arg Arg Trp Leu Ala Glu Lys Leu Gly Ala
        115                 120                 125

Asp Ala Val Thr Asn Glu Leu Glu Phe Thr Lys Lys Ile Phe Ser Gln
    130                 135                 140

Asp Ala Lys Asn Tyr His Ala Trp Ser His Arg Gln Trp Val Leu Gln
145                 150                 155                 160

Ala Leu Gly Gly Trp Glu Asp Glu Leu Ala Tyr Cys Gln Gln Leu Leu
                165                 170                 175

Glu Asp Asp Ile Tyr Asn Asn Ser Ala Trp Asn Gln Arg Tyr Phe Val
            180                 185                 190

Val Thr Arg Ser Pro Leu Leu Gly Gly Leu Val Ala Met Arg Glu Leu
        195                 200                 205

Glu Val Asn Tyr Thr Val Gln Ala Ile Arg Ala Ser Pro Glu Asn Glu
    210                 215                 220

Ser Pro Trp Arg Tyr Leu Arg Gly Leu Tyr Lys Asn Asp Thr Gln Ser
225                 230                 235                 240

Leu Val Gln Asp Ser Gln Val Ala Ser Val Leu Trp Asp Val Leu Thr
                245                 250                 255

Ser Gln Asn Ser His Val His Ala Leu Arg Phe Leu Leu Asp Leu Leu
            260                 265                 270

Cys His Asp Leu Glu Pro Ser Gln Glu Leu Lys Ser Ala Val Asp Val
        275                 280                 285

Leu Thr Pro Gln Ser Cys Ser Pro Asp Leu Ala Leu Thr Lys Lys Ile
    290                 295                 300

Cys Ser Ile Leu Glu His Ala Asp Pro Met Arg Val Lys Tyr Trp Asn
```

-continued

```
305                 310                 315                 320

Trp Arg Lys Ser Met Val Arg Val Gln Leu Leu Gln Ser Gln Asn Ala
                325                 330                 335

Glu Arg Leu Ala Asn Leu Ser Val Gln Glu
            340                 345


<210> SEQ ID NO 68
<211> LENGTH: 339
<212> TYPE: PRT
<213> ORGANISM: Oryza sp.

<400> SEQUENCE: 68

Met Ala Pro Ser Ser Thr Ser Ser Glu Gly Ala Ser Asp Glu Trp Leu
 1               5                  10                  15

Pro Pro Ser Arg Arg Pro Glu Leu Ala Asp Val Val Pro Val Thr Gln
            20                  25                  30

Asp Asp Gly Pro His Pro Val Val Ala Ile Ala Tyr Arg Asp Glu Phe
        35                  40                  45

Arg Glu Val Met Asp Tyr Phe Arg Ala Leu Tyr Phe Ala Gly Glu Arg
    50                  55                  60

Ser Val Arg Ala Leu His Leu Thr Ala Glu Val Ile Asp Leu Asn Pro
65                  70                  75                  80

Gly Asn Tyr Thr Val Trp His Phe Arg Arg Leu Val Leu Glu Ala Leu
                85                  90                  95

Asp Ala Asp Leu Arg Glu Glu Met Asp Phe Val Asp Arg Ile Val Glu
            100                 105                 110

Cys Asn Pro Lys Asn Tyr Gln Ile Trp His His Lys Arg Trp Leu Ala
        115                 120                 125

Glu Lys Leu Gly Pro Asp Ile Ala Asn Lys Glu His Glu Phe Thr Arg
    130                 135                 140

Lys Ile Leu Ser Met Asp Ala Lys Asn Tyr His Ala Trp Ser His Arg
145                 150                 155                 160

Gln Trp Val Leu Gln Ala Leu Gly Gly Trp Glu Thr Glu Leu Gln Tyr
                165                 170                 175

Cys Asn Gln Leu Leu Glu Glu Asp Val Phe Asn Asn Ser Ala Trp Asn
            180                 185                 190

Gln Arg Tyr Leu Val Ile Thr Ser Ser Pro Leu Leu Gly Gly Leu Ala
        195                 200                 205

Ala Met Arg Asp Ser Glu Val Asp Tyr Thr Val Gly Ala Ile Leu Ala
    210                 215                 220

Asn Pro Gln Asn Glu Ser Pro Trp Arg Tyr Leu Lys Gly Leu Tyr Lys
225                 230                 235                 240

Gly Glu Asn Asn Leu Leu Met Ala Asp Glu Arg Ile Ser Asp Val Cys
                245                 250                 255

Leu Lys Val Leu Lys His Asp Ser Thr Cys Val Phe Ala Leu Ser Leu
            260                 265                 270

Leu Leu Asp Leu Leu Gln Ile Gly Leu Gln Pro Ser Asp Glu Leu Lys
        275                 280                 285

Gly Thr Ile Glu Ala Ile Lys Asn Ser Asp Pro Glu Ala Asp Glu Ala
    290                 295                 300

Val Asp Ala Asp Leu Ala Thr Ala Ile Cys Ser Ile Leu Gln Arg Cys
305                 310                 315                 320

Asp Pro Leu Arg Ile Asn Tyr Trp Ser Trp Tyr Arg Thr Thr Ile Ser
                325                 330                 335
```

-continued

Ser Gln Thr

<210> SEQ ID NO 69
<211> LENGTH: 326
<212> TYPE: PRT
<213> ORGANISM: Zea mays

<400> SEQUENCE: 69

```
Met Glu His Thr Leu Ser Gly Pro Ser Ser Trp Pro Glu Leu Ala Asp
 1               5                  10                  15

Val Val Pro Val Pro Gln Asp Asp Gly Pro Ser Pro Val Val Ser Ile
            20                  25                  30

Ala Tyr Arg Asp Asp Phe Arg Gly Val Met Asp Tyr Phe Arg Ala Leu
        35                  40                  45

Tyr Leu Thr Gly Glu Arg Ser Pro Arg Ala Leu Arg Leu Thr Ala Glu
    50                  55                  60

Ala Ile Glu Leu Asn Pro Gly Asn Tyr Thr Val Trp His Phe Arg Arg
65                  70                  75                  80

Leu Ile Leu Glu Ser Leu Asp Phe Asp Leu Leu Glu Glu Met Lys Phe
                85                  90                  95

Val Glu Leu Ile Ala Glu Cys Asn Pro Lys Asn Tyr Gln Ile Trp His
            100                 105                 110

His Leu Arg Trp Leu Ala Glu Lys Leu Gly Pro Gly Ile Ala Asn Lys
        115                 120                 125

Glu His Glu Phe Thr Met Lys Ile Leu Ala Ile Asp Ala Leu Asn Tyr
    130                 135                 140

His Ala Trp Ser His Arg Gln Trp Val Leu Gln Ala Leu Gly Gly Trp
145                 150                 155                 160

Glu Thr Glu Leu Glu Tyr Cys Asp His Leu Leu Lys Glu Asp Val Phe
                165                 170                 175

Asn Asn Ser Ala Trp Asn Gln Arg Tyr Phe Val Ile Thr Arg Ser Pro
            180                 185                 190

Phe Leu Gly Gly Leu Ala Ala Met Arg Asp Ser Gly Val Asp Tyr Thr
        195                 200                 205

Ile Glu Ala Ile Leu Ala Asn Ala Gln Asn Gly Ser Pro Trp Arg Tyr
    210                 215                 220

Leu Lys Gly Leu Tyr Lys Gly Glu Asn Asn Leu Leu Val Glu Asp Gly
225                 230                 235                 240

Arg Ile Ser Ala Val Cys Phe Lys Val Leu Lys Asn Asp Trp Thr Cys
                245                 250                 255

Val Phe Ala Leu Ser Leu Leu Leu Asp Leu Leu Cys Thr Gly Leu Gln
            260                 265                 270

Pro Ser Asp Gly Leu Arg Ser Thr Leu Gly Thr Ile Arg Ser Ser His
        275                 280                 285

Pro Glu Thr Ala Asp Asp Asp Pro Ala Ala Ala Val Cys Cys Ile Leu
    290                 295                 300

Gln Lys Cys Asp Pro Leu Ala Val Asn Tyr Trp Ser Trp Phe Lys Asp
305                 310                 315                 320

Thr Leu Ser Gln Ile Ser
                325
```

<210> SEQ ID NO 70
<211> LENGTH: 346
<212> TYPE: PRT
<213> ORGANISM: Glycine max -continued

<400> SEQUENCE: 70

Met Glu Ser Gly Ser Ser Glu Gly Glu Glu Val Gln Gln Arg Val Pro
1 5 10 15

Leu Arg Glu Arg Val Glu Trp Ser Asp Val Thr Pro Val Pro Gln Asn
20 25 30

Asp Gly Pro Asn Pro Val Val Pro Ile Gln Tyr Thr Glu Glu Phe Ser
35 40 45

Glu Val Met Asp Tyr Phe Arg Ala Val Tyr Leu Thr Asp Glu Arg Ser
50 55 60

Pro Arg Ala Leu Ala Leu Thr Ala Glu Ala Val Gln Phe Asn Ser Gly
65 70 75 80

Asn Tyr Thr Val Trp His Phe Arg Arg Leu Leu Leu Glu Ser Leu Lys
85 90 95

Val Asp Leu Asn Asp Glu Leu Asp Phe Val Glu Arg Met Ala Ala Gly
100 105 110

Asn Ser Lys Asn Tyr Gln Met Trp His His Arg Arg Trp Val Ala Glu
115 120 125

Lys Leu Gly Pro Glu Ala Arg Asn Asn Glu Leu Glu Phe Thr Lys Lys
130 135 140

Ile Leu Ser Val Asp Ala Lys His Tyr His Ala Trp Ser His Arg Gln
145 150 155 160

Trp Ala Leu Gln Thr Leu Gly Gly Trp Glu Asp Glu Leu Asn Tyr Cys
165 170 175

Thr Glu Leu Leu Lys Glu Asp Ile Phe Asn Asn Ser Ala Trp Asn Gln
180 185 190

Arg Tyr Phe Val Ile Thr Arg Ser Pro Phe Leu Gly Gly Leu Lys Ala
195 200 205

Met Arg Glu Ser Glu Val Leu Tyr Thr Ile Glu Ala Ile Ile Ala Tyr
210 215 220

Pro Glu Asn Glu Ser Ser Trp Arg Tyr Leu Arg Gly Leu Tyr Lys Gly
225 230 235 240

Glu Thr Thr Ser Trp Val Asn Asp Pro Gln Val Ser Ser Val Cys Leu
245 250 255

Lys Ile Leu Arg Thr Lys Ser Asn Tyr Val Phe Ala Leu Ser Thr Ile
260 265 270

Leu Asp Leu Ile Cys Phe Gly Tyr Gln Pro Asn Glu Asp Ile Arg Asp
275 280 285

Ala Ile Asp Ala Leu Lys Thr Ala Asp Met Asp Lys Gln Asp Leu Asp
290 295 300

Asp Asp Glu Lys Gly Glu Gln Gln Asn Leu Asn Ile Ala Arg Asn Ile
305 310 315 320

Cys Ser Ile Leu Lys Gln Val Asp Pro Ile Arg Thr Asn Tyr Trp Ile
325 330 335

Trp Arg Lys Ser Arg Leu Pro Leu Ser Ala
340 345

<210> SEQ ID NO 71
<211> LENGTH: 358
<212> TYPE: PRT
<213> ORGANISM: Glycine max

<400> SEQUENCE: 71

Met Glu Ser Gly Ser Ser Glu Gly Glu Glu Val Gln Gln Arg Val Pro
1 5 10 15

-continued

```
Leu Arg Glu Arg Val Glu Trp Ser Asp Val Thr Pro Val Pro Gln Asn
            20                  25                  30

Asp Gly Pro Asn Pro Val Val Pro Ile Gln Tyr Thr Glu Glu Phe Ser
        35                  40                  45

Glu Val Met Asp Tyr Phe Arg Ala Val Tyr Leu Thr Asp Glu Arg Ser
    50                  55                  60

Pro Arg Ala Leu Ala Leu Thr Ala Glu Ala Val Gln Phe Asn Ser Gly
65                  70                  75                  80

Asn Tyr Thr Val Trp His Phe Arg Arg Leu Leu Leu Glu Ser Leu Lys
                85                  90                  95

Val Asp Leu Asn Asp Glu Leu Glu Phe Val Glu Arg Met Ala Ala Gly
            100                 105                 110

Asn Ser Lys Asn Tyr Gln Met Trp Cys Asp Ala Leu Leu Cys Ser Phe
        115                 120                 125

Phe His Thr Leu His His Arg Arg Trp Val Ala Glu Lys Leu Gly Pro
    130                 135                 140

Glu Ala Arg Asn Asn Glu Leu Glu Phe Thr Lys Lys Ile Leu Ser Val
145                 150                 155                 160

Asp Ala Lys His Tyr His Ala Trp Ser His Arg Gln Trp Ala Leu Gln
                165                 170                 175

Thr Leu Gly Gly Trp Glu Asp Glu Leu Asn Tyr Cys Thr Glu Leu Leu
            180                 185                 190

Lys Glu Asp Ile Phe Asn Asn Ser Ala Trp Asn Gln Arg Tyr Phe Val
        195                 200                 205

Ile Thr Arg Ser Pro Phe Leu Gly Gly Leu Lys Ala Met Arg Glu Ser
    210                 215                 220

Glu Val Leu Tyr Thr Ile Glu Ala Ile Ile Ala Tyr Pro Glu Asn Glu
225                 230                 235                 240

Ser Ser Trp Arg Tyr Leu Arg Gly Leu Tyr Lys Gly Glu Thr Thr Ser
                245                 250                 255

Trp Val Asn Asp Pro Gln Val Ser Ser Val Cys Leu Lys Ile Leu Arg
            260                 265                 270

Thr Lys Ser Asn Tyr Val Phe Ala Leu Ser Thr Ile Leu Asp Leu Ile
        275                 280                 285

Cys Phe Gly Tyr Gln Pro Asn Glu Asp Ile Arg Asp Ala Ile Asp Ala
    290                 295                 300

Leu Lys Thr Ala Asp Met Asp Lys Gln Asp Leu Asp Asp Asp Glu Lys
305                 310                 315                 320

Gly Glu Gln Gln Asn Leu Asn Ile Ala Arg Asn Ile Cys Ser Ile Leu
                325                 330                 335

Lys Gln Val Asp Pro Ile Arg Thr Asn Tyr Trp Ile Trp Arg Lys Ser
            340                 345                 350

Arg Leu Pro Leu Ser Ala
        355


<210> SEQ ID NO 72
<211> LENGTH: 309
<212> TYPE: PRT
<213> ORGANISM: Triticum sp.

<400> SEQUENCE: 72

Asp Val Ala Pro Leu Pro Gln Ala Asp Gly Pro Cys Pro Val Val Ser
 1               5                  10                  15

Ile Ala Tyr Arg Gly Asp Phe Arg Glu Val Met Asp Tyr Phe Arg Ala
            20                  25                  30
```

-continued

```
Leu Tyr Ala Ala Gly Glu Arg Ser Pro Arg Ala Leu Arg Leu Thr Ala
        35                  40                  45

Asp Ala Ile His Leu Asn Pro Gly Asn Tyr Thr Val Trp His Phe Arg
    50                  55                  60

Arg Val Val Leu Gly Ala Leu Asp Ala Asp Leu Leu Leu Glu Met His
65                  70                  75                  80

Phe Val Asp Gln Ile Ala Glu Ser Asn Pro Leu Asn Tyr Gln Val Trp
                85                  90                  95

His His Lys Arg Trp Leu Ala Glu Lys Ile Gly Pro Asp Ala Ala Asn
            100                 105                 110

Ser Glu His Asp Phe Thr Arg Lys Ile Leu Ala Met Asp Ala Lys Asn
        115                 120                 125

Tyr His Ala Trp Ser His Arg Gln Trp Val Leu Gln Ala Leu Gly Gly
    130                 135                 140

Trp Glu Ser Glu Leu Gln Tyr Cys Asn Gln Leu Leu Glu Glu Asp Val
145                 150                 155                 160

Phe Asn Asn Ser Ala Trp Asn Gln Arg Tyr Leu Val Val Thr Arg Ser
                165                 170                 175

Pro Ile Leu Gly Gly Leu Ala Ala Met Arg Asp Ser Glu Val Asp Tyr
            180                 185                 190

Thr Val Glu Ala Ile Met Val Asn Pro Gln Asn Glu Ser Pro Trp Arg
        195                 200                 205

Tyr Leu Arg Gly Leu Tyr Lys Asp Asp Asn Asn Leu Leu Val Ala Asp
    210                 215                 220

Asn Arg Ile Ser Asp Ala Cys Leu Lys Val Leu Asn Lys Asp Trp Thr
225                 230                 235                 240

Cys Val Phe Ala Leu Ser Phe Leu Leu Asp Leu Leu Arg Met Gly Leu
                245                 250                 255

Gln Pro Ser Asn Glu Leu Lys Gly Thr Ile Glu Ala Met Glu Asn Ser
            260                 265                 270

Asp Pro Glu Thr Gly His Ala Asp Ile Ala Val Ala Val Cys Ser Ile
        275                 280                 285

Leu Gln Lys Cys Asp Pro Leu Arg Ile Asn Tyr Trp Ser Trp Tyr Gln
    290                 295                 300

Thr Thr Leu Ser Ser
305
```

<210> SEQ ID NO 73
<211> LENGTH: 1290
<212> TYPE: DNA
<213> ORGANISM: Unknown Organism
<220> FEATURE:
<223> OTHER INFORMATION: Description of Unknown Organism: Protein similar to FT Beta subunit

<400> SEQUENCE: 73

```
atggagattc agcgagataa gcaattggat tatctgatga aaggcttaag gcagcttggt      60

ccgcagtttt cttccttaga tgctaatcga ccttggcttt gttactggat tcttcattca     120

atagctttgc ttggggagac tgtggatgat gaattagaaa gcaatgccat tgacttcctt     180

ggacgctgcc agggctctga aggtggatac ggtggtggtc ctggccaact tccacatctt     240

gcaactactt atgctgcagt gaatgcactt gttactttag gaggtgacaa agccctttct     300

tcaattaata gagaaaaaat gtcttgtttt ttaagacgga tgaaggatac aagtggaggt     360

ttcaggatgc atgatatggg agaaattgat gttcgtgcat gctacactgc aatttcggtt     420
```

-continued

```
gcaagcatcc taaatattat ggatgatgaa ctcacccagg gcctaggaga ttacatcttg    480

agttgccaaa cttatgaagg tggcattgga ggggaacctg gctccgaagc tcacggtggg    540

tatacctact gtggtttggc tgctatgatt ttaatcaatg aggtcgaccg tttgaatttg    600

gattcattaa tgaattgggc tgtacatcga caaggagtag aaatgggatt tcaaggtagg    660

acgaacaaat tggtcgatgg ttgctacaca ttttggcagg cagccccttg tgttctacta    720

caaagattat attcaaccaa tgatcatgac gttcatggat catcacatat atcagaaggg    780

acaaatgaag aacatcatgc tcatgatgaa gatgaccttg aagacagtga tgatgatgat    840

gattctgatg aggacaacga tgaagattca gtgaatggtc acagaatcca tcatacatcc    900

acctacatta acaggagaat gcaactggtt tttgatagcc tcggcttgca gagatatgta    960

ctcttgtgct ctaagatccc tgacggtgga ttcagagaca agccgaggaa accccgtgac   1020

ttctaccaca catgttactg cctgagcggc ttgtctgtgg ctcagcacgc ttggttaaaa   1080

gacgaggaca ctcctccttt gactcgcgac attatgggtg gctactcgaa tctccttgaa   1140

cctgttcaac ttcttcacaa cattgtcatg gatcagtata atgaagctat cgagttcttc   1200

tttaaagcag catgacccgt tgttgctaat gtatgggaaa ccccaaacat aagagtttcc   1260

gtagtgttgt aacttgtaag atttcaaaag                                    1290
```

<210> SEQ ID NO 74
<211> LENGTH: 1627
<212> TYPE: DNA
<213> ORGANISM: Arabidopsis thaliana

<400> SEQUENCE: 74

```
atgccagtag taacccgctt gattcgtttg aagtgtgtag ggctcagact tgaccggagt     60

ggactcaatc ggcgaatctg tcacggagga cacggggaat caacgcggcg gagagtgatg    120

gaagagcttt caagcctaac cgtgagtcag cgcgagcaat ttctggtgga gaacgatgtg    180

ttcgggatct ataattactt cgacgccagc gacgtttcta ctcaaaaata catgatggag    240

attcagcgag ataagcaatt ggattatctg atgaaaggct taaggcagct tggtccgcag    300

ttttcttcct tagatgctaa tcgaccttgg ctttgttact ggattcttca ttcaatagct    360

ttgcttgggg agactgtgga tgatgaatta gaaagcaatg ccattgactt ccttggacgc    420

tgccagggct ctgaaggtgg atacggtggt ggtcctggcc aacttccaca tcttgcaact    480

acttatgctg cagtgaatgc acttgttact ttaggaggtg acaaagccct ttcttcaatt    540

aatagagaaa aaatgtcttg ttttttaaga cggatgaagg atacaagtgg aggtttcagg    600

atgcatgata tgggagaaat ggatgttcgt gcatgctaca ctgcaatttc ggttgcaagc    660

atcctaaata ttatggatga tgaactcacc cagggcctag gagattacat cttgagttgc    720

caaacttatg aaggtggcat tggaggggaa cctggctccg aagctcacgg tgggtatacc    780

tactgtggtt tggctgctat gattttaatc aatgaggtcg accgtttgaa tttggattca    840

ttaatgaatt gggctgtaca tcgacaagga gtagaaatgg gatttcaagg taggacgaac    900

aaattggtcg atggttgcta cacattttgg caggcagccc cttgtgttct actacaaaga    960

ttatattcaa ccaatgatca tgacgttcat ggatcatcac atatatcaga agggacaaat   1020

gaagaacatc atgctcatga tgaagatgac cttgaagaca gtgatgatga tgatgattct   1080

gatgaggaca acgatgaaga ttcagtgaat ggtcacagaa tccatcatac atccacctac   1140

attaacagga gaatgcaact ggtttttgat agcctcggct tgcagagata tgtactcttg   1200
```

-continued

```
tgctctaaga tccctgacgg tggattcaga gacaagccga ggaaaccccg tgacttctac   1260

cacacatgtt actgcctgag cggcttgtct gtggctcagc acgcttggtt aaaagacgag   1320

gacactcctc ctttgactcg cgacattatg ggtggctact cgaatctcct tgaacctgtt   1380

caacttcttc acaacattgt catggatcag tataatgaag ctatcgagtt cttctttaaa   1440

gcagcatgac ccgttgttgc taatgtatgg gaaactccaa acataagagt tttcgtagtg   1500

ttgtaacttg taagatttca aaagaagttt cactaattta accttaaaac ctgttacttt   1560

tttattacgt atataccatt tatcatatct ttggtttacg acttaaagaa tttgatgatt   1620

gttgaaa                                                             1627
```

<210> SEQ ID NO 75
<211> LENGTH: 1135
<212> TYPE: DNA
<213> ORGANISM: Glycine max

<400> SEQUENCE: 75

```
gccaccattc ctcgcaacgc ccaaaccctc atgttggagc ttcaacgcga taatcacatg     60

cagtatgtct ccaaaggcct tcgccatctc agttccgcat tttccgtttt ggacgctaat    120

cgaccctggc tctgctactg gatcttccac tccattgctt tgtcgggaga atccgtcgat    180

gatgaactcg aagataacgc tatcgatttt cttaaccgtt gccaggatcc gaatggtgga    240

tatgccgggg gaccaggcca gatgcctcat attgccacaa cttatgctgc tgttaattca    300

cttattactt tgggtggtga gaaatccctg gcatcaatta atagagataa actgtatggg    360

tttctgcggc ggatgaagca accaaatggt ggattcagga tgcatgatga aggtgaaatt    420

gatgttcgag cttgctacac tgccatttct gttgcaagtg ttttgaacat tttggatgat    480

gagctgatcc agaatgttgg agactacatt ataagctgtc aaacatatga gggtggcatt    540

gctggtgagc ctggttctga ggctcatggt gggtacacct tttgtggatt agctacaatg    600

attctgattg gtgaggttaa tcacttggat ctgcctcgat tagttgactg ggtggtattc    660

cgacaaggta aggaatgtgg attccagggg agaacaaata aactggtgga tggatgctat    720

tccttttggc agggaggtgc tgttgctcta ttgcaaagat tatcttctat tatcaacaaa    780

cagatggaag agacatcaca gatttttgcg gtatcttatg tatctgaagc aaaagaaagt    840

ttggatggaa cctctagtca tgcaacatgc cgtggtgagc atgaaggcac cagtgaatcc    900

agttcatctg attttaaaaa tattgcctat aaatttatta atgagtggag agcacaagaa    960

ccactttttc acagtattgc tttacagcaa tatattctct tatgtgcaca ggagcaagag   1020

ggtggactga gagacaaacc gggtaaacgt agagatcatt atcacacatg ttactgttta   1080

agtggactct cattgtgcca gtatagttgg tcaaagcacc cagattctcc accac        1135
```

<210> SEQ ID NO 76
<211> LENGTH: 1245
<212> TYPE: DNA
<213> ORGANISM: Zea mays

<400> SEQUENCE: 76

```
ggcggatccc gacctaccga ggctcacggt gacgcaggtg gagcagatga aggtggaggc     60

cagggttggc gacatctacc gctccctctt cggggccgcg cccaacacga aatccatcat    120

gctagagctg tggcgtgatc agcatatcga gtatctgacg cctgggctga ggcatatggg    180

accagccttt catgttctag atgccaatcg ccccttggcta tgctactgga tggttcatcc    240

acttgctttg ctggatgaag cacttgatga tgatcttgag aatgatatca tagacttctt    300
```

-continued

```
agctcgatgt caggataaag atggtggata tagtggtgga cctggacagt tgcctcacct    360

agctacgact tatgctgctg taaatacact tgtgacaata gggagccaaa gagcattgtc    420

atcaatcaat aggggcaacc tgtacaattt tatgctgcag atgaaagatg tatcaggtgc    480

tttcagaatg catgatggtg gcgaaattga tgtccgtgct tcctacaccg ctatatcggt    540

tgccagcctt gtgaatattc ttgattttaa actggcaaaa ggtgtaggcg actacatagc    600

aagatgtcaa acttatgaag gtggtattgc tggggagcct tatgctgaag cacatggtgg    660

gtatacattc tgtggattgg ctgctttgat cctgcttaat gaggcagaga aagttgactt    720

gcctagtttg attggctggg tggcttttcg tcaaggagtg gaatgcggat ttcaaggacg    780

aactaataaa ttggttgatg gttgctactc cttttggcag ggagctgcca ttgctttcac    840

acaaaagtta attacgattg ttgataagca attgaagtcc tcgtattcct gcaaaaggcc    900

atcaggagag gatgcctgca gcaccagttc atatgggtgc accgcgaaaa agtcttcctc    960

tgctgtggac tatgcgaagt ttggatttga ttttatacaa cagagcaacc aaattggccc   1020

actcttccat aacattgccc tgcaacaata catcctactt tgttctcagg tactagaggg   1080

aggcttgagg gataagcctg gaaagaacag agatcactac cattcatgct actgcctcag   1140

tggcctcgca gttagccagt acagtgccat gactgatact ggttcgtgcc cattacctca   1200

gcatgtgctt ggaccgtact ctaatttgct ggagccaatc catcc                   1245
```

```
<210> SEQ ID NO 77
<211> LENGTH: 1648
<212> TYPE: DNA
<213> ORGANISM: Pisum sativum

<400> SEQUENCE: 77

cggacccccc cgtccacaat cgtgatgatg acgtctccgc gagcatttca acaaccagtt     60

actcaaacca ccgcggagta acacatggaa gcttcaaccg cggcggagac accaactccg    120

acggtgagtc agagagatca atggatagta gaatcacagg tctttcatat ttatcaactc    180

ttcgccaata ttcctcctaa cgcccaatct atcattcgac cttggctgtg ttactggatt    240

attcattcaa ttgctttgtt gggagaatct attgatgatg atctcgaaga taacactgtc    300

gattttctta accgttgcca ggatccaaat ggtggatatg ctgggggacc tggtcagatg    360

cctcatcttg ccacaactta tgctgcagtc aatactctta ttactctggg tggtgagaaa    420

tctttggcat ctattaatag aaataagttg tacgggttta tgcggcggat gaaacagcca    480

aacggcggat tcaggatgca tgacgaggga gaaattgacg ttcgagcttg ctacactgcc    540

atctctgtgg caagtgttct gaacattttg gatgatgagc tgatcaagaa tgttggagac    600

ttcattttaa gctgtcaaac atatgaggga ggccttgctg gtgagcctgg gtctgaggct    660

catggcgggt ataccttttg tgggttagct gcaatgattc tgattggtga ggttaatcgc    720

ttggatctgc ctcgtttact tgattgggtt gtgtttcggc aaggtaaaga gtgtggattt    780

caggggagaa cgaataaatt ggtagatgga tgctactcgt tttggcaggg aggtgctgtt    840

gccctattgc aaagattaca ttctattatc gacgaacaaa tggcagaggc atcacagttt    900

gttacagtat ctgatgcacc tgaagaaaag gaatgtttgg acggaacctc aagtcatgca    960

acttcccata ttaggcatga aggcatgaat gaatcctgct catctgacgt taaaaatatt   1020

ggttataact ttattagtga gtggagacaa agtgaaccac tttttcacag cattgcctta   1080

cagcaatata ttcttttatg ttcacaggag caagatggtg ggctcaggga caaaccgggt   1140
```

-continued

```
aaacgcaggg atcattatca ttcatgttac tgtttaagtg ggttgtcact gtgccagtat   1200

agttggtcga agcgcccaga ttctccaccg ctgcctaagg tagtaatggg cccatactcc   1260

aatctcttag aacccatcca tcctctcttt aatgttgttt tggatcgata tcgtgaagct   1320

catgaattct tttctcagtt gtgacggatg acaaggtttt agctaccaat agctcgatca   1380

ttagaatgta aaatgtaaac taaaatatga aatatgaaat accaaaaaga tattattgga   1440

tgaaattcac gtggatctaa tacaactgcg tggttttcat tcctgatttg attttgattt   1500

acatgagtta aaacgttaaa cccttcttat tcatacattt gttaagagct taaggcttaa   1560

tggttaagcc aatgatataa atatttatgc agaaagctgt tgcttatcac caacggtaat   1620

attaataagc aaacaagtat tctgtgat                                      1648
```

<210> SEQ ID NO 78
<211> LENGTH: 1832
<212> TYPE: DNA
<213> ORGANISM: Lycopersicon esculentum

<400> SEQUENCE: 78

```
gtaaacgagc gttgatttgt cgctgacgaa atttacagtc aagagtagta accggttgta     60

gtgaaaaaat ggagtcgagg aaagtgacga agacgctgga agatcaatgg gtggtggagc    120

gtcgagtccg agagatatac gattatttct acagcatttc ccccaactct ccgtccgacc    180

tcatagagat cgaacgtgac aaacacttcg gttatctaag ccaaggtctc agaaaacttg    240

gtccgtcgtt ttccgttttg gatgccagtc gaccatggct ttgctactgg acacttcatt    300

caatcgcttt gttgggagaa tctattggtg gcaaactgga aaatgatgca attgactttc    360

tgacccgttg ccaggataaa gatggtggct atggaggtgg acctggtcag atgcctcatc    420

ttgcaactac ttatgctgca gtcaattcac taataacttt gggcaaacct gaagctctgt    480

catcaattaa tagagaaaag ttgtacacat ttttgctgcg aatgaaagac gcaagtggtg    540

gattcaggat gcacgatggt ggagaagtag atgttcgtgc ctgttatact gccatttctg    600

ttgcaaatat attaaacatt gtggatgacg agctgattca tggtgttgga aattacatcc    660

taagttgtca gacttatgaa ggtggaattg ctggcgaacc aggttctgaa gctcatggtg    720

ggtatacttt ctgtgggttg gctgcaatga ttctgatcaa cgaagtagat cgattggact    780

tgccaggttt aattgattgg gtggtattta gacaaggggt cgaaggtgga tttcaaggca    840

ggacaaataa attagtcgat ggctgctatt cctttggca gggcgcggta gtgtttctta    900

tacaaagact aaatttgata gtccatgaac aactagggct gtcaaatgac ctcagtacag    960

aaagtgctga tgattcttca gagtcagagt tatctgatga agaagagcat ttggaaggga   1020

tatcctctca tgttcaggat actttccctc ttggacaagc aggtgcttgt caagaaaatg   1080

cttctcatag cccaaaaata gcagatactg gatatgagtt tatcaaccga cccatagcta   1140

tgaggcctct ctttgacagc atgtatctgc agcaatatgt tcttctttgc tctcagattg   1200

aagttggtgg tttcagagac aaacctggga agggtagaga ctactaccat acctgttact   1260

gtttaagtgg tctttcaatt gctcagtata gctggaccga cgaagctgat tctacaccat   1320

tacccaggga tgtatttggt ccttattcca aatgtctgtt ggaacaggtt cacccactct   1380

tcaacgtagt gttggatcgg tattatgaag ctcgcgaata ctctcaggct tgtgagactg   1440

tttcaccact ttcattagca ccaacttttt cagaaactta gttgcaatcc agaagttaaa   1500

agtgtcattg ggttcaaaag agttgtgatc gtttatgtac atatccttgc atttgtatac   1560

gtgatacaag ttgagagaat aacgggtact ttctgaactt gctgaactag cacgtaaatt   1620
```

-continued

```
cgtctctggt ttagtgaggt ctgtaaacat caatgtgaaa ttgcgagata tgcatgtaat   1680

agtggctaag atttacaaat ctggataccg gttattagtg atcagaaatt tcattcaatt   1740

tcccaaacgg tcacctaagt ttaggatatt gctttaaaat attatttatt tttcatttaa   1800

gaatcaaaaa aaaaaaaaaa aaaaaaaaaa aa                                 1832
```

<210> SEQ ID NO 79
<211> LENGTH: 1449
<212> TYPE: DNA
<213> ORGANISM: Nicotiana tabacum
<220> FEATURE:
<221> NAME/KEY: misc_feature
<222> LOCATION: (87)...(87)
<223> OTHER INFORMATION: Wherein "n" is A, T, C or G
<220> FEATURE:
<221> NAME/KEY: misc_difference
<222> LOCATION: (1038)...(1038)
<223> OTHER INFORMATION: Wherein "n" is A, T, C or G

<400> SEQUENCE: 79

```
ggcacgagcg gcacgaggac actggaagat caatggatgg tggagcgtca agttcgggag     60

atatacaatt ttttctacag cattccnccc aattcccact tagagacttc aacagaaaag    120

cacttcgatt atctcactcg aggtctcaga aaacttggtc cgtcgttctc cgtcttggat    180

gctaatcgac catggctttg ctactggata cttcattcaa tcgctttgtt gggagaatct    240

attgatgccc aactggaaaa tgatgcaatt gactttctga gccgttgcca ggatgaagat    300

ggtggctatg gtggtggacc tggtcagatg cctcatcttg caactactta tgctgcagtc    360

aattcactca taactttggg cagccctaaa gctctgtcat caatcaatag agaaaaattg    420

tatacatttt ggctgcaaat gaaagacaca agtggtggct tcaggatgca tgatggtgga    480

gaagtagatg ttcgtgcctg ttatactgcc atttctgttg caagtatatt gcaaattgtg    540

gatgatgaac tgattaatga tgttgggaat tacatcctaa gttgtcagac ttatgaaggt    600

ggaattgctg gcgaaccagg ttctgaagct catggtgggt ataccttctg tgggttggct    660

gcaatgattc tgattaacga agcgaatcga ttggacttgc caagattaat tgattgggtg    720

gtatttagac aaggagtcga aggtggattt caaggcagga caaataaatt agtcgatggc    780

tgctattcct tttggcaggc cgcggtagct tttcttatac aaagattaaa atcgacagtc    840

catgaacaac tagggctgtc aaatgaactc agtacagaaa gtgctgatga ttcttcggag    900

tcagagttat ctgatgaaga gcatttgcaa gggacatcat ctcatgttca gaagacttgc    960

cctcttggac aagaaggaca ggaaaatgct tcagatccca caaagatagc agatactggt   1020

tatgattttg tcaatcgnac gatagctatg cgacctgtgt ttgacagctt ttatctgcag   1080

caatacgttc ttctctgctc ccagatagat ggaggtttca gagacaaacc tgggaagggt   1140

agagaccact accatacttg ctactgttta agtggtcttt caattgctca atatagctgg   1200

accaacgaag ctgatgcgcc accattaccc agggatgtat ttggtcctta ttctcaaaat   1260

cttttggaac agattcaccc actttacaac gtagtgttgg atcggtatta tgaagctcgt   1320

agcttcttct catgcttgtg ataatatttt acgcgatagc tgtagctgga atgttacctc   1380

tagttgttca gaatcagaga ctaatctatt attttgaggg attggattca aaaaaaaaaa   1440

aaaaaaaaa                                                           1449
```

<210> SEQ ID NO 80
<211> LENGTH: 404
<212> TYPE: PRT

-continued

<213> ORGANISM: Unknown
<220> FEATURE:
<223> OTHER INFORMATION: Description of Unknown: Protein similar to FT Beta Subunit

<400> SEQUENCE: 80

```
Met Glu Ile Gln Arg Asp Lys Gln Leu Asp Tyr Leu Met Lys Gly Leu
 1               5                  10                  15

Arg Gln Leu Gly Pro Gln Phe Ser Ser Leu Asp Ala Asn Arg Pro Trp
            20                  25                  30

Leu Cys Tyr Trp Ile Leu His Ser Ile Ala Leu Leu Gly Glu Thr Val
        35                  40                  45

Asp Asp Glu Leu Glu Ser Asn Ala Ile Asp Phe Leu Gly Arg Cys Gln
    50                  55                  60

Gly Ser Glu Gly Gly Tyr Gly Gly Gly Pro Gly Gln Leu Pro His Leu
65                  70                  75                  80

Ala Thr Thr Tyr Ala Ala Val Asn Ala Leu Val Thr Leu Gly Gly Asp
                85                  90                  95

Lys Ala Leu Ser Ser Ile Asn Arg Glu Lys Met Ser Cys Phe Leu Arg
            100                 105                 110

Arg Met Lys Asp Thr Ser Gly Gly Phe Arg Met His Asp Met Gly Glu
        115                 120                 125

Ile Asp Val Arg Ala Cys Tyr Thr Ala Ile Ser Val Ala Ser Ile Leu
    130                 135                 140

Asn Ile Met Asp Asp Glu Leu Thr Gln Gly Leu Gly Asp Tyr Ile Leu
145                 150                 155                 160

Ser Cys Gln Thr Tyr Glu Gly Gly Ile Gly Gly Glu Pro Gly Ser Glu
                165                 170                 175

Ala His Gly Gly Tyr Thr Tyr Cys Gly Leu Ala Ala Met Ile Leu Ile
            180                 185                 190

Asn Glu Val Asp Arg Leu Asn Leu Asp Ser Leu Met Asn Trp Ala Val
        195                 200                 205

His Arg Gln Gly Val Glu Met Gly Phe Gln Gly Arg Thr Asn Lys Leu
    210                 215                 220

Val Asp Gly Cys Tyr Thr Phe Trp Gln Ala Ala Pro Cys Val Leu Leu
225                 230                 235                 240

Gln Arg Leu Tyr Ser Thr Asn Asp His Asp Val His Gly Ser Ser His
                245                 250                 255

Ile Ser Glu Gly Thr Asn Glu Glu His His Ala His Asp Glu Asp Asp
            260                 265                 270

Leu Glu Asp Ser Asp Asp Asp Asp Asp Ser Asp Glu Asp Asn Asp Glu
        275                 280                 285

Asp Ser Val Asn Gly His Arg Ile His His Thr Ser Thr Tyr Ile Asn
    290                 295                 300

Arg Arg Met Gln Leu Val Phe Asp Ser Leu Gly Leu Gln Arg Tyr Val
305                 310                 315                 320

Leu Leu Cys Ser Lys Ile Pro Asp Gly Gly Phe Arg Asp Lys Pro Arg
                325                 330                 335

Lys Pro Arg Asp Phe Tyr His Thr Cys Tyr Cys Leu Ser Gly Leu Ser
            340                 345                 350

Val Ala Gln His Ala Trp Leu Lys Asp Glu Asp Thr Pro Pro Leu Thr
        355                 360                 365

Arg Asp Ile Met Gly Gly Tyr Ser Asn Leu Leu Glu Pro Val Gln Leu
    370                 375                 380
```

-continued

```
Leu His Asn Ile Val Met Asp Gln Tyr Asn Glu Ala Ile Glu Phe Phe
385                 390                 395                 400

Phe Lys Ala Ala


<210> SEQ ID NO 81
<211> LENGTH: 482
<212> TYPE: PRT
<213> ORGANISM: Arabidopsis thaliana

<400> SEQUENCE: 81

Met Pro Val Val Thr Arg Leu Ile Arg Leu Lys Cys Val Gly Leu Arg
 1               5                  10                  15

Leu Asp Arg Ser Gly Leu Asn Arg Arg Ile Cys His Gly Gly His Gly
            20                  25                  30

Glu Ser Thr Arg Arg Arg Val Met Glu Glu Leu Ser Ser Leu Thr Val
        35                  40                  45

Ser Gln Arg Glu Gln Phe Leu Val Glu Asn Asp Val Phe Gly Ile Tyr
    50                  55                  60

Asn Tyr Phe Asp Ala Ser Asp Val Ser Thr Gln Lys Tyr Met Met Glu
65                  70                  75                  80

Ile Gln Arg Asp Lys Gln Leu Asp Tyr Leu Met Lys Gly Leu Arg Gln
                85                  90                  95

Leu Gly Pro Gln Phe Ser Ser Leu Asp Ala Asn Arg Pro Trp Leu Cys
            100                 105                 110

Tyr Trp Ile Leu His Ser Ile Ala Leu Leu Gly Glu Thr Val Asp Asp
        115                 120                 125

Glu Leu Glu Ser Asn Ala Ile Asp Phe Leu Gly Arg Cys Gln Gly Ser
    130                 135                 140

Glu Gly Gly Tyr Gly Gly Gly Pro Gly Gln Leu Pro His Leu Ala Thr
145                 150                 155                 160

Thr Tyr Ala Ala Val Asn Ala Leu Val Thr Leu Gly Gly Asp Lys Ala
                165                 170                 175

Leu Ser Ser Ile Asn Arg Glu Lys Met Ser Cys Phe Leu Arg Arg Met
            180                 185                 190

Lys Asp Thr Ser Gly Gly Phe Arg Met His Asp Met Gly Glu Met Asp
        195                 200                 205

Val Arg Ala Cys Tyr Thr Ala Ile Ser Val Ala Ser Ile Leu Asn Ile
    210                 215                 220

Met Asp Asp Glu Leu Thr Gln Gly Leu Gly Asp Tyr Ile Leu Ser Cys
225                 230                 235                 240

Gln Thr Tyr Glu Gly Gly Ile Gly Gly Glu Pro Gly Ser Glu Ala His
                245                 250                 255

Gly Gly Tyr Thr Tyr Cys Gly Leu Ala Ala Met Ile Leu Ile Asn Glu
            260                 265                 270

Val Asp Arg Leu Asn Leu Asp Ser Leu Met Asn Trp Ala Val His Arg
        275                 280                 285

Gln Gly Val Glu Met Gly Phe Gln Gly Arg Thr Asn Lys Leu Val Asp
    290                 295                 300

Gly Cys Tyr Thr Phe Trp Gln Ala Ala Pro Cys Val Leu Leu Gln Arg
305                 310                 315                 320

Leu Tyr Ser Thr Asn Asp His Asp Val His Gly Ser Ser His Ile Ser
                325                 330                 335

Glu Gly Thr Asn Glu Glu His His Ala His Asp Glu Asp Asp Leu Glu
            340                 345                 350
```

-continued

```
Asp Ser Asp Asp Asp Asp Asp Ser Asp Glu Asp Asn Asp Glu Asp Ser
        355                 360                 365

Val Asn Gly His Arg Ile His His Thr Ser Thr Tyr Ile Asn Arg Arg
    370                 375                 380

Met Gln Leu Val Phe Asp Ser Leu Gly Leu Gln Arg Tyr Val Leu Leu
385                 390                 395                 400

Cys Ser Lys Ile Pro Asp Gly Gly Phe Arg Asp Lys Pro Arg Lys Pro
                405                 410                 415

Arg Asp Phe Tyr His Thr Cys Tyr Cys Leu Ser Gly Leu Ser Val Ala
            420                 425                 430

Gln His Ala Trp Leu Lys Asp Glu Asp Thr Pro Pro Leu Thr Arg Asp
        435                 440                 445

Ile Met Gly Gly Tyr Ser Asn Leu Leu Glu Pro Val Gln Leu Leu His
    450                 455                 460

Asn Ile Val Met Asp Gln Tyr Asn Glu Ala Ile Glu Phe Phe Phe Lys
465                 470                 475                 480

Ala Ala


<210> SEQ ID NO 82
<211> LENGTH: 378
<212> TYPE: PRT
<213> ORGANISM: Glycine max

<400> SEQUENCE: 82

Ala Thr Ile Pro Arg Asn Ala Gln Thr Leu Met Leu Glu Leu Gln Arg
 1               5                  10                  15

Asp Asn His Met Gln Tyr Val Ser Lys Gly Leu Arg His Leu Ser Ser
            20                  25                  30

Ala Phe Ser Val Leu Asp Ala Asn Arg Pro Trp Leu Cys Tyr Trp Ile
        35                  40                  45

Phe His Ser Ile Ala Leu Ser Gly Glu Ser Val Asp Asp Glu Leu Glu
    50                  55                  60

Asp Asn Ala Ile Asp Phe Leu Asn Arg Cys Gln Asp Pro Asn Gly Gly
65                  70                  75                  80

Tyr Ala Gly Gly Pro Gly Gln Met Pro His Ile Ala Thr Thr Tyr Ala
                85                  90                  95

Ala Val Asn Ser Leu Ile Thr Leu Gly Gly Glu Lys Ser Leu Ala Ser
            100                 105                 110

Ile Asn Arg Asp Lys Leu Tyr Gly Phe Leu Arg Arg Met Lys Gln Pro
        115                 120                 125

Asn Gly Gly Phe Arg Met His Asp Glu Gly Glu Ile Asp Val Arg Ala
    130                 135                 140

Cys Tyr Thr Ala Ile Ser Val Ala Ser Val Leu Asn Ile Leu Asp Asp
145                 150                 155                 160

Glu Leu Ile Gln Asn Val Gly Asp Tyr Ile Ile Ser Cys Gln Thr Tyr
                165                 170                 175

Glu Gly Gly Ile Ala Gly Glu Pro Gly Ser Glu Ala His Gly Gly Tyr
            180                 185                 190

Thr Phe Cys Gly Leu Ala Thr Met Ile Leu Ile Gly Glu Val Asn His
        195                 200                 205

Leu Asp Leu Pro Arg Leu Val Asp Trp Val Val Phe Arg Gln Gly Lys
    210                 215                 220

Glu Cys Gly Phe Gln Gly Arg Thr Asn Lys Leu Val Asp Gly Cys Tyr
225                 230                 235                 240
```

-continued

```
Ser Phe Trp Gln Gly Gly Ala Val Ala Leu Leu Gln Arg Leu Ser Ser
                245                 250                 255

Ile Ile Asn Lys Gln Met Glu Glu Thr Ser Gln Ile Phe Ala Val Ser
            260                 265                 270

Tyr Val Ser Glu Ala Lys Glu Ser Leu Asp Gly Thr Ser Ser His Ala
        275                 280                 285

Thr Cys Arg Gly Glu His Glu Gly Thr Ser Glu Ser Ser Ser Ser Asp
    290                 295                 300

Phe Lys Asn Ile Ala Tyr Lys Phe Ile Asn Glu Trp Arg Ala Gln Glu
305                 310                 315                 320

Pro Leu Phe His Ser Ile Ala Leu Gln Gln Tyr Ile Leu Leu Cys Ala
                325                 330                 335

Gln Glu Gln Glu Gly Gly Leu Arg Asp Lys Pro Gly Lys Arg Arg Asp
            340                 345                 350

His Tyr His Thr Cys Tyr Cys Leu Ser Gly Leu Ser Leu Cys Gln Tyr
        355                 360                 365

Ser Trp Ser Lys His Pro Asp Ser Pro Pro
    370                 375


<210> SEQ ID NO 83
<211> LENGTH: 414
<212> TYPE: PRT
<213> ORGANISM: Zea mays

<400> SEQUENCE: 83

Ala Asp Pro Asp Leu Pro Arg Leu Thr Val Thr Gln Val Glu Gln Met
 1               5                  10                  15

Lys Val Glu Ala Arg Val Gly Asp Ile Tyr Arg Ser Leu Phe Gly Ala
            20                  25                  30

Ala Pro Asn Thr Lys Ser Ile Met Leu Glu Leu Trp Arg Asp Gln His
        35                  40                  45

Ile Glu Tyr Leu Thr Pro Gly Leu Arg His Met Gly Pro Ala Phe His
    50                  55                  60

Val Leu Asp Ala Asn Arg Pro Trp Leu Cys Tyr Trp Met Val His Pro
65                  70                  75                  80

Leu Ala Leu Leu Asp Glu Ala Leu Asp Asp Asp Leu Glu Asn Asp Ile
                85                  90                  95

Ile Asp Phe Leu Ala Arg Cys Gln Asp Lys Asp Gly Gly Tyr Ser Gly
            100                 105                 110

Gly Pro Gly Gln Leu Pro His Leu Ala Thr Thr Tyr Ala Ala Val Asn
        115                 120                 125

Thr Leu Val Thr Ile Gly Ser Gln Arg Ala Leu Ser Ser Ile Asn Arg
    130                 135                 140

Gly Asn Leu Tyr Asn Phe Met Leu Gln Met Lys Asp Val Ser Gly Ala
145                 150                 155                 160

Phe Arg Met His Asp Gly Gly Glu Ile Asp Val Arg Ala Ser Tyr Thr
                165                 170                 175

Ala Ile Ser Val Ala Ser Leu Val Asn Ile Leu Asp Phe Lys Leu Ala
            180                 185                 190

Lys Gly Val Gly Asp Tyr Ile Ala Arg Cys Gln Thr Tyr Glu Gly Gly
        195                 200                 205

Ile Ala Gly Glu Pro Tyr Ala Glu Ala His Gly Gly Tyr Thr Phe Cys
    210                 215                 220

Gly Leu Ala Ala Leu Ile Leu Leu Asn Glu Ala Glu Lys Val Asp Leu
225                 230                 235                 240
```

-continued

```
Pro Ser Leu Ile Gly Trp Val Ala Phe Arg Gln Gly Val Glu Cys Gly
                245                 250                 255

Phe Gln Gly Arg Thr Asn Lys Leu Val Asp Gly Cys Tyr Ser Phe Trp
            260                 265                 270

Gln Gly Ala Ala Ile Ala Phe Thr Gln Lys Leu Ile Thr Ile Val Asp
        275                 280                 285

Lys Gln Leu Lys Ser Ser Tyr Ser Cys Lys Arg Pro Ser Gly Glu Asp
    290                 295                 300

Ala Cys Ser Thr Ser Ser Tyr Gly Cys Thr Ala Lys Lys Ser Ser Ser
305                 310                 315                 320

Ala Val Asp Tyr Ala Lys Phe Gly Phe Asp Phe Ile Gln Gln Ser Asn
                325                 330                 335

Gln Ile Gly Pro Leu Phe His Asn Ile Ala Leu Gln Gln Tyr Ile Leu
            340                 345                 350

Leu Cys Ser Gln Val Leu Glu Gly Gly Leu Arg Asp Lys Pro Gly Lys
        355                 360                 365

Asn Arg Asp His Tyr His Ser Cys Tyr Cys Leu Ser Gly Leu Ala Val
    370                 375                 380

Ser Gln Tyr Ser Ala Met Thr Asp Thr Gly Ser Cys Pro Leu Pro Gln
385                 390                 395                 400

His Val Leu Gly Pro Tyr Ser Asn Leu Leu Glu Pro Ile His
                405                 410


<210> SEQ ID NO 84
<211> LENGTH: 420
<212> TYPE: PRT
<213> ORGANISM: Pisum sativum

<400> SEQUENCE: 84

Met Glu Ala Ser Thr Ala Ala Glu Thr Pro Thr Pro Thr Val Ser Gln
 1               5                  10                  15

Arg Asp Gln Trp Ile Val Glu Ser Gln Val Phe His Ile Tyr Gln Leu
            20                  25                  30

Phe Ala Asn Ile Pro Pro Asn Ala Gln Ser Ile Ile Arg Pro Trp Leu
        35                  40                  45

Cys Tyr Trp Ile Ile His Ser Ile Ala Leu Leu Gly Glu Ser Ile Asp
    50                  55                  60

Asp Asp Leu Glu Asp Asn Thr Val Asp Phe Leu Asn Arg Cys Gln Asp
65                  70                  75                  80

Pro Asn Gly Gly Tyr Ala Gly Gly Pro Gly Gln Met Pro His Leu Ala
                85                  90                  95

Thr Thr Tyr Ala Ala Val Asn Thr Leu Ile Thr Leu Gly Gly Glu Lys
            100                 105                 110

Ser Leu Ala Ser Ile Asn Arg Asn Lys Leu Tyr Gly Phe Met Arg Arg
        115                 120                 125

Met Lys Gln Pro Asn Gly Gly Phe Arg Met His Asp Glu Gly Glu Ile
    130                 135                 140

Asp Val Arg Ala Cys Tyr Thr Ala Ile Ser Val Ala Ser Val Leu Asn
145                 150                 155                 160

Ile Leu Asp Asp Glu Leu Ile Lys Asn Val Gly Asp Phe Ile Leu Ser
                165                 170                 175

Cys Gln Thr Tyr Glu Gly Gly Leu Ala Gly Glu Pro Gly Ser Glu Ala
            180                 185                 190

His Gly Gly Tyr Thr Phe Cys Gly Leu Ala Ala Met Ile Leu Ile Gly
```

-continued

```
        195                 200                 205

Glu Val Asn Arg Leu Asp Leu Pro Arg Leu Leu Asp Trp Val Val Phe
    210                 215                 220

Arg Gln Gly Lys Glu Cys Gly Phe Gln Gly Arg Thr Asn Lys Leu Val
225                 230                 235                 240

Asp Gly Cys Tyr Ser Phe Trp Gln Gly Gly Ala Val Ala Leu Leu Gln
                245                 250                 255

Arg Leu His Ser Ile Ile Asp Glu Gln Met Ala Glu Ala Ser Gln Phe
            260                 265                 270

Val Thr Val Ser Asp Ala Pro Glu Glu Lys Glu Cys Leu Asp Gly Thr
        275                 280                 285

Ser Ser His Ala Thr Ser His Ile Arg His Glu Gly Met Asn Glu Ser
    290                 295                 300

Cys Ser Ser Asp Val Lys Asn Ile Gly Tyr Asn Phe Ile Ser Glu Trp
305                 310                 315                 320

Arg Gln Ser Glu Pro Leu Phe His Ser Ile Ala Leu Gln Gln Tyr Ile
                325                 330                 335

Leu Leu Cys Ser Gln Glu Gln Asp Gly Gly Leu Arg Asp Lys Pro Gly
            340                 345                 350

Lys Arg Arg Asp His Tyr His Ser Cys Tyr Cys Leu Ser Gly Leu Ser
        355                 360                 365

Leu Cys Gln Tyr Ser Trp Ser Lys Arg Pro Asp Ser Pro Pro Leu Pro
    370                 375                 380

Lys Val Val Met Gly Pro Tyr Ser Ser Asn Leu Leu Glu Pro Ile His
385                 390                 395                 400

Pro Leu Phe Asn Val Val Leu Asp Arg Tyr Arg Glu Ala His Glu Phe
                405                 410                 415

Phe Ser Gln Leu
            420


<210> SEQ ID NO 85
<211> LENGTH: 470
<212> TYPE: PRT
<213> ORGANISM: Lycopersicon esculentum

<400> SEQUENCE: 85

Met Glu Ser Arg Lys Val Thr Lys Thr Leu Glu Asp Gln Trp Val Val
 1               5                  10                  15

Glu Arg Arg Val Arg Glu Ile Tyr Asp Tyr Phe Tyr Ser Ile Ser Pro
            20                  25                  30

Asn Ser Pro Ser Asp Leu Ile Glu Ile Glu Arg Asp Lys His Phe Gly
        35                  40                  45

Tyr Leu Ser Gln Gly Leu Arg Lys Leu Gly Pro Ser Phe Ser Val Leu
    50                  55                  60

Asp Ala Ser Arg Pro Trp Leu Cys Tyr Trp Thr Leu His Ser Ile Ala
65                  70                  75                  80

Leu Leu Gly Glu Ser Ile Gly Gly Lys Leu Glu Asn Asp Ala Ile Asp
                85                  90                  95

Phe Leu Thr Arg Cys Gln Asp Lys Asp Gly Gly Tyr Gly Gly Gly Pro
            100                 105                 110

Gly Gln Met Pro His Leu Ala Thr Thr Tyr Ala Ala Val Asn Ser Leu
        115                 120                 125

Ile Thr Leu Gly Lys Pro Glu Ala Leu Ser Ser Ile Asn Arg Glu Lys
    130                 135                 140
```

-continued

Leu Tyr Thr Phe Leu Leu Arg Met Lys Asp Ala Ser Gly Gly Phe Arg
145 150 155 160

Met His Asp Gly Gly Glu Val Asp Val Arg Ala Cys Tyr Thr Ala Ile
165 170 175

Ser Val Ala Asn Ile Leu Asn Ile Val Asp Asp Glu Leu Ile His Gly
180 185 190

Val Gly Asn Tyr Ile Leu Ser Cys Gln Thr Tyr Glu Gly Gly Ile Ala
195 200 205

Gly Glu Pro Gly Ser Glu Ala His Gly Gly Tyr Thr Phe Cys Gly Leu
210 215 220

Ala Ala Met Ile Leu Ile Asn Glu Val Asp Arg Leu Asp Leu Pro Gly
225 230 235 240

Leu Ile Asp Trp Val Val Phe Arg Gln Gly Val Glu Gly Gly Phe Gln
245 250 255

Gly Arg Thr Asn Lys Leu Val Asp Gly Cys Tyr Ser Phe Trp Gln Gly
260 265 270

Ala Val Val Phe Leu Ile Gln Arg Leu Asn Leu Ile Val His Glu Gln
275 280 285

Leu Gly Leu Ser Asn Asp Leu Ser Thr Glu Ser Ala Asp Asp Ser Ser
290 295 300

Glu Ser Glu Leu Ser Asp Glu Glu Glu His Leu Glu Gly Ile Ser Ser
305 310 315 320

His Val Gln Asp Thr Phe Pro Leu Gly Gln Ala Gly Ala Cys Gln Glu
325 330 335

Asn Ala Ser His Ser Pro Lys Ile Ala Asp Thr Gly Tyr Glu Phe Ile
340 345 350

Asn Arg Pro Ile Ala Met Arg Pro Leu Phe Asp Ser Met Tyr Leu Gln
355 360 365

Gln Tyr Val Leu Leu Cys Ser Gln Ile Glu Val Gly Gly Phe Arg Asp
370 375 380

Lys Pro Gly Lys Gly Arg Asp Tyr Tyr His Thr Cys Tyr Cys Leu Ser
385 390 395 400

Gly Leu Ser Ile Ala Gln Tyr Ser Trp Thr Asp Glu Ala Asp Ser Thr
405 410 415

Pro Leu Pro Arg Asp Val Phe Gly Pro Tyr Ser Lys Cys Leu Leu Glu
420 425 430

Gln Val His Pro Leu Phe Asn Val Val Leu Asp Arg Tyr Tyr Glu Ala
435 440 445

Arg Glu Tyr Ser Gln Ala Cys Glu Thr Val Ser Pro Leu Ser Leu Ala
450 455 460

Pro Thr Phe Ser Glu Thr
465 470

<210> SEQ ID NO 86
<211> LENGTH: 446
<212> TYPE: PRT
<213> ORGANISM: Nicotiana tabacum

<400> SEQUENCE: 86

Gly Thr Ser Gly Thr Arg Thr Leu Glu Asp Gln Trp Met Val Glu Arg
1 5 10 15

Gln Val Arg Glu Ile Tyr Asn Phe Phe Tyr Ser Ile Pro Pro Asn Ser
20 25 30

His Leu Glu Thr Ser Thr Glu Lys His Phe Asp Tyr Leu Thr Arg Gly
35 40 45

-continued

```
Leu Arg Lys Leu Gly Pro Ser Phe Ser Val Leu Asp Ala Asn Arg Pro
    50                  55                  60

Trp Leu Cys Tyr Trp Ile Leu His Ser Ile Ala Leu Leu Gly Glu Ser
65                  70                  75                  80

Ile Asp Ala Gln Leu Glu Asn Asp Ala Ile Asp Phe Leu Ser Arg Cys
                85                  90                  95

Gln Asp Glu Asp Gly Gly Tyr Gly Gly Gly Pro Gly Gln Met Pro His
            100                 105                 110

Leu Ala Thr Thr Tyr Ala Ala Val Asn Ser Leu Ile Thr Leu Gly Ser
        115                 120                 125

Pro Lys Ala Leu Ser Ser Ile Asn Arg Glu Lys Leu Tyr Thr Phe Trp
    130                 135                 140

Leu Gln Met Lys Asp Thr Ser Gly Gly Phe Arg Met His Asp Gly Gly
145                 150                 155                 160

Glu Val Asp Val Arg Ala Cys Tyr Thr Ala Ile Ser Val Ala Ser Ile
                165                 170                 175

Leu Gln Ile Val Asp Asp Glu Leu Ile Asn Asp Val Gly Asn Tyr Ile
            180                 185                 190

Leu Ser Cys Gln Thr Tyr Glu Gly Gly Ile Ala Gly Glu Pro Gly Ser
        195                 200                 205

Glu Ala His Gly Gly Tyr Thr Phe Cys Gly Leu Ala Ala Met Ile Leu
    210                 215                 220

Ile Asn Glu Ala Asn Arg Leu Asp Leu Pro Arg Leu Ile Asp Trp Val
225                 230                 235                 240

Val Phe Arg Gln Gly Val Glu Gly Gly Phe Gln Gly Arg Thr Asn Lys
                245                 250                 255

Leu Val Asp Gly Cys Tyr Ser Phe Trp Gln Ala Ala Val Ala Phe Leu
            260                 265                 270

Ile Gln Arg Leu Lys Ser Thr Val His Glu Gln Leu Gly Leu Ser Asn
        275                 280                 285

Glu Leu Ser Thr Glu Ser Ala Asp Asp Ser Ser Glu Ser Glu Leu Ser
    290                 295                 300

Asp Glu Glu His Leu Gln Gly Thr Ser Ser His Val Gln Lys Thr Cys
305                 310                 315                 320

Pro Leu Gly Gln Glu Gly Gln Glu Asn Ala Ser Asp Pro Thr Lys Ile
                325                 330                 335

Ala Asp Thr Gly Tyr Asp Phe Val Asn Arg Thr Ile Ala Met Arg Pro
            340                 345                 350

Val Phe Asp Ser Phe Tyr Leu Gln Gln Tyr Val Leu Leu Cys Ser Gln
        355                 360                 365

Ile Asp Gly Gly Phe Arg Asp Lys Pro Gly Lys Gly Arg Asp His Tyr
    370                 375                 380

His Thr Cys Tyr Cys Leu Ser Gly Leu Ser Ile Ala Gln Tyr Ser Trp
385                 390                 395                 400

Thr Asn Glu Ala Asp Ala Pro Pro Leu Pro Arg Asp Val Phe Gly Pro
                405                 410                 415

Tyr Ser Gln Asn Leu Leu Glu Gln Ile His Pro Leu Tyr Asn Val Val
            420                 425                 430

Leu Asp Arg Tyr Tyr Glu Ala Arg Ser Phe Phe Ser Cys Leu
        435                 440                 445
```

<210> SEQ ID NO 87
<211> LENGTH: 323

-continued

<212> TYPE: PRT
<213> ORGANISM: Artificial Sequence
<220> FEATURE:
<223> OTHER INFORMATION: Description of Artificial Sequence:Consensus
sequence where Xaa can be any amino acid
<220> FEATURE:
<221> NAME/KEY: VARIANT
<222> LOCATION: (1)...(6)
<223> OTHER INFORMATION: Wherein “Xaa” is any amino acid
<220> FEATURE:
<221> NAME/KEY: VARIANT
<222> LOCATION: (10)...(11)
<223> OTHER INFORMATION: Wherein “Xaa” is any amino acid
<220> FEATURE:
<221> NAME/KEY: VARIANT
<222> LOCATION: (13)
<223> OTHER INFORMATION: Wherein “Xaa” is any amino acid
<220> FEATURE:
<221> NAME/KEY: VARIANT
<222> LOCATION: (19)
<223> OTHER INFORMATION: Wherein “Xaa” is any amino acid
<220> FEATURE:
<221> NAME/KEY: VARIANT
<222> LOCATION: (21)...(22)
<223> OTHER INFORMATION: Wherein “Xaa” is any amino acid
<220> FEATURE:
<221> NAME/KEY: VARIANT
<222> LOCATION: (24)
<223> OTHER INFORMATION: Wherein “Xaa” is any amino acid
<220> FEATURE:
<221> NAME/KEY: VARIANT
<222> LOCATION: (34)
<223> OTHER INFORMATION: Wherein “Xaa” is any amino acid
<220> FEATURE:
<221> NAME/KEY: VARIANT
<222> LOCATION: (36)
<223> OTHER INFORMATION: Wherein “Xaa” is any amino acid
<220> FEATURE:
<221> NAME/KEY: VARIANT
<222> LOCATION: (40)
<223> OTHER INFORMATION: Wherein “Xaa” is any amino acid
<220> FEATURE:
<221> NAME/KEY: VARIANT
<222> LOCATION: (42)
<223> OTHER INFORMATION: Wherein “Xaa” is any amino acid
<220> FEATURE:
<221> NAME/KEY: VARIANT
<222> LOCATION: (68)
<223> OTHER INFORMATION: Wherein “Xaa” is any amino acid
<220> FEATURE:
<221> NAME/KEY: VARIANT
<222> LOCATION: (86)
<223> OTHER INFORMATION: Wherein “Xaa” is any amino acid
<220> FEATURE:
<221> NAME/KEY: VARIANT
<222> LOCATION: (89)
<223> OTHER INFORMATION: Wherein “Xaa” is any amino acid
<220> FEATURE:
<221> NAME/KEY: VARIANT
<222> LOCATION: (92)
<223> OTHER INFORMATION: Wherein “Xaa” is any amino acid
<220> FEATURE:
<221> NAME/KEY: VARIANT
<222> LOCATION: (129)
<223> OTHER INFORMATION: Wherein “Xaa” is any amino acid
<220> FEATURE:
<221> NAME/KEY: VARIANT
<222> LOCATION: (194)
<223> OTHER INFORMATION: Wherein “Xaa” is any amino acid
<220> FEATURE:
<221> NAME/KEY: VARIANT
<222> LOCATION: (218)
<223> OTHER INFORMATION: Wherein “Xaa” is any amino acid
<220> FEATURE:
<221> NAME/KEY: VARIANT
<222> LOCATION: (284)
<223> OTHER INFORMATION: Wherein “Xaa” is any amino acid
<220> FEATURE:
<221> NAME/KEY: VARIANT -continued

```
<222> LOCATION: (304)
<223> OTHER INFORMATION: Wherein "Xaa" is any amino acid
<220> FEATURE:
<221> NAME/KEY: VARIANT
<222> LOCATION: (320)...(323)
<223> OTHER INFORMATION: Wherein "Xaa" is any amino acid

<400> SEQUENCE: 87

Xaa Xaa Xaa Xaa Xaa Xaa Val Pro Leu Xaa Xaa Arg Xaa Glu Trp Ser
 1               5                  10                  15

Asp Val Xaa Pro Xaa Xaa Gln Xaa Asp Gly Pro Asn Pro Val Val Pro
            20                  25                  30

Ile Xaa Tyr Xaa Glu Glu Phe Xaa Glu Xaa Met Asp Tyr Phe Arg Ala
        35                  40                  45

Ile Tyr Phe Ser Asp Glu Arg Ser Pro Arg Ala Leu Arg Leu Thr Glu
    50                  55                  60

Glu Ala Leu Xaa Leu Asn Ser Gly Asn Tyr Thr Val Trp His Phe Arg
65                  70                  75                  80

Arg Leu Val Leu Glu Xaa Leu Asn Xaa Asp Leu Xaa Glu Glu Leu Glu
                85                  90                  95

Phe Ile Glu Arg Ile Ala Glu Asp Asn Ser Lys Asn Tyr Gln Leu Trp
            100                 105                 110

His His Arg Arg Trp Val Ala Glu Lys Leu Gly Pro Asp Val Ala Gly
        115                 120                 125

Xaa Glu Leu Glu Phe Thr Arg Arg Val Leu Ser Leu Asp Ala Lys His
    130                 135                 140

Tyr His Ala Trp Ser His Arg Gln Trp Ala Leu Gln Ala Leu Gly Gly
145                 150                 155                 160

Trp Glu Asp Glu Leu Asn Tyr Cys His Glu Leu Leu Glu Ala Asp Val
                165                 170                 175

Phe Asn Asn Ser Ala Trp Asn Gln Arg Tyr Tyr Val Ile Thr Arg Ser
            180                 185                 190

Pro Xaa Leu Gly Gly Leu Glu Ala Met Arg Glu Ser Glu Val Ser Tyr
        195                 200                 205

Thr Ile Lys Ala Ile Leu Ala Asn Pro Xaa Asn Glu Ser Ser Trp Arg
    210                 215                 220

Tyr Leu Lys Ala Leu Tyr Lys Asp Asp Thr Glu Ser Trp Ile Ser Asp
225                 230                 235                 240

Pro Ser Val Ser Ser Val Cys Leu Lys Val Leu Ser Arg Thr Asp Cys
                245                 250                 255

Phe His Gly Phe Ala Leu Ser Thr Leu Leu Asp Leu Leu Cys Asp Gly
            260                 265                 270

Leu Arg Pro Thr Asn Glu His Arg Asp Ser Val Xaa Ala Leu Ala Asn
        275                 280                 285

Glu Glu Pro Glu Thr Asn Leu Ala Asn Leu Val Cys Thr Ile Leu Xaa
    290                 295                 300

Arg Val Asp Pro Ile Arg Ala Asn Tyr Trp Ala Trp Arg Lys Ser Xaa
305                 310                 315                 320

Xaa Xaa Xaa


<210> SEQ ID NO 88
<211> LENGTH: 394
<212> TYPE: PRT
<213> ORGANISM: Artificial Sequence
<220> FEATURE:
<223> OTHER INFORMATION: Description of Artificial Sequence: Consensus
      sequence where X can be any amino acid
```

-continued

<220> FEATURE:
<221> NAME/KEY: VARIANT
<222> LOCATION: (1)
<223> OTHER INFORMATION: Wherein "Xaa" is any amino acid
<220> FEATURE:
<221> NAME/KEY: VARIANT
<222> LOCATION: (3)...(5)
<223> OTHER INFORMATION: Wherein "Xaa" is any amino acid
<220> FEATURE:
<221> NAME/KEY: VARIANT
<222> LOCATION: (7)...(10)
<223> OTHER INFORMATION: Wherein "Xaa" is any amino acid
<220> FEATURE:
<221> NAME/KEY: VARIANT
<222> LOCATION: (15)
<223> OTHER INFORMATION: Wherein "Xaa" is any amino acid
<220> FEATURE:
<221> NAME/KEY: VARIANT
<222> LOCATION: (18)
<223> OTHER INFORMATION: Wherein "Xaa" is any amino acid
<220> FEATURE:
<221> NAME/KEY: VARIANT
<222> LOCATION: (20)...(21)
<223> OTHER INFORMATION: Wherein "Xaa" is any amino acid
<220> FEATURE:
<221> NAME/KEY: VARIANT
<222> LOCATION: (23)...(25)
<223> OTHER INFORMATION: Wherein "Xaa" is any amino acid
<220> FEATURE:
<221> NAME/KEY: VARIANT
<222> LOCATION: (30)...(32)
<223> OTHER INFORMATION: Wherein "Xaa" is any amino acid
<220> FEATURE:
<221> NAME/KEY: VARIANT
<222> LOCATION: (35)
<223> OTHER INFORMATION: Wherein "Xaa" is any amino acid
<220> FEATURE:
<221> NAME/KEY: VARIANT
<222> LOCATION: (49)
<223> OTHER INFORMATION: Wherein "Xaa" is any amino acid
<220> FEATURE:
<221> NAME/KEY: VARIANT
<222> LOCATION: (72)
<223> OTHER INFORMATION: Wherein "Xaa" is any amino acid
<220> FEATURE:
<221> NAME/KEY: VARIANT
<222> LOCATION: (77)
<223> OTHER INFORMATION: Wherein "Xaa" is any amino acid
<220> FEATURE:
<221> NAME/KEY: VARIANT
<222> LOCATION: (82)
<223> OTHER INFORMATION: Wherein "Xaa" is any amino acid
<220> FEATURE:
<221> NAME/KEY: VARIANT
<222> LOCATION: (116)...(117)
<223> OTHER INFORMATION: Wherein "Xaa" is any amino acid
<220> FEATURE:
<221> NAME/KEY: VARIANT
<222> LOCATION: (120)
<223> OTHER INFORMATION: Wherein "Xaa" is any amino acid
<220> FEATURE:
<221> NAME/KEY: VARIANT
<222> LOCATION: (128)
<223> OTHER INFORMATION: Wherein "Xaa" is any amino acid
<220> FEATURE:
<221> NAME/KEY: VARIANT
<222> LOCATION: (137)
<223> OTHER INFORMATION: Wherein "Xaa" is any amino acid
<220> FEATURE:
<221> NAME/KEY: VARIANT
<222> LOCATION: (154)
<223> OTHER INFORMATION: Wherein "Xaa" is any amino acid
<220> FEATURE:
<221> NAME/KEY: VARIANT
<222> LOCATION: (163)...(164)
<223> OTHER INFORMATION: Wherein "Xaa" is any amino acid
<220> FEATURE:
<221> NAME/KEY: VARIANT
<222> LOCATION: (171)

-continued

<223> OTHER INFORMATION: Wherein "Xaa" is any amino acid
<220> FEATURE:
<221> NAME/KEY: VARIANT
<222> LOCATION: (207)...(208)
<223> OTHER INFORMATION: Wherein "Xaa" is any amino acid
<220> FEATURE:
<221> NAME/KEY: VARIANT
<222> LOCATION: (215)...(216)
<223> OTHER INFORMATION: Wherein "Xaa" is any amino acid
<220> FEATURE:
<221> NAME/KEY: VARIANT
<222> LOCATION: (248)
<223> OTHER INFORMATION: Wherein "Xaa" is any amino acid
<220> FEATURE:
<221> NAME/KEY: VARIANT
<222> LOCATION: (255)
<223> OTHER INFORMATION: Wherein "Xaa" is any amino acid
<220> FEATURE:
<221> NAME/KEY: VARIANT
<222> LOCATION: (258)
<223> OTHER INFORMATION: Wherein "Xaa" is any amino acid
<220> FEATURE:
<221> NAME/KEY: VARIANT
<222> LOCATION: (262)...(264)
<223> OTHER INFORMATION: Wherein "Xaa" is any amino acid
<220> FEATURE:
<221> NAME/KEY: VARIANT
<222> LOCATION: (267)...(269)
<223> OTHER INFORMATION: Wherein "Xaa" is any amino acid
<220> FEATURE:
<221> NAME/KEY: VARIANT
<222> LOCATION: (271)...(276)
<223> OTHER INFORMATION: Wherein "Xaa" is any amino acid
<220> FEATURE:
<221> NAME/KEY: VARIANT
<222> LOCATION: (278)...(280)
<223> OTHER INFORMATION: Wherein "Xaa" is any amino acid
<220> FEATURE:
<221> NAME/KEY: VARIANT
<222> LOCATION: (285)...(287)
<223> OTHER INFORMATION: Wherein "Xaa" is any amino acid
<220> FEATURE:
<221> NAME/KEY: VARIANT
<222> LOCATION: (289)...(296)
<223> OTHER INFORMATION: Wherein "Xaa" is any amino acid
<220> FEATURE:
<221> NAME/KEY: VARIANT
<222> LOCATION: (300)...(301)
<223> OTHER INFORMATION: Wherein "Xaa" is any amino acid
<220> FEATURE:
<221> NAME/KEY: VARIANT
<222> LOCATION: (303)...(304)
<223> OTHER INFORMATION: Wherein "Xaa" is any amino acid
<220> FEATURE:
<221> NAME/KEY: VARIANT
<222> LOCATION: (306)...(309)
<223> OTHER INFORMATION: Wherein "Xaa" is any amino acid
<220> FEATURE:
<221> NAME/KEY: VARIANT
<222> LOCATION: (312)...(314)
<223> OTHER INFORMATION: Wherein "Xaa" is any amino acid
<220> FEATURE:
<221> NAME/KEY: VARIANT
<222> LOCATION: (316)
<223> OTHER INFORMATION: Wherein "Xaa" is any amino acid
<220> FEATURE:
<221> NAME/KEY: VARIANT
<222> LOCATION: (318)
<223> OTHER INFORMATION: Wherein "Xaa" is any amino acid
<220> FEATURE:
<221> NAME/KEY: VARIANT
<222> LOCATION: (337)
<223> OTHER INFORMATION: Wherein "Xaa" is any amino acid
<220> FEATURE:
<221> NAME/KEY: VARIANT
<222> LOCATION: (348)
<223> OTHER INFORMATION: Wherein "Xaa" is any amino acid
<220> FEATURE:
<221> NAME/KEY: VARIANT
<222> LOCATION: (364)
<223> OTHER INFORMATION: Wherein “Xaa” is any amino acid
<220> FEATURE:
<221> NAME/KEY: VARIANT
<222> LOCATION: (372)
<223> OTHER INFORMATION: Wherein “Xaa” is any amino acid
<220> FEATURE:
<221> NAME/KEY: VARIANT
<222> LOCATION: (378)...(381)
<223> OTHER INFORMATION: Wherein “Xaa” is any amino acid
<220> FEATURE:
<221> NAME/KEY: VARIANT
<222> LOCATION: (384)
<223> OTHER INFORMATION: Wherein “Xaa” is any amino acid
<220> FEATURE:
<221> NAME/KEY: VARIANT
<222> LOCATION: (386)
<223> OTHER INFORMATION: Wherein “Xaa” is any amino acid
<220> FEATURE:
<221> NAME/KEY: VARIANT
<222> LOCATION: (388)
<223> OTHER INFORMATION: Wherein “Xaa” is any amino acid
<220> FEATURE:
<221> NAME/KEY: VARIANT
<222> LOCATION: (392)
<223> OTHER INFORMATION: Wherein “Xaa” is any amino acid
<220> FEATURE:
<221> NAME/KEY: VARIANT
<222> LOCATION: (394)
<223> OTHER INFORMATION: Wherein “Xaa” is any amino acid

<400> SEQUENCE: 88

```
Xaa Thr Xaa Xaa Xaa Asn Xaa Xaa Xaa Xaa Met Leu Glu Leu Xaa Arg
 1               5                  10                  15

Asp Xaa His Xaa Xaa Tyr Xaa Xaa Xaa Gly Leu Arg His Xaa Xaa Xaa
            20                  25                  30

Ala Phe Xaa Val Leu Asp Ala Asn Arg Pro Trp Leu Cys Tyr Trp Ile
        35                  40                  45

Xaa His Ser Ile Ala Leu Leu Gly Glu Ser Val Asp Asp Asp Leu Glu
    50                  55                  60

Asn Asn Ala Ile Asp Phe Leu Xaa Arg Cys Gln Asp Xaa Asp Gly Gly
65                  70                  75                  80

Tyr Xaa Gly Gly Pro Gly Gln Leu Pro His Leu Ala Thr Thr Tyr Ala
                85                  90                  95

Ala Val Asn Thr Leu Val Thr Leu Gly Gly Glu Lys Ala Leu Ser Ser
            100                 105                 110

Ile Asn Arg Xaa Xaa Leu Tyr Xaa Phe Leu Arg Arg Met Lys Asp Xaa
        115                 120                 125

Asn Gly Gly Phe Arg Met His Asp Xaa Gly Glu Ile Asp Val Arg Ala
    130                 135                 140

Cys Tyr Thr Ala Ile Ser Val Ala Ser Xaa Leu Asn Ile Leu Asp Asp
145                 150                 155                 160

Glu Leu Xaa Xaa Gly Val Gly Asp Tyr Ile Xaa Ser Cys Gln Thr Tyr
                165                 170                 175

Glu Gly Gly Ile Ala Gly Glu Pro Gly Ser Glu Ala His Gly Gly Tyr
            180                 185                 190

Thr Phe Cys Gly Leu Ala Thr Met Ile Leu Ile Asn Glu Val Xaa Xaa
        195                 200                 205

Leu Asp Leu Pro Ser Leu Xaa Xaa Trp Val Val Phe Arg Gln Gly Val
    210                 215                 220

Glu Cys Gly Phe Gln Gly Arg Thr Asn Lys Leu Val Asp Gly Cys Tyr
225                 230                 235                 240

Ser Phe Trp Gln Gly Ala Ala Xaa Ala Leu Leu Gln Arg Leu Xaa Ser
```

-continued 245 250 255

Ile Xaa Asp Lys Gln Xaa Xaa Xaa Ser Ser Xaa Xaa Xaa Ser Xaa Xaa
260 265 270

Xaa Xaa Xaa Xaa Glu Xaa Xaa Xaa Gly Thr Ser Ser Xaa Xaa Xaa Cys
275 280 285

Xaa Xaa Xaa Xaa Xaa Xaa Xaa Xaa Glu Ser Ser Xaa Xaa Asp Xaa Xaa
290 295 300

Asn Xaa Xaa Xaa Xaa Phe Ile Xaa Xaa Xaa Arg Xaa Ile Xaa Pro Leu
305 310 315 320

Phe His Ser Ile Ala Leu Gln Gln Tyr Ile Leu Leu Cys Ser Gln Val
325 330 335

Xaa Glu Gly Gly Leu Arg Asp Lys Pro Gly Lys Xaa Arg Asp His Tyr
340 345 350

His Thr Cys Tyr Cys Leu Ser Gly Leu Ser Val Xaa Gln Tyr Ser Trp
355 360 365

Ser Lys Asp Xaa Asp Ser Pro Pro Leu Xaa Xaa Xaa Xaa Leu Gly Xaa
370 375 380

Tyr Xaa Asn Xaa Leu Glu Pro Xaa His Xaa
385 390

<210> SEQ ID NO 89
<211> LENGTH: 1018
<212> TYPE: DNA
<213> ORGANISM: Artificial Sequence
<220> FEATURE:
<223> OTHER INFORMATION: farnesyl transferase alpha consensus sequence
<220> FEATURE:
<221> NAME/KEY: misc_feature
<222> LOCATION: (1)...(4)
<223> OTHER INFORMATION: Wherein “n” is A, T, C or G
<220> FEATURE:
<221> NAME/KEY: misc_feature
<222> LOCATION: (7)...(8)
<223> OTHER INFORMATION: Wherein “n” is A, T, C or G
<220> FEATURE:
<221> NAME/KEY: misc_feature
<222> LOCATION: (10)...(10)
<223> OTHER INFORMATION: Wherein “n” is A, T, C or G
<220> FEATURE:
<221> NAME/KEY: misc_feature
<222> LOCATION: (12)...(12)
<223> OTHER INFORMATION: Wherein “n” is A, T, C or G
<220> FEATURE:
<221> NAME/KEY: misc_feature
<222> LOCATION: (14)...(14)
<223> OTHER INFORMATION: Wherein “n” is A, T, C or G
<220> FEATURE:
<221> NAME/KEY: misc_feature
<222> LOCATION: (17)...(18)
<223> OTHER INFORMATION: Wherein “n” is A, T, C or G
<220> FEATURE:
<221> NAME/KEY: misc_feature
<222> LOCATION: (20)...(20)
<223> OTHER INFORMATION: Wherein “n” is A, T, C or G
<220> FEATURE:
<221> NAME/KEY: misc_feature
<222> LOCATION: (22)...(23)
<223> OTHER INFORMATION: Wherein “n” is A, T, C or G
<220> FEATURE:
<221> NAME/KEY: misc_feature
<222> LOCATION: (25)...(25)
<223> OTHER INFORMATION: Wherein “n” is A, T, C or G
<220> FEATURE:
<221> NAME/KEY: misc_feature
<222> LOCATION: (27)...(28)
<223> OTHER INFORMATION: Wherein “n” is A, T, C or G
<220> FEATURE:
<221> NAME/KEY: misc_feature
<222> LOCATION: (35)...(36)

-continued

<223> OTHER INFORMATION: Wherein “n” is A, T, C or G
<220> FEATURE:
<221> NAME/KEY: misc_feature
<222> LOCATION: (41)...(42)
<223> OTHER INFORMATION: Wherein “n” is A, T, C or G
<220> FEATURE:
<221> NAME/KEY: misc_feature
<222> LOCATION: (44)...(45)
<223> OTHER INFORMATION: Wherein “n” is A, T, C or G
<220> FEATURE:
<221> NAME/KEY: misc_feature
<222> LOCATION: (48)...(48)
<223> OTHER INFORMATION: Wherein “n” is A, T, C or G
<220> FEATURE:
<221> NAME/KEY: misc_feature
<222> LOCATION: (62)...(62)
<223> OTHER INFORMATION: Wherein “n” is A, T, C or G
<220> FEATURE:
<221> NAME/KEY: misc_feature
<222> LOCATION: (65)...(68)
<223> OTHER INFORMATION: Wherein “n” is A, T, C or G
<220> FEATURE:
<221> NAME/KEY: misc_feature
<222> LOCATION: (71)...(72)
<223> OTHER INFORMATION: Wherein “n” is A, T, C or G
<220> FEATURE:
<221> NAME/KEY: misc_feature
<222> LOCATION: (74)...(75)
<223> OTHER INFORMATION: Wherein “n” is A, T, C or G
<220> FEATURE:
<221> NAME/KEY: misc_feature
<222> LOCATION: (80)...(81)
<223> OTHER INFORMATION: Wherein “n” is A, T, C or G
<220> FEATURE:
<221> NAME/KEY: misc_feature
<222> LOCATION: (86)...(86)
<223> OTHER INFORMATION: Wherein “n” is A, T, C or G
<220> FEATURE:
<221> NAME/KEY: misc_feature
<222> LOCATION: (89)...(89)
<223> OTHER INFORMATION: Wherein “n” is A, T, C or G
<220> FEATURE:
<221> NAME/KEY: misc_feature
<222> LOCATION: (92)...(92)
<223> OTHER INFORMATION: Wherein “n” is A, T, C or G
<220> FEATURE:
<221> NAME/KEY: misc_feature
<222> LOCATION: (95)...(95)
<223> OTHER INFORMATION: Wherein “n” is A, T, C or G
<220> FEATURE:
<221> NAME/KEY: misc_feature
<222> LOCATION: (98)...(98)
<223> OTHER INFORMATION: Wherein “n” is A, T, C or G
<220> FEATURE:
<221> NAME/KEY: misc_feature
<222> LOCATION: (101)...(101)
<223> OTHER INFORMATION: Wherein “n” is A, T, C or G
<220> FEATURE:
<221> NAME/KEY: misc_feature
<222> LOCATION: (104)...(104)
<223> OTHER INFORMATION: Wherein “n” is A, T, C or G
<220> FEATURE:
<221> NAME/KEY: misc_feature
<222> LOCATION: (107)...(107)
<223> OTHER INFORMATION: Wherein “n” is A, T, C or G
<220> FEATURE:
<221> NAME/KEY: misc_feature
<222> LOCATION: (110)...(113)
<223> OTHER INFORMATION: Wherein “n” is A, T, C or G
<220> FEATURE:
<221> NAME/KEY: misc_feature
<222> LOCATION: (22)...(23)
<223> OTHER INFORMATION: Wherein “n” is A, T, C or G
<220> FEATURE:
<221> NAME/KEY: misc_feature
<222> LOCATION: (118)...(119)
<223> OTHER INFORMATION: Wherein “n” is A, T, C or G
<220> FEATURE:
<221> NAME/KEY: misc_feature -continued
<222> LOCATION: (128)...(130)
<223> OTHER INFORMATION: Wherein "n" is A, T, C or G
<220> FEATURE:
<221> NAME/KEY: misc_feature
<222> LOCATION: (134)...(136)
<223> OTHER INFORMATION: Wherein "n" is A, T, C or G
<220> FEATURE:
<221> NAME/KEY: misc_feature
<222> LOCATION: (176)...(188)
<223> OTHER INFORMATION: Wherein "n" is A, T, C or G
<220> FEATURE:
<221> NAME/KEY: misc_feature
<222> LOCATION: (191)...(191)
<223> OTHER INFORMATION: Wherein "n" is A, T, C or G
<220> FEATURE:
<221> NAME/KEY: misc_feature
<222> LOCATION: (214)...(214)
<223> OTHER INFORMATION: Wherein "n" is A, T, C or G
<220> FEATURE:
<221> NAME/KEY: misc_feature
<222> LOCATION: (236)...(236)
<223> OTHER INFORMATION: Wherein "n" is A, T, C or G
<220> FEATURE:
<221> NAME/KEY: misc_feature
<222> LOCATION: (249)...(249)
<223> OTHER INFORMATION: Wherein "n" is A, T, C or G
<220> FEATURE:
<221> NAME/KEY: misc_feature
<222> LOCATION: (276)...(276)
<223> OTHER INFORMATION: Wherein "n" is A, T, C or G
<220> FEATURE:
<221> NAME/KEY: misc_feature
<222> LOCATION: (342)...(342)
<223> OTHER INFORMATION: Wherein "n" is A, T, C or G
<220> FEATURE:
<221> NAME/KEY: misc_feature
<222> LOCATION: (395)...(395)
<223> OTHER INFORMATION: Wherein "n" is A, T, C or G
<220> FEATURE:
<221> NAME/KEY: misc_feature
<222> LOCATION: (398)...(398)
<223> OTHER INFORMATION: Wherein "n" is A, T, C or G
<220> FEATURE:
<221> NAME/KEY: misc_feature
<222> LOCATION: (416)...(416)
<223> OTHER INFORMATION: Wherein "n" is A, T, C or G
<220> FEATURE:
<221> NAME/KEY: misc_feature
<222> LOCATION: (425)...(425)
<223> OTHER INFORMATION: Wherein "n" is A, T, C or G
<220> FEATURE:
<221> NAME/KEY: misc_feature
<222> LOCATION: (473)...(473)
<223> OTHER INFORMATION: Wherein "n" is A, T, C or G
<220> FEATURE:
<221> NAME/KEY: misc_feature
<222> LOCATION: (554)...(554)
<223> OTHER INFORMATION: Wherein "n" is A, T, C or G
<220> FEATURE:
<221> NAME/KEY: misc_feature
<222> LOCATION: (581)...(581)
<223> OTHER INFORMATION: Wherein "n" is A, T, C or G
<220> FEATURE:
<221> NAME/KEY: misc_feature
<222> LOCATION: (664)...(664)
<223> OTHER INFORMATION: Wherein "n" is A, T, C or G
<220> FEATURE:
<221> NAME/KEY: misc_feature
<222> LOCATION: (677)...(677)
<223> OTHER INFORMATION: Wherein "n" is A, T, C or G
<220> FEATURE:
<221> NAME/KEY: misc_feature
<222> LOCATION: (695)...(695)
<223> OTHER INFORMATION: Wherein "n" is A, T, C or G
<220> FEATURE:
<221> NAME/KEY: misc_feature
<222> LOCATION: (716)...(716)
<223> OTHER INFORMATION: Wherein "n" is A, T, C or G
<220> FEATURE:

-continued

<221> NAME/KEY: misc_feature
<222> LOCATION: (719)...(719)
<223> OTHER INFORMATION: Wherein "n" is A, T, C or G
<220> FEATURE:
<221> NAME/KEY: misc_feature
<222> LOCATION: (758)...(758)
<223> OTHER INFORMATION: Wherein "n" is A, T, C or G
<220> FEATURE:
<221> NAME/KEY: misc_feature
<222> LOCATION: (764)...(764)
<223> OTHER INFORMATION: Wherein "n" is A, T, C or G
<220> FEATURE:
<221> NAME/KEY: misc_feature
<222> LOCATION: (767)...(767)
<223> OTHER INFORMATION: Wherein "n" is A, T, C or G
<220> FEATURE:
<221> NAME/KEY: misc_feature
<222> LOCATION: (773)...(773)
<223> OTHER INFORMATION: Wherein "n" is A, T, C or G
<220> FEATURE:
<221> NAME/KEY: misc_feature
<222> LOCATION: (776)...(776)
<223> OTHER INFORMATION: Wherein "n" is A, T, C or G
<220> FEATURE:
<221> NAME/KEY: misc_feature
<222> LOCATION: (827)...(827)
<223> OTHER INFORMATION: Wherein "n" is A, T, C or G
<220> FEATURE:
<221> NAME/KEY: misc_feature
<222> LOCATION: (857)...(857)
<223> OTHER INFORMATION: Wherein "n" is A, T, C or G
<220> FEATURE:
<221> NAME/KEY: misc_feature
<222> LOCATION: (914)...(914)
<223> OTHER INFORMATION: Wherein "n" is A, T, C or G
<220> FEATURE:
<221> NAME/KEY: misc_feature
<222> LOCATION: (921)...(921)
<223> OTHER INFORMATION: Wherein "n" is A, T, C or G
<220> FEATURE:
<221> NAME/KEY: misc_feature
<222> LOCATION: (960)...(962)
<223> OTHER INFORMATION: Wherein "n" is A, T, C or G
<220> FEATURE:
<221> NAME/KEY: misc_feature
<222> LOCATION: (965)...(965)
<223> OTHER INFORMATION: Wherein "n" is A, T, C or G
<220> FEATURE:
<221> NAME/KEY: misc_feature
<222> LOCATION: (967)...(970)
<223> OTHER INFORMATION: Wherein "n" is A, T, C or G
<220> FEATURE:
<221> NAME/KEY: misc_feature
<222> LOCATION: (974)...(976)
<223> OTHER INFORMATION: Wherein "n" is A, T, C or G
<220> FEATURE:
<221> NAME/KEY: misc_feature
<222> LOCATION: (978)...(978)
<223> OTHER INFORMATION: Wherein "n" is A, T, C or G
<220> FEATURE:
<221> NAME/KEY: misc_feature
<222> LOCATION: (980)...(980)
<223> OTHER INFORMATION: Wherein "n" is A, T, C or G
<220> FEATURE:
<221> NAME/KEY: misc_feature
<222> LOCATION: (982)...(982)
<223> OTHER INFORMATION: Wherein "n" is A, T, C or G
<220> FEATURE:
<221> NAME/KEY: misc_feature
<222> LOCATION: (984)...(984)
<223> OTHER INFORMATION: Wherein "n" is A, T, C or G
<220> FEATURE:
<221> NAME/KEY: misc_feature
<222> LOCATION: (988)...(988)
<223> OTHER INFORMATION: Wherein "n" is A, T, C or G
<220> FEATURE:
<221> NAME/KEY: misc_feature
<222> LOCATION: (990)...(994)
<223> OTHER INFORMATION: Wherein "n" is A, T, C or G
<220> FEATURE:
<221> NAME/KEY: misc_feature
<222> LOCATION: (997)...(997)
<223> OTHER INFORMATION: Wherein "n" is A, T, C or G
<220> FEATURE:
<221> NAME/KEY: misc_feature
<222> LOCATION: (1000)...(1000)
<223> OTHER INFORMATION: Wherein "n" is A, T, C or G
<220> FEATURE:
<221> NAME/KEY: misc_feature
<222> LOCATION: (1004)...(1006)
<223> OTHER INFORMATION: Wherein "n" is A, T, C or G
<220> FEATURE:
<221> NAME/KEY: misc_feature
<222> LOCATION: (1008)...(1009)
<223> OTHER INFORMATION: Wherein "n" is A, T, C or G
<220> FEATURE:
<221> NAME/KEY: misc_feature
<222> LOCATION: (1011)...(1015)
<223> OTHER INFORMATION: Wherein "n" is A, T, C or G
<220> FEATURE:
<221> NAME/KEY: misc_feature
<222> LOCATION: (1017)...(1017)
<223> OTHER INFORMATION: Wherein "n" is A, T, C or G

<400> SEQUENCE: 89

```
nnnncgnngn anangannth cnncnanncg tgccnntgag nnanngantg gagtggtcag        60
angtnnnncc nntnnctcan nacganggnc cnaanccngt ngtnccnatn nnntacanng       120
aagagttnnn cgannntatg gattacttcc gtgcgattta cttctccgac gagcgntctc       180
ctcgcgcnct ncgactcacg gaagaagccc tccncttaaa ctccggcaac tacacngtgt       240
ggcatttcng gcgcttagta ctcgaggcgc ttaatnacga cttgtatgaa gaactcgagt       300
tcatcgaacg cattgctgag gataactcta agaactacca gntgtggcat catcgacgat       360
gggttgcaga gaaactgggt cctgatgttg caggnaanga acttgagttt acccgnaggg       420
tactntcact tgatgccaaa cattatcatg cttggtcaca taggcagtgg gcnctacaag       480
cattaggagg atgggaagat gagcttaatt actgccacga gctccttgaa gctgacgtct       540
ttaacaattc tgcntggaat cagaggtatt atgtcataac nagatctcct ttgttgggag       600
gcctagaagc catgagagaa tctgaagtaa gctacacaat caaagccatt ttagccaatc       660
ctgnaaacga gagctcntgg agatacctaa aagcncttta caaagacgac acagantcnt       720
ggattagtga tccaagtgtt tcctcagtct gtttgaangt tctntcncgc acngantgct       780
tccatggatt cgctctgagc acccttttgg atcttctatg cgatggnttg agaccaacca       840
acgagcatag agactcngtg aaagctctag ctaatgaaga accagagact aacttggcca       900
atttggtgtg tacnattctg ngtcgtgtag atccaataag agctaactat tgggcatggn       960
nnaanannnn gatnnnantn gnancaantn nnnnatntgn cgcnnnanna nnnnncnt        1018
```

<210> SEQ ID NO 90
<211> LENGTH: 1237
<212> TYPE: DNA
<213> ORGANISM: Artificial Sequence
<220> FEATURE:
<223> OTHER INFORMATION: Description of Artificial Sequence: farnesyl
      transferase beta Consensus sequence
<220> FEATURE:
<221> NAME/KEY: misc_feature
<222> LOCATION: (1)...(34)
<223> OTHER INFORMATION: Wherein "n" is A, T, C or G
<220> FEATURE:
<221> NAME/KEY: misc_feature
<222> LOCATION: (36)...(36)
<223> OTHER INFORMATION: Wherein "n" is A, T, C or G
<220> FEATURE:
<221> NAME/KEY: misc_feature -continued
<222> LOCATION: (40)...(40)
<223> OTHER INFORMATION: Wherein “n” is A, T, C or G
<220> FEATURE:
<221> NAME/KEY: misc_feature
<222> LOCATION: (42)...(45)
<223> OTHER INFORMATION: Wherein “n” is A, T, C or G
<220> FEATURE:
<221> NAME/KEY: misc_feature
<222> LOCATION: (48)...(48)
<223> OTHER INFORMATION: Wherein “n” is A, T, C or G
<220> FEATURE:
<221> NAME/KEY: misc_feature
<222> LOCATION: (52)...(52)
<223> OTHER INFORMATION: Wherein “n” is A, T, C or G
<220> FEATURE:
<221> NAME/KEY: misc_feature
<222> LOCATION: (54)...(54)
<223> OTHER INFORMATION: Wherein “n” is A, T, C or G
<220> FEATURE:
<221> NAME/KEY: misc_feature
<222> LOCATION: (57)...(58)
<223> OTHER INFORMATION: Wherein “n” is A, T, C or G
<220> FEATURE:
<221> NAME/KEY: misc_feature
<222> LOCATION: (60)...(61)
<223> OTHER INFORMATION: Wherein “n” is A, T, C or G
<220> FEATURE:
<221> NAME/KEY: misc_feature
<222> LOCATION: (63)...(63)
<223> OTHER INFORMATION: Wherein “n” is A, T, C or G
<220> FEATURE:
<221> NAME/KEY: misc_feature
<222> LOCATION: (67)...(67)
<223> OTHER INFORMATION: Wherein “n” is A, T, C or G
<220> FEATURE:
<221> NAME/KEY: misc_feature
<222> LOCATION: (69)...(75)
<223> OTHER INFORMATION: Wherein “n” is A, T, C or G
<220> FEATURE:
<221> NAME/KEY: misc_feature
<222> LOCATION: (78)...(79)
<223> OTHER INFORMATION: Wherein “n” is A, T, C or G
<220> FEATURE:
<221> NAME/KEY: misc_feature
<222> LOCATION: (81)...(82)
<223> OTHER INFORMATION: Wherein “n” is A, T, C or G
<220> FEATURE:
<221> NAME/KEY: misc_feature
<222> LOCATION: (84)...(84)
<223> OTHER INFORMATION: Wherein “n” is A, T, C or G
<220> FEATURE:
<221> NAME/KEY: misc_feature
<222> LOCATION: (87)...(88)
<223> OTHER INFORMATION: Wherein “n” is A, T, C or G
<220> FEATURE:
<221> NAME/KEY: misc_feature
<222> LOCATION: (90)...(91)
<223> OTHER INFORMATION: Wherein “n” is A, T, C or G
<220> FEATURE:
<221> NAME/KEY: misc_feature
<222> LOCATION: (93)...(94)
<223> OTHER INFORMATION: Wherein “n” is A, T, C or G
<220> FEATURE:
<221> NAME/KEY: misc_feature
<222> LOCATION: (96)...(99)
<223> OTHER INFORMATION: Wherein “n” is A, T, C or G
<220> FEATURE:
<221> NAME/KEY: misc_feature
<222> LOCATION: (103)...(109)
<223> OTHER INFORMATION: Wherein “n” is A, T, C or G
<220> FEATURE:
<221> NAME/KEY: misc_feature
<222> LOCATION: (111)...(111)
<223> OTHER INFORMATION: Wherein “n” is A, T, C or G
<220> FEATURE:
<221> NAME/KEY: misc_feature
<222> LOCATION: (114)...(114)
<223> OTHER INFORMATION: Wherein “n” is A, T, C or G
<220> FEATURE:

-continued

<221> NAME/KEY: misc_feature
<222> LOCATION: (117)...(117)
<223> OTHER INFORMATION: Wherein "n" is A, T, C or G
<220> FEATURE:
<221> NAME/KEY: misc_feature
<222> LOCATION: (123)...(123)
<223> OTHER INFORMATION: Wherein "n" is A, T, C or G
<220> FEATURE:
<221> NAME/KEY: misc_feature
<222> LOCATION: (126)...(126)
<223> OTHER INFORMATION: Wherein "n" is A, T, C or G
<220> FEATURE:
<221> NAME/KEY: misc_feature
<222> LOCATION: (132)...(132)
<223> OTHER INFORMATION: Wherein "n" is A, T, C or G
<220> FEATURE:
<221> NAME/KEY: misc_feature
<222> LOCATION: (135)...(135)
<223> OTHER INFORMATION: Wherein "n" is A, T, C or G
<220> FEATURE:
<221> NAME/KEY: misc_feature
<222> LOCATION: (144)...(145)
<223> OTHER INFORMATION: Wherein "n" is A, T, C or G
<220> FEATURE:
<221> NAME/KEY: misc_feature
<222> LOCATION: (165)...(165)
<223> OTHER INFORMATION: Wherein "n" is A, T, C or G
<220> FEATURE:
<221> NAME/KEY: misc_feature
<222> LOCATION: (168)...(168)
<223> OTHER INFORMATION: Wherein "n" is A, T, C or G
<220> FEATURE:
<221> NAME/KEY: misc_feature
<222> LOCATION: (171)...(172)
<223> OTHER INFORMATION: Wherein "n" is A, T, C or G
<220> FEATURE:
<221> NAME/KEY: misc_feature
<222> LOCATION: (174)...(174)
<223> OTHER INFORMATION: Wherein "n" is A, T, C or G
<220> FEATURE:
<221> NAME/KEY: misc_feature
<222> LOCATION: (177)...(177)
<223> OTHER INFORMATION: Wherein "n" is A, T, C or G
<220> FEATURE:
<221> NAME/KEY: misc_feature
<222> LOCATION: (186)...(187)
<223> OTHER INFORMATION: Wherein "n" is A, T, C or G
<220> FEATURE:
<221> NAME/KEY: misc_feature
<222> LOCATION: (189)...(189)
<223> OTHER INFORMATION: Wherein "n" is A, T, C or G
<220> FEATURE:
<221> NAME/KEY: misc_feature
<222> LOCATION: (195)...(195)
<223> OTHER INFORMATION: Wherein "n" is A, T, C or G
<220> FEATURE:
<221> NAME/KEY: misc_feature
<222> LOCATION: (201)...(201)
<223> OTHER INFORMATION: Wherein "n" is A, T, C or G
<220> FEATURE:
<221> NAME/KEY: misc_feature
<222> LOCATION: (204)...(204)
<223> OTHER INFORMATION: Wherein "n" is A, T, C or G
<220> FEATURE:
<221> NAME/KEY: misc_feature
<222> LOCATION: (207)...(207)
<223> OTHER INFORMATION: Wherein "n" is A, T, C or G
<220> FEATURE:
<221> NAME/KEY: misc_feature
<222> LOCATION: (210)...(210)
<223> OTHER INFORMATION: Wherein "n" is A, T, C or G
<220> FEATURE:
<221> NAME/KEY: misc_feature
<222> LOCATION: (215)...(216)
<223> OTHER INFORMATION: Wherein "n" is A, T, C or G
<220> FEATURE:
<221> NAME/KEY: misc_feature
<222> LOCATION: (219)...(219)
<223> OTHER INFORMATION: Wherein "n" is A, T, C or G -continued
<220> FEATURE:
<221> NAME/KEY: misc_feature
<222> LOCATION: (227)...(227)
<223> OTHER INFORMATION: Wherein "n" is A, T, C or G
<220> FEATURE:
<221> NAME/KEY: misc_feature
<222> LOCATION: (229)...(229)
<223> OTHER INFORMATION: Wherein "n" is A, T, C or G
<220> FEATURE:
<221> NAME/KEY: misc_feature
<222> LOCATION: (231)...(231)
<223> OTHER INFORMATION: Wherein "n" is A, T, C or G
<220> FEATURE:
<221> NAME/KEY: misc_feature
<222> LOCATION: (252)...(252)
<223> OTHER INFORMATION: Wherein "n" is A, T, C or G
<220> FEATURE:
<221> NAME/KEY: misc_feature
<222> LOCATION: (261)...(262)
<223> OTHER INFORMATION: Wherein "n" is A, T, C or G
<220> FEATURE:
<221> NAME/KEY: misc_feature
<222> LOCATION: (264)...(264)
<223> OTHER INFORMATION: Wherein "n" is A, T, C or G
<220> FEATURE:
<221> NAME/KEY: misc_feature
<222> LOCATION: (267)...(267)
<223> OTHER INFORMATION: Wherein "n" is A, T, C or G
<220> FEATURE:
<221> NAME/KEY: misc_feature
<222> LOCATION: (276)...(276)
<223> OTHER INFORMATION: Wherein "n" is A, T, C or G
<220> FEATURE:
<221> NAME/KEY: misc_feature
<222> LOCATION: (279)...(279)
<223> OTHER INFORMATION: Wherein "n" is A, T, C or G
<220> FEATURE:
<221> NAME/KEY: misc_feature
<222> LOCATION: (291)...(291)
<223> OTHER INFORMATION: Wherein "n" is A, T, C or G
<220> FEATURE:
<221> NAME/KEY: misc_feature
<222> LOCATION: (294)...(294)
<223> OTHER INFORMATION: Wherein "n" is A, T, C or G
<220> FEATURE:
<221> NAME/KEY: misc_feature
<222> LOCATION: (298)...(298)
<223> OTHER INFORMATION: Wherein "n" is A, T, C or G
<220> FEATURE:
<221> NAME/KEY: misc_feature
<222> LOCATION: (315)...(315)
<223> OTHER INFORMATION: Wherein "n" is A, T, C or G
<220> FEATURE:
<221> NAME/KEY: misc_feature
<222> LOCATION: (321)...(321)
<223> OTHER INFORMATION: Wherein "n" is A, T, C or G
<220> FEATURE:
<221> NAME/KEY: misc_feature
<222> LOCATION: (328)...(328)
<223> OTHER INFORMATION: Wherein "n" is A, T, C or G
<220> FEATURE:
<221> NAME/KEY: misc_feature
<222> LOCATION: (330)...(330)
<223> OTHER INFORMATION: Wherein "n" is A, T, C or G
<220> FEATURE:
<221> NAME/KEY: misc_feature
<222> LOCATION: (333)...(333)
<223> OTHER INFORMATION: Wherein "n" is A, T, C or G
<220> FEATURE:
<221> NAME/KEY: misc_feature
<222> LOCATION: (348)...(348)
<223> OTHER INFORMATION: Wherein "n" is A, T, C or G
<220> FEATURE:
<221> NAME/KEY: misc_feature
<222> LOCATION: (352)...(352)
<223> OTHER INFORMATION: Wherein "n" is A, T, C or G
<220> FEATURE:
<221> NAME/KEY: misc_feature
<222> LOCATION: (356)...(356)

-continued

<223> OTHER INFORMATION: Wherein “n” is A, T, C or G
<220> FEATURE:
<221> NAME/KEY: misc_feature
<222> LOCATION: (358)...(358)
<223> OTHER INFORMATION: Wherein “n” is A, T, C or G
<220> FEATURE:
<221> NAME/KEY: misc_feature
<222> LOCATION: (364)...(364)
<223> OTHER INFORMATION: Wherein “n” is A, T, C or G
<220> FEATURE:
<221> NAME/KEY: misc_feature
<222> LOCATION: (336)...(367)
<223> OTHER INFORMATION: Wherein “n” is A, T, C or G
<220> FEATURE:
<221> NAME/KEY: misc_feature
<222> LOCATION: (369)...(369)
<223> OTHER INFORMATION: Wherein “n” is A, T, C or G
<220> FEATURE:
<221> NAME/KEY: misc_feature
<222> LOCATION: (382)...(382)
<223> OTHER INFORMATION: Wherein “n” is A, T, C or G
<220> FEATURE:
<221> NAME/KEY: misc_feature
<222> LOCATION: (386)...(386)
<223> OTHER INFORMATION: Wherein “n” is A, T, C or G
<220> FEATURE:
<221> NAME/KEY: misc_feature
<222> LOCATION: (390)...(390)
<223> OTHER INFORMATION: Wherein “n” is A, T, C or G
<220> FEATURE:
<221> NAME/KEY: misc_feature
<222> LOCATION: (409)...(411)
<223> OTHER INFORMATION: Wherein “n” is A, T, C or G
<220> FEATURE:
<221> NAME/KEY: misc_feature
<222> LOCATION: (414)...(414)
<223> OTHER INFORMATION: Wherein “n” is A, T, C or G
<220> FEATURE:
<221> NAME/KEY: misc_feature
<222> LOCATION: (426)...(426)
<223> OTHER INFORMATION: Wherein “n” is A, T, C or G
<220> FEATURE:
<221> NAME/KEY: misc_feature
<222> LOCATION: (429)...(429)
<223> OTHER INFORMATION: Wherein “n” is A, T, C or G
<220> FEATURE:
<221> NAME/KEY: misc_feature
<222> LOCATION: (432)...(432)
<223> OTHER INFORMATION: Wherein “n” is A, T, C or G
<220> FEATURE:
<221> NAME/KEY: misc_feature
<222> LOCATION: (444)...(444)
<223> OTHER INFORMATION: Wherein “n” is A, T, C or G
<220> FEATURE:
<221> NAME/KEY: misc_feature
<222> LOCATION: (460)...(460)
<223> OTHER INFORMATION: Wherein “n” is A, T, C or G
<220> FEATURE:
<221> NAME/KEY: misc_feature
<222> LOCATION: (462)...(463)
<223> OTHER INFORMATION: Wherein “n” is A, T, C or G
<220> FEATURE:
<221> NAME/KEY: misc_feature
<222> LOCATION: (468)...(468)
<223> OTHER INFORMATION: Wherein “n” is A, T, C or G
<220> FEATURE:
<221> NAME/KEY: misc_feature
<222> LOCATION: (472)...(472)
<223> OTHER INFORMATION: Wherein “n” is A, T, C or G
<220> FEATURE:
<221> NAME/KEY: misc_feature
<222> LOCATION: (486)...(486)
<223> OTHER INFORMATION: Wherein “n” is A, T, C or G
<220> FEATURE:
<221> NAME/KEY: misc_feature
<222> LOCATION: (492)...(492)
<223> OTHER INFORMATION: Wherein “n” is A, T, C or G
<220> FEATURE:
<221> NAME/KEY: misc_feature -continued
<222> LOCATION: (495)...(496)
<223> OTHER INFORMATION: Wherein "n" is A, T, C or G
<220> FEATURE:
<221> NAME/KEY: misc_feature
<222> LOCATION: (504)...(504)
<223> OTHER INFORMATION: Wherein "n" is A, T, C or G
<220> FEATURE:
<221> NAME/KEY: misc_feature
<222> LOCATION: (510)...(511)
<223> OTHER INFORMATION: Wherein "n" is A, T, C or G
<220> FEATURE:
<221> NAME/KEY: misc_feature
<222> LOCATION: (513)...(513)
<223> OTHER INFORMATION: Wherein "n" is A, T, C or G
<220> FEATURE:
<221> NAME/KEY: misc_feature
<222> LOCATION: (516)...(516)
<223> OTHER INFORMATION: Wherein "n" is A, T, C or G
<220> FEATURE:
<221> NAME/KEY: misc_feature
<222> LOCATION: (519)...(519)
<223> OTHER INFORMATION: Wherein "n" is A, T, C or G
<220> FEATURE:
<221> NAME/KEY: misc_feature
<222> LOCATION: (542)...(543)
<223> OTHER INFORMATION: Wherein "n" is A, T, C or G
<220> FEATURE:
<221> NAME/KEY: misc_feature
<222> LOCATION: (549)...(549)
<223> OTHER INFORMATION: Wherein "n" is A, T, C or G
<220> FEATURE:
<221> NAME/KEY: misc_feature
<222> LOCATION: (555)...(555)
<223> OTHER INFORMATION: Wherein "n" is A, T, C or G
<220> FEATURE:
<221> NAME/KEY: misc_feature
<222> LOCATION: (558)...(558)
<223> OTHER INFORMATION: Wherein "n" is A, T, C or G
<220> FEATURE:
<221> NAME/KEY: misc_feature
<222> LOCATION: (576)...(576)
<223> OTHER INFORMATION: Wherein "n" is A, T, C or G
<220> FEATURE:
<221> NAME/KEY: misc_feature
<222> LOCATION: (579)...(579)
<223> OTHER INFORMATION: Wherein "n" is A, T, C or G
<220> FEATURE:
<221> NAME/KEY: misc_feature
<222> LOCATION: (581)...(581)
<223> OTHER INFORMATION: Wherein "n" is A, T, C or G
<220> FEATURE:
<221> NAME/KEY: misc_feature
<222> LOCATION: (588)...(588)
<223> OTHER INFORMATION: Wherein "n" is A, T, C or G
<220> FEATURE:
<221> NAME/KEY: misc_feature
<222> LOCATION: (595)...(595)
<223> OTHER INFORMATION: Wherein "n" is A, T, C or G
<220> FEATURE:
<221> NAME/KEY: misc_feature
<222> LOCATION: (604)...(604)
<223> OTHER INFORMATION: Wherein "n" is A, T, C or G
<220> FEATURE:
<221> NAME/KEY: misc_feature
<222> LOCATION: (606)...(606)
<223> OTHER INFORMATION: Wherein "n" is A, T, C or G
<220> FEATURE:
<221> NAME/KEY: misc_feature
<222> LOCATION: (609)...(609)
<223> OTHER INFORMATION: Wherein "n" is A, T, C or G
<220> FEATURE:
<221> NAME/KEY: misc_feature
<222> LOCATION: (618)...(618)
<223> OTHER INFORMATION: Wherein "n" is A, T, C or G
<220> FEATURE:
<221> NAME/KEY: misc_feature
<222> LOCATION: (621)...(621)
<223> OTHER INFORMATION: Wherein "n" is A, T, C or G
<220> FEATURE:

-continued

<221> NAME/KEY: misc_feature
<222> LOCATION: (623)...(624)
<223> OTHER INFORMATION: Wherein "n" is A, T, C or G
<220> FEATURE:
<221> NAME/KEY: misc_feature
<222> LOCATION: (628)...(628)
<223> OTHER INFORMATION: Wherein "n" is A, T, C or G
<220> FEATURE:
<221> NAME/KEY: misc_feature
<222> LOCATION: (634)...(635)
<223> OTHER INFORMATION: Wherein "n" is A, T, C or G
<220> FEATURE:
<221> NAME/KEY: misc_feature
<222> LOCATION: (637)...(639)
<223> OTHER INFORMATION: Wherein "n" is A, T, C or G
<220> FEATURE:
<221> NAME/KEY: misc_feature
<222> LOCATION: (645)...(646)
<223> OTHER INFORMATION: Wherein "n" is A, T, C or G
<220> FEATURE:
<221> NAME/KEY: misc_feature
<222> LOCATION: (648)...(648)
<223> OTHER INFORMATION: Wherein "n" is A, T, C or G
<220> FEATURE:
<221> NAME/KEY: misc_feature
<222> LOCATION: (654)...(654)
<223> OTHER INFORMATION: Wherein "n" is A, T, C or G
<220> FEATURE:
<221> NAME/KEY: misc_feature
<222> LOCATION: (658)...(659)
<223> OTHER INFORMATION: Wherein "n" is A, T, C or G
<220> FEATURE:
<221> NAME/KEY: misc_feature
<222> LOCATION: (672)...(672)
<223> OTHER INFORMATION: Wherein "n" is A, T, C or G
<220> FEATURE:
<221> NAME/KEY: misc_feature
<222> LOCATION: (676)...(678)
<223> OTHER INFORMATION: Wherein "n" is A, T, C or G
<220> FEATURE:
<221> NAME/KEY: misc_feature
<222> LOCATION: (684)...(684)
<223> OTHER INFORMATION: Wherein "n" is A, T, C or G
<220> FEATURE:
<221> NAME/KEY: misc_feature
<222> LOCATION: (690)...(690)
<223> OTHER INFORMATION: Wherein "n" is A, T, C or G
<220> FEATURE:
<221> NAME/KEY: misc_feature
<222> LOCATION: (693)...(693)
<223> OTHER INFORMATION: Wherein "n" is A, T, C or G
<220> FEATURE:
<221> NAME/KEY: misc_feature
<222> LOCATION: (696)...(696)
<223> OTHER INFORMATION: Wherein "n" is A, T, C or G
<220> FEATURE:
<221> NAME/KEY: misc_feature
<222> LOCATION: (699)...(699)
<223> OTHER INFORMATION: Wherein "n" is A, T, C or G
<220> FEATURE:
<221> NAME/KEY: misc_feature
<222> LOCATION: (708)...(708)
<223> OTHER INFORMATION: Wherein "n" is A, T, C or G
<220> FEATURE:
<221> NAME/KEY: misc_feature
<222> LOCATION: (721)...(721)
<223> OTHER INFORMATION: Wherein "n" is A, T, C or G
<220> FEATURE:
<221> NAME/KEY: misc_feature
<222> LOCATION: (723)...(723)
<223> OTHER INFORMATION: Wherein "n" is A, T, C or G
<220> FEATURE:
<221> NAME/KEY: misc_feature
<222> LOCATION: (734)...(734)
<223> OTHER INFORMATION: Wherein "n" is A, T, C or G
<220> FEATURE:
<221> NAME/KEY: misc_feature
<222> LOCATION: (738)...(739)
<223> OTHER INFORMATION: Wherein "n" is A, T, C or G -continued
<220> FEATURE:
<221> NAME/KEY: misc_feature
<222> LOCATION: (741)...(743)
<223> OTHER INFORMATION: Wherein "n" is A, T, C or G
<220> FEATURE:
<221> NAME/KEY: misc_feature
<222> LOCATION: (746)...(746)
<223> OTHER INFORMATION: Wherein "n" is A, T, C or G
<220> FEATURE:
<221> NAME/KEY: misc_feature
<222> LOCATION: (751)...(751)
<223> OTHER INFORMATION: Wherein "n" is A, T, C or G
<220> FEATURE:
<221> NAME/KEY: misc_feature
<222> LOCATION: (764)...(764)
<223> OTHER INFORMATION: Wherein "n" is A, T, C or G
<220> FEATURE:
<221> NAME/KEY: misc_feature
<222> LOCATION: (768)...(768)
<223> OTHER INFORMATION: Wherein "n" is A, T, C or G
<220> FEATURE:
<221> NAME/KEY: misc_feature
<222> LOCATION: (770)...(774)
<223> OTHER INFORMATION: Wherein "n" is A, T, C or G
<220> FEATURE:
<221> NAME/KEY: misc_feature
<222> LOCATION: (779)...(779)
<223> OTHER INFORMATION: Wherein "n" is A, T, C or G
<220> FEATURE:
<221> NAME/KEY: misc_feature
<222> LOCATION: (781)...(787)
<223> OTHER INFORMATION: Wherein "n" is A, T, C or G
<220> FEATURE:
<221> NAME/KEY: misc_feature
<222> LOCATION: (789)...(789)
<223> OTHER INFORMATION: Wherein "n" is A, T, C or G
<220> FEATURE:
<221> NAME/KEY: misc_feature
<222> LOCATION: (791)...(793)
<223> OTHER INFORMATION: Wherein "n" is A, T, C or G
<220> FEATURE:
<221> NAME/KEY: misc_feature
<222> LOCATION: (799)...(811)
<223> OTHER INFORMATION: Wherein "n" is A, T, C or G
<220> FEATURE:
<221> NAME/KEY: misc_feature
<222> LOCATION: (813)...(813)
<223> OTHER INFORMATION: Wherein "n" is A, T, C or G
<220> FEATURE:
<221> NAME/KEY: misc_feature
<222> LOCATION: (815)...(816)
<223> OTHER INFORMATION: Wherein "n" is A, T, C or G
<220> FEATURE:
<221> NAME/KEY: misc_feature
<222> LOCATION: (818)...(819)
<223> OTHER INFORMATION: Wherein "n" is A, T, C or G
<220> FEATURE:
<221> NAME/KEY: misc_feature
<222> LOCATION: (821)...(821)
<223> OTHER INFORMATION: Wherein "n" is A, T, C or G
<220> FEATURE:
<221> NAME/KEY: misc_feature
<222> LOCATION: (823)...(823)
<223> OTHER INFORMATION: Wherein "n" is A, T, C or G
<220> FEATURE:
<221> NAME/KEY: misc_feature
<222> LOCATION: (825)...(826)
<223> OTHER INFORMATION: Wherein "n" is A, T, C or G
<220> FEATURE:
<221> NAME/KEY: misc_feature
<222> LOCATION: (828)...(828)
<223> OTHER INFORMATION: Wherein "n" is A, T, C or G
<220> FEATURE:
<221> NAME/KEY: misc_feature
<222> LOCATION: (831)...(834)
<223> OTHER INFORMATION: Wherein "n" is A, T, C or G
<220> FEATURE:
<221> NAME/KEY: misc_feature
<222> LOCATION: (836)...(836)

-continued

<223> OTHER INFORMATION: Wherein “n” is A, T, C or G
<220> FEATURE:
<221> NAME/KEY: misc_feature
<222> LOCATION: (838)...(838)
<223> OTHER INFORMATION: Wherein “n” is A, T, C or G
<220> FEATURE:
<221> NAME/KEY: misc_feature
<222> LOCATION: (840)...(841)
<223> OTHER INFORMATION: Wherein “n” is A, T, C or G
<220> FEATURE:
<221> NAME/KEY: misc_feature
<222> LOCATION: (845)...(845)
<223> OTHER INFORMATION: Wherein “n” is A, T, C or G
<220> FEATURE:
<221> NAME/KEY: misc_feature
<222> LOCATION: (847)...(847)
<223> OTHER INFORMATION: Wherein “n” is A, T, C or G
<220> FEATURE:
<221> NAME/KEY: misc_feature
<222> LOCATION: (850)...(850)
<223> OTHER INFORMATION: Wherein “n” is A, T, C or G
<220> FEATURE:
<221> NAME/KEY: misc_feature
<222> LOCATION: (852)...(856)
<223> OTHER INFORMATION: Wherein “n” is A, T, C or G
<220> FEATURE:
<221> NAME/KEY: misc_feature
<222> LOCATION: (861)...(863)
<223> OTHER INFORMATION: Wherein “n” is A, T, C or G
<220> FEATURE:
<221> NAME/KEY: misc_feature
<222> LOCATION: (865)...(871)
<223> OTHER INFORMATION: Wherein “n” is A, T, C or G
<220> FEATURE:
<221> NAME/KEY: misc_feature
<222> LOCATION: (873)...(875)
<223> OTHER INFORMATION: Wherein “n” is A, T, C or G
<220> FEATURE:
<221> NAME/KEY: misc_feature
<222> LOCATION: (879)...(879)
<223> OTHER INFORMATION: Wherein “n” is A, T, C or G
<220> FEATURE:
<221> NAME/KEY: misc_feature
<222> LOCATION: (882)...(883)
<223> OTHER INFORMATION: Wherein “n” is A, T, C or G
<220> FEATURE:
<221> NAME/KEY: misc_feature
<222> LOCATION: (885)...(885)
<223> OTHER INFORMATION: Wherein “n” is A, T, C or G
<220> FEATURE:
<221> NAME/KEY: misc_feature
<222> LOCATION: (889)...(889)
<223> OTHER INFORMATION: Wherein “n” is A, T, C or G
<220> FEATURE:
<221> NAME/KEY: misc_feature
<222> LOCATION: (891)...(891)
<223> OTHER INFORMATION: Wherein “n” is A, T, C or G
<220> FEATURE:
<221> NAME/KEY: misc_feature
<222> LOCATION: (893)...(893)
<223> OTHER INFORMATION: Wherein “n” is A, T, C or G
<220> FEATURE:
<221> NAME/KEY: misc_feature
<222> LOCATION: (895)...(895)
<223> OTHER INFORMATION: Wherein “n” is A, T, C or G
<220> FEATURE:
<221> NAME/KEY: misc_feature
<222> LOCATION: (897)...(898)
<223> OTHER INFORMATION: Wherein “n” is A, T, C or G
<220> FEATURE:
<221> NAME/KEY: misc_feature
<222> LOCATION: (902)...(906)
<223> OTHER INFORMATION: Wherein “n” is A, T, C or G
<220> FEATURE:
<221> NAME/KEY: misc_feature
<222> LOCATION: (912)...(914)
<223> OTHER INFORMATION: Wherein “n” is A, T, C or G
<220> FEATURE:
<221> NAME/KEY: misc_feature -continued
<222> LOCATION: (917)...(918)
<223> OTHER INFORMATION: Wherein "n" is A, T, C or G
<220> FEATURE:
<221> NAME/KEY: misc_feature
<222> LOCATION: (920)...(920)
<223> OTHER INFORMATION: Wherein "n" is A, T, C or G
<220> FEATURE:
<221> NAME/KEY: misc_feature
<222> LOCATION: (922)...(922)
<223> OTHER INFORMATION: Wherein "n" is A, T, C or G
<220> FEATURE:
<221> NAME/KEY: misc_feature
<222> LOCATION: (925)...(926)
<223> OTHER INFORMATION: Wherein "n" is A, T, C or G
<220> FEATURE:
<221> NAME/KEY: misc_feature
<222> LOCATION: (929)...(932)
<223> OTHER INFORMATION: Wherein "n" is A, T, C or G
<220> FEATURE:
<221> NAME/KEY: misc_feature
<222> LOCATION: (936)...(937)
<223> OTHER INFORMATION: Wherein "n" is A, T, C or G
<220> FEATURE:
<221> NAME/KEY: misc_feature
<222> LOCATION: (939)...(939)
<223> OTHER INFORMATION: Wherein "n" is A, T, C or G
<220> FEATURE:
<221> NAME/KEY: misc_feature
<222> LOCATION: (942)...(944)
<223> OTHER INFORMATION: Wherein "n" is A, T, C or G
<220> FEATURE:
<221> NAME/KEY: misc_feature
<222> LOCATION: (946)...(951)
<223> OTHER INFORMATION: Wherein "n" is A, T, C or G
<220> FEATURE:
<221> NAME/KEY: misc_feature
<222> LOCATION: (955)...(957)
<223> OTHER INFORMATION: Wherein "n" is A, T, C or G
<220> FEATURE:
<221> NAME/KEY: misc_feature
<222> LOCATION: (961)...(962)
<223> OTHER INFORMATION: Wherein "n" is A, T, C or G
<220> FEATURE:
<221> NAME/KEY: misc_feature
<222> LOCATION: (967)...(968)
<223> OTHER INFORMATION: Wherein "n" is A, T, C or G
<220> FEATURE:
<221> NAME/KEY: misc_feature
<222> LOCATION: (974)...(974)
<223> OTHER INFORMATION: Wherein "n" is A, T, C or G
<220> FEATURE:
<221> NAME/KEY: misc_feature
<222> LOCATION: (980)...(980)
<223> OTHER INFORMATION: Wherein "n" is A, T, C or G
<220> FEATURE:
<221> NAME/KEY: misc_feature
<222> LOCATION: (982)...(982)
<223> OTHER INFORMATION: Wherein "n" is A, T, C or G
<220> FEATURE:
<221> NAME/KEY: misc_feature
<222> LOCATION: (984)...(984)
<223> OTHER INFORMATION: Wherein "n" is A, T, C or G
<220> FEATURE:
<221> NAME/KEY: misc_feature
<222> LOCATION: (991)...(993)
<223> OTHER INFORMATION: Wherein "n" is A, T, C or G
<220> FEATURE:
<221> NAME/KEY: misc_feature
<222> LOCATION: (998)...(998)
<223> OTHER INFORMATION: Wherein "n" is A, T, C or G
<220> FEATURE:
<221> NAME/KEY: misc_feature
<222> LOCATION: (1000)...(1000)
<223> OTHER INFORMATION: Wherein "n" is A, T, C or G
<220> FEATURE:
<221> NAME/KEY: misc_feature
<222> LOCATION: (1006)...(1006)
<223> OTHER INFORMATION: Wherein "n" is A, T, C or G
<220> FEATURE:

-continued

<221> NAME/KEY: misc_feature
<222> LOCATION: (1009)...(1009)
<223> OTHER INFORMATION: Wherein "n" is A, T, C or G
<220> FEATURE:
<221> NAME/KEY: misc_feature
<222> LOCATION: (1018)...(1018)
<223> OTHER INFORMATION: Wherein "n" is A, T, C or G
<220> FEATURE:
<221> NAME/KEY: misc_feature
<222> LOCATION: (1020)...(1021)
<223> OTHER INFORMATION: Wherein "n" is A, T, C or G
<220> FEATURE:
<221> NAME/KEY: misc_feature
<222> LOCATION: (1024)...(1024)
<223> OTHER INFORMATION: Wherein "n" is A, T, C or G
<220> FEATURE:
<221> NAME/KEY: misc_feature
<222> LOCATION: (1033)...(1033)
<223> OTHER INFORMATION: Wherein "n" is A, T, C or G
<220> FEATURE:
<221> NAME/KEY: misc_feature
<222> LOCATION: (1046)...(1046)
<223> OTHER INFORMATION: Wherein "n" is A, T, C or G
<220> FEATURE:
<221> NAME/KEY: misc_feature
<222> LOCATION: (1048)...(1048)
<223> OTHER INFORMATION: Wherein "n" is A, T, C or G
<220> FEATURE:
<221> NAME/KEY: misc_feature
<222> LOCATION: (1053)...(1053)
<223> OTHER INFORMATION: Wherein "n" is A, T, C or G
<220> FEATURE:
<221> NAME/KEY: misc_feature
<222> LOCATION: (1055)...(1055)
<223> OTHER INFORMATION: Wherein "n" is A, T, C or G
<220> FEATURE:
<221> NAME/KEY: misc_feature
<222> LOCATION: (1057)...(1057)
<223> OTHER INFORMATION: Wherein "n" is A, T, C or G
<220> FEATURE:
<221> NAME/KEY: misc_feature
<222> LOCATION: (1060)...(1062)
<223> OTHER INFORMATION: Wherein "n" is A, T, C or G
<220> FEATURE:
<221> NAME/KEY: misc_feature
<222> LOCATION: (1066)...(1066)
<223> OTHER INFORMATION: Wherein "n" is A, T, C or G
<220> FEATURE:
<221> NAME/KEY: misc_feature
<222> LOCATION: (1084)...(1084)
<223> OTHER INFORMATION: Wherein "n" is A, T, C or G
<220> FEATURE:
<221> NAME/KEY: misc_feature
<222> LOCATION: (1087)...(1087)
<223> OTHER INFORMATION: Wherein "n" is A, T, C or G
<220> FEATURE:
<221> NAME/KEY: misc_feature
<222> LOCATION: (1090)...(1090)
<223> OTHER INFORMATION: Wherein "n" is A, T, C or G
<220> FEATURE:
<221> NAME/KEY: misc_feature
<222> LOCATION: (1093)...(1093)
<223> OTHER INFORMATION: Wherein "n" is A, T, C or G
<220> FEATURE:
<221> NAME/KEY: misc_feature
<222> LOCATION: (1096)...(1096)
<223> OTHER INFORMATION: Wherein "n" is A, T, C or G
<220> FEATURE:
<221> NAME/KEY: misc_feature
<222> LOCATION: (1100)...(1102)
<223> OTHER INFORMATION: Wherein "n" is A, T, C or G
<220> FEATURE:
<221> NAME/KEY: misc_feature
<222> LOCATION: (1106)...(1106)
<223> OTHER INFORMATION: Wherein "n" is A, T, C or G
<220> FEATURE:
<221> NAME/KEY: misc_feature
<222> LOCATION: (1109)...(1110)
<223> OTHER INFORMATION: Wherein "n" is A, T, C or G -continued
<220> FEATURE:
<221> NAME/KEY: misc_feature
<222> LOCATION: (1116)...(1116)
<223> OTHER INFORMATION: Wherein "n" is A, T, C or G
<220> FEATURE:
<221> NAME/KEY: misc_feature
<222> LOCATION: (1120)...(1120)
<223> OTHER INFORMATION: Wherein "n" is A, T, C or G
<220> FEATURE:
<221> NAME/KEY: misc_feature
<222> LOCATION: (1124)...(1126)
<223> OTHER INFORMATION: Wherein "n" is A, T, C or G
<220> FEATURE:
<221> NAME/KEY: misc_feature
<222> LOCATION: (1129)...(1130)
<223> OTHER INFORMATION: Wherein "n" is A, T, C or G
<220> FEATURE:
<221> NAME/KEY: misc_feature
<222> LOCATION: (1135)...(1135)
<223> OTHER INFORMATION: Wherein "n" is A, T, C or G
<220> FEATURE:
<221> NAME/KEY: misc_feature
<222> LOCATION: (1138)...(1138)
<223> OTHER INFORMATION: Wherein "n" is A, T, C or G
<220> FEATURE:
<221> NAME/KEY: misc_feature
<222> LOCATION: (1141)...(1142)
<223> OTHER INFORMATION: Wherein "n" is A, T, C or G
<220> FEATURE:
<221> NAME/KEY: misc_feature
<222> LOCATION: (1146)...(1148)
<223> OTHER INFORMATION: Wherein "n" is A, T, C or G
<220> FEATURE:
<221> NAME/KEY: misc_feature
<222> LOCATION: (1150)...(1151)
<223> OTHER INFORMATION: Wherein "n" is A, T, C or G
<220> FEATURE:
<221> NAME/KEY: misc_feature
<222> LOCATION: (1153)...(1154)
<223> OTHER INFORMATION: Wherein "n" is A, T, C or G
<220> FEATURE:
<221> NAME/KEY: misc_feature
<222> LOCATION: (1156)...(1156)
<223> OTHER INFORMATION: Wherein "n" is A, T, C or G
<220> FEATURE:
<221> NAME/KEY: misc_feature
<222> LOCATION: (1159)...(1162)
<223> OTHER INFORMATION: Wherein "n" is A, T, C or G
<220> FEATURE:
<221> NAME/KEY: misc_feature
<222> LOCATION: (1166)...(1166)
<223> OTHER INFORMATION: Wherein "n" is A, T, C or G
<220> FEATURE:
<221> NAME/KEY: misc_feature
<222> LOCATION: (1168)...(1168)
<223> OTHER INFORMATION: Wherein "n" is A, T, C or G
<220> FEATURE:
<221> NAME/KEY: misc_feature
<222> LOCATION: (1171)...(1174)
<223> OTHER INFORMATION: Wherein "n" is A, T, C or G
<220> FEATURE:
<221> NAME/KEY: misc_feature
<222> LOCATION: (1177)...(1177)
<223> OTHER INFORMATION: Wherein "n" is A, T, C or G
<220> FEATURE:
<221> NAME/KEY: misc_feature
<222> LOCATION: (1180)...(1180)
<223> OTHER INFORMATION: Wherein "n" is A, T, C or G
<220> FEATURE:
<221> NAME/KEY: misc_feature
<222> LOCATION: (1183)...(1184)
<223> OTHER INFORMATION: Wherein "n" is A, T, C or G
<220> FEATURE:
<221> NAME/KEY: misc_feature
<222> LOCATION: (1186)...(1186)
<223> OTHER INFORMATION: Wherein "n" is A, T, C or G
<220> FEATURE:
<221> NAME/KEY: misc_feature
<222> LOCATION: (1189)...(1189)

-continued

```
<223> OTHER INFORMATION: Wherein "n" is A, T, C or G
<220> FEATURE:
<221> NAME/KEY: misc_feature
<222> LOCATION: (1191)...(1237)
<223> OTHER INFORMATION: Wherein "n" is A, T, C or G

<400> SEQUENCE: 90

nnnnnnnnnn nnnnnnnnnn nnnnnnnnnn nnnntngagn tnnnncgnga tnancanntn     60

nantatntnn nnnnnggnnt nngncanntn ngnncnnnnt ttnnnnnnnt ngangcnaat    120

cgnccntggc tntgntactg gatnnttcat tcaattgctt tgctnggnga nncngtngat    180

gatganntng aaaanaatgc natnganttn cttgnncgnt gccaggntnc ngatggtgga    240

tatggtggtg gncctggcca nntnccncat cttgcnacna cttatgctgc ngtnaatnca    300

cttgttactt taggngtga naaagccntn tcntcaatta atagaganaa antgtntngt    360

tttntnngnc ggatgaagga tncaantggn ggtttcagga tgcatgatnn nggngaaatt    420

gatgtncgng cntgctacac tgcnatttcg gttgcaagcn tnntgaanat tntggatgat    480

gaactnaccc anggnntagg agantacatn ntnagntgnc aaacttatga aggtggcatt    540

gnnggggganc ctggntcnga agctcatggt gggtanacnt nctgtggntt ggctnctatg    600

attntnatna atgaggtnga ncnnttgnat ttgnntnnnt taatnnantg ggtngtannt    660

cgacaaggag tngaannngg attncaaggn agnacnaana aattggtnga tggttgctac    720

ncnttttggc aggnagcnnc nnntgntcta ntacaaagat tatnttcnan nnnngatang    780

nnnnnnnang nnncatcann nnnnnnnnnn ngngnnannt nangnncntg nnnnanangn    840

ncatnangan gnnnnncctg nnnannnnnn ngnnnatgnt gnntntgang ngnanannga    900

tnnnnnttca gngnatnntn anaannttnn nnatanntnt annnannnnn ncagnnnaat    960

nnaaccnntt tttnatagcn tngncttgca nnnatatntn ctcttntgnt ctcaggtncn   1020

nganggtgga ttnagagaca agccgngnaa acncngngan nnctancaca catgttactg   1080

cctnagnggn ctntcngtgn nncagnacnn ttggtnaaan gacnnngann ctccnccntt   1140

nnctcnnnan ntnntnggnn nntacncnaa nnnnctngan ccnntncanc nnnnnnnnnn   1200

nnnnnnnnnn nnnnnnnnnn nnnnnnnnnn nnnnnnn                            1237
```

COMPOSITIONS AND METHODS OF INCREASING STRESS TOLERANCE IN PLANTS

RELATED APPLICATIONS

This application is a continuation of U.S. Ser. No. 10/160,764, filed May 31, 2002, now issued U.S. Pat. No. 7,172,881, which claims the benefit of U.S. Ser. No. 60/294,766, filed May 31, 2001 and U.S. Ser. No. 60/348,909 filed Oct. 22, 2001 each of which are incorporated herein by reference in their entireties.

FIELD OF THE INVENTION

The invention relates in part to novel plant farnesyl transferase alpha and beta subunit polynucleotides and polypeptides. Also included are transgenic plants expressing the novel polynucleotides and polypeptides. The invention also includes transgenic plant cells, tissues and plants having novel phenotypes resulting from the expression of these polynucleotides in either the sense or antisense orientation.

BACKGROUND OF THE INVENTION

Most higher plants encounter at least transient decreases in relative water content at some stage of their life cycle and, as a result, have evolved a number of desiccation protection mechanisms. If however, the change in water deficit is prolonged the effects on the plants growth and development can be profound. Decreased water content due to drought, cold or salt stress can irreparably damage plant cells which in turn limits plant growth and crop productivity in agriculture.

Plants respond to adverse conditions of drought, salinity and cold with a variety of morphological and physiological changes. Although our understanding of plant tolerance mechanisms to these stresses is incomplete, the plant hormone abscisic acid (ABA) is believed to be an essential mediator between environmental stimulus and plant responses. ABA levels increase in response to water deficits and exogenously applied ABA mimics many of the responses induced by water-stress. Once ABA is synthesized it causes the closure of the leaf stomata thereby decreasing water loss through transpiration.

The identification of genes that transduce ABA into a cellular response opens the possibility of exploiting these regulators to enhance desiccation tolerance in crop species. In principle, these ABA signaling genes can be coupled with the appropriate controlling elements to allow optimal plant growth, development and productivity. Thus, not only would these genes allow the genetic tailoring of crops to withstand transitory environmental stresses, but they should also broaden the environments where traditional crops can be grown.

The recent isolation of an *Arabidopsis thaliana* mutant, era1, is hypersensitive to ABA and has been shown to also be tolerant to conditions of water deprivation. ERA1 has been identified as a β subunit of farnesyl transferase. Farnesyl transferase is a heterodimeric enzyme that provides the specific addition of a farnesyl pyrophosphate moiety onto the substrate target sequence. The target sequence is defined as a sequence of four amino acids which are present at the carboxy terminus of the protein and is referred to as a CaaX motif in which the "C" is cysteine, "a" is any aliphatic amino acid and "X" is any amino acid. The α subunit is common with a second prenylation enzyme, geranylgeranyl transferase, that has a different β subunit and adds a geranylgeranyl isoprenyl pyrophosphate moiety to the target sequence.

Prenylation is a multistep pathway which includes prenylation of the cysteine residue of the CaaX site, cleavage of the -aaX tripeptide and methylation of the prenyl-cysteine residue. Potentially, each of these steps could represent a target for genetic manipulation of the prenylation process to generate a desired phenotype such as stress tolerance.

In plants, prenylation has been linked to cell cycle control, meristem development, and phytohormone signal transduction, however, few details of the role of prenylation, the substrate proteins or the extent to which the plant system will be analogous to the mammalian and yeast systems are known. The most characterized substrates for CaaX modification are the Ras and a-factor proteins of yeast. Although there are three steps to complete protein maturation, abolition or modification of any one step does not necessarily result in cessation of target biological activities. Ras function is attenuated if the -aaX tripeptide is not cleaved but not abolished and some proteins retain the -aaX tripeptide after farnesylation. These observations may be substrate specific as, in contrast, there are examples indicating some proteins are fully functional only after being properly prenylated such as in regulating processes such as mitogen response in mammals and mating pheromone in yeast.

In *Arabidopsis thaliana*, more than 600 proteins contain a CaaX motif, suggesting a role for the post-translational modification by prenylation in numerous cellular processes. In *Arabidopsis thaliana*, it has been demonstrated that the loss-of-function of the β-subunit of farnesyl transferase will result in a ABA-hypersensitive phenotype. Although it is still not clear why plants lacking the functional β-subunit of farnesyl transferase become more sensitive to ABA, it clearly suggests that protein prenylation is involved in regulation of the homeostasis of ABA sensitivity. The balance of ABA cellular responses, whether more sensitive or less sensitive to ABA, is possibly regulated by the relative activities of prenylated proteins.

This invention is directed at the manipulation of the farnesyl transferase (FT) subunits, either α or β (FTA, FTB) to alter farnesyl transferase enzyme expression and activity. Farnesyl transferase catalyses the first step of farnesylation in which a 15-carbon farnesyl moiety is added to the cysteine residue of the target sequence CaaX. Included in this invention are vector constructs containing FTA or FTB sequences under the control of appropriate regulatory sequences to produce phenotypes such as, but not limited to, water-stress tolerance, increased biomass accumulation, increased yield or delayed senescence. Manipulation of the FTA subunit may also affect the activity of geranylgeranyl transferase and the phenoytypes associated with this manipulation are encompassed by this invention.

SUMMARY OF THE INVENTION

The present invention is based in part upon the discovery of novel farnesyl transferase nucleic acid sequences and polypeptides from *Arabidopsis thaliana, Brassica napus, Glycine max* and *Zea maize*. The nucleic acids, polynucleotides, proteins and polypeptides, or fragments thereof described herein are collectively referred to as FT nucleic acids and polypeptides.

Accordingly, in one aspect, the invention provides an isolated nucleic acid molecule that includes the sequence of SEQ ID NO:1, SEQ ID NO:6, SEQ ID NO:8, SEQ ID NO:31, SEQ ID NO:34, or SEQ ID NO:37, or a fragment, homolog, analog or derivative thereof. The nucleic acid can include, e.g., a nucleic acid sequence encoding a polypeptide at least 99% identical to a polypeptide that includes the amino acid sequences of SEQ ID NO:5, SEQ ID NO:7, or SEQ ID NO:9, SEQ ID NO:33, SEQ ID NO:36, or SEQ ID NO:37, a nucleic acid sequence encoding a polypeptide at least 85% identical to a polypeptide that includes the amino acid sequences of SEQ ID NO:5, SEQ ID NO:7, or SEQ ID NO:9 or a nucleic acid sequence encoding a polypeptide at least 99% identical to a polypeptide that includes the amino acid sequences of SEQ ID NO:33, SEQ ID NO:36, or SEQ ID NO:39 The nucleic acid can be, e.g., a genomic DNA fragment, or a cDNA molecule.

The invention also includes the nucleic acid sequences of SEQ ID NO: 2, 3, 4, 29, 30, 32, 35, 38, 40-57 or 58. Also included in the invention is a vector containing one or more of the nucleic acids described herein, and a cell containing the vectors or nucleic acids described herein. In some aspects the FT nucleic acid is operably linked to a promoter. Examples of promoter includes a constitutive promoter (e.g., 35S CaMV, MuA), an ABA inducible promoter (e.g., RD29A), tissue specific promoters (e.g., CUT1) or a guard cell-specific promoter (e.g., 35S, MuA and RD29A)

The invention is also directed to host cells transformed with a vector comprising any of the nucleic acid molecules described herein.

The invention is also directed to plants and cells transformed with a FT nucleic acid or a vector comprising a FT nucleic acid. Also included in the invention is the seed, and progeny of the transformed plants or cells.

The invention is also further directed to the use of plants and cells transformed with a FT nucleic acid or a vector comprising a FT nucleic acid in generation of mutant libraries and genetic screening protocols.

In a further aspect, the invention includes a substantially purified FT polypeptide, e.g., any of the FT polypeptides encoded by an FT nucleic acid, and fragments, homologs, analogs, and derivatives thereof.

In still a further aspect, the invention provides an antibody that binds specifically to an FT polypeptide. The antibody can be, e.g., a monoclonal or polyclonal antibody, and fragments, homologs, analogs, and derivatives thereof. The invention is also directed to isolated antibodies that bind to an epitope on a polypeptide encoded by any of the nucleic acid molecules described above.

The invention also includes a method of producing a transgenic plant which has increased stress resistance such as, but not limited to, water deficit, or increased biomass, increased yield; delayed senescence or increases ABA sensitivity by introducing into one or more cells of a plant a compound that alters FT expression or activity in the plant. In one aspect the compound is a FT nucleic acid. The nucleic acid can be for example a inhibitor or farnesylation or genanylgerylation. Alternatively, the compound is a FT double stranded RNA-inhibition hair-pin nucleic acid or FT antisense nucleic acid.

The invention further provides a method for producing a FT polypeptide by providing a cell containing an FT nucleic acid, e.g., a vector that includes a FT nucleic acid, and culturing the cell under conditions sufficient to express the FT polypeptide encoded by the nucleic acid. The expressed FT polypeptide is then recovered from the cell. Preferably, the cell produces little or no endogenous FT polypeptide. The cell can be, e.g., a prokaryotic cell or eukaryotic cell.

The invention is also directed to methods of identifying a FT polypeptide or nucleic acid in a sample by contacting the sample with a compound that specifically binds to the polypeptide or nucleic acid, and detecting complex formation, if present.

The invention further provides methods of identifying a compound that modulates the activity of a FT polypeptide by contacting a FT polypeptide with a compound and determining whether the FT polypeptide activity is modified.

The invention is also directed to compounds that modulate FT polypeptide activity identified by contacting a FT polypeptide with the compound and determining whether the compound modifies activity of the FT polypeptide, binds to the FT polypeptide, or binds to a nucleic acid molecule encoding a FT polypeptide.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 8 is an illustration of the homology among FTA nucleic acid (A) and amino acid (B) sequences from various plant species based on ClustalW analysis (percent identity shown).

FIG. 9 is an illustration of the homology among FTB nucleic acid and amino acid sequences from various plant species based on ClustalW analysis (percent identity shown).

DETAILED DESCRIPTION OF INVENTION

Figure 1:
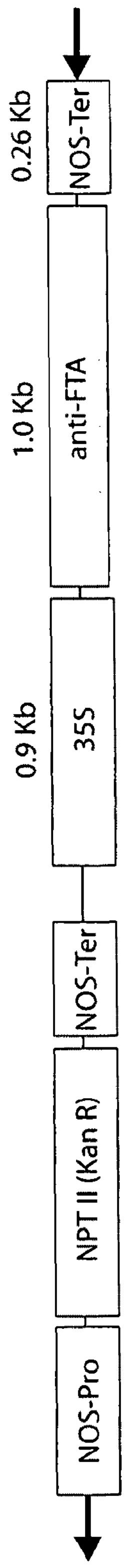
FIG. 1 is an illustration depicting the pBI121 antisense FTA vector construct.

The present invention provides a novel farnesyl transferase (FT) nucleic acid sequences (SEQ ID NO:1, SEQ ID NO:6, SEQ ID NO:8, SEQ ID NO:31, SEQ ID NO:34, or SEQ ID NO:37) and their encoded polypeptides (SEQ ID NO:5, SEQ ID NO:7, SEQ ID NO:9, SEQ ID NO:33, SEQ ID NO:36 or SEQ ID NO:39) isolated from *Brassica napus* (Bn), *Arabidopsis thaliana* (At), *Glycine max* (Gm) and *Zea maize* (Zm). The sequences are collectively referred to as "FT nucleic acids" or FT polynucleotides" and the corresponding encoded polypeptide is referred to as a "FT polypeptide" or "FT protein". Farnesyl transferase subunits, Alpha (α) and Beta (β) are referred to as FTA and FTB, respectively. *Glycine max* is also referred to as soy or soybean throughout the specification. *Zea maize* is also referred to as *Zea mays* or corn throughout the specification. These terms are interchangeable. Unless indicated otherwise, "FT" is meant to refer to any of the novel sequences disclosed herein.

Table A provides a summary of the FT nucleic acids and their encoded polypeptides.

TABLE A

Sequences and Corresponding SEQ ID Numbers

| FT Assignment | Identification | SEQ ID NO (nucleic acid) | SEQ ID NO (polypeptide) |
|---|---|---|---|
| 1 | *Arabidopsis thaliana* farnesyl transerase alpha subunit | 1 | 5 |
| 2 | *Brassica napus* farnesyl transerase alpha subunit | 6 | 7 |
| 3 | *Brassica napus* farnesyl transerase beta subunit | 8 | 9 |
| 4 | *Glycine max* alpha subunit | 31 | 33 |
| 5 | *Glycine max* beta subunit | 34 | 36 |
| 6 | *Zea maize* beta subunit | 37 | 39 |

Also included in the invention are nucleic acids that are complementary to the disclosed FT nucleic acid sequences. For example, SEQ ID NO: 2, 3, 29, 30, 32, 35 or 38. Further provide by the invention are constructs comprising FT antisense nucleic acid molecules as disclosed in for example SEQ ID NO:4, 40-58.

Based on their structural and functional relatedness to known farnesyl transferase proteins, the FT proteins are novel members of the farnesyl transferase family of proteins. (See, Example 3) FT nucleic acids, and their encoded polypeptides, according to the invention are useful in a variety of applications and contexts. For example, the nucleic acids can be used produce transgenic plants that have an increase resistance to biotic and abiotic stresses, e.g., chilling stress, salt stress, heat stress, water stress, wound healing, pathogen challenge, or herbicides.

This invention includes methods to up-regulate the FT enzyme activity in transgenic plants, cells and tissue cultures by using an over-expression vector construct and methods to down-regulate the FT enzyme activity in transgenic plants, cells and tissue cultures by using a double stranded RNA-inhibition, hairpin vector construct. These methods are by way of example to produce the up-regulation or down-regulation effects and are not meant to be limiting as to the method of achieving this outcome.

Additionally, the nucleic acids and polypeptides according to the invention may be used as targets for the identification of small molecules that modulate or inhibit, FT activity. Alternatively, the FT nucleic acids and polypeptides can be used to identify proteins that are members of the farnesyl transferase family of associated proteins.

Further, the modulation or inhibition of FT activity maybe achieved by modifications to the nucleic acid sequences of FTA or FTB by the actions of chemical mutagens or irradiation. Expression of FT nucleic acids which encode enzymatically non-functional FT polypeptides can be used to evoke a dominant-negative inhibitory effect on FT activity.

Additional utilities for FT nucleic acids and polypeptides according to the invention are disclosed herein.

FT Nucleic Acids

The nucleic acids of the invention include those that encode a FT polypeptide or protein. As used herein, the terms polypeptide and protein are interchangeable.

In some embodiments, a FT nucleic acid encodes a mature FT polypeptide. As used herein, a "mature" form of a polypeptide or protein described herein relates to the product of a naturally occurring polypeptide or precursor form or proprotein. The naturally occurring polypeptide, precursor or proprotein includes, by way of nonlimiting example, the full length gene product, encoded by the corresponding gene. Alternatively, it may be defined as the polypeptide, precursor or proprotein encoded by an open reading frame described herein. The product "mature" form arises, again by way of nonlimiting example, as a result of one or more naturally occurring processing steps that may take place within the cell in which the gene product arises. Examples of such processing steps leading to a "mature" form of a polypeptide or protein include the cleavage of the N-terminal methionine residue encoded by the initiation codon of an open reading frame, or the proteolytic cleavage of a signal peptide or leader sequence. Thus a mature form arising from a precursor polypeptide or protein that has residues 1 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Further as used herein, a "mature" form of a polypeptide or protein may arise from a step of post-translational modification other than a proteolytic cleavage event. Such additional processes include, by way of non-limiting example, glycosylation, myristoylation or phosphorylation. In general, a mature polypeptide or protein may result from the operation of only one of these processes, or a combination of any of them.

Among the FT nucleic acids is the nucleic acid whose sequence is provided in SEQ ID NO:1, SEQ ID NO:6, SEQ ID NO:8, SEQ ID NO:31, SEQ ID NO:34, or SEQ ID NO:37 or a fragment thereof. Additionally, the invention includes mutant or variant nucleic acids of SEQ ID NO:1, SEQ ID NO:6, SEQ ID NO:8, SEQ ID NO:31, SEQ ID NO:34, or SEQ ID NO:37, or a fragment thereof, any of whose bases may be changed from the corresponding base shown in SEQ ID NO:1, SEQ ID NO:6, SEQ ID NO:8, SEQ ID NO:31, SEQ ID NO:34, or SEQ ID NO:37, while still encoding a protein that maintains at least one of its FT-like activities and physiological functions. The invention further includes the complement of the nucleic acid sequence of SEQ ID NO:1, SEQ ID NO:6, SEQ ID NO:8, SEQ ID NO:31, SEQ ID NO:34, or SEQ ID NO:37, including fragments, derivatives, analogs and homologs thereof. The invention additionally includes nucleic acids or nucleic acid fragments, or complements thereto, whose structures include chemical modifications.

One aspect of the invention pertains to isolated nucleic acid molecules that encode FT proteins or biologically active portions thereof. Also included are nucleic acid fragments sufficient for use as hybridization probes to identify FT-encoding nucleic acids (e.g., FT mRNA) and fragments for use as polymerase chain reaction (PCR) primers for the amplification or mutation of FT nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but preferably is double-stranded DNA.

"Probes" refer to nucleic acid sequences of variable length, preferably between at least about 10 nucleotides (nt), 100 nt, or as many as about, e.g., 6,000 nt, depending on use. Probes are used in the detection of identical, similar, or complementary nucleic acid sequences. Longer length probes are usually obtained from a natural or recombinant source, are highly specific and much slower to hybridize than oligomers. Probes may be single- or double-stranded and designed to have specificity in PCR, membrane-based hybridization technologies, or ELISA-like technologies.

An "isolated" nucleic acid molecule is one that is separated from other nucleic acid molecules that are present in the natural source of the nucleic acid. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated FT nucleic acid molecule can contain less than about 50 kb, 25 kb, 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the present invention, e.g., a nucleic acid molecule having the nucleotide sequence of SEQ ID NO:1, SEQ ID NO:6, SEQ ID NO:8, SEQ ID NO:31, SEQ ID NO:34, or SEQ ID NO:37, or a complement of any one of the nucleotide sequences, can be isolated using standard molecular biology techniques and the sequence information provided herein. Using all or a portion of the nucleic acid sequence of SEQ ID NO:1, SEQ ID NO:6, SEQ ID NO:8, SEQ ID NO:31, SEQ ID NO:34, or SEQ ID NO:37 as a hybridization probe, FT nucleic acid sequences can be isolated using standard hybridization and cloning techniques (e.g., as described in Sambrook et al., eds., MOLECULAR CLONING: A LABORATORY MANUAL $2^{nd}$ Ed., Cold Spring Harbor Laboratory Press, Cold Spring Harbor, N.Y., 1989; and Ausubel, et al., eds., CURRENT PROTOCOLS IN MOLECULAR BIOLOGY, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to FT nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. In one embodiment, an oligonucleotide comprising a nucleic acid molecule less than 100 nt in length would further comprise at least 6 contiguous nucleotides of SEQ ID NO:1, SEQ ID NO:6, SEQ ID NO:8, SEQ ID NO:31, SEQ ID NO:34, or SEQ ID NO:37, or a complement thereof. Oligonucleotides may be chemically synthesized and may be used as probes.

In another embodiment, an isolated nucleic acid molecule of the invention includes a nucleic acid molecule that is a complement of the nucleotide sequence shown in SEQ ID NO:1, SEQ ID NO:6, SEQ ID NO:8, SEQ ID NO:31, SEQ ID NO:34, or SEQ ID NO:37. For example, a complimentary nucleic acid sequence of SEQ ID NO:2, SEQ ID NO:3, SEQ ID NO:29, SEQ ID NO:30, SEQ ID NO:32, SEQ ID NO:35 or SEQ ID NO:38. In another embodiment, an isolated nucleic acid molecule of the invention comprises a nucleic acid molecule that is a complement of the nucleotide sequence shown in SEQ ID NO:1, SEQ ID NO:6, SEQ ID NO:8, SEQ ID NO:31, SEQ ID NO:34, or SEQ ID NO:37, or a portion of this nucleotide sequence. A nucleic acid molecule that is complementary to the nucleotide sequence shown in SEQ ID NO:1, SEQ ID NO:6, SEQ ID NO:8, SEQ ID NO:31, SEQ ID NO:34, or SEQ ID NO:37 is one that is sufficiently complementary to the nucleotide sequence shown in SEQ ID NO:1, SEQ ID NO:6, SEQ ID NO:8, SEQ ID NO:31, SEQ ID NO:34, or SEQ ID NO:37 that it can hydrogen bond with little or no mismatches to the nucleotide sequence shown in SEQ ID NO:1, SEQ ID NO:6, SEQ ID NO:8, SEQ ID NO:31, SEQ ID NO:34, or SEQ ID NO:37, thereby forming a stable duplex.

As used herein, the term "complementary" refers to Watson-Crick or Hoogsteen base pairing between nucleotide units of a nucleic acid molecule, and the term "binding" means the physical or chemical interaction between two polypeptides or compounds or associated polypeptides or compounds or combinations thereof. Binding includes ionic, non-ionic, Von der Waals, hydrophobic interactions, etc. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Moreover, the nucleic acid molecule of the invention can comprise only a portion of the nucleic acid sequence of SEQ ID NO:1, SEQ ID NO:6, SEQ ID NO:8, SEQ ID NO:31, SEQ ID NO:34, or SEQ ID NO:37, e.g., a fragment that can be used as a probe or primer, or a fragment encoding a biologically active portion of FT. Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 70%, 80%, 85%, 90%, 95%, 98%, or even 99% identity (with a preferred identity of 80-99%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., Current Protocols in Molecular Biology, John Wiley & Sons, New York, N.Y., 1993, and below. An exemplary program is the Gap program (Wisconsin Sequence Analysis Package, Version 8 for UNIX, Genetics Computer Group, University Research Park, Madison, Wis.) using the default settings, which uses the algorithm of Smith and Waterman (Adv. Appl. Math., 1981, 2: 482-489, which is incorporated herein by reference in its entirety).

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of a FT polypeptide. Isoforms can be expressed in different tissues of the same organism as a result of, for example, alternative splicing of RNA. Alternatively, isoforms can be encoded by different genes. Homologous nucleotide sequences also include, but are not limited to, naturally occurring allelic variations and mutations of the nucleotide sequences set forth herein. Homologous nucleic acid sequences include those nucleic acid sequences that encode conservative amino acid substitutions (see below) in SEQ ID NO:5, SEQ ID NO:7, SEQ ID NO:9, SEQ ID NO:33, SEQ ID NO:36 or SEQ ID NO:39, as well as a polypeptide having FT activity, e.g. substrate binding.

The nucleotide sequence determined from the cloning of the *Arabidopsis thaliana* FT gene allows for the generation of probes and primers designed for use in identifying and/or cloning FT homologues in other cell types, e.g., from other tissues, as well as FT homologues from other plants. The probe/primer typically comprises a substantially purified oligonucleotide. The oligonucleotide typically comprises a region of nucleotide sequence that hybridizes under stringent conditions to at least about 12, 25, 50, 100, 150, 200, 250, 300, 350 or 400 or more consecutive sense strand nucleotide sequence of SEQ ID NO:1, SEQ ID NO:6, SEQ ID NO:8, SEQ ID NO:31, SEQ ID NO:34, or SEQ ID NO:37; or an anti-sense strand nucleotide sequence of SEQ ID NO:1, SEQ ID NO:6, SEQ ID NO:8, SEQ ID NO:31, SEQ ID NO:34, or SEQ ID NO:37; or of a naturally occurring mutant of SEQ ID NO:1, SEQ ID NO:6, SEQ ID NO:8, SEQ ID NO:31, SEQ ID NO:34, or SEQ ID NO:37.

Probes based on the *Arabidopsis thaliana* FT nucleotide sequence can be used to detect transcripts or genomic sequences encoding the same or homologous proteins. In various embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a FT protein, such as by measuring a level of a FT-encoding nucleic acid in a sample of cells from a subject e.g., detecting FT mRNA levels or determining whether a genomic FT gene has been mutated or deleted.

A "polypeptide having a biologically active portion of FT" refers to polypeptides exhibiting activity similar, but not necessarily identical to, an activity of a polypeptide of the present invention, including mature forms, as measured in a particular biological assay, with or without dose dependency. A nucleic acid fragment encoding a "biologically active portion of FT" can be prepared by isolating a portion of SEQ ID NO:1, SEQ ID NO:6, SEQ ID NO:8, SEQ ID NO:31, SEQ ID NO:34, or SEQ ID NO:37 that encodes a polypeptide having a FT biological activity (biological activities of the FT proteins are described below), expressing the encoded portion of FT protein (e.g., by recombinant expression in vitro) and assessing the activity of the encoded portion of FT. In another embodiment, a nucleic acid fragment encoding a biologically active portion of FT includes one or more regions.

FT Variants

The invention further encompasses nucleic acid molecules that differ from the nucleotide sequences shown in SEQ ID NO:1, SEQ ID NO:6, SEQ ID NO:8, SEQ ID NO:31, SEQ ID NO:34, or SEQ ID NO:37 due to the degeneracy of the genetic code. These nucleic acids thus encode the same FT protein as that encoded by the nucleotide sequence shown in SEQ ID NO:1, SEQ ID NO:6, SEQ ID NO:8, SEQ ID NO:31, SEQ ID NO:34, or SEQ ID NO:37, e.g., the polypeptide of SEQ ID NO:5, SEQ ID NO:7, SEQ ID NO:9, SEQ ID NO:33, SEQ ID NO:36 or SEQ ID NO:39. In another embodiment, an isolated nucleic acid molecule of the invention has a nucleotide sequence encoding a protein having an amino acid sequence shown in SEQ ID NO:5, SEQ ID NO:7, SEQ ID NO:9, SEQ ID NO:33, SEQ ID NO:36 or SEQ ID NO:39.

In addition to the *Arabidopsis thaliana* FT nucleotide sequence shown in SEQ ID NO:1, SEQ ID NO:6, SEQ ID NO:8, SEQ ID NO:31, SEQ ID NO:34, or SEQ ID NO:37, it will be appreciated by those skilled in the art that DNA sequence polymorphisms that lead to changes in the amino acid sequences of FT may exist within a population (e.g., the plant). Such genetic polymorphism in the FT gene may exist among individuals within a population due to natural allelic variation. As used herein, the terms "gene" and "recombinant gene" refer to nucleic acid molecules comprising an open reading frame encoding a FT protein, preferably a plant FT protein. Such natural allelic variations can typically result in 1-5% variance in the nucleotide sequence of the FT gene. Any and all such nucleotide variations and resulting amino acid polymorphisms in FT that are the result of natural allelic variation and that do not alter the functional activity of FT are intended to be within the scope of the invention.

Moreover, nucleic acid molecules encoding FT proteins from other species, and thus that have a nucleotide sequence that differs from the sequence of SEQ ID NO:1, SEQ ID NO:6, SEQ ID NO:8, SEQ ID NO:31, SEQ ID NO:34, or SEQ ID NO:37 are intended to be within the scope of the invention. Nucleic acid molecules corresponding to natural allelic variants and homologues of the FT cDNAs of the invention can be isolated based on their homology to the *Arabidopsis thaliana* FT nucleic acids disclosed herein using the cDNAs, or a portion thereof, as a hybridization probe according to standard hybridization techniques under stringent hybridization conditions.

Accordingly, in another embodiment, an isolated nucleic acid molecule of the invention is at least 6 nucleotides in length and hybridizes under stringent conditions to the nucleic acid molecule comprising the nucleotide sequence of SEQ ID NO:1, SEQ ID NO:6, SEQ ID NO:8, SEQ ID NO:31, SEQ ID NO:34, or SEQ ID NO:37. In another embodiment, the nucleic acid is at least 10, 25, 50, 100, 250, 500 or 750 nucleotides in length. In another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding FT proteins derived from species other than *Arabidopsis thaliana*) or other related sequences (e.g., paralogs) can be obtained by low, moderate or high stringency hybridization with all or a portion of the particular sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point ($T_m$) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in CURRENT PROTOCOLS IN MOLECULAR BIOLOGY, John Wiley & Sons, N.Y. (1989), 6.3.1-6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C. This hybridization is followed by one or more washes in 0.2×SSC, 0.01% BSA at 50° C. An isolated nucleic acid molecule of the invention that hybridizes under stringent conditions to the sequence of SEQ ID NO:1, SEQ ID NO:6, SEQ ID NO:8, SEQ ID NO:31, SEQ ID NO:34, or SEQ ID NO:37 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of SEQ ID NO:1, SEQ ID NO:6, SEQ ID NO:8, SEQ ID NO:31, SEQ ID NO:34, or SEQ ID NO:37, or fragments, analogs or derivatives thereof, under conditions of moderate stringency is provided. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well known in the art. See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY.

In a third embodiment, a nucleic acid that is hybridizable to the nucleic acid molecule comprising the nucleotide sequence of SEQ ID NO:1, SEQ ID NO:6, SEQ ID NO:8, SEQ ID NO:31, SEQ ID NO:34, or SEQ ID NO:37, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY; Shilo and Weinberg, 1981, *Proc Natl Acad Sci USA* 78: 6789-6792.

Conservative Mutations

In addition to naturally-occurring allelic variants of the FT sequence that may exist in the population, the skilled artisan will further appreciate that changes can be introduced by mutation into the nucleotide sequence of SEQ ID NO:1, SEQ ID NO:6, SEQ ID NO:8, SEQ ID NO:31, SEQ ID NO:34, or SEQ ID NO:37, thereby leading to changes in the amino acid sequence of the encoded FT protein, without altering the functional ability of the FT protein. For example, nucleotide substitutions leading to amino acid substitutions at "non-essential" amino acid residues can be made in the sequence of SEQ ID NO:1, SEQ ID NO:6, SEQ ID NO:8, SEQ ID NO:31, SEQ ID NO:34, or SEQ ID NO:37. A "non-essential" amino acid residue is a residue that can be altered from the wild-type sequence of FT without altering the biological activity, whereas an "essential" amino acid residue is required for biological activity. For example, amino acid residues that are conserved among the FT proteins of the present invention, are predicted to be particularly unamenable to alteration.

Another aspect of the invention pertains to nucleic acid molecules encoding FT proteins that contain changes in amino acid residues that are not essential for activity. Such FT proteins differ in amino acid sequence from SEQ ID NO:5, SEQ ID NO:7, SEQ ID NO:9, SEQ ID NO:33, SEQ ID NO:36 or SEQ ID NO:39, yet retain biological activity. In one embodiment, the isolated nucleic acid molecule comprises a nucleotide sequence encoding a protein, wherein the protein comprises an amino acid sequence at least about 75% homologous to the amino acid sequence of SEQ ID NO:5, SEQ ID NO:7, SEQ ID NO:9, SEQ ID NO:33, SEQ ID NO:36 or SEQ ID NO:39. Preferably, the protein encoded by the nucleic acid is at least about 80% homologous to SEQ ID NO:5, SEQ ID NO:7, SEQ ID NO:9, SEQ ID NO:33, SEQ ID NO:36 or SEQ ID NO:39, more preferably at least about 90%, 95%, 98%, and most preferably at least about 99% homologous to SEQ ID NO:5, SEQ ID NO:7, SEQ ID NO:9, SEQ ID NO:33, SEQ ID NO:36 or SEQ ID NO:39.

An isolated nucleic acid molecule encoding a FT protein homologous to the protein of SEQ ID NO:5, SEQ ID NO:7, SEQ ID NO:9, SEQ ID NO:33, SEQ ID NO:36 or SEQ ID NO:39 can be created by introducing one or more nucleotide substitutions, additions or deletions into the nucleotide sequence of SEQ ID NO:1, SEQ ID NO:6, SEQ ID NO:8, SEQ ID NO:31, SEQ ID NO:34, or SEQ ID NO:37, such that one or more amino acid substitutions, additions or deletions are introduced into the encoded protein.

Mutations can be introduced into the nucleotide sequence of SEQ ID NO:1, SEQ ID NO:6, SEQ ID NO:8, SEQ ID NO:31, SEQ ID NO:34, or SEQ ID NO:37 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in FT is replaced with another amino acid residue from the same side chain family. Alternatively, in another embodiment, mutations can be introduced randomly along all or part of a FT coding sequence, such as by saturation mutagenesis, and the resultant mutants can be screened for FT biological activity to identify mutants that retain activity. Following mutagenesis of SEQ ID NO:1, SEQ ID NO:6, SEQ ID NO:8, SEQ ID NO:31, SEQ ID NO:34, or SEQ ID NO:37 the encoded protein can be expressed by any recombinant technology known in the art and the activity of the protein can be determined.

In one embodiment, a mutant FT protein can be assayed for (1) the ability to form protein:protein interactions with other FT proteins, other cell-surface proteins, or biologically active portions thereof, (2) complex formation between a mutant FT protein and a FT receptor; (3) the ability of a mutant FT protein to bind to an intracellular target protein or biologically active portion thereof, (e.g., avidin proteins); (4) the ability to bind FT protein; or (5) the ability to specifically bind an anti-FT protein antibody.

Antisense FT Nucleic Acids

Another aspect of the invention pertains to isolated antisense nucleic acid molecules that are hybridizable to or complementary to the nucleic acid molecule comprising the nucleotide sequence of SEQ ID NO:1, SEQ ID NO:6, SEQ ID NO:8, SEQ ID NO:31, SEQ ID NO:34, or SEQ ID NO:37, or fragments, analogs or derivatives thereof. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. In specific aspects, antisense nucleic acid molecules are provided that comprise a sequence complementary to at least about 10, 25, 50, 100, 250 or 500 nucleotides or an entire FT coding strand, or to only a portion thereof. Nucleic acid molecules encoding fragments, homologs, derivatives and analogs of a FT protein of SEQ ID NO:5, SEQ ID NO:7, SEQ ID NO:9, SEQ ID NO:33, SEQ ID NO:36 or SEQ ID NO:39, or antisense nucleic acids complementary to a FT nucleic acid sequence of SEQ ID NO:1, SEQ ID NO:6, SEQ ID NO:8, SEQ ID NO:31, SEQ ID NO:34, or SEQ ID NO:37 are additionally provided.

In one embodiment, an antisense nucleic acid molecule is antisense to a "coding region" of the coding strand of a nucleotide sequence encoding FT (e.g. SEQ ID NO:1, SEQ ID NO:6, SEQ ID NO:8, SEQ ID NO:31, SEQ ID NO:34, or SEQ ID NO:37). The term "coding region" refers to the region of the nucleotide sequence comprising codons which are translated into amino acid residues (e.g., the protein coding region of *Arabidopsis thaliana* FT corresponds to SEQ ID NO:5, SEQ ID NO:7, SEQ ID NO:9, SEQ ID NO:33, SEQ ID NO:36 or SEQ ID NO:39). In another embodiment, the antisense nucleic acid molecule is antisense to a "noncoding region" of the coding strand of a nucleotide sequence encoding FT (e.g. SEQ ID NO:1, SEQ ID NO:6, SEQ ID NO:8, SEQ ID NO:31, SEQ ID NO:34, or SEQ ID NO:37). The term "noncoding region" refers to 5' and 3' sequences which flank the coding region that are not translated into amino acids (i.e., also referred to as 5' and 3' untranslated regions).

In various embodiments the anti-sense FT nucleic acid molecule includes the sequences of SEQ ID NO: 2, 3, 29, 30, 32, 35 or 38.

Given the coding strand sequences encoding FT disclosed herein (e.g., SEQ ID NO:1, SEQ ID NO:6, SEQ ID NO:8, SEQ ID NO:31, SEQ ID NO:34, or SEQ ID NO:37), antisense nucleic acids of the invention can be designed according to the rules of Watson and Crick or Hoogsteen base pairing. The antisense nucleic acid molecule can be complementary to the entire coding region of FT mRNA, but more preferably is an oligonucleotide that is antisense to only a portion of the coding or noncoding region of FT mRNA. For example, the antisense oligonucleotide can be complementary to the region surrounding the translation start site of FT mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta- D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are generated in situ such that they hybridize with or bind to cellular mRNA and/or genomic DNA encoding a FT protein to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res* 15: 6625-6641). The antisense nucleic acid molecule can also comprise a 2'-o-methylribonucleotide (Inoue et al. (1987) *Nucleic Acids Res* 15: 6131-6148) or a chimeric RNA-DNA analogue (Inoue et al. (1987) *FEBS Lett* 215: 327-330).

Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in applications.

Double Stranded RNA Inhibition (RNAi) by Hairpin Nucleic Acids

Another aspect of the invention pertains to the use of post transcriptional gene silencing (PTGS) to repress gene expression. Double stranded RNA can initiate the sequence specific repression of gene expression in plants and animals. Double stranded RNA is processed to short duplex oligomers of 21-23 nucleotides in length. These small interfering RNA's suppress the expression of endogenous and heterologous genes in a sequence specific manner (Fire et al. Nature 391: 806-811, Carthew, Curr. Opin. in Cell Biol., 13:244-248, Elbashir et al., Nature 411:494-498). A RNAi suppressing construct can be designed in a number of ways, for example, transcription of a inverted repeat which can form a long hair pin molecule, inverted repeats separated by a spacer sequence that could be an unrelated sequence such as GUS or an intron sequence. Transcription of sense and antisense strands by opposing promoters or cotranscription of sense and antisense genes.

FT Ribozymes and PNA Moieties

In still another embodiment, an antisense nucleic acid of the invention is a ribozyme. Ribozymes are catalytic RNA molecules with ribonuclease activity that are capable of cleaving a single-stranded nucleic acid, such as a mRNA, to which they have a complementary region. Thus, ribozymes (e.g., hammerhead ribozymes (described in Haselhoff and Gerlach (1988) *Nature* 334:585-591)) can be used to catalytically cleave FT mRNA transcripts to thereby inhibit translation of FT mRNA. A ribozyme having specificity for a FT-encoding nucleic acid can be designed based upon the nucleotide sequence of a FT DNA disclosed herein (i.e., SEQ ID NO:1, SEQ ID NO:6, SEQ ID NO:8, SEQ ID NO:31, SEQ ID NO:34, or SEQ ID NO:37). For example, a derivative of a Tetrahymena L-19 IVS RNA can be constructed in which the nucleotide sequence of the active site is complementary to the nucleotide sequence to be cleaved in a FT-encoding mRNA. See, e.g., Cech et al. U.S. Pat. No. 4,987,071; and Cech et al. U.S. Pat. No. 5,116,742. Alternatively, FT mRNA can be used to select a catalytic RNA having a specific ribonuclease activity from a pool of RNA molecules. See, e.g., Bartel et al., (1993) *Science* 261:1411-1418.

Alternatively, FT gene expression can be inhibited by targeting nucleotide sequences complementary to the regulatory region of the FT (e.g., the FT promoter and/or enhancers) to form triple helical structures that prevent transcription of the FT gene in target cells. See generally, Helene. (1991) *Anticancer Drug Des.* 6: 569-84; Helene. et al. (1992) *Ann. N.Y. Acad. Sci.* 660:27-36; and Maher (1992) *Bioassays* 14: 807-15.

In various embodiments, the nucleic acids of FT can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorg Med Chem* 4: 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) above; Perry-O'Keefe et al. (1996) *PNAS* 93: 14670-675.

PNAs of FT can be used in therapeutic and diagnostic applications. For example, PNAs can be used as antisense or antigene agents for sequence-specific modulation of gene expression by, e.g., inducing transcription or translation arrest or inhibiting replication. PNAs of FT can also be used, e.g., in the analysis of single base pair mutations in a gene by, e.g., PNA directed PCR clamping; as artificial restriction enzymes when used in combination with other enzymes, e.g., S1 nucleases (Hyrup B. (1996) above); or as probes or primers for DNA sequence and hybridization (Hyrup et al. (1996), above; Perry-O'Keefe (1996), above).

In another embodiment, PNAs of FT can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of FT can be generated that may combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) above). The synthesis of PNA-DNA chimeras can be performed as described in Hyrup (1996) above and Finn et al. (1996) *Nucl Acids Res* 24: 3357-63. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA (Mag et al. (1989) *Nucl Acid Res* 17: 5973-88). PNA monomers are then coupled in a stepwise manner to produce a chimeric molecule with a 5' PNA segment and a 3' DNA segment (Finn et al. (1996) above). Alternatively, chimeric molecules can be synthesized with a 5' DNA segment and a 3' PNA segment. See, Petersen et al. (1975) *Bioorg Med Chem Lett* 5: 1119-11124.

FT Polypeptides

A FT polypeptide of the invention includes the protein whose sequence is provided in SEQ ID NO:5, SEQ ID NO:7, OR SEQ ID NO:9. The invention also includes a mutant or variant protein any of whose residues may be changed from the corresponding residue shown in SEQ ID NO:5, SEQ ID NO:7, SEQ ID NO:9, SEQ ID NO:33, SEQ ID NO:36 or SEQ ID NO:39 while still encoding a protein that maintains its FT-like activities and physiological functions, or a functional fragment thereof. In some embodiments, up to 20% or more of the residues may be so changed in the mutant or variant protein. In some embodiments, the FT polypeptide according to the invention is a mature polypeptide.

In general, a FT-like variant that preserves FT-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

One aspect of the invention pertains to isolated FT proteins, and biologically active portions thereof, or derivatives, fragments, analogs or homologs thereof. Also provided are polypeptide fragments suitable for use as immunogens to raise anti-FT antibodies. In one embodiment, native FT proteins can be isolated from cells or tissue sources by an appropriate purification scheme using standard protein purification techniques. In another embodiment, FT proteins are produced by recombinant DNA techniques. Alternative to recombinant expression, a FT protein or polypeptide can be synthesized chemically using standard peptide synthesis techniques.

An "isolated" or "purified" protein or biologically active portion thereof is substantially free of cellular material or other contaminating proteins from the cell or tissue source from which the FT protein is derived, or substantially free from chemical precursors or other chemicals when chemically synthesized. The language "substantially free of cellular material" includes preparations of FT protein in which the protein is separated from cellular components of the cells from which it is isolated or recombinantly produced. In one embodiment, the language "substantially free of cellular material" includes preparations of FT protein having less than about 30% (by dry weight) of non-FT protein (also referred to herein as a "contaminating protein"), more preferably less than about 20% of non-FT protein, still more preferably less than about 10% of non-FT protein, and most preferably less than about 5% non-FT protein. When the FT protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of FT protein in which the protein is separated from chemical precursors or other chemicals that are involved in the synthesis of the protein. In one embodiment, the language "substantially free of chemical precursors or other chemicals" includes preparations of FT protein having less than about 30% (by dry weight) of chemical precursors or non-FT chemicals, more preferably less than about 20% chemical precursors or non-FT chemicals, still more preferably less than about 10% chemical precursors or non-FT chemicals, and most preferably less than about 5% chemical precursors or non-FT chemicals.

Biologically active portions of a FT protein include peptides comprising amino acid sequences sufficiently homologous to or derived from the amino acid sequence of the FT protein, e.g., the amino acid sequence shown in SEQ ID NO:5, SEQ ID NO:7, SEQ ID NO:9, SEQ ID NO:33, SEQ ID NO:36 or SEQ ID NO:39 that include fewer amino acids than the full length FT proteins, and exhibit at least one activity of a FT protein, e.g. substrate binding. Typically, biologically active portions comprise a domain or motif with at least one activity of the FT protein. A biologically active portion of a FT protein can be a polypeptide which is, for example, 10, 25, 50, 100 or more amino acids in length.

A biologically active portion of a FT protein of the present invention may contain at least one of the above-identified domains conserved between the FT proteins. Moreover, other biologically active portions, in which other regions of the protein are deleted, can be prepared by recombinant techniques and evaluated for one or more of the functional activities of a native FT protein.

A biologically active portion or a FT protein can be the N-terminal domain of the FT polypeptide. Alternatively, a biologically active portion or a FT protein can be the C-terminal domain of the FT polypeptide. Preferably, the biologically active portion comprises at least 75 amino acids of the C-terminal domain. More preferably, the biologically active portion comprises at least 25 amino acids of the C-terminal domain. Most preferably, the biologically active portion comprises at least 10 amino acids of the C-terminal.

In an embodiment, the FT protein has an amino acid sequence of SEQ ID NO:5, SEQ ID NO:7, SEQ ID NO:9, SEQ ID NO:33, SEQ ID NO:36 or SEQ ID NO:39. In other embodiments, the FT protein is substantially homologous to SEQ ID NO:5, SEQ ID NO:7, SEQ ID NO:9, SEQ ID NO:33, SEQ ID NO:36 or SEQ ID NO:39 and retains the functional activity of the protein of SEQ ID NO:5, SEQ ID NO:7, SEQ ID NO:9, SEQ ID NO:33, SEQ ID NO:36 or SEQ ID NO:39, yet differs in amino acid sequence due to natural allelic variation or mutagenesis, as described in detail below. Accordingly, in another embodiment, the FT protein is a protein that comprises an amino acid sequence at least 45% homologous to the amino acid sequence of SEQ ID NO:5, SEQ ID NO:7, SEQ ID NO:9, SEQ ID NO:33, SEQ ID NO:36 or SEQ ID NO:39 and retains the functional activity of the FT proteins of SEQ ID NO:5, SEQ ID NO:7, SEQ ID NO:9, SEQ ID NO:33, SEQ ID NO:36 or SEQ ID NO:39.

Determining Homology Between Two or More Sequence

To determine the percent homology of two amino acid sequences or of two nucleic acids, the sequences are aligned for optimal comparison purposes (e.g., gaps can be introduced in either of the sequences being compared for optimal alignment between the sequences). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See, Needleman and Wunsch 1970 *J Mol Biol* 48: 443-453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in SEQ ID NO:1, SEQ ID NO:6, SEQ ID NO:8, SEQ ID NO:31, SEQ ID NO:34, or SEQ ID NO:37.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region. The term "percentage of positive residues" is calculated by comparing two optimally aligned sequences over that region of comparison, determining the number of positions at which the identical and conservative amino acid substitutions, as defined above, occur in both sequences to yield the number of matched positions, dividing the number of matched positions by the total number of positions in the region of comparison (i.e., the window size), and multiplying the result by 100 to yield the percentage of positive residues.

Chimeric and Fusion Proteins

The invention also provides FT chimeric or fusion proteins. As used herein, a FT "chimeric protein" or "fusion protein" comprises a FT polypeptide operatively linked to a non-FT polypeptide. An "FT polypeptide" refers to a polypeptide having an amino acid sequence corresponding to FT, whereas a "non-FT polypeptide" refers to a polypeptide having an amino acid sequence corresponding to a protein that is not substantially homologous to the FT protein, e.g., a protein that is different from the FT protein and that is derived from the same or a different organism. Within a FT fusion protein the FT polypeptide can correspond to all or a portion of a FT protein. In one embodiment, a FT fusion protein comprises at least one biologically active portion of a FT protein. In another embodiment, a FT fusion protein comprises at least two biologically active portions of a FT protein. Within the fusion protein, the term "operatively linked" is intended to indicate that the FT polypeptide and the non-FT polypeptide are fused in-frame to each other. The non-FT polypeptide can be fused to the N-terminus or C-terminus of the FT polypeptide.

A FT chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) Current Protocols in Molecular Biology, John Wiley & Sons, 1992). Moreover, many expression vectors are commercially available that already encode a fusion moiety (e.g., a GST polypeptide, a 6×His-tag). A FT-encoding nucleic acid can be cloned into such an expression vector such that the fusion moiety is linked in-frame to the FT protein.

FT Agonists and Antagonists

The present invention also pertains to variants of the FT proteins that function as either FT agonists (mimetics) or as FT antagonists. An agonist can be for example an antisense nucleic acid molecule. Variants of the FT protein can be generated by mutagenesis, e.g., discrete point mutation or truncation of the FT protein. An agonist of the FT protein can retain substantially the same, or a subset of, the biological activities of the naturally occurring form of the FT protein. An antagonist of the FT protein can inhibit one or more of the activities of the naturally occurring form of the FT protein by, for example, competitively binding to a downstream or upstream member of a cellular signaling cascade which includes the FT protein. Thus, specific biological effects can be elicited by treatment with a variant of limited function.

Variants of the FT protein that function as either FT agonists (mimetics) or as FT antagonists can be identified by screening combinatorial libraries of mutants, e.g., truncation mutants, of the FT protein for FT protein agonist or antagonist activity. In one embodiment, a variegated library of FT variants is generated by combinatorial mutagenesis at the nucleic acid level and is encoded by a variegated gene library. A variegated library of FT variants can be produced by, for example, enzymatically ligating a mixture of synthetic oligonucleotides into gene sequences such that a degenerate set of potential FT sequences is expressible as individual polypeptides, or alternatively, as a set of larger fusion proteins (e.g., for phage display) containing the set of FT sequences therein. There are a variety of methods which can be used to produce libraries of potential FT variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential FT sequences. Methods for synthesizing degenerate oligonucleotides are known in the art (see, e.g., Narang (1983) *Tetrahedron* 39:3; Itakura et al. (1984) *Annu Rev Biochem* 53:323; Itakura et al. (1984) *Science* 198:1056; Ike et al. (1983) *Nucl Acid Res* 11:477.

Polypeptide Libraries

In addition, libraries of fragments of the FT protein coding sequence can be used to generate a variegated population of FT fragments for screening and subsequent selection of variants of a FT protein. In one embodiment, a library of coding sequence fragments can be generated by treating a double stranded PCR fragment of a FT coding sequence with a nuclease under conditions wherein nicking occurs only about once per molecule, denaturing the double stranded DNA, renaturing the DNA to form double stranded DNA that can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the FT protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of FT proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique that enhances the frequency of functional mutants in the libraries, can be used in combination with the screening assays to identify FT variants (Arkin and Yourvan (1992) PNAS 89:7811-7815; Delgrave et al. (1993) Protein Engineering 6:327-331).

FT Antibodies

FT polypeptides, including chimeric polypeptides, or derivatives, fragments, analogs or homologs thereof, may be utilized as immunogens to generate antibodies that immunospecifically-bind these peptide components. Such antibodies include, e.g., polyclonal, monoclonal, chimeric, single chain, Fab fragments and a Fab expression library. In a specific embodiment, fragments of the FT polypeptides are used as immunogens for antibody production. Various procedures known within the art may be used for the production of polyclonal or monoclonal antibodies to a FT polypeptides, or derivative, fragment, analog or homolog thereof.

For the production of polyclonal antibodies, various host animals may be immunized by injection with the native peptide, or a synthetic variant thereof, or a derivative of the foregoing. Various adjuvants may be used to increase the immunological response and include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.) and human adjuvants such as Bacille Calmette-Guerin and *Corynebacterium parvum.*

For preparation of monoclonal antibodies directed towards a FT polypeptides, or derivatives, fragments, analogs or homologs thereof, any technique that provides for the production of antibody molecules by continuous cell line culture may be utilized. Such techniques include, but are not limited to, the hybridoma technique (see, Kohler and Milstein, 1975. *Nature* 256: 495-497); the trioma technique; the human B-cell hybridoma technique (see, Kozbor, et al., 1983. *Immunol Today* 4: 72) and the EBV hybridoma technique to produce human monoclonal antibodies (see, Cole, et al., 1985. In: *Monoclonal Antibodies and Cancer Therapy*, Alan R. Liss, Inc., pp. 77-96). Human monoclonal antibodies may be utilized in the practice of the present invention and may be produced by the use of human hybridomas (see, Cote, et al., 1983. *Proc Natl Acad Sci USA* 80: 2026-2030) or by transforming human B-cells with Epstein Barr Virus in vitro (see, Cole, et al., 1985. In: *Monoclonal Antibodies and Cancer Therapy* (Alan R. Liss, Inc., pp. 77-96).

According to the invention, techniques can be adapted for the production of single-chain antibodies specific to a FT polypeptides (see, e.g., U.S. Pat. No. 4,946,778). In addition, methodologies can be adapted for the construction of Fab expression libraries (see, e.g., Huse, et al., 1989. *Science* 246: 1275-1281) to allow rapid and effective identification of monoclonal Fab fragments with the desired specificity for a FT polypeptides or derivatives, fragments, analogs or homologs thereof. Antibody fragments that contain the idiotypes to a FT polypeptides may be produced by techniques known in the art including, e.g., (i) an $F(ab')_2$ fragment produced by pepsin digestion of an antibody molecule; (ii) an Fab fragment generated by reducing the disulfide bridges of an $F(ab')_2$ fragment; (iii) an Fab fragment generated by the treatment of the antibody molecule with papain and a reducing agent and (iv) Fv fragments.

In one embodiment, methodologies for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of a FT polypeptides is facilitated by generation of hybridomas that bind to the fragment of a FT polypeptides possessing such a domain. Antibodies that are specific for a domain within a FT polypeptides, or derivative, fragments, analogs or homologs thereof, are also provided herein. The anti-FT polypeptide antibodies may be used in methods known within the art relating to the localization and/or quantitation of a FT polypeptide (e.g., for use in measuring levels of the peptide within appropriate physiological samples, for use in diagnostic methods, for use in imaging the peptide, and the like).

FT Recombinant Expression Vectors and Host Cells

Another aspect of the invention pertains to vectors, preferably expression vectors, containing a nucleic acid encoding a FT protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication). Other vectors are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors or plant transformation vectors, binary or otherwise, which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., FT proteins, mutant forms of FT proteins, fusion proteins, etc.).

The recombinant expression vectors of the invention can be designed for expression of FT proteins in prokaryotic or eukaryotic cells. For example, FT proteins can be expressed in bacterial cells such as *Escherichia coli*, insect cells (using baculovirus expression vectors) yeast cells, plant cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein, however carboxy terminus fusions are also common. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301-315) and pET 11d (Studier et al., Gene Expression Technology: Methods in Enzymology 185, Academic Press, San Diego, Calif. (1990) 60-89).

One strategy to maximize recombinant protein expression in *E. coli* is to express the protein in a host bacteria with an impaired capacity to proteolytically cleave the recombinant protein. See, e.g., Gottesman, Gene Expression Technology: Methods in Enzymology 185, Academic Press, San Diego, Calif. (1990) 119-128. Another strategy is to alter the nucleic acid sequence of the nucleic acid to be inserted into an expression vector so that the individual codons for each amino acid are those preferentially utilized in *E. coli* (see, e.g., Wada, et al., 1992. *Nucl. Acids Res.* 20: 2111-2118). Such alteration of nucleic acid sequences of the invention can be carried out by standard DNA synthesis techniques.

In another embodiment, the FT expression vector is a yeast expression vector. Examples of vectors for expression in yeast *Saccharomyces cerevisiae* include pYepSec1 (Baldari, et al., 1987. *EMBO J.* 6: 229-234), pMFa (Kurjan and Herskowitz, 1982. *Cell* 30: 933-943), pJRY88 (Schultz et al., 1987. *Gene* 54: 113-123), pYES2 (Invitrogen Corporation, San Diego, Calif.), and picZ (InVitrogen Corp, San Diego, Calif.).

Alternatively, FT can be expressed in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156-2165) and the pVL series (Lucklow and Summers, 1989. *Virology* 170: 31-39).

In yet another embodiment, a nucleic acid of the invention is expressed in mammalian cells using a mammalian expression vector. Examples of mammalian expression vectors include pCDM8 (Seed, 1987. *Nature* 329: 840) and pMT2PC (Kaufman, et al., 1987. *EMBO J.* 6: 187-195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., Molecular Cloning: A Laboratory Manual. 2nd ed., Cold Spring Harbor Laboratory, Cold Spring Harbor Laboratory Press, Cold Spring Harbor, N.Y., 1989.

In yet another embodiment, a nucleic acid of the invention is expressed in plants cells using a plant expression vector. Examples of plant expression vectors systems include tumor inducing (Ti) plasmid or portion thereof found in *Agrobacterium*, cauliflower mosaic virus (CAMV) DNA and vectors such as pBI121.

For expression in plants, the recombinant expression cassette will contain in addition to the FT nucleic acids, a plant promoter region, a transcription initiation site (if the coding sequence to transcribed lacks one), and a transcription termination/polyadenylation sequence. The termination/polyadenylation region may be obtained from the same gene as the promoter sequence or may be obtained from different genes. Unique restriction enzyme sites at the 5' and 3' ends of the cassette are typically included to allow for easy insertion into a pre-existing vector.

Examples of suitable promotors include promoters from plant viruses such as the 35S promoter from cauliflower mosaic virus (CaMV). Odell, et al., Nature, 313: 810-812 (1985). and promoters from genes such as rice actin (McElroy, et al., Plant Cell, 163-171 (1990)); ubiquitin (Christensen, et al., Plant Mol. Biol., 12: 619-632 (1992); and Christensen, et al., Plant Mol. Biol., 18: 675-689 (1992)); pEMU (Last, et al., Theor. Appl. Genet., 81: 581-588 (1991)); MAS (Velten, et al., EMBO J., 3: 2723-2730 (1984)); maize H3 histone (Lepetit, et al., Mol. Gen. Genet., 231: 276-285 (1992); and Atanassvoa, et al., Plant Journal, 2(3): 291-300 (1992)), the 5'- or 3'-promoter derived from T-DNA of *Agrobacterium tumefaciens*, the Smas promoter, the cinnamyl alcohol dehydrogenase promoter (U.S. Pat. No. 5,683,439), the Nos promoter, the rubisco promoter, the GRP1-8 promoter, ALS promoter, (WO 96/30530), a synthetic promoter, such as, Rsyn7, SCP and UCP promoters, ribulose-1,3-diphosphate carboxylase, fruit-specific promoters, heat shock promoters, seed-specific promoters and other transcription initiation regions from various plant genes, for example, include the various opine initiation regions, such as for example, octopine, mannopine, and nopaline.

Additional regulatory elements that may be connected to a FT encoding nucleic acid sequence for expression in plant cells include terminators, polyadenylation sequences, and nucleic acid sequences encoding signal peptides that permit localization within a plant cell or secretion of the protein from the cell. Such regulatory elements and methods for adding or exchanging these elements with the regulatory elements FT gene are known, and include, but are not limited to, 3' termination and/or polyadenylation regions such as those of the *Agrobacterium tumefaciens* nopaline synthase (nos) gene (Bevan, et al., Nucl. Acids Res., 12: 369-385 (1983)); the potato proteinase inhibitor II (PINII) gene (Keil, et al., Nucl. Acids Res., 14: 5641-5650 (1986) and hereby incorporated by reference); and An, et al., Plant Cell, 1: 115-122 (1989)); and the CaMV 19S gene (Mogen, et al., Plant Cell, 2: 1261-1272 (1990)).

Plant signal sequences, including, but not limited to, signal-peptide encoding DNA/RNA sequences which target proteins to the extracellular matrix of the plant cell (Dratewka-Kos, et al., J. Biol. Chem., 264: 4896-4900 (1989)) and the *Nicotiana plumbaginifolia* extension gene (DeLoose, et al., Gene, 99: 95-100 (1991)), or signal peptides which target proteins to the vacuole like the sweet potato sporamin gene (Matsuka, et al., Proc. Nat'l Acad. Sci. (USA), 88: 834 (1991)) and the barley lectin gene (Wilkins, et al., Plant Cell, 2: 301-313 (1990)), or signals which cause proteins to be secreted such as that of PRIb (Lind, et al., Plant Mol. Biol., 18: 47-53 (1992)), or those which target proteins to the plastids such as that of rapeseed enoyl-ACP reductase (Verwaert, et al., Plant Mol. Biol., 26: 189-202 (1994)) are useful in the invention.

In another embodiment, the recombinant expression vector is capable of directing expression of the nucleic acid preferentially in a particular cell type (e.g., tissue-specific regulatory elements are used to express the nucleic acid). Tissue-specific regulatory elements are known in the art. Especially useful in connection with the nucleic acids of the present invention are expression systems which are operable in plants. These include systems which are under control of a tissue-specific promoter, as well as those which involve promoters that are operable in all plant tissues.

Organ-specific promoters are also well known. For example, the patatin class I promoter is transcriptionally activated only in the potato tuber and can be used to target gene expression in the tuber (Bevan, M., 1986, *Nucleic Acids Research* 14:4625-4636). Another potato-specific promoter is the granule-bound starch synthase (GBSS) promoter (Visser, R. G. R, et al., 1991, *Plant Molecular Biology* 17:691-699).

Other organ-specific promoters appropriate for a desired target organ can be isolated using known procedures. These control sequences are generally associated with genes uniquely expressed in the desired organ. In a typical higher plant, each organ has thousands of mRNAs that are absent from other organ systems (reviewed in Goldberg, P., 1986, *Trans. R. Soc. London* B314:343).

For in situ production of the antisense mRNA of GST, those regions of the GST gene which are transcribed into GST mRNA, including the untranslated regions thereof, are inserted into the expression vector under control of the promoter system in a reverse orientation. The resulting transcribed mRNA is then complementary to that normally produced by the plant.

The resulting expression system or cassette is ligated into or otherwise constructed to be included in a recombinant vector which is appropriate for plant transformation. The vector may also contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow on a medium containing the particular antibiotic. Replication sequences, of bacterial or viral origin, are generally also included to allow the vector to be cloned in a bacterial or phage host, preferably a broad host range prokaryotic origin of replication is included. A selectable marker for bacteria should also be included to allow selection of bacterial cells bearing the desired construct. Suitable prokaryotic selectable markers also include resistance to antibiotics such as kanamycin or tetracycline.

Other DNA sequences encoding additional functions may also be present in the vector, as is known in the art. For instance, in the case of *Agrobacterium* transformations, T-DNA sequences will also be included for subsequent transfer to plant chromosomes.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell.

A host cell of the invention, such as a prokaryotic or eukaryotic host cell in culture, can be used to produce (i.e., express) a polypeptide of the invention encoded in a an open reading frame of a polynucleotide of the invention. Accordingly, the invention further provides methods for producing a polypeptide using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

A number of types of cells may act as suitable host cells for expression of a polypeptide encoded by an open reading frame in a polynucleotide of the invention. Plant host cells include, for example, plant cells that could function as suitable hosts for the expression of a polynucleotide of the invention include epidermal cells, mesophyll and other ground tissues, and vascular tissues in leaves, stems, floral organs, and roots from a variety of plant species, such as *Arabidopsis thaliana, Nicotiana tabacum, Brassica napus, Zea mays*, and *Glycine max*.

Alternatively, it may be possible to produce a polypeptide in lower eukaryotes such as yeast or in prokaryotes such as bacteria. Potentially suitable yeast strains include *Saccharomyces cerevisiae, Schizosaccharomyces pombe, Kluyveromyces strains, Candida*, or any yeast strain capable of expressing heterologous proteins. Potentially suitable bacterial strains include *Escherichia coli, Bacillus subtilis, Salmonella typhimurium*, or any bacterial strain capable of expressing heterologous polypeptides. If the polypeptide is made in yeast or bacteria, it may be necessary to modify the polypeptide produced therein, for example by phosphorylation or glycosylation of the appropriate sites, in order to obtain a functional polypeptide, if the polypeptide is of sufficient length and conformation to have activity. Such covalent attachments may be accomplished using known chemical or enzymatic methods.

A polypeptide may be prepared by culturing transformed host cells under culture conditions suitable to express the recombinant protein. The resulting expressed polypeptide or protein may then be purified from such culture (e.g., from culture medium or cell extracts) using known purification processes, such as gel filtration and ion exchange chromatography. The purification of the polypeptide or protein may also include an affinity column containing agents which will bind to the protein; one or more column steps over such affinity resins as concanavalin A-agarose, Heparin-Toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, a polypeptide or protein may also be expressed in a form which will facilitate purification. For example, it may be expressed as a fusion protein containing a six-residue histidine tag. The histidine-tagged protein will then bind to a Ni-affinity column. After elution of all other proteins, the histidine-tagged protein can be eluted to achieve rapid and efficient purification. One or more reverse-phase high performance liquid chromatography (RP-HPLC) steps employing hydrophobic RP-HPLC media, e.g., silica gel having pendant methyl or other aliphatic groups, can be employed to further purify a polypeptide. Some or all of the foregoing purification steps, in various combinations, can also be employed to provide a substantially homogeneous isolated recombinant polypeptide. The protein or polypeptide thus purified is substantially free of other plant proteins or polypeptides and is defined in accordance with the present invention as "isolated."

Transformed Plants Cells and Transgenic Plants

The invention includes protoplast, plants cells, plant tissue and plants (e.g., monocots and dicots transformed with a FT nucleic acid, a vector containing a FT nucleic acid or an expression vector containing a FT nucleic acid. Examples of nucleic acids suitable for transforming plant cells and plants include those nucleic acid sequences of SEQ ID NO: 4, 40-57 or 58. As used herein, "plant" is meant to include not only a whole plant but also a portion thereof (i.e., cells, and tissues, including for example, leaves, stems, shoots, roots, flowers, fruits and seeds).

The plant can be any plant type including, for example, species from the genera *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Picea, Caco*, and *Populus*.

In some aspects of the invention, the transformed plant is resistant to biotic and abiotic stresses, e.g., chilling stress, salt stress, heat stress, water stress, disease, grazing pests and wound healing. Additionally, the invention also includes a transgenic plant that is resistant to pathogens such as for example fungi, bacteria, nematodes, viruses and parasitic weeds. Alternatively, the transgenic plant is resistant to herbicides. By resistant is meant the plant grows under stress conditions (e.g., high salt, decreased water, low temperatures) or under conditions that normally inhibit, to some degree, the growth of an untransformed plant. Methodologies to determine plant growth or response to stress include for example, height measurements, weight measurements, leaf area, ability to flower, water use, transpiration rates and yield.

The invention also includes cells, tissues, including for example, leaves, stems, shoots, roots, flowers, fruits and seeds and the progeny derived from the transformed plant.

Numerous methods for introducing foreign genes into plants are known and can be used to insert a gene into a plant host, including biological and physical plant transformation protocols. See, for example, Miki et al., (1993) "Procedure for Introducing Foreign DNA into Plants", In: Methods in Plant Molecular Biology and Biotechnology, Glick and Thompson, eds., CRC Press, Inc., Boca Raton, pages 67-88 and Andrew Bent in, Clough S J and Bent A F, 1998. Floral dipping: a simplified method for *Agrobacterium*-mediated transformation of *Arabidopsis thaliana*. The methods chosen vary with the host plant, and include chemical transfection methods such as calcium phosphate, polyethylene glycol (PEG) transformation, microorganism-mediated gene transfer such as *Agrobacterium* (Horsch, et al., Science, 227: 1229-31 (1985)), electroporation, protoplast transformation, micro-injection, flower dipping and particle or non-particle biolistic bombardment.

*Agrobacterium*-mediated Transformation

The most widely utilized method for introducing an expression vector into plants is based on the natural transformation system of *Agrobacterium. A. tumefaciens* and *A. rhizogenes* are plant pathogenic soil bacteria which genetically transform plant cells. The Ti and Ri plasmids of *A. tumefaciens* and *A. rhizogenes*, respectfully, carry genes responsible for genetic transformation of plants. See, for example, Kado, Crit. Rev. Plant Sci., 10:1-32 (1991). Descriptions of the *Agrobacterium* vector systems and methods for *Agrobacterium*-mediated gene transfer are provided in Gruber et al., supra; and Moloney, et al, Plant Cell Reports, 8: 238-242 (1989).

Transgenic *Arabidopsis* plants can be produced easily by the method of dipping flowering plants into an *Agrobacterium* culture, based on the method of Andrew Bent in, Clough S J and Bent A F, 1998. Floral dipping: a simplified method for *Agrobacterium*-mediated transformation of *Arabidopsis thaliana*. Wild type plants are grown until the plant has both developing flowers and open flowers. The plant are inverted for 1 minutes into a solution of *Agrobacterium* culture carrying the appropriate gene construct. Plants are then left horizontal in a tray and kept covered for two days to maintain humidity and then righted and bagged to continue growth and seed development. Mature seed was bulk harvested.

Direct Gene Transfer

A generally applicable method of plant transformation is microprojectile-mediated transformation, where DNA is carried on the surface of microprojectiles measuring about 1 to 4 mu.m. The expression vector is introduced into plant tissues with a biolistic device that accelerates the microprojectiles to speeds of 300 to 600 m/s which is sufficient to penetrate the plant cell walls and membranes. (Sanford, et al., Part. Sci. Technol., 5: 27-37 (1987); Sanford, Trends Biotech, 6: 299-302 (1988); Sanford, Physiol. Plant, 79: 206-209 (1990); Klein, et al., Biotechnology, 10: 286-291 (1992)).

Another method for physical delivery of DNA to plants is sonication of target cells as described in Zang, et al., BioTechnology, 9: 996-996 (1991). Alternatively, liposome or spheroplast fusions have been used to introduce expression vectors into plants. See, for example, Deshayes, et al., EMBO J., 4: 2731-2737 (1985); and Christou, et al., Proc. Nat'l. Acad. Sci. (USA), 84: 3962-3966 (1987). Direct uptake of DNA into protoplasts using $CaCl_2$ precipitation, polyvinyl alcohol or poly-L-ornithine have also been reported. See, for example, Hain, et al., Mol. Gen. Genet., 199: 161 (1985); and Draper, et al., Plant Cell Physiol., 23: 451-458 (1982).

Electroporation of protoplasts and whole cells and tissues has also been described. See, for example, Donn, et al., (1990) In: Abstracts of the VIIth Int;l. Congress on Plant Cell and Tissue Culture IAPTC, A2-38, page 53; D'Halluin et al., Plant Cell, 4: 1495-1505 (1992); and Spencer et al., Plant Mol. Biol., 24: 51-61 (1994).

Plants may also be transformed using the method of Held et al. (U.S. Application 20010026941). The method utilizes an accelerated aerosol beam of droplets which carries the desired molecules, DNA, into the target cells. The size of droplets produced by this method are reported to be sufficiently small as to transform bacterial cells of 1 to 2 microns in length.

Particle Wounding/Agrobacterium Delivery

Another useful basic transformation protocol involves a combination of wounding by particle bombardment, followed by use of *Agrobacterium* for DNA delivery, as described by Bidney, et al., Plant Mol. Biol., 18: 301-31 (1992). Useful plasmids for plant transformation include Bin 19. See Bevan, Nucleic Acids Research, 12: 8711-8721 (1984), and hereby incorporated by reference.

In general, the intact meristem transformation method involves imbibing seed for 24 hours in the dark, removing the cotyledons and root radical, followed by culturing of the meristem explants. Twenty-four hours later, the primary leaves are removed to expose the apical meristem. The explants are placed apical dome side up and bombarded, e.g., twice with particles, followed by co-cultivation with *Agrobacterium*. To start the co-cultivation for intact meristems, *Agrobacterium* is placed on the meristem. After about a 3-day co-cultivation period the meristems are transferred to culture medium with cefotaxime plus kanamycin for the NPTII selection.

The split meristem method involves imbibing seed, breaking of the cotyledons to produce a clean fracture at the plane of the embryonic axis, excising the root tip and then bisecting the explants longitudinally between the primordial leaves. The two halves are placed cut surface up on the medium then bombarded twice with particles, followed by co-cultivation with *Agrobacterium*. For split meristems, after bombardment, the meristems are placed in an *Agrobacterium* suspension for 30 minutes. They are then removed from the suspension onto solid culture medium for three day co-cultivation. After this period, the meristems are transferred to fresh medium with cefotaxime plus kanamycin for selection.

Transfer by Plant Breeding

Alternatively, once a single transformed plant has been obtained by the foregoing recombinant DNA method, conventional plant breeding methods can be used to transfer the gene and associated regulatory sequences via crossing and backcrossing. Such intermediate methods will comprise the further steps of: (1) sexually crossing the disease-resistant plant with a plant from the disease susceptible taxon; (2) recovering reproductive material from the progeny of the cross; and (3) growing disease-resistant plants from the reproductive material. Where desirable or necessary, the agronomic characteristics of the susceptible taxon can be substantially preserved by expanding this method to include the further steps of repetitively: (1) backcrossing the disease-resistant progeny with disease-susceptible plants from the susceptible taxon; and (2) selecting for expression of a hydrogen peroxide producing enzyme activity (or an associated marker gene) among the progeny of the backcross, until the desired percentage of the characteristics of the susceptible taxon are present in the progeny along with the gene or genes imparting oxalic acid degrading and/or hydrogen peroxide enzyme activity.

By the term "taxon" herein is meant a unit of botanical classification. It thus includes, genus, species, cultivars, varieties, variants and other minor taxonomic groups which lack a consistent nomenclature.

Regeneration of Transformants

The development or regeneration of plants from either single plant protoplasts or various explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by *Agrobacterium* from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983). In particular, U.S. Pat. No. 5,349,124 (specification incorporated herein by reference) details the creation of genetically transformed lettuce cells and plants resulting therefrom which express hybrid crystal proteins conferring insecticidal activity against Lepidopteran larvae to such plants.

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, or pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

A preferred transgenic plant is an independent segregant and can transmit the FT gene and its activity to its progeny. A more preferred transgenic plant is homozygous for the gene, and transmits that gene to all of its offspring on sexual mating. Seed from a transgenic plant may be grown in the field or greenhouse, and resulting sexually mature transgenic plants are self-pollinated to generate true breeding plants. The progeny from these plants become true breeding lines that are evaluated for increased expression of the FT transgene.

Method of Producing Transgenic Plants

Included in the invention are methods of producing a transgenic plant that has increased stress resistance, delayed senescence or increased sensitivity to ABA. The method includes introducing into one or more plant cells a compound that alters farnesyl transferase expression (i.e. farnesyl transferase alpha or beta) or activity in the plant. The compound can be, e.g., (i) a farnesyl transferase polypeptide inhibitor; (ii) a nucleic acid encoding a farnesyl transferase polypeptide inhibitor; (iii) a nucleic acid that decreases expression of a nucleic acid that encodes a farnesyl transferase polypeptide and, derivatives, fragments, analogs and homologs thereof, (iv) an antisense farnesyl transferase nucleic acid. A nucleic acid that decreases expression of a nucleic acid that encodes a farnesyl transferase polypeptide includes, e.g., antisense nucleic acids or RNA inhibitory nucleic acids. The nucleic acid can be either endogenous or exogenous. Preferably the compound is a farnesyl transferase polypeptide or a nucleic acid encoding a farnesyl transferase polypeptide. For example the compound is the nucleic acid sequence of SEQ ID NO:1, SEQ ID NO:6, SEQ ID NO:8, SEQ ID NO:31, SEQ ID NO:34, or SEQ ID NO:37. More preferably the compound is a nucleic acid complementarity to a nucleic acid encoding a farnesyl transferase polypeptide. For example an anti-sense nucleic acid molecule. Exemplary compounds include SEQ ID NO:1, 3, 4, 29, 30, 32, 35, 38, 40-57 and 58.

Also included in the invention is a plant where a mutation has been introduced in the gene encoding farnesyl transferase (i.e. alpha or beta) which results in a plant that has decreased farnesyl transferase activity and increased tolerance to stress as compared to a wild type plant. The mutation may be introduced by chemical or mechanical means.

Examples of stresses include, for example, chilling stress, heat stress, salt stress, water stress, nutrient limitation stress, disease, grazing pests, wound healing, pathogens such as for example fungi, bacteria, nematodes, viruses or parasitic weed and herbicides.

Increases stress resistance is meant that the transgenic plant can grows under stress conditions (e.g., high salt, decreased water, low temperatures) or under conditions that normally inhibit the growth of an untransformed plant. Methodologies to determine plant growth or response to stress include for example, height measurements, weight measurements, leaf area, ability to flower, water use, transpiration rates and yield Sensitivity to ABA can be assessed using a concentration curve of ABA and germinating seeds on plates as described in Example 11. Often germination is assessed and used to determine sensitivity. However, sensitivity can be observed at more developmental stages than simply germination. For example, increased sensitivity may be observed at the stage of cotyledon expansion, expansion of the first true leaf, or developmental arrest in the seedling stage.

The concentration of ABA at which sensitivity is observed varies in a species dependent manner. For example, transgenic *Arabidopsis thaliana* will demonstrate sensitivity at a lower concentration than observed in *Brassica* or soybean.

By increased ABA sensitivity it is meant that the transgenic plant is seen to display a phenotype at a lower concentration of ABA than that used to observe the same phenotype in a wild type plant. Methodologies to determine ABA sensitivity include for example, plant germination, growth or development.

The plant can be any plant type including, for example, species from the genera *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Picea, Caco*, and *Populus.*

Screening Methods

The isolated nucleic acid molecules of the invention (e.g., SEQ ID NO:1, SEQ ID NO:6, SEQ ID NO:8, SEQ ID NO:31, SEQ ID NO:34, or SEQ ID NO:37) can be used to express FT protein (e.g., via a recombinant expression vector in a host cell), to detect FT mRNA (e.g., in a biological sample) or a genetic lesion in a FT gene, and to modulate FT activity, as described further, below. In addition, the FT proteins can be used to screen compounds that modulate the FT protein activity or expression. In addition, the anti-FT antibodies of the invention can be used to detect and isolate FT proteins and modulate FT activity.

The invention provides a method (also referred to herein as a "screening assay") for identifying modulators, i.e., candidate or test compounds or agents (e.g., peptides, peptidomimetics, small molecules or other drugs) that bind to FT proteins or have a stimulatory or inhibitory effect on, e.g., FT protein expression or FT protein activity. The invention also includes compounds identified in the screening assays described herein. The invention also includes methods of identifying related genes using the transgenic plants of this invention in screening protocols utilizing mutagenesis, gene tagging, insertional gene tagging, activation tagging or other such methods of gene or phenotype identification.

In one embodiment, the invention provides assays for screening candidate or test compounds which bind to a FT protein or polypeptide or biologically-active portion thereof. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. See, e.g., Lam, 1997. Anticancer Drug Design 12: 145.

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. *Proc. Natl. Acad. Sci. U.S.A.* 90: 6909; Erb, et al., 1994. *Proc. Natl. Acad. Sci. U.S.A.* 91: 11422; Zuckermann, et al., 1994. *J. Med. Chem.* 37: 2678; Cho, et al., 1993. *Science* 261: 1303; Carrell, et al., 1994. *Angew. Chem. Int. Ed. Engl.* 33: 2059; Carell, et al., 1994. *Angew. Chem. Int. Ed. Engl.* 33: 2061; and Gallop, et al., 1994. *J. Med. Chem.* 37: 1233.

Libraries of compounds may be presented in solution (e.g., Houghten, 1992. *Biotechniques* 13: 412-421), or on beads (Lam, 1991. *Nature* 354: 82-84), on chips (Fodor, 1993. *Nature* 364: 555-556), bacteria (Ladner, U.S. Pat. No. 5,223,409), spores (Ladner, U.S. Pat. No. 5,233,409), plasmids (Cull, et al., 1992. *Proc. Natl. Acad. Sci. USA* 89: 1865-1869) or on phage (Scott and Smith, 1990. *Science* 249: 386-390; Devlin, 1990. *Science* 249: 404-406; Cwirla, et al., 1990. *Proc. Natl. Acad. Sci. U.S.A.* 87: 6378-6382; Felici, 1991. *J. Mol. Biol.* 222: 301-310; Ladner, U.S. Pat. No. 5,233,409.).

In one embodiment, an assay is a cell-based assay in which a cell which expresses a FT protein, or a biologically-active portion thereof, is contacted with a test compound and the ability of the test compound to bind to a FT protein determined. The cell, for example, can be of mammalian origin, plant cell or a yeast cell. Determining the ability of the test compound to bind to the FT protein can be accomplished, for example, by coupling the test compound with a radioisotope or enzymatic label such that binding of the test compound to the FT protein or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product. In one embodiment, the assay comprises contacting a cell which expresses a FT protein, or a biologically-active portion thereof, with a known compound which binds FT to form an assay mixture, contacting the assay mixture with a test compound, and determining the ability of the test compound to interact with a FT protein, wherein determining the ability of the test compound to interact with a FT protein comprises determining the ability of the test compound to preferentially bind to FT protein or a biologically-active portion thereof as compared to the known compound.

In another embodiment, an assay is a cell-based assay comprising contacting a cell expressing a FT protein, or a biologically-active portion thereof, with a test compound and determining the ability of the test compound to modulate (e.g., stimulate or inhibit) the activity of the FT protein or biologically-active portion thereof. Determining the ability of the test compound to modulate the activity of FT or a biologically-active portion thereof can be accomplished, for example, by determining the ability of the FT protein to bind to or interact with a FT target molecule. As used herein, a "target molecule" is a molecule with which a FT protein binds or interacts in nature, for example, a molecule on the surface of a cell which expresses a FT interacting protein, a molecule on the surface of a second cell, a molecule in the extracellular milieu, a molecule associated with the internal surface of a cell membrane or a cytoplasmic molecule. A FT target molecule can be a non-FT molecule or a FT protein or polypeptide of the invention In one embodiment, a FT target molecule is a component of a signal transduction pathway that facilitates transduction of an extracellular signal (e.g. a signal generated by binding of a compound to a membrane-bound molecule) through the cell membrane and into the cell. The target, for example, can be a second intercellular protein that has catalytic activity or a protein that facilitates the association of downstream signaling molecules with FT.

Determining the ability of the FT protein to bind to or interact with a FT target molecule can be accomplished by one of the methods described above for determining direct binding. In one embodiment, determining the ability of the FT protein to bind to or interact with a FT target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising a FT-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the invention is a cell-free assay comprising contacting a FT protein or biologically-active portion thereof with a test compound and determining the ability of the test compound to bind to the FT protein or biologically-active portion thereof. Binding of the test compound to the FT protein can be determined either directly or indirectly as described above. In one such embodiment, the assay comprises contacting the FT protein or biologically-active portion thereof with a known compound which binds FT to form an assay mixture, contacting the assay mixture with a test compound, and determining the ability of the test compound to interact with a FT protein, wherein determining the ability of the test compound to interact with a FT protein comprises determining the ability of the test compound to preferentially bind to FT or biologically-active portion thereof as compared to the known compound.

In still another embodiment, an assay is a cell-free assay comprising contacting FT protein or biologically-active portion thereof with a test compound and determining the ability of the test compound to modulate (e.g. stimulate or inhibit) the activity of the FT protein or biologically-active portion thereof. Determining the ability of the test compound to modulate the activity of FT can be accomplished, for example, by determining the ability of the FT protein to bind to a FT target molecule by one of the methods described above for determining direct binding. In an alternative embodiment, determining the ability of the test compound to modulate the activity of FT protein can be accomplished by determining the ability of the FT protein further modulate a FT target molecule. For example, the catalytic/enzymatic activity of the target molecule on an appropriate substrate can be determined as described above.

In yet another embodiment, the cell-free assay comprises contacting the FT protein or biologically-active portion thereof with a known compound which binds FT protein to form an assay mixture, contacting the assay mixture with a test compound, and determining the ability of the test compound to interact with a FT protein, wherein determining the ability of the test compound to interact with a FT protein comprises determining the ability of the FT protein to preferentially bind to or modulate the activity of a FT target molecule.

The cell-free assays of the invention are amenable to use of both the soluble form or the membrane-bound form of FT protein. In the case of cell-free assays comprising the membrane-bound form of FT protein, it may be desirable to utilize a solubilizing agent such that the membrane-bound form of FT protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly (ethylene glycol ether)$_n$, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-2-hydroxy-1-propane sulfonate (CHAPSO).

In more than one embodiment of the above assay methods of the invention, it may be desirable to immobilize either FT protein or its target molecule to facilitate separation of complexed from uncomplexed forms of one or both of the proteins, as well as to accommodate automation of the assay. Binding of a test compound to FT protein, or interaction of FT protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-FT fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or FT protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described, supra. Alternatively, the complexes can be dissociated from the matrix, and the level of FT protein binding or activity determined using standard techniques.

Other techniques for immobilizing proteins on matrices can also be used in the screening assays of the invention. For example, either the FT protein or its target molecule can be immobilized utilizing conjugation of biotin and streptavidin. Biotinylated FT protein or target molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, antibodies reactive with FT protein or target molecules, but which do not interfere with binding of the FT protein to its target molecule, can be derivatized to the wells of the plate, and unbound target or FT protein trapped in the wells by antibody conjugation. Methods for detecting such complexes, in addition to those described above for the GST-immobilized complexes, include immunodetection of complexes using antibodies reactive with the FT protein or target molecule, as well as enzyme-linked assays that rely on detecting an enzymatic activity associated with the FT protein or target molecule.

In another embodiment, modulators of FT protein expression are identified in a method wherein a cell is contacted with a candidate compound and the expression of FT mRNA or protein in the cell is determined. The level of expression of FT mRNA or protein in the presence of the candidate compound is compared to the level of expression of FT mRNA or protein in the absence of the candidate compound. The candidate compound can then be identified as a modulator of FT mRNA or protein expression based upon this comparison. For example, when expression of FT mRNA or protein is greater (i.e., statistically significantly greater) in the presence of the candidate compound than in its absence, the candidate compound is identified as a stimulator of FT mRNA or protein expression. Alternatively, when expression of FT mRNA or protein is less (statistically significantly less) in the presence of the candidate compound than in its absence, the candidate compound is identified as an inhibitor of FT mRNA or protein expression. The level of FT mRNA or protein expression in the cells can be determined by methods described herein for detecting FT mRNA or protein.

In yet another aspect of the invention, the FT proteins can be used as "bait proteins" in a two-hybrid assay or three hybrid assay (see, e.g., U.S. Pat. No. 5,283,317; Zervos, et al., 1993. *Cell* 72: 223-232; Madura, et al., 1993. *J. Biol. Chem.* 268: 12046-12054; Bartel, et al., 1993. *Biotechniques* 14: 920-924; Iwabuchi, et al., 1993. *Oncogene* 8: 1693-1696; and Brent WO 94/10300), to identify other proteins that bind to or interact with FT ("FT-binding proteins" or "FT-bp") and modulate FT activity. Such FT-binding proteins are also likely to be involved in the propagation of signals by the FT proteins as, for example, upstream or downstream elements of the FT pathway.

The two-hybrid system is based on the modular nature of most transcription factors, which consist of separable DNA-binding and activation domains. Briefly, the assay utilizes two different DNA constructs. In one construct, the gene that codes for FT is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a FT-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with FT.

In yet another aspect of the invention are methods which utilize the transgenic plants of the invention to identify FT-interacting components via genetic screening protocols. These components can be for example, regulatory elements which modify FT-gene expression, interacting proteins which directly modify FT activity or interacting proteins which modify components of the same signal transduction pathway and thereby exert an effect on the expression or activity of FT. Briefly, genetic screening protocols are applied to the transgenic plants of the invention and in so doing identify related genes which are not identified using a wild type background for the screen. For example an activation tagged library (Weigel, et al., 2000. *Plant Physiol.* 122: 1003-1013), can be produced using the transgenic plants of the invention as the genetic background. Plants are then screened for altered phenotypes from that displayed by the parent plants. Alternative methods of generating libraries from the transgenic plants of the invention can be used, for example, chemical or irradiation induced mutations, insertional inactivation or activation methods.

The invention further pertains to novel agents identified by the aforementioned screening assays and uses thereof.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

The invention will be further described in the following examples, which do not limit the scope of the invention described in the claims.

EXAMPLES

Example 1

Cloning of *Arabidopsis thaliana* FTA and Construction of Transformation Vector The *Arabidopsis thaliana* FTA sequence was obtained by RT-PCR from total RNA isolated from leaf tissue using primers corresponding to SEQ ID NO:11 and SEQ ID NO:12. The resulting fragment was digested with BamHI and SmaI and cloned into the plasmid pCR2.1 The Clonetech vector pBI121 was used as the backbone for the antisense construct. The GUS gene was removed by BamHI and Eco1CRI digestion and replaced with the FTA insert that was cut from pCR2.1-FTA using SmaI and BamHI and ligated into the vector SEQ ID NO:4.

TABLE 1

| | |
|---|---|
| SEQ ID NO: 11: | 5'-AAAGGATCCTCAAATTGCTGCCACTGTAAT-3' |
| SEQ ID NO: 12: | 5'-AAACCCGGGATGAATTTCGACGAGAACGTG-3' |

Example 2

Cloning of Non-Full Length *Brassica napus* FTA and FTB Nucleic Acid Sequences RNA was isolated from leaf and root tissue using the Qiagen RNeasy kit. RT-PCR was performed by known techniques using the primers shown in Table 2. The FTA sequence was obtained using the primer pair SEQ ID NO:19 and SEQ ID NO:20. The FTB sequence was obtained using the primer pair SEQ ID NO:21 and SEQ ID NO:22.

TABLE 2

| | |
|---|---|
| SEQ ID NO: 19: | 5'-GGATCCATGGATTACTTCCGTGCGATTTACTTCTCC-3' |
| SEQ ID NO: 20: | 5'-AAAAAGCTTCCATGCCCAATAGTTAGCTCTTATTGGATC-3' |
| SEQ ID NO: 21: | 5'-AAAAAGCTTTGGCTTTGTTACTGGATTCTTCATTCAAT-3' |
| SEQ ID NO: 22: | 5'-AAATCTAGAAGCTTCATAATACCGATCCAAGACAATGTT-3' |

PCR products were separated from the RT-PCR reaction mixture using the Qiagen PCR column spin kit and ligated into the cloning vector pBluescript KS+. The vector was digested with EcoRV and treated with Taq polymerase in the presence of dTTP to produce a 3' overhang for ligation with the PCR products. The ligation products were transformed into *E. coli* DH5α cells, positive colonies were selected and the resulting inserts sequenced.

Example 3

Cloning of Non-Full Length FTA and FTB Nucleic Acid Sequences from *Glycine max* and *Zea maize*

RNA was isolated from leaf and root tissue using the Qiagen RNeasy kit. RT-PCR was performed by known techniques using the primers shown in Table 3. The *Glycine max* FTA sequence was obtained using the primer pair SEQ ID NO:23 and SEQ ID NO:24. The *Glycine max* FTB sequence was obtained using the primer pair SEQ ID NO:25 and SEQ ID NO:26. The *Zea maize* FTB sequence was obtained using the primer pair SEQ ID NO:27 and SEQ ID NO:28.

TABLE 3

| | |
|---|---|
| SEQ ID NO: 23: | 5'-AAAGGATCCATGGAATCTGGGTCTAGCGA-3' |
| SEQ ID NO: 24: | 5'-AAATCTAGAAGGAAGTCTGCTCTTGCGC-3' |
| SEQ ID NO: 25: | 5'-AAATCTAGAGCCACCATTCCTCGCAACG-3' |
| SEQ ID NO: 26: | 5'-AAAGAGCTCGTGGTGGAGAATCTGGGTGC-3' |
| SEQ ID NO: 27: | 5'-GGCGGATCCCGACCTACCGAGG-3' |
| SEQ ID NO: 28: | 5'-AAAGAGCTCGTGGATGGATTGGCTCCAGC-3' |

PCR products were separated from the RT-PCR reaction mixture using the Qiagen PCR column spin kit and ligated into the cloning vector pBluescript KS+. The vector was digested with EcoRV and treated with Taq polymerase in the presence of dTTP to produce a 3' overhang for ligation with the PCR products. The ligation products were transformed into *E. coli* DH5α cells, positive colonies were selected and the resulting inserts sequenced.

Example 4

Sequence Analysis

*Arabidopsis thaliana* FTA

A disclosed nucleic acid of 999 nucleotides (also referred to as FT1) is shown in Table 4A. The primers used in the PCR are depicted in bold.

TABLE 4A

| FT1 Nucleotide Sequence (SEQ ID NO: 1). |
|---|
| **aaacccgggatgaatttcgacgagaccgtg**ccactgagccaacgattggagtggtcagacgtggt |
| cccattgactcaggacgatggtccgaatccagtggtgccaattgcctacaaggaagagttccgcg |
| agactatggattacttccgtgcgatttacttttccgacgagcgatctcctcgcgcactacgactc |
| acggaagaaaccctcctcttaaactccggcaactacacagtgtggcatttcaggcgcctagtact |
| cgaggcccttaatcacgacttgtttgaagaactcgagttcatcgaacgcattgctgaggataact |
| ctaagaactaccaactgtggcatcatcggcgatgggttgcagagaaactgggtcctgatgttgca |
| gggagagaacttgaatttacccgtagagtactttcacttgatgccaaacattatcatgcttggtc |
| acataggcagtggacactacgggcattaggaggatgggaagatgagctcgattactgtcacgagc |
| tccttgaagctgacgtctttaacaattccgcctggaatcagaggtattatgtcatcacccaatct |
| cctttgttgggaggcctagaagccatgagagaatctgaagtaagctacacaatcaaagccatttt |
| aaccaatcctgcaaacgagagctcatggcgatacctaaaagcgctttacaaagacgacaaagaat |
| cctggattagtgatccaagtgtttcctcagtctgtttgaatgttctatcccgcacagattgcttc |
| catggattcgctctgagcaccctttggatcttctatgtgatggactgagaccaaccaacgagca |
| taaagactcagtgagagctctagctaatgaagaaccagagactaacttggccaatttggtgtgta |
| ctattcttggtcgtgtagatcctataagagctaactattgggcatggaggaagagcaagatt**aca** |
| **gtggcagcaatttgaggatccttt** |

A disclosed FT1 polypeptide (SEQ ID NO:5) encoded by SEQ ID NO:1 has 326 amino acid residues and is presented in Table 4B using the one-letter amino acid code.

TABLE 4B

| Encoded FT1 protein sequence (SEQ ID NO: 5). |
|---|
| MNFDETVPLSQRLEWSDVVPLTQDDGPNPVVPIAYKEEFRETMDYFRAIYFSDERSPRALRLTE |
| ETLLLNSGNYTVWHFRRLVLEALNHDLFEELEFIERIAEDNSKNYQLWHHRRWVAEKLGPDVAG |
| RELEFTRRVLSLDAKHYHAWSHRQWTLRALGGWEDELDYCHELLEADVFNNSAWNQRYYVITQS |
| PLLGGLEAMRESEVSYTIKAILTNPANESSWRYLKALYKDDKESWISDPSVSSVCLNVLSRTDC |
| FHGFALSTLLDLLCDGLRPTNEHKDSVRALANEEPETNLANLVCTILGRVDPIRANYWAWRKSK |
| ITVAAI |

Due to the nature of the cloning strategy the sequence presented does not contain any 5' or 3' non-translated sequence. Using the sequences disclosed herein as hybridization probes, one is able to screen and isolate full length sequences from cDNA or genomic libraries or use the rapid amplification of cDNA ends (RACE) technology or other such PCR techniques. The percent identity of the *Arabidopsis thaliana* nucleotide sequence and its encoded amino acid sequence to that of published sequences is shown in FIG. 8.

The present invention also includes a nucleic acid sequence complimentary to the *Arabidopsis thaliana* farnesyl transferase alpha subunit of SEQ ID NO:1. The disclosed complimentary sequence is shown as SEQ ID NO:2. The nucleic acid sequence of SEQ ID NO:3 shows the nucleic acid sequence of SEQ ID NO:2 that has been prepared for ligation into an expression vector.

SEQ ID NO: 2 aaaggatcctcaaattgctgccactgtaatcttgctcttcctccatgccc
aatagttagctcttataggatctacacgaccaagaatagtacacaccaaa
ttggccaagttagtctctggttcttcattagctagagctctcactgagtc
tttatgctcgttggttggtctcagtccatcacatagaagatccaaaaggg
tgctcagagcgaatccatggaagcaatctgtgcgggatagaacattcaaa
cagactgaggaaacacttggatcactaatccaggattctttgtcgtcttt
gtaaagcgcttttaggtatcgccatgagctctcgtttgcaggattggtta
aaatggctttgattgtgtagcttacttcagattctctcatggcttctagg -continued cctcccaacaaaggagattgggtgatgacataatacctctgattccaggc
ggaattgttaaagacgtcagcttcaaggagctcgtgacagtaatcgagct
catcttcccatcctcctaatgcccgtagtgtccactgcctatgtgaccaa
gcatgataatgtttggcatcaagtgaaagtactctacgggtaaattcaag
ttctctccctgcaacatcaggacccagtttctctgcaacccatcgccgat
gatgccacagttggtagttcttagagttatcctcagcaatgcgttcgatg
aactcgagttcttcaaacaagtcgtgattaagggcctcgagtactaggcg
cctgaaatgccacactgtgtagttgccggagtttaagaggagggtttctt
ccgtgagtcgtagtgcgcgaggagatcgctcgtcggaaaagtaaatcgca
cggaagtaatccatagtctcgcggaactcttccttgtaggcaattggcac
cactggattcggaccatcgtcctgagtcaatgggaccacgtctgaccact
ccaatcgttggctcagtggcacggtctcgtcgaaattcatcccgggttt

SEQ ID NO: 3

*gatcc*tcaaattgctgccactgtaatcttgctcttcctccatgcccaata
gttagctcttataggatctacacgaccaagaatagtacacaccaaattgg
ccaagttagtctctggttcttcattagctagagctctcactgagtcttta
tgctcgttggttggtctcagtccatcacatagaagatccaaaagggtgct
cagagcgaatccatggaagcaatctgtgcgggatagaacattcaaacaga
ctgaggaaacacttggatcactaatccaggattctttgtcgtctttgtaa
agcgcttttaggtatcgccatgagctctcgtttgcaggattggttaaaat
ggctttgattgtgtagcttacttcagattctctcatggcttctaggcctc
ccaacaaaggagattgggtgatgacataatacctctgattccaggcggaa
ttgttaaagacgtcagcttcaaggagctcgtgacagtaatcgagctcatc
ttcccatcctcctaatgcccgtagtgtccactgcctatgtgaccaagcat
gataatgtttggcatcaagtgaaagtactctacgggtaaattcaagttct
ctccctgcaacatcaggacccagtttctctgcaacccatcgccgatgatg
ccacagttggtagttcttagagttatcctcagcaatgcgttcgatgaact
cgagttcttcaaacaagtcgtgattaagggcctcgagtactaggcgcctg
aaatgccacactgtgtagttgccggagtttaagaggagggtttcttccgt
gagtcgtagtgcgcgaggagatcgctcgtcggaaaagtaaatcgcacgga
agtaatccatagtctcgcggaactcttccttgtaggcaattggcaccact
ggattcggaccatcgtcctgagtcaatgggaccacgtctgaccactccaa
tcgttggctcagtggcacggtctcgtcgaaattcat*ccc*

*Brassica napus* FTA

A disclosed nucleic acid of 822 nucleotides (also referred to as FT2) is shown in Table 5A.

TABLE 5A

| FT2 Nucleotide Sequence (SEQ ID NO: 6). |
|---|
| ATGGATTACTTCCGTGCGATTTACTTCTCCGACGAGCGTTCTGCTCGCGC |
| GCTGCGACTCACGGAAGAAGCTCTCCGCTTAAACTCGGGCAACTACACCG |
| TGTGGCACTTCGGGCGCTTAGTACTCGAGGAGCTTAATAACGACTTGTAT |
| GAAGAGCTCAAGTTCATCGAAAGCATTGCTGAGGATAACTCTAAGAACTA |
| CCAGTTGTGGCATCATCGACGATGGGTCGCAGAGAAACTGGGTCCTGATG |
| TTGCAGGAAAGGAACTTGAGTTTACTCGGAGGGTACTATCACTTGATGCC |
| AAGCATTATCATGCTTGGTCACATAGGCAGTGGGCGCTACAAGCATTAGG |
| AGGATGGGAAAATGAGCTTAACTACTGCCACGAGCTCCTTGAAGCTGACG |
| TCTTTAACAACTCTGCATGGAATCAGAGGTATTACGTTATAACTAGATCA |
| CCTTCGTTGGGAGGCCTAGAAGCCATGAGAGAATCTGAAGTAAGCTACAC |
| AGTCAAAGCCATTTTAGCAAATCCCGGGAACGAGAGCTCTTGGAGGTACC |
| TGAAAGCCCTTTACAAAGACGACACAGAGTCTTGGATTAGTGATCCAAGT |
| GTTTCCTCAGTCTGTTTGAAAGTTCTCTCACGCGCGGACTGCTTCCATGG |
| ATTCGCTCTGAGCACCCTTTTGGATCTTCTGTGCGATGGGTTGAGACCAA |
| CCAACGAGCATAGAGACTCGGTGAAAGCTCTAGCTAATGAAGAACCAGAG |
| ACTAACTTGGCCAATTTGGTGTGTACCATTCTGTGTCGTGTTGATCCAAT |
| AAGAGCTAACTATTGGGCATGG |

A disclosed FT2 polypeptide (SEQ ID NO:7) encoded by SEQ ID NO:6 has 274 amino acid residues and is presented in Table 5B using the one-letter amino acid code.

TABLE 5B

| Encoded FT2 protein sequence (SEQ ID NO: 7). |
|---|
| MDYFRAIYFSDERSARALRLTEEALRLNSGNYTVWHFGRLVLEELNNDLY |
| EELKFIESIAEDNSKNYQLWHHRRWVAEKLGPDVAGLEKEFTRRVLSLDA |
| KHYHAWSHRQWALQALGGWENELNYCHELLEADVFNNSAWNQRYYVITRS |
| PSLGGLEAMRESEVSYTVKAILANPGNESSWRYLKALYKDDTESWISDPS |
| VSSVCLKVLSRADCFHGFALSTLLDLLCDGLRPTNEHRDSVKALANEEPE |
| TNLANLVCTILCRVDPIRANYWAWKL |

Due to the nature of the cloning strategy the sequence presented is not full length. Compared to the *Arabidopsis thaliana* sequence there are 42 amino acids missing from the amino terminus and 10 amino acids from the carboxy terminus. The percent identity of the *Brassica napus* nucleotide sequence and its encoded amino acid sequence to that of published sequences is shown in FIG. 8.

Using the sequences disclosed herein as hybridization probes, one is able to screen and isolate full length sequences from cDNA or genomic libraries or use the rapid amplification of cDNA ends (RACE) technology or other such PCR techniques.

The present invention also includes a nucleic acid sequence complimentary to the *Brassica napus* farnesyl transferase alpha subunit of SEQ ID NO:6. The disclosed complimentary sequence is shown as SEQ ID NO:29.

SEQ ID NO: 29

CCATGCCCAATAGTTAGCTCTTATTGGATCAACACGACACAGAATGGTAC
ACACCAAATTGGCCAAGTTAGTCTCTGGTTCTTCATTAGCTAGAGCTTTC
ACCGAGTCTCTATGCTCGTTGGTTGGTCTCAACCCATCGCACAGAAGATC
CAAAAGGGTGCTCAGAGCGAATCCATGGAAGCAGTCCGCGCGTGAGAGAA
CTTTCAAACAGACTGAGGAAACACTTGGATCACTAATCCAAGACTCTGTG
TCGTCTTTGTAAAGGGCTTTCAGGTACCTCCAAGAGCTCTCGTTCCCGGG
ATTTGCTAAAATGGCTTTGACTGTGTAGCTTACTTCAGATTCTCTCATGG
CTTCTAGGCCTCCCAACGAAGGTGATCTAGTTATAACGTAATACCTCTGA
TTCCATGCAGAGTTGTTAAAGACGTCAGCTTCAAGGAGCTCGTGGCAGTA
GTTAAGCTCATTTTCCCATCCTCCTAATGCTTGTAGCGCCCACTGCCTAT
GTGACCAAGCATGATAATGCTTGGCATCAAGTGATAGTACCCTCCGAGTA
AACTCAAGTTCCTTTCCTGCAACATCAGGACCCAGTTTCTCTGCGACCCA
TCGTCGATGATGCCACAACTGGTAGTTCTTAGAGTTATCCTCAGCAATGC
TTTCGATGAACTTGAGCTCTTCATACAAGTCGTTATTAAGCTCCTCGAGT
ACTAAGCGCCCGAAGTGCCACACGGTGTAGTTGCCCGAGTTTAAGCGGAG
AGCTTCTTCCGTGAGTCGCAGCGCGCGAGCAGAACGCTCGTCGGAGAAGT
AAATCGCACGGAAGTAATCCAT

*Brassica napus* FTB

A disclosed nucleic acid of 1110 nucleotides (also referred to as FT3) is shown in Table 6A.

TABLE 6A

| FT3 Nucleotide Sequence (SEQ ID NO: 8). |
|---|
| TGGCTTTGTTACTGGATTCTTCATTCAATTGCTTTGCTTGGGGAGTCTGT |
| GGATGATGACTTAGAAAACAATGCAATCGATTTTCTTGGACGTTGCCAGG |
| GTTCTGATGGTGGATATGGTGGTGGTCCTGGCCAACTTCCACATCTTGCA |
| ACAAGTTATGCTGCAGTGAATACACTTGTTACTTTAGGAGGTGAGAAAGC |
| CTTCTCTTCAATTAACAGAGAACAAATGGCTTGTTTCTTAAGACGAATGA |
| AGGATACAAATGGAGGTTTCAGGATGCATAATATGGGAGAAATAGATGTG |
| CGAGCGTGCTACACTGCGATTTTGATTGCAAGCATCCTGAACATTGTGGA |
| TGATGAACTCACCCGCGGCTTAGGAGATTACATTTTGAGTTGCCAAACTT |
| ATGAAGGTGGCATTGGAGGGGAACCTGGCTCCGAAGCTCATGGTGGGTAC |
| ACGTACTGTGGGTTGGCTACTATGATTTTAATCAATGAAGTCGACCGCTT |
| GAATTTGGATTCGTTAATGAATTGGGTTGTACATCGACAAGGAGTAGAAA |
| TGGGATTCCAAGGTAGGACGAACAAATTGGTCGACGGTTGCTACACGTTT |
| TGGCAGGCAGCCCCCTGTGTTCTACTACAGCGATTTTTTTCATCCCAGGA |
| TATGGCACCTCATGGATCATCATCACATATGTCACAAGGGACAGATGAAG |
| ATCACGAGGAACATGGTCATGATGAAGATGATCCTGAAGACAGTGATGAA |
| GATGATTCTGATGAGGATAGCGATGAAGATTCAGGGAATGGTCACCAAGT |
| TCATCATACGTCTACCTACATTGACAGGAGAATTCAACCTGTTTTTGATA |
| GCCTCGGCTTGCAAAGATATGTGCTCTTGTGCTCTCAGGTTGCTGATGGT |

TABLE 6A-continued

| FT3 Nucleotide Sequence (SEQ ID NO: 8). |
|---|
| GGATTCAGAGACAAGCTGAGGAAACCCCGTGACTTCTACCACACATGTTA |
| CTGCCTAAGCGGTCTTTCCGTGGCTCAACACGCTTGGTCAAAAGACGAGG |
| ACACTCCTCCTTTGACTCGTGACATTTTGGGTGGCTACGCAAACCACCTT |
| GAACCTGTTCACCTCCTCCACAACATTGTCTTGGATCGGTATTATGAAGC |
| TTCTAGATTT |

A disclosed FT3 polypeptide (SEQ ID NO:9) encoded by SEQ ID NO:7 has 370 amino acid residues and is presented in Table 6B using the one-letter amino acid code.

TABLE 6B

| Encoded FT3 protein sequence (SEQ ID NO: 9). |
|---|
| WLCYWILHSIALLGESVDDDLENNAIDFLGRCQGSDGGYGGGPGQLPHLA |
| TSYAAVNTLVTLGGEKAFSSINREQMACFLRRMKDTNGGFRMHNMGEIDV |
| RACYTAILIASILNIVDDELTRGLGDYILSCQTYEGGIGGEPGSEAHGGY |
| TYCGLATMILINEVDRLNLDSLMNWVVHRQGVEMGFQGRTNKLVDGCYTF |
| WQAAPCVLLQRFFSSQDMAPHGSSSHMSQGTDEDHEEHGHDEDDPEDSDE |
| DDSDEDSDEDSGNGHQVHHTSTYIDRRIQPVFDSLGLQRYVLLCSQVADG |
| GFRDKLRKPRDFYHTCYCLSGLSVAQHAWSKDEDTPPLTRDILGGYANHL |
| EPVHLLHNILVDRYYEASRF |

Due to the nature of the cloning strategy the sequence presented is not full length. Compared to the *Arabidopsis thaliana* sequence there are 31 amino acids missing from the amino terminus and 5 amino acids from the carboxy terminus. The percent identity of the *Brassica napus* nucleotide sequence and its encoded amino acid sequence to that of published sequences is shown in FIG. 9.

Using the sequences disclosed herein as hybridization probes, one is able to screen and isolate full length sequences from cDNA or genomic libraries or use the rapid amplification of cDNA ends (RACE) technology or other such PCR techniques. Sequence comparisons have been performed and percent identities are shown in FIG. 8 and FIG. 9.

The present invention also includes a nucleic acid sequence complimentary to the *Brassica napus* farnesyl transferase beta subunit of SEQ ID NO:8. The disclosed complimentary sequence is shown as SEQ ID NO:30.

SEQ ID NO: 30

AAATCTAGAAGCTTCATAATACCGATCCAAGACAATGTTGTGGAGGAGGT
GAACAGGTTCAAGGTGGTTTGCGTAGCCACCCAAAATGTCACGAGTCAAA
GGAGGAGTGTCCTCGTCTTTTGACCAAGCGTGTTGAGCCACGGAAAGACC
GCTTAGGCAGTAACATGTGTGGTAGAAGTCACGGGGTTTCCTCAGCTTGT
CTCTGAATCCACCATCAGCAACCTGAGAGCACAAGAGCACATATCTTTGC
AAGCCGAGGCTATCAAAAACAGGTTGAATTCTCCTGTCAATGTAGGTAGA
CGTATGATGAACTTGGTGACCATTCCCTGAATCTTCATCGCTATCCTCAT

-continued

CAGAATCATCTTCATCACTGTCTTCAGGATCATCTTCATCATGACCATGT

TCCTCGTGATCTTCATCTGTCCCTTGTGACATATGTGATGATGATCCATG

AGGTGCCATATCCTGGGATGAAAAAAATCGCTGTAGTAGAACACAGGGGG

CTGCCTGCCAAAACGTGTAGCAACCGTCGACCAATTTGTTCGTCCTACCT

TGGAATCCCATTTCTACTCCTTGTCGATGTACAACCCAATTCATTAACGA

ATCCAAATTCAAGCGGTCGACTTCATTGATTAAAATCATAGTAGCCAACC

CACAGTACGTGTACCCACCATGAGCTTCGGAGCCAGGTTCCCCTCCAATG

CCACCTTCATAAGTTTGGCAACTCAAAATGTAATCTCCTAAGCCGCGGGT

GAGTTCATCATCCACAATGTTCAGGATGCTTGCAATCAAAATCGCAGTGT

AGCACGCTCGCACATCTATTTCTCCCATATTATGCATCCTGAAACCTCCA

TTTGTATCCTTCATTCGTCTTAAGAAACAAGCCATTTGTTCTCTGTTAAT

TGAAGAGAAGGCTTTCTCACCTCCTAAAGTAACAAGTGTATTCACTGCAG

CATAACTTGTTGCAAGATGTGGAAGTTGGCCAGGACCACCACCATATCCA

CCATCAGAACCCTGGCAACGTCCAAGAAAATCGATTGCATTGTTTTCTAA

GTCATCATCCACAGACTCCCCAAGCAAAGCAATTGAATGAAGAATCCAGT

AACAAAGCCA

*Glycine max* FTA

A disclosed nucleic acid of 1041 nucleotides (also referred to as FT4) is shown in Table 7A.

TABLE 7A

| FT4 Nucleotide Sequence (SEQ ID NO: 31). |
|---|
| ATGGAATCTGGGTCTAGCGAAGGAGAAGAGGTGCAGCAACGCGTGCCGTT |
| GAGGGAGAGAGTGGAGTGGTCAGATGTTACTCCGGTTCCTCAAAACGACG |
| GCCCTAACCCTGTCGTTCCGATCCAGTACACTGAAGAGTTTTCCGAAGTT |
| ATGGATTACTTTCGCGCCGTTTACCTCACCGATGAACGCTCCCCTCGCGC |
| CCTCGCTCTCACAGCCGAAGCCGTTCAATTCAACTCCGGCAACTACACTG |
| TGTGGCATTTCCGACGGTTGTTACTTGAGTCGCTAAAAGTCGACTTGAAC |
| GATGAACTGGAGTTTGTGGAGCGTATGGCCGCTGGAAATTCTAAAAATTA |
| TCAGATGTGnATGTTCTGTAGGCATCCTAGACGATGGGTTGCCGAGAAGT |
| TAGGTCCTGAAGCTAGAAACAATGAGCTCGAGTTCACCAAAAAGATACTG |
| TCCGTTGATGCCAAACATTATCATGCATGGTCTCATAGACAGTGGGCTCT |
| TCAAACACTAGGAGGATGGGAAGATGAACTTAATTATTGCACAGAACTAC |
| TTAAAGAAGACATTTTTAACAATTCTGCTTGGAATCAGAGATATTTTGTC |
| ATAACAAGGTCTCCTTTCTTGGGGGGCCTAAAAGCTATGAGAGAGTCTGA |
| AGTGCTTTACACCATCGAAGCCATTATAGCCTACCCTGAAAATGAAAGCT |
| CGTGGAGATATCTACGAGGACTTTATAAAGGTGAAACTACTTCATGGGTA |
| AATGATCCTCAAGTTTCTTCAGTATGCTTAAAGATTTTGAGAACTAAGAG |
| CAACTACGTGTTTGCTCTTAGCACTATTTTAGATCTTATATGCTTTGGTT |
| ATCAACCAAATGAAGACATTAGAGATGCCATTGACGCCTTAAAGACCGCA |
| GATATGGATAAACAAGATTTAGATGATGATGAGAAAGGGGAACAACAAAA |

TABLE 7A-continued

| FT4 Nucleotide Sequence (SEQ ID NO: 31). |
|---|
| TTTAAATATAGCACGAAATATTTGTTCTATCCTAAAACAAGTTGATCCAA |
| TTAGAACCAACTATTGGATTTGGCGCAAGAGCAGACTTCCT |

A disclosed FT4 polypeptide (SEQ ID NO:33) encoded by SEQ ID NO:31 has 347 amino acid residues and is presented in Table 7B using the one-letter amino acid code.

TABLE 7B

| Encoded FT4 protein sequence (SEQ ID NO: 33). |
|---|
| MESGSSEGEEVQQRVPLRERVEWSDVTPVPQNDGPNPVVPIQYTEEFSEV |
| MDYFRAVYLTDERSPRALALTAEAVQFNSGNYTVWHFRRLLLESLKVDLN |
| DELEFVERMAAGNSKNYQMXMFCRHPRRWVAEKLGPEARNNELEFTKKIL |
| SVDAKHYHAWSHRQWALQTLGGWEDELNYCTELLKEDIFNNSAWNQRYFV |
| ITRSPFLGGLKAMRESEVLYTIEAIIAYPENESSWRYLRGLYKGETTSWV |
| NDPQVSSVCLKILRTKSNYVFALSTILDLICFGYQPNEDIRDAIDALKTA |
| DMDKQDLDDDEKGEQQNLNIARNICSILKQVDPIRTNYWIWRKSRLP |

Due to the nature of the cloning strategy the sequence presented is not full length. The percent identity of the *Glycine max* nucleotide sequence and its encoded amino acid sequence to that of other sequences is shown in FIG. 8.

Using the sequences disclosed herein as hybridization probes, one is able to screen and isolate full length sequences from cDNA or genomic libraries or use the rapid amplification of cDNA ends (RACE) technology or other such PCR techniques.

The present invention also includes a nucleic acid sequence complimentary to the *Glycine max* alpha subunit of SEQ ID NO:31. The disclosed complimentary sequence is shown as SEQ ID NO:32.

SEQ ID NO: 32

AGGAAGTCTGCTCTTGCGCCAAATCCAATAGTTGGTTCTAATTGGATCAA

CTTGTTTTAGGATAGAACAAATATTTCGTGCTATATTTAAATTTTGTTGT

TCCCCTTTCTCATCATCATCTAAATCTTGTTTATCCATATCTGCGGTCTT

TAAGGCGTCAATGGCATCTCTAATGTCTTCATTTGGTTGATAACCAAAGC

ATATAAGATCTAAAATAGTGCTAAGAGCAAACACGTAGTTGCTCTTAGTT

CTCAAAATCTTTAAGCATACTGAAGAAACTTGAGGATCATTTACCCATGA

AGTAGTTTCACCTTTATAAAGTCCTCGTAGATATCTCCACGAGCTTTCAT

TTTCAGGGTAGGCTATAATGGCTTCGATGGTGTAAAGCACTTCAGACTCT

CTCATAGCTTTTAGGCCCCCCAAGAAAGGAGACCTTGTTATGACAAAATA

TCTCTGATTCCAAGCAGAATTGTTAAAAATGTCTTCTTTAAGTAGTTCTG

TGCAATAATTAAGTTCATCTTCCCATCCTCCTAGTGTTTGAAGAGCCCAC

TGTCTATGAGACCATGCATGATAATGTTTGGCATCAACGGACAGTATCTT

TTTGGTGAACTCGAGCTCATTGTTTCTAGCTTCAGGACCTAACTTCTCGG

CAACCCATCGTCTAGGATGCCTACAGAACATNCACATCTGATAATTTTTA

-continued

```
GAATTTCCAGCGGCCATACGCTCCACAAACTCCAGTTCATCGTTCAAGTC
GACTTTTAGCGACTCAAGTAACAACCGTCGGAAATGCCACACAGTGTAGT
TGCCGGAGTTGAATTGAACGGCTTCGGCTGTGAGAGCGAGGGCGCGAGGG
GAGCGTTCATCGGTGAGGTAAACGGCGCGAAAGTAATCCATAACTTCGGA
AAACTCTTCAGTGTACTGGATCGGAACGACAGGGTTAGGGCCGTCGTTTT
GAGGAACCGGAGTAACATCTGACCACTCCACTCTCTCCCTCAACGGCACG
CGTTGCTGCACCTCTTCTCCTTCGCTAGACCCAGATTCCAT
```

*Glycine max* FTB

A disclosed nucleic acid of 1035 nucleotides (also referred to as FT5) is shown in Table 8A.

TABLE 8A

| FT5 Nucleotide Sequence (SEQ ID NO: 34). |
|---|
| GCCACCATTCCTCGCAACGCCCAAACCCTCATGTTGGAGCTTCAACGCGA |
| TAATCACATGCAGTATGTCTCCAAAGGCCTTCGCCATCTCAGTTCCGCAT |
| TTTCCGTTTTGGACGCTAATCGACCCTGGCTCTGCTACTGGATCTTCCAC |
| TCCATTGCTTTGTTGGGAGAATCCGTCGATGATGAACTCGAAGATAACGC |
| TATCGATTTTCTTAACCGTTGCCAGGATCCGAATGGTGGATATGCCGGGG |
| GACCAGGCCAGATGCCTCATATTGCCACAACTTATGCTGCTGTTAATTCA |
| CTTATTACTTTGGGTGGTGAGAAATCCCTGGCATCAATTAATAGAGATAA |
| ACTGTATGGGTTTCTGCGGCGGATGAAGCAACCAAATGGTGGATTCAGGA |
| TGCATGATGAAGGTGAAATTGATGTTCGAGCTTGCTACACTGCCATTTCT |
| GTTGCAAGTGTTTTGAACATTTTGGATGATGAGCTGATCCAGAATGTTGG |
| AGACTACATTATAAGCTGTCAAACATATGAGGGTGGCATTGCTGGTGAGC |
| CTGGTTCTGAGGCTCATGGTGGGTACACCTTTTGTGGATTAGCTACAATG |
| ATTCTGATTGGTGAGGTTAATCACTTGGATCTGCCTCGATTAGTTGACTG |
| GGTGGTATTCCGACAAGGTAAGGAATGTGGATTCCAGGGGAGAACAAATA |
| AACTGGTGGATGGATGCTATTCCTTTTGGCAGGGAGGTGCTGTTGCTCTA |
| TTGCAAAGATTATCTTCTATTATCAACAAACAGATGGAAGAGACATCACA |
| GATTTTTGCGGTATCTTATGTATCTGAAGCAAAAGAAAGTTTGGATGGAA |
| CCTCTAGTCATGCAACATGCCGTGGTGAGCATGAAGGCACCAGTGAATCC |
| AGTTCATCTGATTTTAAAAATATTGCCTATAAATTTATTAATGAGTGGAG |
| AGCACAAGAACCACTTTTTCACAGTATTGCTTTACAGCAATATATTCTCT |
| TATGTGCACAGGAGCAAGAGGGTGGACTGAGAGACAAACCGGGTAAACGT |
| AGAGATCATTATCACACATGTTACTGTTTAAGTGGACTCTCATTGTGCCA |
| GTATAGTTGGTCAAAGCACCCAGATTCTCCACCAC |

A disclosed FT5 polypeptide (SEQ ID NO:36) encoded by SEQ ID NO:34 has 378 amino acid residues and is presented in Table 8B using the one-letter amino acid code.

TABLE 8B

| Encoded FT5 protein sequence (SEQ ID NO: 36). |
|---|
| ATIPRNAQTLMLELQRDNHMQYVSKGLRHLSSAFSVLDANRPWLCYWIFH |
| SIALLGESVDDELEDNAIDFLNRCQDPNGGYAGGPGQMPHIATTYAAVNS |
| LITLGGEKSLASINRDKLYGFLRRMKQPNGGFRMHDEGEIDVRACYTAIS |
| VASVLNILDDELIQNVGDYIISCQTYEGGIAGEPGSEAHGGYTFCGLATM |
| ILIGEVNHLDLPRLVDWVVFRQGKECGFQGRTNKLVDGCYSFWQGGAVAL |
| LQRLSSIINKQMEETSQIFAVSYVSEAKESLDGTSSHATCRGEHEGTSES |
| SSSDFKNIAYKFINEWRAQEPLFHSIALQQYILLCAQEQEGGLRDKPGKR |
| RDHYHTCYCLSGLSLCQYSWSKHPDSPP |

Due to the nature of the cloning strategy the sequence presented is not full length. The percent identity of the *Glycine max* nucleotide sequence and its encoded amino acid sequence to that of other sequences is shown in FIG. 8.

Using the sequences disclosed herein as hybridization probes, one is able to screen and isolate full length sequences from cDNA or genomic libraries or use the rapid amplification of cDNA ends (RACE) technology or other such PCR techniques.

The present invention also includes a nucleic acid sequence complimentary to the *Glycine max* beta subunit of SEQ ID NO:34. The disclosed complimentary sequence is shown as SEQ ID NO:35.

SEQ ID NO: 35

```
GTGGTGGAGAATCTGGGTGCTTTGACCAACTATACTGGCACAATGAGAGT
CCACTTAAACAGTAACATGTGTGATAATGATCTCTACGTTTACCCGGTTT
GTCTCTCAGTCCACCCTCTTGCTCCTGTGCACATAAGAGAATATATTGCT
GTAAAGCAATACTGTGAAAAAGTGGTTCTTGTGCTCTCCACTCATTAATA
AATTTATAGGCAATATTTTTAAAATCAGATGAACTGGATTCACTGGTGCC
TTCATGCTCACCACGGCATGTTGCATGACTAGAGGTTCCATCCAAACTTT
CTTTTGCTTCAGATACATAAGATACCGCAAAAATCTGTGATGTCTCTTCC
ATCTGTTTGTTGATAATAGAAGATAATCTTTGCAATAGAGCAACAGCACC
TCCCTGCCAAAAGGAATAGCATCCATCCACCAGTTTATTTGTTCTCCCCT
GGAATCCACATTCCTTACCTTGTCGGAATACCACCCAGTCAACTAATCGA
GGCAGATCCAAGTGATTAACCTCACCAATCAGAATCATTGTAGCTAATCC
ACAAAAGGTGTACCCACCATGAGCCTCAGAACCAGGCTCACCAGCAATGC
CACCCTCATATGTTTGACAGCTTATAATGTAGTCTCCAACATTCTGGATC
AGCTCATCATCCAAAATGTTCAAAACACTTGCAACAGAAATGGCAGTGTA
GCAAGCTCGAACATCAATTTCACCTTCATCATGCATCCTGAATCCACCAT
TTGGTTGCTTCATCCGCCGCAGAAACCCATACAGTTTATCTCTATTAATT
GATGCCAGGGATTTCTCACCACCCAAAGTAATAAGTGAATTAACAGCAGC
ATAAGTTGTGGCAATATGAGGCATCTGGCCTGGTCCCCCGGCATATCCAC
CATTCGGATCCTGGCAACGGTTAAGAAAATCGATAGCGTTATCTTCGAGT
TCATCATCGACGGATTCTCCCAACAAAGCAATGGAGTGGAAGATCCAGTA
```

-continued

GCAGAGCCAGGGTCGATTAGCGTCCAAAACGGAAAATGCGGAACTGAGAT

GGCGAAGGCCTTTGGAGACATACTGCATGTGATTATCGCGTTGAAGCTCC

AACATGAGGGTTTGGGCGTTGCGAGGAATGGTGGC

*Zea maize* FTB

A disclosed nucleic acid of 1235 nucleotides (also referred to as FT6) is shown in Table 9A.

TABLE 9A

| FT6 Nucleotide Sequence (SEQ ID NO: 37). |
|---|
| GGCGGATCCCGACCTACCGAGGCTCACGGTGACGCAGGTGGAGCAGATGA |
| AGGTGGAGGCCAGGGTTGGCGACATCTACCGCTCCCTCTTCGGGGCCGCG |
| CCCAACACGAAATCCATCATGCTAGAGCTGTGGCGTGATCAGCATATCGA |
| GTATCTGACGCCTGGGCTGAGGCATATGGGACCAGCCTTTCATGTTCTAG |
| ATGCCAATCGCCCTTGGCTATGCTACTGGATGGTTCATCCACTTGCTTTG |
| CTGGATGAAGCACTTGATGATGATCTTGAGAATGATATCATAGACTTCTT |
| AGCTCGATGTCAGGATAAAGATGGTGGATATAGTGGTGGACCTGGACAGT |
| TGCCTCACCTAGCTACGACTTATGCTGCTGTAAATACACTTGTGACAATA |
| GGGAGCGAAAGAGCATTGTCATCAATCAATAGGGGCAACCTGTACAATTT |
| TATGCTGCAGATGAAAGATGTATCAGGTGCTTTCAGAATGCATGATGGTG |
| GCGAAATTGATGTCCGTGCTTCCTACACCGCTATATCGGTTGCCAGCCTT |
| GTGAATATTCTTGATTTTAAACTGGCAAAAGGTGTAGGCGACTACATAGC |
| AAGATGTCAAACTTATGAAGGTGGTATTGCTGGGGAGCCTTATGCTGAAG |
| CACATGGTGGGTATACATTCTGTGGATTGGCTGCTTTGATCCTGCTTAAT |
| GAGGCAGAGAAAGTTGACTTGCCTAGTTTGATTGGCTGGGTGGCTTTTCG |
| TCAAGGAGTGGAATGCGGATTTCAAGGACGAACTAATAAATTGGTTGATG |
| GTTGCTACTCCTTTTGGCAGGGAGCTGCCATTGCTTTCACACAAAAGTTA |
| ATTACGATTGTTGATAAGCAATTGAGGTCCTCGTATTCCTGCAAAAGGCC |
| ATCAGGAGAGGATGCCTGCAGCACCAGTTCATATGGGTGCACCGCGAATA |
| AGTCTTCCTCTGCTGTGGACTATGCGAAGTTTGGATTTGATTTTATACAA |
| CAGAGCAACCAAATTGGCCCACTCTTCCATAACATTGCCCTGCAACAATA |
| CATCCTACTTTGTTCTCAGGTACTAGAGGGAGGCTTGAGGGATAAGCCTG |
| GAAAGAACAGAGATCACTATCATTCATGCTACTGCCTCAGTGGCCTCGCA |
| GTTAGCCAGTACAGTGCCATGACTGATACTGGTTCGTGCCCATTACCTCA |
| GCATGTGCTTGGACCGTACTCTAATTTGCTGGAGCCAATCCATCC |

A disclosed FT6 polypeptide (SEQ ID NO:39) encoded by SEQ ID NO:37 has 414 amino acid residues and is presented in Table 9B using the one-letter amino acid code.

TABLE 9B

| Encoded FT6 protein sequence (SEQ ID NO: 39). |
|---|
| ADPDLPRLTVTQVEQMKVEARVGDIYRSLFGAAPNTKSIMLELWRDQHIE |
| YLTPGLRHMGPAFHVLDANRPWLCYWMVHPLALLDEALDDDLENDIIDFL |
| ARCQDKDGGYSGGPGQLPHLATTYAAVNTLVTIGSERALSSINRGNLYNF |
| MLQMKDVSGAFRMHDGGEIDVRASYTAISVASLVNILDFKLAKGVGDYIA |
| RCQTYEGGIAGEPYAEAHGGYTFCGLAALILLNEAEKVDLPSLIGWVAFR |
| QGVECGFQGRTNKLVDGCYSFWQGAAIAFTQKLITIVDKQLRSSYSCKRP |
| SGEDACSTSSYGCTANKSSSAVDYAKFGFDFIQQSNQIGPLFHNIALQQY |
| ILLCSQVLEGGLRDKPGKNRDHYHSCYCLSGLAVSQYSAMTDTGSCPLPQ |
| HVLGPYSNLLEPIH |

Due to the nature of the cloning strategy the sequence presented is not full length. The percent identity of the *Glycine max* nucleotide sequence and its encoded amino acid sequence to that of other sequences is shown in FIG. 8.

Using the sequences disclosed herein as hybridization probes, one is able to screen and isolate full length sequences from cDNA or genomic libraries or use the rapid amplification of cDNA ends (RACE) technology or other such PCR techniques.

The present invention also includes a nucleic acid sequence complimentary to the *Zea maize* beta subunit of SEQ ID NO:37. The disclosed complimentary sequence is shown as SEQ ID NO:38.

SEQ ID NO: 38

GGATGGATTGGCTCCAGCAAATTAGAGTACGGTCCAAGCACATGCTGAGG

TAATGGGCACGAACCAGTATCAGTCATGGCACTGTACTGGCTAACTGCGA

GGCCACTGAGGCAGTAGCATGAATGATAGTGATCTCTGTTCTTTCCAGGC

TTATCCCTCAAGCCTCCCTCTAGTACCTGAGAACAAAGTAGGATGTATTG

TTGCAGGGCAATGTTATGGAAGAGTGGGCCAATTTGGTTGCTCTGTTGTA

TAAAATCAAATCCAAACTTCGCATAGTCCACAGCAGAGGAAGACTTATTC

GCGGTGCACCCATATGAACTGGTGCTGCAGGCATCCTCTCCTGATGGCCT

TTTGCAGGAATACGAGGACCTCAATTGCTTATCAACAATCGTAATTAACT

TTTGTGTGAAAGCAATGGCAGCTCCCTGCCAAAAGGAGTAGCAACCATCA

ACCAATTTATTAGTTCGTCCTTGAAATCCGCATTCCACTCCTTGACGAAA

AGCCACCCAGCCAATCAAACTAGGCAAGTCAACTTTCTCTGCCTCATTAA

GCAGGATCAAAGCAGCCAATCCACAGAATGTATACCCACCATGTGCTTCA

GCATAAGGCTCCCCAGCAATACCACCTTCATAAGTTTGACATCTTGCTAT

GTAGTCGCCTACACCTTTTGCCAGTTTAAAATCAAGAATATTCACAAGGC

TGGCAACCGATATAGCGGTGTAGGAAGCACGGACATCAATTTCGCCACCA

TCATGCATTCTGAAAGCACCTGATACATCTTTCATCTGCAGCATAAAATT

GTACAGGTTGCCCCTATTGATTGATGACAATGCTCTTTCGCTCCCTATTG

TCACAAGTGTATTTACAGCAGCATAAGTCGTAGCTAGGTGAGGCAACTGT

CCAGGTCCACCACTATATCCACCATCTTTATCCTGACATCGAGCTAAGAA

GTCTATGATATCATTCTCAAGATCATCATCAAGTGCTTCATCCAGCAAAG

CAAGTGGATGAACCATCCAGTAGCATAGCCAAGGGCGATTGGCATCTAGA

-continued

```
ACATGAAAGGCTGGTCCCATATGCCTCAGCCCAGGCGTCAGATACTCGAT

ATGCTGATCACGCCACAGCTCTAGCATGATGGATTTCGTGTTGGGCGCGG

CCCCGAAGAGGGAGCGGTAGATGTCGCCAACCCTGGCCTCCACCTTCATC

TGCTCCACCTGCGTCACCGTGAGCCTCGGTAGGTCGGGATCCGCC
```

The FTA and FTB nucleic acids and amino acids disclosed above have homology to other members of the FT protein family (GenBank ID NOs: U63298, U83707, and U73203; WO 00/14207; Cutler et al., Science 273(5279):1239-41, 1996; Ziegelhoffer et al., Proc Natl Acad Sci USA. 97(13): 7633-8, 2000). The homology between these and other sequences is shown graphically in the ClustalW analysis shown in Tables 10A-10D. In the ClustalW alignment, the black outlined amino acid residues indicate regions of conserved sequence (i.e., regions that may be required to preserve structural or functional properties), whereas non-highlighted amino acid residues are less conserved and can potentially be altered to a much broader extent without altering protein structure or function.

TABLE 10A

ClustalW Nucleic Acid Analysis of FT Alpha Subunits

1) BNA-12; FT2 (SEQ ID NO: 6)
2) At-FT-A; FT1 (SEQ ID NO: 1)
3) PPI-Soy-FTA; FT4 (SEQ ID NO: 31)
4) Pea-FT-A (SEQ ID NO: 59)
5) Tomato-FTA (SEQ ID NO: 60)
6) Rice-FT-A (SEQ ID NO: 61)
7) *Zea mays*-FT-A (SEQ ID NO: 62)
8) Soy1-FT-A (SEQ ID NO: 63)
9) Soy2-FT-A (SEQ ID NO: 64)
10) Triticum-FT-A (SEQ ID NO: 65)

```
                        10        20        30        40        50        60        70
                ....|....|....|....|....|....|....|....|....|....|....|....|....|....|
BnA-12          ----------------------------------------------------------------------
At-FT-A         ----------------------------------------------------------------------
PPI-Soy-FTA     ---------------------------------------------------------------AT--GGA
Pea-FT-A        CAACACCTACCTAGTGCTTCTAGTTCTGGTTCTAGGACTGAGAGTAAACAGAAGTGAAGAAGAATCCAGA
Tomato-FTA      ---TACCCCGAAGGCAATTCCAGTATTGAACTACCGCCGGCAGTTTTCCGATCGGATCCCGGAGCCGAGT
Rice-FT-A       -----------GCACGAGGTTCTAACGCCGCCGCCGCCGCCGTCTCCGCA-GAATCTGATCGATGGC
Zea mays-FT-A   -----------------GCACGAGACAGCGCAATTACTTAAGCTATTTGTATTCGGATCTGATCCAACCC
Soy1-FT-A       --------------------------------------------GCACGAGGATTAACGAAGGAT--GGA
Soy2-FT-A       ------------------------GCACGAGCTTGCGTGTGGAGTGAAGAAGATTAACGAAGGAT--GGA
Triticum-FT-A   ----------------------------------------------------------------------

                        80        90       100       110       120       130       140
                ....|....|....|....|....|....|....|....|....|....|....|....|....|....|
BnA-12          ----------------------------------------------------------------------
At-FT-A         ---GAGTCGGGGAACATGAATTTCGACGAG---A-CCGTG----CCACTGAGCCAACGATTGGAGTGGTC
PPI-Soy-FTA     AT----CTGGGTCTAGCGAAGGAGAAGAGGTGCAGCAACGCGTGCCGTTGAGGGAGAGAGTGGAGTGGTC
Pea-FT-A        ACATGGCCGGGAATATCGAAGTTGAAGAAG---ACGATCGTGTGCCGCTAAGATTACGACCTGAGTGGTC
Tomato-FTA      ATCAAATGGACAGTTGTGAGGT--GACGAA---A-ACGCGAATTCCTTTCAAGGAAAGGCCCGACTGGGC
Rice-FT-A       GCCGTCGTCGACGTCGTCGGAGGGTGCCTC-CGACGAGTGGTTGCCACCCAGCCGGCGGCCGGAGCTGGC
Zea mays-FT-A   TGGTGGTCAGCTGGACTCATCGCCCATGGA-GCACACTAAGTCAGGCCCCAGCAGTTGGCCAGAACTGGC
Soy1-FT-A       AT----CTGGGTCTAGCGAAGGAGAAGAGGTGCAGCAACGCGTGCCGTTGAGGGAGAGAGTGGAGTGGTC
Soy2-FT-A       AT----CTGGGTCTAGCGAAGGAGAAGAGGTGCAGCAACGCGTGCCGTTGAGGGAGAGAGTGGAGTGGTC
Triticum-FT-A   ---------------------------------------------------------------------C

                       150       160       170       180       190       200       210
                ....|....|....|....|....|....|....|....|....|....|....|....|....|....|
BnA-12          ----------------------------------------------------------------------
At-FT-A         AGACGTGGTCCCATTGACTCAGGACGATGGTCCGAATCCAGTGGTGCCAATTGCCTACAAGGAAGAGTTC
PPI-Soy-FTA     AGATGTTACTCCGGTTCCTCAAAACGACGGCCCTAACCCTGTCGTTCCGATCCAGTACACTGAAGAGTTT
Pea-FT-A        AGATGTTACTCCGATCCCACAAGACGATGGCCCTAGTCCCGTCGTGCCGATCAACTACTCCGAAGAGTTT
Tomato-FTA      CGATGTGAAGCCCGTTCCGCAAGACGACGGCCCTGCCCGGTTGTTCCCATAGCCTACACAGAAGACTTC
Rice-FT-A       GGACGTGGTCCCCGTGACGCAGGACGACGGGCCCCACCCCGTGGTGGCCATCGCCTACCGGGACGAGTTC
Zea mays-FT-A   CGACGTGGTGCCGGTGCCGCAGGACGATGGGCCTAGCCCTGTGGTGTCCATCGCCTATCGAGATGACTTT
Soy1-FT-A       AGATGTTACTCCGGTTCCTCAAAACGACGGCCCTAACCCTGTCGTTCCGATCCAGTACACTGAAGAGTTT
Soy2-FT-A       AGATGTTACTCCGGTTCCTCAAAACGACGGCCCTAACCCTGTCGTTCCGATCCAGTACACTGAAGAGTTT
Triticum-FT-A   GGACGTGGCGCCGCTGCCGCAGGCCGACGGGCCCTGCCCCGTCGTCTCCATCGCTTACCGCGGCGACTTC
```

TABLE 10A-continued

ClustalW Nucleic Acid Analysis of FT Alpha Subunits

```
                        220        230        240        250        260        270        280
                ....|....|....|....|....|....|....|....|....|....|....|....|....|....|
BnA-12          ---------ATGGATTACTTCCGTGCGATTTACTTCTCCGACGAGCGTTCTGCTCGCGCGCTGCGACTCA
At-FT-A         CGCGAGACTATGGATTACTTCCGTGCGATTTACTTTTCCGACGAGCGATCTCCTCGCGCACTACGACTCA
PPI-Soy-FTA     TCCGAAGTTATGGATTACTTTCGCGCCGTTTACCTCACCGATGAACGCTCCCCTCGCGCCCTCGCTCTCA
Pea-FT-A        TCAGAAGTTATGGATTACTTTCGTGCTGTTTACTTCGCCAAAGAACTTTCCTCTCGCGCTCTTGCTCTCA
Tomato-FTA      TCTGAAACCATGGACTACTTCCGGGCAATTTACGTAGCCGATGAGCGATCTACACGCGCCCTCCAGCTTA
Rice-FT-A       CGCGAGGTCATGGACTACTTCCGCGCCCTCTACTTCGCCGGCGAGCGCAGCGTCCGCGCCCTCCACCTCA
Zea mays-FT-A   CGTGAGGTCATGGATTACTTCCGCGCCCTCTACCTCACCGGTGAGCGAAGCCCTCGCGCTCTCCGCCTCA
Soy1-FT-A       TCCGAAGTTATGGATTACTTTCGCGCCGTTTACCTCACCGATGAACGCTCCCCTCGCGCCCTCGCTCTCA
Soy2-FT-A       TCCGAAGTTATGGATTACTTTCGCGCCGTTTACCTCACCGATGAACGCTCCCCTCGCGCCCTCGCTCTCA
Triticum-FT-A   CGCGAGGTCATGGACTACTTCCGCGCCCTCTACGCCGCCGGCGAGCGCAGCCCCCGCGCCCTCCGCCTCA

                        290        300        310        320        330        340        350
                ....|....|....|....|....|....|....|....|....|....|....|....|....|....|
BnA-12          CGGAAGAAGCTCTCCGCTTAAACTCGGGCAACTACACCGTGTGGCACTTCGGGCGCTTAGTACTCGAGGA
At-FT-A         CGGAAGAAACCCTCCTCTTAAACTCCGGCAACTACACAGTGTGGCATTTCAGGCGCCTAGTACTCGAGGC
PPI-Soy-FTA     CAGCCGAAGCCGTTCAATTCAACTCCGGCAACTACACTGTGTGGCATTTCCGACGGTTGTTACTTGAGTC
Pea-FT-A        CCGCCGAAGCTATCGGTTTAAACGCCGGAAACTACACTGTGTGGCATTTCCGGCGGTTATTACTTGAGTC
Tomato-FTA      CTGGTGAAGCTATTCAGCTAAACCCTGGAAATTACACTGTATGGCAATTTAGGCGTGTTGTGCTGGAGGC
Rice-FT-A       CCGCCGAGGTCATCGACCTTAATCCCGGCAACTACACGGTGTGGCATTTTAGGCGTCTTGTTCTAGAGGC
Zea mays-FT-A   CCGCCGAGGCCATCGAGCTCAACCCCGGCAACTACACTGTCTGGCATTTCCGGCGCCTTATTCTGGAGTC
Soy1-FT-A       CAGCCGAAGCCGTTCAATTCAACTCCGGCAACTACACTGTGTGGCATTTCCGACGGTTGTTACTTGAGTC
Soy2-FT-A       CAGCCGAAGCCGTTCAATTCAACTCCGGCAACTACACTGTGTGGCATTTCCGACGGTTGTTACTTGAGTC
Triticum-FT-A   CCGCCGACGCCATCCACCTCAACCCCGGCAACTACACTGTATGGCATTTCAGGCGCGTTGTTCTAGAGGC

                        360        370        380        390        400        410        420
                ....|....|....|....|....|....|....|....|....|....|....|....|....|....|
BnA-12          GCTTAATAACGACTTGTATGAAGAGCTCAAGTTCATCGAAAGCATTGCTGAGGATAACTCTAAGAACTAC
At-FT-A         CCTTAATCACGACTTGTTTGAAGAACTCGAGTTCATCGAACGCATTGCTGAGGATAACTCTAAGAACTAC
PPI-Soy-FTA     GCTAAAAGTCGACTTGAACGATGAACTGGAGTTTGTGGAGCGTATGGCCGCTGGAAATTCTAAAAATTAT
Pea-FT-A        ACTGAAAGTTGACCTACATGTTGAACGGGAATTCGTGGAGCGTGTTGCCAGTGGCAATTCAAAAAATTAT
Tomato-FTA      ATTGGGTGTTGATTTACGTGAAGAATTGAAGTTTGTTGATCGCATTGCTGGGGAGAATACCAAAAATTAT
Rice-FT-A       ACTGGATGCTGATCTGCGTGAGGAAATGGATTTTGTGGACCGAATTGTCGAATGTAACCCAAAAAATTAT
Zea mays-FT-A   ACTAGATTTTGATTTACTAGAGGAGATGAAATTTGTCGAAAAAATTGCTGAATGCAATCCAAAAAATTAC
Soy1-FT-A       GCTAAAAGTCGACTTGAACGATGAACTGGATTTTGTGGAGCGTATGGCCGCTGGAAATTCTAAAAATTAT
Soy2-FT-A       GCTAAAAGTCGACTTGAACGATGAACTGGAGTTTGTGGAGCGTATGGCCGCTGGAAATTCTAAAAATTAT
Triticum-FT-A   ACTGGATGCTGATTTATTGCTAGAAATGCATTTTGTGGACCAAATTGCTGAATCTAATCCAAAAAATTAC

                        430        440        450        460        470        480        490
                ....|....|....|....|....|....|....|....|....|....|....|....|....|....|
BnA-12          CAGTTGTGG------------------------------------CATCATCGACGATGGGTCGCAGAGA
At-FT-A         CAACTGTGG------------------------------------CATCATCGGCGATGGGTTGCAGAGA
PPI-Soy-FTA     CAGATGTGN----ATGTTCTG----------TAG----------GCATCCTAGACGATGGGTTGCCGAGA
Pea-FT-A        CAGATTTGG------------------------------------CATCATAGACGATGGGTTGCTGAGA
Tomato-FTA      CAAATATGG------------------------------------CATCATAGACGGTGGCTTGCTGAGA
Rice-FT-A       CAAATCTGG------------------------------------CATCAC AGAGATGGCTTGCGGAGA
Zea mays-FT-A   CAAATCTGG------------------------------------CACCATAAGAGATGGCTTGCTGAGA
Soy1-FT-A       CAGATGTGG------------------------------------CATCATAGACGATGGGTTGCCGAGA
Soy2-FT-A       CAGATGTGGTGTGATGCTCTGCTCTGCTCTTTCTTCCATACTTTGCATCATAGACGATGGGTTGCCGAGA
Triticum-FT-A   CAAGTCTGG------------------------------------CATCACAAGAGATGGCTTGCTGAGA
```

TABLE 10A-continued

ClustalW Nucleic Acid Analysis of FT Alpha Subunits

| | 500 510 520 530 540 550 560 |
|---|---|
| BnA-12 | AACTGGGTCCTGATGTTGCAGGAAAGGAACTTGAGTTTACTCGGAGGGTACTATCACTTGATGCCAAGCA |
| At-FT-A | AACTGGGTCCTGATGTTGCAGGGAGAGAACTTGAATTTACCCGTAGAGTACTTTCACTTGATGCCAAACA |
| PPI-Soy-FTA | AGTTAGGTCCTGAAGCTAGAAACAATGAGCTCGAGTTCACCAAAAAGATACTGTCCGTTGATGCCAAACA |
| Pea-FT-A | AATTAGGACCTGAAGCTAGAAACAGTGAACTTGAGTTCACCAAAAAGATTCTGTCTGTTGACGCCAAACA |
| Tomato-FTA | AGCTGGGAGCTGATGCTGTGACAAATGAGCTAGAATTCACCAAGAAAATATTTTCTCAGGATGCAAAAAA |
| Rice-FT-A | AATTAGGACCAGATATTGCAAATAAAGAGCACGAATTTACAAGGAAGATACTTTCTATGGATGCTAAAAA |
| *Zea mays*-FT-A | AATTAGGACCTGGTATTGCAAACAAAGAGCATGAATTCACAATGAAGATACTTGCTATTGATGCAAAAAA |
| Soy1-FT-A | AGTTAGGTCCTGAAGCTAGAAACAATGAGCTCGAGTTCACCAAAAAGATACTGTCCGTTGATGCCAAACA |
| Soy2-FT-A | AGTTAGGTCCTGAAGCTAGAAACAATGAGCTCGAGTTCACCAAAAAGATACTGTCCGTTGATGCCAAACA |
| Triticum-FT-A | AAATAGGACCAGATGCTGCAAATAGTGAACATGACTTCACAAGGAAGATACTTGCTATGGATGCTAAAAA |

| | 570 580 590 600 610 620 630 |
|---|---|
| BnA-12 | TTATCATGCTTGGTCACATAGGCAGTGGGCGCTACAAGCATTAGGAGGATGGGAAAATGAGCTTAACTAC |
| At-FT-A | TTATCATGCTTGGTCACATAGGCAGTGGACACTACGGGCATTAGGAGGATGGGAAGATGAGCTCGATTAC |
| PPI-Soy-FTA | TTATCATGCATGGTCTCATAGACAGTGGGCTCTTCAAACACTAGGAGGATGGGAAGATGAACTTAATTAT |
| Pea-FT-A | CTATCATGCATGGTCTCATAGGCAGTGGGTTCTTCAAAATCTAGGAGGATGGGAAGATGAACTCAGTTAT |
| Tomato-FTA | TTATCATGCTTGGTCCCATCGGCAGTGGGTCCTTCAAGCACTTGGAGGATGGGAAGATGAGCTTGCTTAT |
| Rice-FT-A | TTACCATGCTTGGTCTCATAGGCAGTGGGTTCTTCAAGCACTGGGTGGATGGGAGACTGAACTACAGTAT |
| *Zea mays*-FT-A | TTATCATGCTTGGTCTCATAGGCAGTGGGTTCTTCAAGCGTTGGGGGGATGGGAGACTGAATTAGAATAC |
| Soy1-FT-A | TTATCATGCATGGTCTCATAGACAGTGGGCTCTTCAAACACTAGGAGGATGGGAAGATGAACTTAATTAT |
| Soy2-FT-A | TTATCATGCATGGTCTCATAGACAGTGGGCTCTTCAAACACTAGGAGGATGGGAAGATGAACTTAATTAT |
| Triticum-FT-A | CTACCATGCTTGGTCCCATAGGCAGTGGGTTCTTCAAGCATTGGGTGGATGGGAGAGTGAACTGCAGTAC |

| | 640 650 660 670 680 690 700 |
|---|---|
| BnA-12 | TGCCACGAGCTCCTTGAAGCTGACGTCTTTAACAACTCTGCATGGAATCAGAGGTATTACGTTATAACTA |
| At-FT-A | TGTCACGAGCTCCTTGAAGCTGACGTCTTTAACAATTCCGCCTGGAATCAGAGGTATTATGTCATCACCC |
| PPI-Soy-FTA | TGCAGCGAACTACTTAAAGAAGACATTTTTAACAATTCTGCTTGGAATCAGAGATATTTTGTCATAACAA |
| Pea-FT-A | TGTAGTGAACTGCTTGCAGAAGACATATTTAACAATTCTGCTTGGAATCAGAGATACTTCGTCATAACAA |
| Tomato-FTA | TGTCAACAACTCCTTGAAGATGATATTTACAACAATTCTGCTTGGAATCAGAGATACTTTGTCGTAACAC |
| Rice-FT-A | TGCAACCAGCTGCTTGAGGAAGACGTCTTCAATAATTCAGCTTGGAATCAGAGATACCTTGTAATAACAA |
| *Zea mays*-FT-A | TGTGACCACTTACTTAAGGAAGACGTCTTCAATAATTCAGCTTGGAATCAGAGATACTTTGTTATAACAA |
| Soy1-FT-A | TGCACAGAACTACTTAAAGAAGACATTTTTAACAATTCTGCTTGGAATCAGAGATATTTTGTCATAACAA |
| Soy2-FT-A | TGCACAGAACTACTTAAAGAAGACATTTTTAACAATTCTGCTTGGAATCAGAGATATTTTGTCATAACAA |
| Triticum-FT-A | TGCAACCAGCTTCTTGAGGAAGATGTCTTCAATAACTCAGCTTGGAATCAGAGATACCTTGTGGTAACAC |

| | 710 720 730 740 750 760 770 |
|---|---|
| BnA-12 | GATCACCTTCGTTGGGAGGCCTAGAAGCCATGAGAGAATCTGAAGTAAGCTACACAGTCAAAGCCATTTT |
| At-FT-A | AATCTCCTTTGTTGGGAGGCCTAGAAGCCATGAGAGAATCTGAAGTAAGCTACACAATCAAAGCCATTTT |
| PPI-Soy-FTA | GGTCTCCTTTCTTGGGGGGCCTAAAAGCTATGAGAGAGTCTGAAGTGCTTTACACCATCGAAGCCATTAT |
| Pea-FT-A | GGTCTCCCGTCTTGGGAGGGCTAAAAGCCATGAGAGAGTCTGAAGTGCTTTTCACCGTTGAAGCCATTAT |
| Tomato-FTA | GATCACCTCTACTAGGGGGCCTAGTGGCAATGAGGGAATTGGAAGTGAATTACACAGTTCAAGCCATCAG |
| Rice-FT-A | GTTCACCACTTCTTGGAGGCCTTGCAGCAATGCGTGACTCGGAAGTGGATTACACAGTTGGGGCTATTCT |
| *Zea mays*-FT-A | GATCACCATTTCTTGGTGGCCTTGCGGCAATGCGTGATTCAGAAGTAGACTACACAATTGAAGCTATTCT |
| Soy1-FT-A | GGTCTCCTTTCTTGGGGGGCCTAAAAGCTATGAGAGAGTCTGAAGTGCTTTACACCATTGAAGCCATTAT |
| Soy2-FT-A | GGTCTCCTTTCTTGGGGGGCCTAAAAGCTATGAGAGAGTCTGAAGTGCTTTACACCATTGAAGCCATTAT |
| Triticum-FT-A | GATCACCAATTCTTGGGGGCCTTGCGGCAATGCGCGACTCAGAAGTAGATTACACAGTTGAGGCCATTAT |

TABLE 10A-continued

ClustalW Nucleic Acid Analysis of FT Alpha Subunits

```
                           780       790       800       810       820       830       840
                   ....|....|....|....|....|....|....|....|....|....|....|....|....|....|
BnA-12             AGCAAATCCCGGGAACGAGAGCTCTTGGAGGTACCTGAAAGCCCTTTACAAAGACGACACAGAGTCTTGG
At-FT-A            AACCAATCCTGCAAACGAGAGCTCATGGCGATACCTAAAAGCGCTTTACAAAGACGACAAAGAATCCTGG
PPI-Soy-FTA        AGCCTACCCTGAAAATGAAAGCTCGTGGAGATATCTACGAGGACTTTATAAAGGTGAAACTACTTCATGG
Pea-FT-A           TTCTTACCCAGAAAATGAAAGCTCATGGAGATATCTTCGAGGACTTTTCAAAGATGAATCCACGTTATAT
Tomato-FTA         AGCTAGTCCAGAGAATGAAAGTCCTTGGAGGTATCTTCGTGGTCTTTACAAGAATGATACACAATCTCTA
Rice-FT-A          GGCTAACCCTCAGAATGAAAGCCCCTGGAGATACCTCAAAGGCCTGTACAAGGGTGAAAATAACTTGCTG
Zea mays-FT-A      AGCAAACGCTCAGAATGAAAGCC CTGGAGGTACCTCAAGGGTCTATACAAGGGTGAGAATAACCTGCTA
Soy1-FT-A          AGCCTACCCTGAAAATGAAAGCTCGTGGAGATATCTACGAGGACTTTATAAAGGTGAAACTACTTCATGG
Soy2-FT-A          AGCCTACCCTGAAAATGAAAGCTCGTGGAGATATCTACGAGGACTTTATAAAGGTGAAACTACTTCATGG
Triticum-FT-A      GGTGAACCCTCAGAATGAAAGCCCCTGGAGATACCTCAGAGGTTTATATAAGGATGATAACAATTTGCTG

                           850       860       870       880       890       900       910
                   ....|....|....|....|....|....|....|....|....|....|....|....|....|....|
BnA-12             ATTAGTGATC AAGTGTTTCCTCAGTCTGTTTGAAAGTTCTCTCACGCGCGGACTGCTTCCATGGATTCG
At-FT-A            ATTAGTGATCCAAGTGTTTCCTCAGTCTGTTTGAATGTTCTATCCCGCACAGATTGCTTCCATGGATTCG
PPI-Soy-FTA        GTAAATGATCCTCAAGTTTCTTCAGTATGCTTAAAGATTTTGAGAACTAAGAGCAAC---TACGTGTTTG
Pea-FT-A           GTAAATGATGCCCAAGTATCTTCATTATGTTTAAAGATTTTGAAAACTAAGAGCAAC---TATTTGTTTG
Tomato-FTA         GTTCAGGATTCTCAAGTAGCATCAGTACTTTGGGACGTCTTAACCTCCCAAAATAGT---CATGTGCACG
Rice-FT-A          ATGGCTGATGAGCGCATCTCTGATGTTTGTCTCAAGGTCCTGAAACATGATTCGACC---TGCGTATTTG
Zea mays-FT-A      GTAGAGGACGAGCGCATCTCTGCTGTTTGTTTCAAGGTCCTGAAGAATGATTGGACT---TGTGTATTTG
Soy1-FT-A          GTAAATGATCCTCAAGTTTCTTCAGTATGCTTAAAGATTTTGAGAACTAAGAGCAAC---TACGTGTTTG
Soy2-FT-A          GTAAATGATCCTCAAGTTTCTTCAGTATGCTTAAAGATTTTGAGAACTAAGAGCAAC---TACGTGTTTG
Triticum-FT-A      GTGGCTGATAATCGCATTTCTGATGCTTGCCTCAAGGTCCTGAATAAGGATTGGACA---TGCGTATTTG

                           920       930       940       950       960       970       980
                   ....|....|....|....|....|....|....|....|....|....|....|....|....|....|
BnA-12             CTCTGAGCACCCTTTTGGATCTTCTGTGCGATGGGT-TGAGACCAACCAACGAGCATAGAGACTCGGTGA
At-FT-A            CTCTGAGCACCCTTTTGGATCTTCTATGTGATGGAC-TGAGACCAACCAACGAGCATAAAGACTCAGTGA
PPI-Soy-FTA        CTCTTAGCACTATTTTAGATCTTATATGCTTTGGTTAT-CAACCAAATGAAGACATTAGAGATGCCATTG
Pea-FT-A           CTCTAAGTACTCTGCTGGATCT-ATCTGCCTCGGTTATTCAACCAAATGAAGATTTCAGAGATGCCATTG
Tomato-FTA         CTCTGAGGTTCTTGTTGGATCTTCTTTGTCATGATT-TGGAACCGAGCCAAGAATTGAAAAGTGCTGTAG
Rice-FT-A          CTTTGAGCTTGCTGCTCGATCTTCTTCAAATTGGTT-TACAACCTTCAGATGAACTCAAAGGAACTATCG
Zea mays-FT-A      CTTTGAGTTTGCTGCTCGATCTTCTCTGCACTGGTT-TGCAGCCTTCAGATGAACTTAGGTCCACTCTTG
Soy1-FT-A          CTCTTAGCACTATTTTAGATCTTATATGCTTTGGTTAT-CAACCAAATGAAGACATTAGAGATGCCATTG
Soy2-FT-A          CTCTTAGCACTATTTTAGATCTTATATGCTTTGGTTAT-CAACCAAATGAAGACATTAGAGATGCCATTG
Triticum-FT-A      CTTTGAGCTTCCTGCTTGATCTTCTTCGCATGGGTT-TGCAGCCTTCGAATGAACTTAAAGGAACCATCG

                           990      1000      1010      1020      1030      1040      1050
                   ....|....|....|....|....|....|....|....|....|....|....|....|....|....|
BnA-12             AAGCTCTAG---CT------AATGAAGA--------------------------------A-CCAGAGAC
At-FT-A            GAGCTCTAG---CT------AATGAAGA--------------------------------A-CCAGAGAC
PPI-Soy-FTA        ACGCCTTAAAGACCGCAGATATGGATAAACAAGATTTAGATGATGATGAGAAAGGGGAACAACAAAATTT
Pea-FT-A           AGGCTTTAA-GACTTCAGATTTTGATAAA-------------------------------A-CAAGATTC
Tomato-FTA         ATGTTCTTA---CTCCC--CAGTCATGCTC------------------------------A-CCAGATTT
Rice-FT-A          AAGCAATAAAGAACTCTGATCCTGAAGCAGATGA--------------------AG---CA-GTAGATGC
Zea mays-FT-A      AAACAATAAGGAGCTCCCATCCTGAAACCGC---------------------------------GGATGA
Soy1-FT-A          ACGCCTTAAAGACCGCAGATATGGATAAACAAGATTTAGATGATGATGAGAAAGGGGAACAACAAAATTT
Soy2-FT-A          ACGCCTTAAAGACCGCAGATATGGATAAACAAGATTTAGATGATGATGAGAAAGGGGAACAACAAAATTT
Triticum-FT-A      AAGCAATGGAGAACTCTGATCCTGAAACGGG---------------------------------ACATGC
```

TABLE 10A-continued

ClustalW Nucleic Acid Analysis of FT Alpha Subunits

```
                        1060      1070      1080      1090      1100      1110      1120
                ....|....|....|....|....|....|....|....|....|....|....|....|....|....|
BnA-12          TAACTTGGCCAATTTGGTGTGTACCATTCTGTGTCGTGTTGATCCAATAAGAGCTAACTATTGGGCATGG
At-FT-A         TAACTTGGCCAATTTGGTGTGTACTATTCTTGGTCGTGTAGATCCTATAAGAGCTAACTATTGGGCATGG
PPI-Soy-FTA     AAATATAGCACGAAATATTTGTTCTATCCTAAAACAAGTTGATCCAATTAGAACCAACTATTGGATTTGG
Pea-FT-A        AGATATAGCAATAACTATTTGTTCTATTTTAGAACAAGTTGATCCAATTAGAGTCAACTATTGGGTCTGG
Tomato-FTA      AGCACTGACAAAGAAAATTTGTTCCATCTTGGAACATGCTGATCCAATGAGAGTAAAATATTGGAATTGG
Rice-FT-A       TGATCTTGGCGACTGCAATCTGCTCAATATTGCAGAGATGTGATCCCCTGCGGATAAATTACTGGTCCTGG
Zea mays-FT-A   TGATCCTGCAGCCGCTGTTTGCTGTATCCTGCAGAAATGTGATCCCCTGCGGGTAAATTATTGGTCTTGG
Soy1-FT-A       AAATATAGCACGAAATATTTGTTCTATCCTAAAACAAGTTGATCCAATTAGAACCAACTATTGGATTTGG
Soy2-FT-A       AAATATAGCACGAAATATTTGTTCTATCCTAAAACAAGTTGATCCAATTAGAACCAACTATTGGATTTGG
Triticum-FT-A   TGATATTGCAGTAGCTGTCTGCTCAATCCTGCAGAAATGTGATCCCCTGCGGATAAACTACTGGTCATGG

                        1130      1140      1150      1160      1170      1180      1190
                ....|....|....|....|....|....|....|....|....|....|....|....|....|....|
BnA-12          ----------------------------------------------------------------------
At-FT-A         AGGAAGAGCAAGATTACA----GTGGC-AGCAATTTGAATATGTGACGCCCCAAAATCACACTTGAAAAA
PPI-Soy-FTA     CGCAAGAGCAGACTTC-------CT---------------------------------------------
Pea-FT-A        CGGAAGAGTAGACTTC-------CTCA-GGCAGCGTAAAGGACAAACTTATGTCATATGTGTAATTTTTA
Tomato-FTA      CGCAAGAGCATGGTTCGG----GTTCA-ATTACTTCAGAGTCAGAATGCAGAGAGGTTG-GCTAATTTGA
Rice-FT-A       TACAGGACCACTATTTCT----TCTCA-AAC--CTGAAG----CATGCAGTGGCCTCCATGA------GG
Zea mays-FT-A   TTCAAGGACACTCTTTCTCAGATCTCATGACTTCACATGGGTTCACCCCTTGTCCGCGCTGGTCCGGGCT
Soy1-FT-A       CGCAAGAGCAGACTTC-------CTCT-ATCAGCTTAGTAACCAAAGTAATTAAA---GGGCAACTCTGT
Soy2-FT-A       CGCAAGAGCAGACTTC-------CTCT-ATCAGCTTAGTAACCAAAGTAATTAAA---GGGCAACTCTGT
Triticum-FT-A   TACCAGACCACTCTTTCT----TCTTA-GACATCTGAAAA-TTCAGCTGAAGACAGTTTTAG------CA

                        1200      1210      1220      1230      1240      1250      1260
                ....|....|....|....|....|....|....|....|....|....|....|....|....|....|
BnA-12          ----------------------------------------------------------------------
At-FT-A         GACTTGATTAT--TAGT-TTTTACGT----------AATTAACTGCTTATTTATGAATCACATG-TTCAT
PPI-Soy-FTA     ----------------------------------------------------------------------
Pea-FT-A        GTCTATTGGAATTTGACGTCATGGAT----------AACAGGGTGGTTGTTTTTGTTATGATAT-GTTTT
Tomato-FTA      GTGTTCAAGAA--TGAC-TTGTGAGA----------ATATTGTACTGTGTTTACGAAATACATA-CTTGC
Rice-FT-A       TCATAATGGAGATATCTTCTAT-----------------------CTTCGTGTGA---------TTCTG
Zea mays-FT-A   CTGTGAGATAGACATGTTTTAGATAGTTTCATTGGACACCCAAACAGAGCGGACAGAGTGTATGGCTGCT
Soy1-FT-A       GTTATGTGTAACCTAGT-TTATTGA-----------AACTGGATTTTTATTT--ATTATTATTT-TTTAT
Soy2-FT-A       GTTATGTGTAACCTAGT-TTATTGA-----------AACTGGATGTTTATTT--ATTATTATTT-TTTAT
Triticum-FT-A   GCATGATGTAAACTCAATCGAAGGGGTT-------------GACGCAGTGTATGAAAAACCT--TTCCT

                        1270      1280      1290      1300      1310      1320      1330
                ....|....|....|....|....|....|....|....|....|....|....|....|....|....|
BnA-12          ----------------------------------------------------------------------
At-FT-A         GT-TAACATGTATCAAAACAATCTTGATTTCTCAAAAAAAAAAAAAAAAAAAAAAAAAAAA-------
PPI-Soy-FTA     ----------------------------------------------------------------------
Pea-FT-A        CC-AGATGTATTTCTATATTTAACAGCAAAGTTGATTTAACATTGGTGTTAACAAACCAATGATCTCCAA
Tomato-FTA      ATCTAAGGTGATCCTTCGGGCACATGTGCTGGGAAGTGACTGAATATCACGAAGAACTAAAAAAACTGTG
Rice-FT-A       GGCGTTGAGGTGCCT---AGCTACATTTGTTATGAACTTTCCTTGGGCATAACTGATCACTGATATTAC-
Zea mays-FT-A   ACCTTCTCCGTGACTGAAAGCAGTGCTTGTAACGA--TTTTGTTTAGTAAAATTTGTGAGTGTTACTGCT
Soy1-FT-A       GT-TGTCATGTATCTGTTTGT----GCAAATTT------ATCTTTTTGTCATGCCATTACTGGCATTTGA
Soy2-FT-A       GT-TGTCATGTATCTGTTTGT----GCAAATTT------ATCTTTTTGTCATGCCATTACTGGCATTTGA
Triticum-FT-A   GTGATCTTGGTGCGG---AGCAA--TTTGTACTGA--TTTTACTGGGAAAAATCAATCAATGACAGCATG
```

TABLE 10A-continued

ClustalW Nucleic Acid Analysis of FT Alpha Subunits

```
                     1340      1350      1360      1370      1380      1390      1400
                ....|....|....|....|....|....|....|....|....|....|....|....|....|....|
BnA-12          ----------------------------------------------------------------------
At-FT-A         ----------------------------------------------------------------------
PPI-Soy-FTA     ----------------------------------------------------------------------
Pea-FT-A        AAAATCAATGTTTTATTTCTCTTCATTTGTCTGATTTTGTGGCATAACATTCTTGATGAT-TTTGTGGTA
Tomato-FTA      ATTGGCAACATTGTACTACTCCAAATAGGTCACTTTCGATGACTTTTTGTACTGCCTTGA-GTTTTGGCT
Rice-FT-A       TCCAATATTGTGTTCTAAA---------------------------------------------------
Zea mays-FT-A   CCAAACAACACCTTATGCAACCATATTTGAATAT----TTCACATGTAAGCT---TGA--------A-TC
Soy1-FT-A       GTG--TAAGGATTGAAAGCCATGCA-------GAATAAGAAATTTAAGTTTTTT-------TTTCCGTTG
Soy2-FT-A       GTG--TAAGGATTGAAAGCCATGCA-------GAATAAGAAATTTAAGTTTTTT-------TTTCCGTTG
Triticum-FT-A   CCCAACAATGTCTTGTGTGAATATGTTACTGCCTGATATTCACATGTTAGCAGAATGAGAATAACCAATC

                     1410      1420      1430      1440      1450      1460      1470
                ....|....|....|....|....|....|....|....|....|....|....|....|....|....|
BnA-12          ----------------------------------------------------------------------
At-Ft-A         ----------------------------------------------------------------------
PPI-Soy-FTA     ----------------------------------------------------------------------
Pea-FT-A        AAAAAAAAAAAAAAAAAAAA--------------------------------------------------
Tomato-FTA      CTGCTATGTTTTGTAAGTTTTGGATATGGATGCATAGCTTATTGATACTTTTGGTGACTTAAAATACTCT
Rice-FT-A       ----------------------------------------------------------------------
Zea mays-FT-A   CAGGTGTGTTTGTTAATGTATTACACTT--G-CCATGGGAGCCTAAATGAGACCCATAATCACTTCCACT
Soy1-FT-A       AAAA------------------------------------------------------------------
Soy2-FT-A       AAAAAAAAAAAAAAAAAAAA--------------------------------------------------
Triticum-FT-A   AAACTCCAACGAGCAGATTGTTACAGTAACGGCCACTGGTGGTGTGAAAATCCTGAAATCTGCTTCAGTC

                     1480      1490      1500      1510      1520      1530      1540
                ....|....|....|....|....|....|....|....|....|....|....|....|....|....|
BnA-12          ----------------------------------------------------------------------
At-Ft-A         ----------------------------------------------------------------------
PPI-Soy-FTA     ----------------------------------------------------------------------
Pea-FT-A        ----------------------------------------------------------------------
Tomato-FTA      GGAAGGCAGGTAGCATGTGTATAATTCACTGTTACTTCCCATGTCGAGTTAGATGCTTGAAAATTTTAGT
Rice-FT-A       ----------------------------------------------------------------------
Zea mays-FT-A   AGAGTCGGAAGACCGT-GTCGAGCAGTTCACTCATATGGTCACTTAAAGCAAAAAAAAAAAAAAAAAAA-
Soy1-FT-A       ----------------------------------------------------------------------
Soy2-FT-A       ----------------------------------------------------------------------
Triticum-FT-A   ACTTTGCCTTGTTTACAGTTGAGTCTGTTGTTGTGATCTGTACCTAATGCATGTACACAATCATCAAATT

                     1550      1560      1570      1580      1590      1600      1610
                ....|....|....|....|....|....|....|....|....|....|....|....|....|....|
BnA-12          ----------------------------------------------------------------------
At-Ft-A         ----------------------------------------------------------------------
PPI-Soy-FTA     ----------------------------------------------------------------------
Pea-FT-A        ----------------------------------------------------------------------
Tomato-FTA      AGGTGTTCTTTTATGAAGCACACATTAATGTGGAAAAAAAAAAAAAAAAAAAAAAAAAAAAAAAAAAAAA
Rice-FT-A       ----------------------------------------------------------------------
Zea mays-FT-A   ----------------------------------------------------------------------
Soy1-FT-A       ----------------------------------------------------------------------
Soy2-FT-A       ----------------------------------------------------------------------
Triticum-FT-A   ATTAGTTTTTGTACCAATGAGTATTCGATGAAAAAAAAAAAAAAAAA-----------------------

BnA-12          -
At-Ft-A         -
PPI-Soy-FTA     -
Pea-FT-A        -
Tomato-FTA      A
Rice-FT-A       -
Zea mays-FT-A   -
Soy1-FT-A       -
Soy2-FT-A       -
Triticum-FT-A   -
```

TABLE 10B

ClustalW Amino Acid Analysis of FT Alpha Subunits

1) BNA-12; FT2 (SEQ ID NO: 7)
2) At-FT-A; FT1 (SEQ ID NO: 5)
3) PPI-Soy-FTA; FT4 (SEQ ID NO: 33)
4) Pea-FT-A (SEQ ID NO: 66)
5) Tomato-FTA (SEQ ID NO: 67)
6) Rice-FT-A (SEQ ID NO: 68)

TABLE 10B-continued

ClustalW Amino Acid Analysis of FT Alpha Subunits

7) *Zea mays*-FT-A (SEQ ID NO: 69)

8) Soy1-FT-A (SEQ ID NO: 70)

9) Soy2-FT-A (SEQ ID NO: 71)

10) Triticum-FT-A (SEQ ID NO: 72)

```
                        10        20        30        40        50        60        70
                ....|....|....|....|....|....|....|....|....|....|....|....|....|....|
BnA-12          ---------------------------------------------------MDYFRAIYFSDERSARALR
At-Ft-A         ---------MNFDETVPLSQRLEWSDVVPLTQDDGPNPVVPIAYKEEFRETMDYFRAIYFSDERSPRALR
PPI-Soy-FTA     -MESGSSEGEEVQQRVPLRERVEWSDVTPVPQNDGPNPVVPIQYTEEFSEVMDYFRAVYLTDERSPRALA
Pea-FT-A        --MAGNIEVEE-DDRVPLRLRPEWSDVTPIPQDDGPSPVVPINYSEEFSEVMDYFRAVYFAKELSSRALA
Tomato-FT-A     -----MDSCEVTKTRIPFKERPDWADVKPVPQDDGPCPVVPIAYTEDFSETMDYFRAIYVADERSTRALQ
RiceFT-A        MAPSSTSSEGASDEWLPPSRRPELADVVPVTQDDGPHPVVAIAYRDEFREVMDYFRALYFAGERSVRALH
Zea mays-FT-A   ----------MEHTLSGPSSWPELADVVPVPQDDGPSPVVSIAYRDDFRGVMDYFRALYLTGERSPRALR
Soy1-FT-A       -MESGSSEGEEVQQRVPLRERVEWSDVTPVPQNDGPNPVVPIQYTEEFSEVMDYFRAVYLTDERSPRALA
Soy2-FT-A       -MESGSSEGEEVQQRVPLRERVEWSDVTPVPQNDGPNPVVPIQYTEEFSEVMDYFRAVYLTDERSPRALA
Triticum-FT-A   -------------------------DVAPLPQADGPCPVVSIAYRGDFREVMDYFRALYAAGERSPRALR

                        80        90       100       110       120       130       140
                ....|....|....|....|....|....|....|....|....|....|....|....|....|....|
BnA-12          LTEEALRLNSGNYTVWHFGRLVLEELNNDLYEELKFIESIAEDNSKNYQLW------------HHRRWVA
At-Ft-A         LTEETLLLNSGNYTVWHFRRLVLEALNHDLFEELEFIERIAEDNSKNYQLW------------HHRRWVA
PPI-Soy-FTA     LTAEAVQFNSGNYTVWHFRRLLLESLKVDLNDELEFVERMAAGNSKNYQMX--------MFCRHPRRWVA
Pea-FT-A        LTAEAIGLNAGNYTVWHFRRLLLESLKVDLHVEREFVERVASGNSKNYQIW------------HHRRWVA
Tomato-FT-A     LTGEAIQLNPGNYTVWQFRR VLEALGVDLREELKFVDRIAGENTKNYQIW------------HHRRWLA
RiceFT-A        LTAEVIDLNPGNYTVWHFRRLVLEALDADLREEMDFVDRIVECNPKNYQIW------------HHKRWLA
Zea mays-FT-A   LTAEAIELNPGNYTVWHFRRLILESLDFDLLEEMKFVELIAECNPKNYQIW------------HHLRWLA
Soy1-FT-A       LTAEAVQFNSGNYTVWHFRRLLLESLKVDLNDELDFVERMAAGNSKNYQMW------------HHRRWVA
Soy2-FT-A       LTAEAVQFNSGNYTVWHFRRLLLESLKVDLNDELEFVERMAAGNSKNYQMWCDALLCSFFHTLHHRRWVA
Triticum-FT-A   LTADAIHLNPGNYTVWHFRRVVLGALDADLLLEMHFVDQIAESNPLNYQVW------------HHKRWLA

                       150       160       170       180       190       200       210
                ....|....|....|....|....|....|....|....|....|....|....|....|....|....|
BnA-12          EKLGPDVAGLEKEFTRRVLSLDAKHYHAWSHRQWALQALGGWENELNYCHELLEADVFNNSAWNQRYYVI
At-Ft-A         EKLGPDVAGRELEFTRRVLSLDAKHYHAWSHRQWTLRALGGWEDELDYCHELLEADVFNNSAWNQRYYVI
PPI-Soy-FTA     EKLGPEARNNELEFTKKILSVDAKHYHAWSHRQWALQTLGGWEDELNYCTELLKEDIFNNSAWNQRYFVI
Pea-FT-A        EKLGPEARNSELEFTKKILSVDAKHYHAWSHRQWVLQNLGGWEDELSYCSELLAEDIFNNSAWNQRYFVI
Tomato-FT-A     EKLGADAVTNELEFTKKIFSQDAKNYHAWSHRQWVLQALGGWEDELAYCQQLLKDDIYNNSAWNQRYFVV
RiceFT-A        EKLGPEIANKEHEFTRKILSMDAKNYHAWSHRQWVLQALGGWETELQYCNQLLEEDVFNNSAWNQRYLVI
Zea mays-FT-A   EKLGPGIANKEHEFTMKILAIDALNYHAWSHRQWVLQALGGWETELEYCDHLLKEDVFNNSAWNQRYFVI
Soy1-FT-A       EKLGPEARNNELEFTKKILSVDAKHYHAWSHRQWALQTLGGWEDELNYCTELLKEDIFNNSAWNQRYFVI
Soy2-FT-A       EKLGPEARNNELEFTKKILSVDAKHYHAWSHRQWALQTLGGWEDELNYCTELLKEDIFNNSAWNQRYFVI
Triticum-FT-A   EKIGPDAANSEHDFTRKILAMDAKNYHAWSHRQWVLQALGGWESELQYCNQLLEEDVFNNSAWNQRYLVV

                       220       230       240       250       260       270       280
                ....|....|....|....|....|....|....|....|....|....|....|....|....|....|
BnA-12          TRSPSLGGLEAMRESEVSYTVKAILANPGNESSWRYLKALYKDDTESWISDPSVSSVCLKVLSRADCFHG
At-Ft-A         TQSPLLGGLEAMRESEVSYTIKAILTNPANESSWRYLKALYKDDKESWISDPSVSSVCLNVLSRTDCFHG
PPI-Soy-FTA     TRSPFLGGLKAMRESEVLYTIEAIIAYPENESSWRYLRGLYKGETTSWVNDPQVSSVCLKIL-RTKSNYV
Pea-FT-A        TRSPVLGGLKAMRESEVLETVEAIISYPENESSWRYLRGLFKDESTLYVNDAQVSSLCLKIL-KTKSNYL
Tomato-FT-A     TRSPLLGGLVAMRELEVNYTVQAIRASPENESPWRYLRGLYKNDTQSLVQDSQVASVLWDVL-TSQNSHV
RiceFT-A        TSSPLLGGLAAMRDSEVDYTVGAILANPQNESPNRYLKGLYKGENNLLMADERISDVCLKVL-KHDSTQV
Zea mays-FT-A   TRSPFLGGLAAMRDSGVDYTIEAILANAQNGSPNRYLKGLYKGENNLLVEDGRISAVCFKVL-KNDWTQV
Soy1-FT-A       TRSPFLGGLKAMRESEVLYTIEAIIAYPENESSWRYLRGLYKGETTSWVNDPQVSSVCLKIL-RTKSNYV
Soy2-FT-A       TRSPFLGGLKAMRESEVLYTIEAIIAYPENESSWRYLRGLYKGETTSWVNDPQVSSVCLKIL-RTKSNYV
Triticum-FT-A   TRSPILGGLAAMRDSEVDYTVEAIMVNPQNESPWRYLRGLYKDDNNLLVADNRISDACLKVL-NKDWTQV

                       290       300       310       320       330       340       350
                ....|....|....|....|....|....|....|....|....|....|....|....|....|....|
BnA-12          FALSTLLDLLCDGLRPINEHRDSVKALANEEP---ETN--------------LANLVCTILCRVDPIRAN
At-Ft-A         FALSTLLDLLCDGLRPINEHKDSVRALANEEP---ETN--------------LANLVCTILGRVDPIRAN
PPI-Soy-FTA     FALSTILDLICFGYQPNEDIRDAIDALKTADM---DKQDLDDDEKGEQQNLNIARNICSILKQVDPIRTN
Pea-FT-A        FALSTLLDLSASVIQPNEDFRDAIEALRLQIL---IKQ--DSD---------IAITICSILEQVDPIRVN
Tomato-FT-A     HALRFLLDLLCHDLEPSQELKSAVDVLTPQSC---SPD------------LALTKKICSILEHADPNRVK
RiceFT-A        FALSLLLDLLQIGLQPSDELKGTIEAIKNSDPEADEAVDA--D---------LATAICSILQRCDPLRIN
Zea mays-FT-A   FALSLLLDLLCTGLQPSDGLRSTLGTIRSSHP---ETADD--D---------PAAAVCCILQKCDPLAVN
Soy1-FT-A       FALSTILDLICFGYQPNEDIRDAIDALKTADM---DKQDLDDDEKGEQQNLNIARNICSILKQVDPIRTN
Soy2-FT-A       FALSTILDLICFGYQPNEDIRDAIDALKTADM---DKQDLDDDEKGEQQNLNIARNICSILKQVDPIRTN
Triticum-FT-A   FALSFLLDLLRMGLQPSNELKGTIEAMENSDP---ETGHA--D---------IAVAVCSILQKCDPLRIN
```

TABLE 10B-continued

ClustalW Amino Acid Analysis of FT Alpha Subunits

```
                    360       370
                ....|....|....|....|....|....
BnA-12          YWAWKL-----------------------
At-Ft-A         YWAWRKSKITVAAI---------------
PPI-Soy-FTA     YWIWRKSRLP-------------------
Pea-FT-A        YWVWRKSRLPQAA----------------
Tomato-FT-A     YWNWRKSMVRVQLLQSQNAERLANLSVQE
RiceFT-A        YWSWYRTTISSQT----------------
Zea mays-FT-A   YWSWFKDTLSQIS----------------
Soy1-FT-A       YWIWRKSRLPLSA----------------
Soy2-FT-A       YWIWRKSRLPLSA----------------
Triticum-FT-A   YWSWYQTTLSS------------------
```

TABLE 10C

ClustalW Nucleic Acid Analysis of FT Beta Subunits

1) PPI-BnFTb; FT3 (SEQ ID NO: 8)
2) era1 (SEQ ID NO: 73)
3) Wiggum (SEQ ID NO: 74)
4) PPI-Soy-FTB; FT5 (SEQ ID NO: 34)
5) DuP-Soy-FTB (SEQ ID NO: 75)
6) PPI-Corn-FTB; FT6 (SEQ ID NO: 37)
7) DuP-Corn-FTB (SEQ ID NO: 76)
8) Pea-FT-B (SEQ ID NO: 77)
9) Tomato (SEQ ID NO: 78)
10) Tobacco (SEQ ID NO: 79)

```
                       10        20        30        40        50        60        70
               ....|....|....|....|....|....|....|....|....|....|....|....|....|....|
PPI-BnFTb      ----------------------------------------------------------------------
era1           ----------------------------------------------------------------------
Wiggum         ATGCCAGTAGTAACCCGCTTGATTCGTTTGAAGTGTGTAGGGCTCAGACTTGACCGGAGTGGACTCAATC
PPI-Soy-FTB    ----------------------------------------------------------------------
DuP-Soy-FTB    ----------------------------------------------------------------------
PPI-Corn-FTB   ----------------------------------------------------------------------
DuP-Corn-FTB   ----------------------------------------------------------------------
Pea FT-B       ----------------------------------------------------------------------
Tomato         ----------------------------------------------------GTAAACGAGCGTTGATTT
Tobacco        ----------------------------------------------------------------------

                       80        90       100       110       120       130       140
               ....|....|....|....|....|....|....|....|....|....|....|....|....|....|
PPI-BnFTb      ----------------------------------------------------------------------
era1           ----------------------------------------------------------------------
Wiggum         GGCGAATCTGTCACGGAGGACACGGGGAATCAACGCGGCGGAGAGTGATGGAAGAGCTTTCAAGCCTAAC
PPI-Soy-FTB    ----------------------------------------------------------------------
DuP-Soy-FTB    ----------------------------------------------------------------------
PPI-Corn-FTB   -------------------------------------------GGCGGATCCCGACCTACCGAGGCTCAC
DuP-Corn-FTB   -------------------------------------------GGCGGATCCCGACCTACCGAGGCTCAC
Pea FT-B       ---------------------------------------------CGGACCCCCCGTCCACAATCGTGAT
Tomato         GTCGCTGACGAAATTTACAGTCAAGAGTAGTAACCGGTTGTAGTGAAAAAATGGAGTCGAGGAAAGTGAC
Tobacco        -------------------------------------------------------GGCACGAGCGGC-AC

                      150       160       170       180       190       200       210
               ....|....|....|....|....|....|....|....|....|....|....|....|....|....|
PPI-BnFTb      ----------------------------------------------------------------------
era1           ----------------------------------------------------------------------
Wiggum         CGTGAGTCAGCGCGAGCAATTTCTGGTGGAGAACGATGTGTTCGGGATCTATAATTACTTCGACGCCAGC
PPI-Soy-FTB    ------------------------------------------------------------GCCACCATTC
DuP-Soy-FTB    ------------------------------------------------------------GCCACCATTC
PPI-Corn-FTB   GGTGACGCAGGTGGAGCAGATGAAGGTGGAGGCCAGGGTTGGCGACATCTACCGCTCCCTCTTCGGGGCC
DuP-Corn-FTB   GGTGACGCAGGTGGAGCAGATGAAGGTGGAGGCCAGGGTTGGCGACATCTACCGCTCCCTCTTCGGGGCC
Pea FT-B       GATGACGTCTCCGCGAGCATTTCAACAACCAGTTACTCAAACCACCGCGGAGTAACACATGGAAGCTTCA
Tomato         GAAGACGCTGGAAGATCAATGGGTGGTGGAGCGTCGAGTCCGAGAGATATACGATTATTTCTACAGCATT
Tobacco        GAGGACACTGGAAGATCAATGGATGGTGGAGCGTCAAGTTCGGGAGATATACAATTTTTTCTACAGCATT
```

TABLE 10C-continued

ClustalW Nucleic Acid Analysis of FT Beta Subunits

```
                    220       230       240       250       260       270       280
            ....|....|....|....|....|....|....|....|....|....|....|....|....|....|
PPI-BnFTb    ----------------------------------------------------------------------
era1         ------------------------ATGGAGATTCAGCCAGATAAGCAATT-GGATTATC-----TGATGA
Wiggum       GACGTTTCTACTCAAAAATACATGATGGAGATTCAGCCAGATAAGCAATT-GGATTATC-----TGATGA
PPI-Soy-FTB  CTCGCAACGCCCAAACCCTCAT-GTTGGAGCTTCAACGCGATAATCACAT-GCAGTAT-----GTCTCCA
DuP-Soy-FTB  CTCGCAACGCCCAAACCCTCAT-GTTGGAGCTTCAACGCGATAATCACAT-GCAGTAT-----GTCTCCA
PPI-Corn-FTB GCGCCCAACACGAAATCCATCATGCTAGAGCTGTGGCGTGATCAGCATAT-CGAGTATC-----TGACGC
DuP-Corn-FTB GCGCCCAACACGAAATCCATCATGCTAGAGCTGTGGCGTGATCAGCATAT-CGAGTATC-----TGACGC
Pea FT-B     ACCGCGGCGGAGACACCAACTCCGACGGTGAGTCAGAGAGATCAATGGATAGTAGAATCACAGGTCTTTC
Tomato       TCCCCCAACTCTCCGTCCGACCTCATAGAGATCCAACGTGACAAACACTT-CGGTTATC-----TAAGCC
Tobacco      CCNCCCAATTC---------CCACTTAGAGACTTCAACAGAAAAGCACTT-CGATTATC-----TCACTC

                    290       300       310       320       330       340       350
            ....|....|....|....|....|....|....|....|....|....|....|....|....|....|
PPI-BnFTb    --------------------------------------------------------TGGCTTTGTTACTG
era1         AAGGCTTAAGGCAGCTT---GGTCCGCAGTTTTCTTCCTTAGATGCTAATCGACCTTGGCTTTGTTACTG
Wiggum       AAGGCTTAAGGCAGCTT---GGTCCGCAGTTTTCTTCCTTAGATGCTAATCGACCTTGGCTTTGTTACTG
PPI-Soy-FTB  AAGGCCTTCGCCATCTC---AGTTCCGCATTTTCCGTTTTGGACGCTAATCGACCCTGGCTCTGCTACTG
DuP-Soy-FTB  AAGGCCTTCGCCATCTC---AGTTCCGCATTTTCCGTTTTGGACGCTAATCGACCCTGGCTCTGCTACTG
PPI-Corn-FTB CTGGGCTGAGGCATATG---GGACCAGCCTTTCATGTTCTAGATGCCAATCGCCCTTGGCTATGCTACTG
DuP-Corn-FTB CTGGGCTCAGGCATATG---GCACCAGCCTTTCATGTCCTAGATCCCAATCGCCCTTGGCTATCCTACTC
Pea FT-B     ATATTTATCAACTCTTCGCCAATATTCCTCCTAACGCCCAATCTATCATTCGACCTTGGCTGTGTTACTG
Tomato       AAGGTCTCAGAAAACTT---GGTCCGTCGTTTTCCGTTTTGGATGCCAGTCGACCATGGCTTTGCTACTG
Tobacco      GAGGTCTCAGAAAACTT---GGTCCGTCGTTCTCCGTCTTGGATGCTAATCGACCATGGCTTTGCTACTG

                    360       370       380       390       400       410       420
            ....|....|....|....|....|....|....|....|....|....|....|....|....|....|
PPI-BnFTb    GATTCTTCATTCAATTGCTTTGCTTGGGGAGTCTGTGGATGATGACTTAGAAAACAATGCAATCGATTTT
era1         GATTCTTCATTCAATAGCTTTGCTTGGGGAGACTGTGGATGATGAATTAGAAAGCAATGCCATTGACTTC
Wiggum       GATTCTTCATTCAATAGCTTTGCTTGGGGAGACTGTGGATGATGAATTAGAAAGCAATGCCATTGACTTC
PPI-Soy-FTB  GATCTTCCACTCCATTGCTTTGTTGGCAGAATCCGTCGATGATGAACTCGAAGATAACGCTATCGATTTT
DuP-Soy-FTB  GATCTTCCACTCCATTGCTTTGTCGGCAGAATCCGTCGATGATGAACTCGAAGATAACGCTATCGATTTT
PPI-Corn-FTB GATGGTTCATCCACTTGCTTTGCTGGATGAAGCACTTGATGATGATCTTGAGAATGATATCATAGACTTC
DuP-Corn-FTB GATGGTTCATCCACTTGCTTTGCTGGATGAAGCACTTGATGATGATCTTGAGAATGATATCATAGACTTC
Pea FT-B     GATTATTCATTCAATTGCTTTGTTGGGAGAATCTATTGATGATGATCTCGAAGATAACACTGTCGATTTT
Tomato       GACACTTCATTCAATCGCTTTGTTGGGAGAATCTATTGGTGGCAAACTGGAAAATGATGCAATTGACTTT
Tobacco      GATACTTCATTCAATCGCTTTGTTGGGAGAATCTATTGATGCCCAACTGGAAAATGATGCAATTGACTTT

                    430       440       450       460       470       480       490
            ....|....|....|....|....|....|....|....|....|....|....|....|....|....|
PPI-BnFTb    CTTGGACGTTGCCAGGGTTCTGATGGTGGATATGGTGGTGGTCCTGGCCAACTTCCACATCTTGCAACAA
era1         CTTGGACGCTGCCAGGGCTCTGAAGGTGGATACGGTGGTGGTCCTGGCCAACTTCCACATCTTGCAACTA
Wiggum       CTTGGACGCTGCCAGGGCTCTGAAGGTGGATACGGTGGTGGTCCTGGCCAACTTCCACATCTTGCAACTA
PPI-Soy-FTB  CTTAACCGTTGCCAGGATCCGAATGGTGGATA GCCGGGGACCAGGCCAGATGCCTCATATTGCCACAA
DuP-Soy-FTB  CTTAACCGTTGCCAGGATCCGAATGGTGGATATGCCGGGGACCAGGCCAGATGCCTCATATTGCCACAA
PPI-Corn-FTB TTAGCTCGATGTCAGGATAAAGATGGTGGATATAGTGGTGGACCTGGACAGTTGCCTCACCTAGCTACGA
DuP-Corn-FTB TTAGCTCGATGTCAGGATAAAGATGGTGGATATAGTGGTGGACCTGGACAGTTGCCTCACCTAGCTACGA
Pea FT-B     CTTAACCGTTGCCAGGATCCAAATGGTGGATATGCTGGGGGACCTGGTCAGATGCCTCATCTTGCCACAA
Tomato       CTGACCCGTTGCCAGGATAAAGATGGTGGCTATGGAGGTGGACCTGGTCAGATGCCTCATCTTGCAACTA
Tobacco      CTGAGCCGTTGCCAGGATGAAGATGGTGGCTATGGTGGTGGACCTGGTCAGATGCCTCATCTTGCAACTA

                    500       510       520       530       540       550       560
            ....|....|....|....|....|....|....|....|....|....|....|....|....|....|
PPI-BnFTb    GTTATGCTGCAGTGAATACACTTGTTACTTTAGGAGGTGAGAAAGCCTTCTCTTCAATTAACAGAGAACA
era1         CTTATGCTGCAGTGAATGCACTTGTTACTTTAGGAGGTGACAAAGCCCTTTCTTCAATTAATAGAGAAAA
Wiggum       CTTATGCTGCAGTGAATGCACTTGTTACTTTAGGAGGTGACAAAGCCCTTTCTTCAATTAATAGAGAAAA
PPI-Soy-FTB  CTTATGCTGCTGTTAATTCACTTATTACTTTGGGTGGTGAGAAATCCCTGGCATCAATTAATAGAGATAA
DuP-Soy-FTB  CTTATGCTGCTGTTAATTCACTTATTACTTTGGGTGGTGAGAAATCCCTGGCATCAATTAATAGAGATAA
PPI-Corn-FTB CTTATGCTGCTGTAAATACACTTGTGACAATAGGGAGCGAAAGAGCATTGTCATCAATCAATAGGGGCAA
DuP-Corn-FTB CTTATGCTGCTGTAAATACACTTGTGACAATAGGGAGCCAAAGAGCATTGTCATCAATCAATAGGGCCAA
Pea FT-B     CTTATGCTGCAGTCAATACTCTTAT ACTCTGGGTGGTGAGAAATCTTTGGCATCTATTAATAGAAATAA
Tomato       CTTATGCTGCAGTCAATTCACTAATAACTTTGGGCAAACCTGAAGCTCTGTCATCAATTAATAGAGAAAA
Tobacco      CTTATGCTGCAGTCAATTCACTCATAACTTTGGGCAGCCCTAAAGCTCTGTCATCAATCAATAGAGAAAA

                    570       580       590       600       610       620       630
            ....|....|....|....|....|....|....|....|....|....|....|....|....|....|
PPI-BnFTb    AATGGCTTGTTTCTTAAGACGAATGAAGGATACAAATGGAGGTTTCAGGATGCATAATATGGAGAAATA
era1         AATGTCTTGTTTTTTAAGACGGATGAAGGATACAAGTGGAGGTTTCAGGATGCATGATATGGAGAAATT
Wiggum       AATGTCTTGTTTTTTAAGACGGATGAAGGATACAAGTGGAGGTTTCAGGATGCATGATATGGAGAAATG
PPI-Soy-FTB  ACTGTATGGGTTTCTGCGGCGGATGAAGCAACCAAATGGTGGATTCAGGATGCATGATGAAGGTGAAATT
DuP-Soy-FTB  ACTGTATGGGTTTCTGCGGCGGATGAAGCAACCAAATGGTGGATTCAGGATGCATGATGAAGGTGAAATT
PPI-Corn-FTB CCTGTACAATTTTATGCTGCAGATGAAAGATGTATCAGGTGCTTTCAGAATGCATGATGGTGGCGAAATT
DuP-Corn-FTB CCTGTACAATTTTATGCTGCAGATGAAAGATGTATCAGGTGCTTTCAGAATGCATGATGGTGGCGAAATT
Pea FT-B     GTTGTACGGGTTTATGCGGCGGATGAAACAGCCAAACGGCGGATTCAGGATGCATGACGAGGGAGAAATT
Tomato       GTTGTACACATTTTTGCTGCGAATGAAAGACGCAAGTGGTGGATTCAGGATGCACGATGGTGGAGAAGTA
Tobacco      ATTGTATACATTTTGGCTGCAAATGAAAGACACAAGTGGTGGCTTCAGGATGCATGATGGTGGAGAAGTA
```

TABLE 10C-continued

ClustalW Nucleic Acid Analysis of FT Beta Subunits

```
                    640       650       660       670       680       690       700
               ....|....|....|....|....|....|....|....|....|....|....|....|....|....|
PPI-BnFTb      GATGTGCCAGCGTGCTACACTGCGATTTTGATTGCAAGCATCCTGAACATTGTGGATGATGAACTCACCC
era1           GATGTTCGTGCATGCTACACTGCAATTTCGGTTGCAAGCATCCTAAATATTATGGATGATGAACTCACCC
Wiggum         GATGTTCGTGCATGCTACACTGCAATTTCGGTTGCAAGCATCCTAAATATTATGGATGATGAACTCACCC
PPI-Soy-FTB    GATGTTCGAGCTTGCTACACTGCCATTTCTGTTGCAAGTGTTTTGAACATTTTGGATGATGAGCTGATCC
DuP-Soy-FTB    GATGTTCGAGCTTGCTACACTGCCATTTCTGTTGCAAGTGTTTTGAACATTTTGGATGATGAGCTGATCC
PPI-Corn-FTB   GATGTCCGTGCTTCCTACACCGCTATATCGGTTGCCAGCCTTGTGAATATTCTTGATTTTAAACTGGCAA
DuP-Corn-FTB   GATGTCCGTGCTTCCTACACCGCTATATCGGTTGCCAGCCTTGTGAATATTCTTGATTTTAAACTGGCAA
Pea FT-B       GACGTTCGAGCTTGCTACACTGCCATCTCTGTGGCAAGTGTTCTGAACATTTTGGATGATGAGCTGATCA
Tomato         GATGTTCGTGCCTGTTATACTGCCATTTCTGTTGCAAATATATTAAACATTGTGGATGACGAGCTGATTC
Tobacco        GATGTTCGTGCCTGTTATACTGCCATTTCTGTTGCAAGTATATTGCAAATTGTGGATGATGAACTGATTA

                    710       720       730       740       750       760       770
               ....|....|....|....|....|....|....|....|....|....|....|....|....|....|
PPI-BnFTb      GCGGCTTAGGAGATTACATTTTGAGTTGCCAAACTTATGAAGGTGGCATTGGAGGGGAACCTGGCTCCGA
era1           AGGGCCTAGGAGATTACATCTTGAGTTGCCAAACTTATGAAGGTGGCATTGGAGGGGAACCTGGCTCCGA
Wiggum         AGGGCCTAGGAGATTACATCTTGAGTTGCCAAACTTATGAAGGTGGCATTGGAGGGGAACCTGGCTCCGA
PPI-Soy-FTB    AGAATGTTGGAGACTACATTATAAGCTGTCAAACATATGAGGGTGGCATTGCTGGTGAGCCTGGTTCTGA
DuP-Soy-FTB    AGAATGTTGGAGACTACATTATAAGCTGTCAAACATATGAGGGTGGCATTGCTGGTGAGCCTGGTTCTGA
PPI-Corn-FTB   AAGGTGTAGGCGACTACATAGCAAGATGTCAAACTTATGAAGGTGGTATTGCTGGGGAGCCTTATGCTGA
DuP-Corn-FTB   AAGGTGTAGGCGACTACATAGCAAGATGTCAAACTTATGAAGGTGGTATTGCTGGGGAGCCTTATGCTGA
Pea FT-B       AGAATGTTGGAGACTTCATTTTAAGCTGTCAAACATATGAGGGAGGCCTTGCTGGTGAGCCTGGGTCTGA
Tomato         ATGGTGTTGGAAATTACATCCTAAGTTGTCAGACTTATGAAGGTGGAATTGCTGGCGAACCAGGTTCTGA
Tobacco        ATGATGTTGGGAATTACATCCTAAGTTGTCAGACTTATGAAGGTGGAATTGCTGGCGAACCAGGTTCTGA

                    780       790       800       810       820       830       840
               ....|....|....|....|....|....|....|....|....|....|....|....|....|....|
PPI-BnFTb      AGCTCATGGTGGGTACACGTACTGTGGGTTGGCTACTATGATTTTAATCAATGAAGTCGACCGCTTGAAT
era1           AGCTCACGGTGGGTATACCTACTGTGGTTTGGCTGCTATGATTTTAATCAATGAGGTCGACCGTTTGAAT
Wiggum         AGCTCACGGTGGGTATACCTACTGTGGTTTGGCTGCTATGATTTTAATCAATGAGGTCGACCGTTTGAAT
PPI-Soy-FTB    GGCTCATGGTGGGTACACCTTTTGTGGATTAGCTACAATGATTCTGATTGGTGAGGTTAATCACTTGGAT
DuP-Soy-FTB    GGCTCATGGTGGGTACACCTTTTGTGGATTAGCTACAATGATTCTGATTGGTGAGGTTAATCACTTGGAT
PPI-Corn-FTB   AGCACATGGTGGGTATACATTCTGTGGATTGGCTGCTTTGATCCTGCTTAATGAGGCAGAGAAAGTTGAC
DuP-Corn-FTB   AGCACATGGTGGGTATACATTCTGTGGATTGGCTGCTTTGATCCTGCTTAATGAGGCAGAGAAAGTTGAC
Pea FT-B       GGCTCATGGCGGGTATACCTTTTGTGGGTTAGCTGCAATGATTCTGATTGGTGAGGTTAATCGCTTGGAT
Tomato         AGCTCATGGTGGGTATACTTTCTGTGGGTTGGCTGCAATGATTCTGATCAACGAAGTAGATCGATTGGAC
Tobacco        AGCTCATGGTGGGTATACCTTCTGTGGGTTGGCTGCAATGATTCTGATTAACGAAGCGAATCGATTGGAC

                    850       860       870       880       890       900       910
               ....|....|....|....|....|....|....|....|....|....|....|....|....|....|
PPI-BnFTb      TTGGATTCGTTAATGAATTGGGTTGTACATCGACAAGGAGTAGAAATGGGATTCCAAGGTAGGACGAACA
era1           TTGGATTCATTAATGAATTGGGCTGTACATCGACAAGGAGTAGAAATGGGATTTCAAGGTAGGACGAACA
Wiggum         TTGGATTCATTAATGAATTGGGCTGTACATCGACAAGGAGTAGAAATGGGATTTCAAGGTAGGACGAACA
PPI-Soy-FTB    CTGCCTCGATTAGTTGACTGGGTGGTATTCCGACAAGGTAAGGAATGTGGATTCCAGGGGAGAACAAATA
DuP-Soy-FTB    CTGCCTCGATTAGTTGACTGGGTGGTATTCCGACAAGGTAAGGAATGTGGATTCCAGGGGAGAACAAATA
PPI-Corn-FTB   TTGCCTAGTTTGATTGGCTGGGTGGCTTTTCGTCAAGGAGTGGAATGCGGATTTCAAGGACGAACTAATA
DuP-Corn-FTB   TTGCCTAGTTTGATTGGCTGGGTGGCTTTTCGTCAAGGAGTGGAATGCGGATTTCAAGGACGAACTAATA
Pea FT-B       CTGCCTCGTTTACTTGATTGGGTTGTGTTTCGGCAAGGTAAAGAGTGTGGATTTCAGGGGAGAACGAATA
Tomato         TTGCCAGGTTTAATTGATTGGGTGGTATTTAGACAAGGGGTCGAAGGTGGATTTCAAGGCAGGACAAATA
Tobacco        TTGCCAAGATTAATTGATTGGGTGGTATTTAGACAAGGAGTCGAAGGTGGATTTCAAGGCAGGACAAATA

                    920       930       940       950       960       970       980
               ....|....|....|....|....|....|....|....|....|....|....|....|....|....|
PPI-BnFTb      AATTGGTCGACGGTTGCTACACGTTTTGGCAGGCAGCCCCCTGTGTTCTACTACAGCGATTTTTTTCATC
era1           AATTGGTCGATGGTTGCTACACATTTTGGCAGGCAGCCCCTTGTGTTCTACTACAAAGATTATATTCAAC
Wiggum         AATTGGTCGATGGTTGCTACACATTTTGGCAGGCAGCCCCTTGTGTTCTACTACAAAGATTATATTCAAC
PPI-Soy-FTB    AACTGGTGGATGGATGCTATTCCTTTTGGCAGGGAGGTGCTGTTGCTCTATTGCAAAGATTATCTTCTAT
DuP-Soy-FTB    AACTGGTGGATGGATGCTATTCCTTTTGGCAGGGAGGTGCTGTTGCTCTATTGCAAAGATTATCTTCTAT
PPI-Corn-FTB   AATTGGTTGATGGTTGCTACTCCTTTTGGCAGGGAGCTGCCATTGCTTTCACACAAAAGTTAATTACGAT
DuP-Corn-FTB   AATTGGTTGATGGTTGCTACTCCTTTTGGCAGGGAGCTGCCATTGCTTTCACACAAAAGTTAATTACGAT
Pea FT-B       AATTGGTAGATGGATGCTACTCGTTTTGGCAGGGAGGTGCTGTTGCCCTATTGCAAAGATTACATTCTAT
Tomato         AATTAGTCGATGGCTGCTATTCCTTTTGGCAGGGCGCGGTAGTGTTTCTTATACAAAGACTAAATTTGAT
Tobacco        AATTAGTCGATGGCTGCTATTCCTTTTGGCAGGCCGCGGTAGCTTTTCTTATACAAAGATTAAAATCGAC

                    990      1000      1010      1020      1030      1040      1050
               ....|....|....|....|....|....|....|....|....|....|....|....|....|....|
PPI-BnFTb      CCAGGAT-ATGGCACC------TCATGGATCATCATCA------------CATATGTCACAAGGACAGAT
era1           CAATGATCATGACGT-------TCATGGATCATCA---------------CATATATCAGAAGGACAAAT
Wiggum         CAATGATCATGACGT-------TCATGGATCATCA---------------CATATATCAGAAGGACAAAT
PPI-Soy-FTB    TATCAACAAACAGATG------GAAGAGA-CATCA---------------CAGATTTTGCGGTATCTTAT
DuP-Soy-FTB    TATCAACAAACAGATG------GAAGAGA-CATCA---------------CAGATTTTGCGGTATCTTAT
PPI-Corn-FTB   TGTTGATAAGCAATTGAGGTCCTCGTA-----T---------------------TCCTGCAAAA----GG
DuP-Corn-FTB   TGTTGATAAGCAATTGAAGTCCTCGTA-----T---------------------TCCTGCAAAA----GG
Pea FT-B       TATCGACGAACAAATG------GCAGAGG-CATCA--------------CAGTTTGTTACAGTATCTGAT
Tomato         AGTCCATGAACAACTAGGGCTGTCAAATGACCTCAGTACAGAAAGTGCTGATGATTCTTCAGAGTCAGAG
Tobacco        AGTCCATGAACAACTAGGGCTGTCAAATGAACTCAGTACAGAAAGTGCTGATGATTCTTCGGAGTCAGAG
```

TABLE 10C-continued

ClustalW Nucleic Acid Analysis of FT Beta Subunits

```
                     1060       1070       1080       1090       1100       1110       1120
                 ....|....|....|....|....|....|....|....|....|....|....|....|....|....|
PPI-BnFTb      GAAGATCACGAGGA-ACATGGTCATGATGAAGATGATCCTGAAGACAGTGATGAAGATGA---TTCTGAT
era1           GAAGAACAT-------CATGCTCATGATGAAGATGACCTTGAAGACAGTGATGATGATGATGATTCTGAT
Wiggum         GAAGAACAT-------CATGCTCATGATGAAGATGACCTTGAAGACAGTGATGATGATGATGATTCTGAT
PPI-Soy-FTB    GTATCTGAAG------CAAAAGAAAGTTTGGATGGAACCTCTAGTCA-TGCAACATGCCGTGGTGAGCAT
DuP-Soy-FTB    GTATCTGAAG------CAAAAGAAAGTTTGGATGGAACCTCTAGTCA-TGCAACATGCCGTGGTGAGCAT
PPI-Corn-FTB   CCATCAGGAGAG----GATGCCTGCAG----CACCAGTTCATAT----GGGTGCACC--------G-CGA
DuP-Corn-FTB   CCATCAGGAGAG----GATGCCTGCAG----CACCAGTTCATAT----GGGTGCACC--------G-CGA
Pea FT-B       GCACCTGAAG------AAAAGGAATGTTTGGACGGAACCTCAAGTCA-TGCAACTTCCCATATTAGGCAT
Tomato         TTATCTGATGAAGAAGAGCATTTGGAAGGGATATCCTCTCATGTTCA-GGATACTTTCCCTCTTGGACAA
Tobacco        TTATCTGATGAA---GAGCATTTGCAAGGGACATCATCTCATGTTCA-GAAGACTTGCCCTCTTGGACAA

                     1130       1140       1150       1160       1170       1180       1190
                 ....|....|....|....|....|....|....|....|....|....|....|....|....|....|
PPI-BnFTb      GAGGAT---------AGCGATGAA---GATTCAGGGAATGGTCACCAAGTTCATCATACGTCTAC-CTAC
era1           GAGGAC---------AACGATGAA---GATTCAGTGAATGGTCACAGAATCCATCATACATCCAC-CTAC
Wiggum         GAGGAC---------AACGATGAA---GATTCAGTGAATGGTCACAGAATCCATCATACATCCAC-CTAC
PPI-Soy-FTB    GAAGGC---------ACCAGTGAATCCAGTTCATCTGATTTTAAAAATATTGCCTATAAATTTAT-TAAT
DuP-Soy-FTB    GAAGGC---------ACCAGTGAATCCAGTTCATCTGATTTTAAAAATATTGCCTATAAATTTAT-TAAT
PPI-Corn-FTB   ATAAGT----------------CTTCCTCTGCTGTGGACTATGCGAAGTTTGGATTTGATTTTATACAAC
DuP-Corn-FTB   AAAAGT----------------CTTCCTCTGCTGTGGACTATGCGAAGTTTGGATTTGATTTTATACAAC
Pea FT-B       GAAGGC---------ATGAATGAATCCTGCTCATCTGACGTTAAAAATATTGGTTATAACTTTAT-TAGT
Tomato         GCAGGTGCTTGTCAAGAAAATGCTTCTCATAGCCCAAAAATAGCAGATACTGGATATGAGTTTAT-CAAC
Tobacco        GAAGGA------CAGGAAAATGCTTCAGATCCCACAAAGATAGCAGATACTGGTTATGATTTTGT-CAAT

                     1200       1210       1220       1230       1240       1250       1260
                 ....|....|....|....|....|....|....|....|....|....|....|....|....|....|
PPI-BnFTb      ATTGACAGGAGAATTCAACCTGTTTTTGATAGCCTCGGCTTGCAAAGATATGTGCTCTTGTGCTCTCAGG
era1           ATTAACAGGAGAATGCAACTGGTTTTTGATAGCCTCGGCTTGCAGAGATATGTACTCTTGTGCTCTAAGA
Wiggum         ATTAACAGGAGAATGCAACTGGTTTTTGATAGCCTCGGCTTGCAGAGATATGTACTCTTGTGCTCTAAGA
PPI-Soy-FTB    GAGTGGAGAGCACAAGAACCACTTTTTCACAGTATTGCTTTACAGCAATATATTCTCTTATGTGCACAGG
DuP-Soy-FTB    GAGTGGAGAGCACAAGAACCACTTTTTCACAGTATTGCTTTACAGCAATATATTCTCTTATGTGCACAGG
PPI-Corn-FTB   AGAGCAACCAA-ATTGGCCCACTCTTCCATAACATTGCCCTGCAACAATACATCCTACTTTGTTCTCAGG
DuP-Corn-FTB   AGAGCAACCAA-ATTGGCCCACTCTTCCATAACATTGCCCTGCAACAATACATCCTACTTTGTTCTCAGG
Pea FT-B       GAGTGGAGACAAAGTGAACCACTTTTTCACAGCATTGCCTTACAGCAATATATTCTTTTATGTTCACAGG
Tomato         CGACCCATAGCTATGAGGCCTCTCTTTGACAGCATGTATCTGCAGCAATATGTTCTTCTTTGCTCTCAGA
Tobacco        CGNACGATAGCTATGCGACCTGTGTTTGACAGCTTTTATCTGCAGCAATACGTTCTTCTCTGCTCCCAGA

                     1270       1280       1290       1300       1310       1320       1330
                 ....|....|....|....|....|....|....|....|....|....|....|....|....|....|
PPI-BnFTb      TTGCTGATGGTGGATTCAGAGACAAGCTGAGGAAACCCCGTGACTTCTACCACACATGTTACTGCCTAAG
era1           TCCCTGACGGTGGATTCAGAGACAAGCCGAGGAAACCCCGTGACTTCTACCACACATGTTACTGCCTGAG
Wiggum         TCCCTCACGGTGGATTCAGAGACAAGCCGACCAAACCCCGTGACTTCTACCACACATGTTACTGCCTGAG
PPI-Soy-FTB    ACCAAGAGGGTGGACTGACACACAAACCGGGTAAACGTAGAGATCATTATCACACATGTTACTCTTTAAG
DuP-Soy-FTB    AGCAAGAGGGTGGACTGAGAGACAAACCGGGTAAACGTAGAGATCATTATCACACATGTTACTGTTTAAG
PPI-Corn-FTB   TACTAGAGGGAGGCTTGAGGGATAAGCCTGGAAAGAACAGAGATCACTATCATTCATGCTACTGCCTCAG
DuP-Corn-FTB   TACTAGAGGGAGGCTTGAGGGATAAGCCTGGAAAGAACAGAGATCACTACCATTCATGCTACTGCCTCAG
Pea FT-B       AGCAAGATGGTGGGCTCAGGGACAAACCGGGTAAACGCAGGGATCATTATCATTCATGTTACTGTTTAAG
Tomato         TTGAAGTTGGTGGTTTCAGAGACAAACCTGGGAAGGGTAGAGACTACTACCATACCTGTTACTGTTTAAG
Tobacco        T---AGATGGAGGTTTCAGAGACAAACCTGGGAAGGGTAGAGACCACTACCATACTTGCTACTGTTTAAG

                     1340       1350       1360       1370       1380       1390       1400
                 ....|....|....|....|....|....|....|....|....|....|....|....|....|....|
PPI-BnFTb      CGGTCTTTCCGTGGCTCAACACGCTTGGTCAAAAGACGAGGACACTCCTCCTTTGACTCGTGACATTTTG
era1           CGGCTTGTCTGTGGCTCAGCACGCTTGGTTAAAAGACGAGGACACTCCTCCTTTGACTCGCGACATTATG
Wiggum         CGGCTTGTCTGTGGCTCAGCACGCTTGGTTAAAAGACGAGGACACTCCTCCTTTGACTCGCGACATTATG
PPI-Soy-FTB    TGGACTCTCATTGTGCCAGTATAGTTGGTCAAAGCACCCAGATTCTCCACCAC-----------------
DuP-Soy-FTB    TGGACTCTCATTGTGCCAGTATAGTTGGTCAAAGCACCCAGATTCTCCACCAC-----------------
PPI-Corn-FTB   TGGCCTCGCAGTTAGCCAGTACAGTGCCATGACTGATACTGGTTCGTGCCCATTACCTCAGCATGTGCTT
DuP-Corn-FTB   TGGCCTCGCAGTTAGCCAGTACAGTGCCATGACTGATACTGGTTCGTGCCCATTACCTCAGCATGTGCTT
Pea FT-B       TGGGTTGTCACTGTGCCAGTATAGTTGGTCGAAGCGCCCAGATTCTCCACCGCTGCCTAAGGTAGTAATG
Tomato         TGGTCTTTCAATTGCTCAGTATAGCTGGACCGACGAAGCTGATTCTACACCATTACCCAGGGATGTATTT
Tobacco        TGGTCTTTCAATTGCTCAATATAGCTGGACCAACGAAGCTGATGCGCCACCATTACCCAGGGATGTATTT

                     1410       1420       1430       1440       1450       1460       1470
                 ....|....|....|....|....|....|....|....|....|....|....|....|....|....|
PPI-BnFTb      GGTGGCTACGCA-AA--CCACCTTGAACCTGTTCACCTCCTCCACAACATTGTCTTGGATCGGTATTATG
era1           GGTGGCTACTCG-AA--TCTCCTTGAACCTGTTCAACTTCTTCACAACATTGTCATGGATCAGTATAATG
Wiggum         GGTGGCTACTCG-AA--TCTCCTTGAACCTGTTCAACTTCTTCACAACATTGTCATGGATCAGTATAATG
PPI-Soy-FTB    ----------------------------------------------------------------------
DuP-Soy-FTB    ----------------------------------------------------------------------
PPI-Corn-FTB   GGACCGTACTCT-AA--TTTGCTGGAGCCAATCCATCC--------------------------------
DuP-Corn-FTB   GGACCGTACTCT-AA--TTTGCTGGAGCCAATCCATCC--------------------------------
Pea FT-B       GGCCCATACTCC-AA--TCTCTTAGAACCCATCCATCCTCTCTTTAATGTTGTTTTGGATCGATATCGTG
Tomato         GGTCCTTATTCCAAATGTCTGTTGGAACAGGTTCACCCACTCTTCAACGTAGTGTTGGATCGGTATTATG
Tobacco        GGTCCTTATTCTCAAAATCTTTTGGAACAGATTCACCCACTTTACAACGTAGTGTTGGATCGGTATTATG
```

TABLE 10C-continued

ClustalW Nucleic Acid Analysis of FT Beta Subunits

```
                     1480      1490      1500      1510      1520      1530      1540
               ....|....|....|....|....|....|....|....|....|....|....|....|....|....|
PPI-BnFTb      AAGCTTCTAGATTT--------------------------------------------------------
era1           AAGCTATCGAGTTCTTCTTTAAAGCAGCATGACCCGTTGTTGCTAATGTATGGGAAACCCCAAACATAAG
Wiggum         AAGCTATCGAGTTCTTCTTTAAAGCAGCATGACCCGTTGTTGCTAATGTATGGGAAACTCCAAACATAAG
PPI-Soy-FTB    ----------------------------------------------------------------------
DuP-Soy-FTB    ----------------------------------------------------------------------
PPI-Corn-FTB   ----------------------------------------------------------------------
DuP-Corn-FTB   ----------------------------------------------------------------------
Pea FT-B       AAGCTCATGAATTCTTTTCTCAGTTGTGACGGATGACAAGGTTTTAGCTACCAATAGCTC-GATCATTAG
Tomato         AAGCTCGCGAATACT-CTCAGGCTTGTGAGACTGTTTCAC-CACTTTCATTAGCACCAAC--TTTTTCAG
Tobacco        AAGCTCGTAGCTTCTTCTCATGCTTGTGATAATATTTTACGCGATAGCTGTAGCTGGAAT--GTTACC--

                     1550      1560      1570      1580      1590      1600      1610
               ....|....|....|....|....|....|....|....|....|....|....|....|....|....|
PPI-BnFTb      ----------------------------------------------------------------------
era1           AGTTTCCGTAGTGTTGTAACTTGTAAGATTTCAAAAG---------------------------------
Wiggum         AGTTTTCGTAGTGTTGTAACTTGTAAGATTTCAAAAGAAGTTTCACTAATTTAACCTTAAAACCTGTTAC
PPI-Soy-FTB    ----------------------------------------------------------------------
DuP-Soy-FTB    ----------------------------------------------------------------------
PPI-Corn-FTB   ----------------------------------------------------------------------
DuP-Corn-FTB   ----------------------------------------------------------------------
Pea FT-B       AATGTAAAATGTAAACTAAAATATGAAATATGAAATACCAAAAAGATATTATTGGATGAAATTCACGTGG
Tomato         AAACTTAGTTGCAATCCAGAAGTTAAAAGTGTCATTGGGTTCAAAAGAGTTGTGATCGTTTATGTACATA
Tobacco        ---TCTAGTTG---TTCAGAATCAGAGACTAATCTATTATTTTGAGGGATTGGATTCAAAAAAAAAAAAA

                     1620      1630      1640      1650      1660      1670      1680
               ....|....|....|....|....|....|....|....|....|....|....|....|....|....|
PPI-BnFTb      ----------------------------------------------------------------------
era1           ----------------------------------------------------------------------
Wiggum         TTTTTTATTACGTATATACCATTTATCATATCTTTGGTTTACGACTTAAAGAATTTGATGATTGTTGAAA
PPI-Soy-FTB    ----------------------------------------------------------------------
DuP-Soy-FTB    ----------------------------------------------------------------------
PPI-Corn-FTB   ----------------------------------------------------------------------
DuP-Corn-FTB   ----------------------------------------------------------------------
Pea FT-B       ATCTAATACAACTGCGTGGTTTTCATTCCTGATTTGATTTTGATTTACATGAGTTAAAACGTTAAACCCT
Tomato         TCCTTGCATTTGTATACGTGATACAAGTTGAGAGAATAACGGGTACTTTCTGAACTTGCTGAACTAGCAC
Tobacco        AAAAAAA---------------------------------------------------------------

                     1690      1700      1710      1720      1730      1740      1750
               ....|....|....|....|....|....|....|....|....|....|....|....|....|....|
PPI-BnFTb      ----------------------------------------------------------------------
era1           ----------------------------------------------------------------------
Wiggum         ----------------------------------------------------------------------
PPI-Soy-FTB    ----------------------------------------------------------------------
DuP-Soy-FTB    ----------------------------------------------------------------------
PPI-Corn-FTB   ----------------------------------------------------------------------
DuP-Corn-FTB   ----------------------------------------------------------------------
Pea FT-B       TCTTATTCATACATTTGTTAAGAGCTTAAGGCTTAATGGTTAAGCCAATGATATAAATATTTATGCAGAA
Tomato         GTAAATTCGTCTCTGGTTTAGTGAGGTCTGTAAACATCAATGTGAAATTGCGAGATATGCATGTAATAGT
Tobacco        ----------------------------------------------------------------------

                     1760      1770      1780      1790      1800      1810      1820
               ....|....|....|....|....|....|....|....|....|....|....|....|....|....|
PPI-BnFTb      ----------------------------------------------------------------------
era1           ----------------------------------------------------------------------
Wiggum         ----------------------------------------------------------------------
PPI-Soy-FTB    ----------------------------------------------------------------------
DuP-Soy-FTB    ----------------------------------------------------------------------
PPI-Corn-FTB   ----------------------------------------------------------------------
DuP-Corn-FTB   ----------------------------------------------------------------------
Pea FT-B       AGCTGTTGCTTATCACCAACGGTAATATTAATAAGCAAACAAGTATTCTGTGAT----------------
Tomato         GGCTAAGATTTACAAATCTGGATACCGGTTATTAGTGATCAGAAATTTCATTCAATTTCCCAAACGGTCA
Tobacco        ----------------------------------------------------------------------
```

TABLE 10C-continued

ClustalW Nucleic Acid Analysis of FT Beta Subunits

```
                    1830      1840      1850      1860      1870      1880      1890
               ....|....|....|....|....|....|....|....|....|....|....|....|....|....|
PPI-BnFTb      ----------------------------------------------------------------------
era1           ----------------------------------------------------------------------
Wiggum         ----------------------------------------------------------------------
PPI-Soy-FTB    ----------------------------------------------------------------------
DuP-Soy-FTB    ----------------------------------------------------------------------
PPI-Corn-FTB   ----------------------------------------------------------------------
DuP-Corn-FTB   ----------------------------------------------------------------------
Pea FT-B       ----------------------------------------------------------------------
Tomato         CCTAAGTTTAGGATATTGCTTTAAAATATTATTTATTTTTCATTTAAGAATCAAAAAAAAAAAAAAAAAA
Tobacco        ----------------------------------------------------------------------

               ....|....
PPI-BnFTb      ---------
era1           ---------
Wiggum         ---------
PPI-Soy-FTB    ---------
DuP-Soy-FTB    ---------
PPI-Corn-FTB   ---------
DuP-Corn-FTB   ---------
Pea FT-B       ---------
Tomato         AAAAAAAAA
Tobacco        ---------
```

TABLE 10D

ClustalW Amino Acid Analysis of FT Beta Subunits

1) PPI-BnFTB; FT3 (SEQ ID NO: 9)
2) era1 (SEQ ID NO: 80)
3) Wiggum (SEQ ID NO: 81)
4) PPI-Soy-FTB; FT5 (SEQ ID NO: 36)
5) DuP-Soy-FTB (SEQ ID NO: 82)
6) PPI-Corn-FTB; FT6 (SEQ ID NO: 39)
7) DuP-Corn-FTB (SEQ ID NO: 83)
8) Pea-FT-B (SEQ ID NO: 84)
9) Tomato (SEQ ID NO: 85)
10) Tobacco (SEQ ID NO: 86)

```
                        10        20        30        40        50        60        70
               ....|....|....|....|....|....|....|....|....|....|....|....|....|....|
PPI-BnFTb      ----------------------------------------------------------------------
era1           ----------------------------------------------------------------------
Wiggum         MPVVTRLIRLKCVGLRLDRSGLNRRICHGGHGESTRRRVMEELSSLTVSQREQFLVENDVFGIYNYFDAS
PPI-Soy-FTB    -------------------------------------------------------------------ATI
DuP-Soy-FTB    -------------------------------------------------------------------ATI
PPI-Corn-FTB   --------------------------------------ADPDLPRLTVTQVEQMKVEARVGDIYRSLFGA
DuP-Corn-FTB   --------------------------------------ADPDLPRLTVTQVEQMKVEARVGDIYRSLFGA
Pea FT-B       -------------------------------------------------------------------MEA
Tomato         ----------------------------------------MESRKVTKTLEDQWVVERRVREIYDYFYSI
Tobacco        ------------------------------------------GTSGTRTLEDQWMVERQVREIYNFFYSI

                        80        90       100       110       120       130       140
               ....|....|....|....|....|....|....|....|....|....|....|....|....|....|
PPI-BnFTb      --------------------------------------------WLCYWILHSIALLGESVDDDLENNAI
era1           --------MEIQRDKQLDYLMKGLRQLGPQFSSLDAN-----RPWLCYWILHSIALLGETVDDELESNAI
Wiggum         DVSTQKYMMEIQRDKQLDYLMKGLRQLGPQFSSLDAN-----RPWLCYWILHSIALLGETVDDELESNAI
PPI-Soy-FTB    PRNAQTLMLELQRDNHMQYVSKGLRHLSSAFSVLDAN-----RPWLCYWIFHSIALLGESVDDELEDNAI
DuP-Soy-FTB    PRNAQTLMLELQRDNHMQYVSKGLRHLSSAFSVLDAN-----RPWLCYWIFHSIALSGESVDDELEDNAI
PPI-Corn-FTB   APNTKSIMLELWRDQHIEYLTPGLRHMGPAFHVLDAN-----RPWLCYWMVHPLALLDEALDDDLENDII
DuP-Corn-FTB   APNTKSIMLELWRDQHIEYLTPGLRHMGPAFHVLDAN-----RPWLCYWMVHPLALLDEALDDDLENDII
Pea FT-B       STAAETPTPTVSQRDQWIVESQ-VFHIYQLFANIPPNAQSIIRPWLCYWIIHSIALLGESIDDDLEDNTV
Tomato         SPNSPSDLIEIERDKHFGYLSQGLRKLGPSFSVLDAS-----RPWLCYWTLHSIALLGESIGGKLENDAI
Tobacco        PPNS---HLETSTEKHFDYLTRGLRKLGPSFSVLDAN-----RPWLCYWILHSIALLGESIDAQLENDAI
```

TABLE 10D-continued

ClustalW Amino Acid Analysis of FT Beta Subunits

```
                     150       160       170       180       190       200       210
             ....|....|....|....|....|....|....|....|....|....|....|....|....|....|
PPI-BnFTb    DFLGRCQGSDGGYGGGPGQLPHLATSYAAVNTLVTLGGEKAFSSINREQMACFLRRMKDTNGGFRMHNMG
era1         DFLGRCQGSEGGYGGGPGQLPHLATTYAAVNALVTLGGDKALSSINREKMSCFLRRMKDTSGGFRMHDMG
Wiggum       DFLGRCQGSEGGYGGGPGQLPHLATTYAAVNALVTLGGDKALSSINREKMSCFLRRMKDTSGGFRMHDMG
PPI-Soy-FTB  DFLNRCQDPNGGYAGGPGQMPHIATTYAAVNSLITLGGEKSLASINRDKLYGFLRRMKQPNGGFRMHDEG
DuP-Soy-FTB  DFLNRCQDPNGGYAGGPGQMPHIATTYAAVNSLITLGGEKSLASINRDKLYGFLRRMKQPNGGFRMHDEG
PPI-Corn-FTB DFLARCQDKDGGYSGGPGQLPHLATTYAAVNTLVTIGSERALSSINRGNLYNFMLQMKDVSGAFRMHDGG
DuP-Corn-FTB DFLARCQDKDGGYSGGPGQLPHLATTYAAVNTLVTIGSQRALSSINRGNLYNFMLQMKDVSGAFRMHDGG
Pea FT-B     DFLNRCQDPNGGYAGGPGQMPHLATTYAAVNTLITLGGEKSLASINRNKLYGFMRRMKQPNGGFRMHDEG
Tomato       DFLTRCQDKDGGYGGGPGQMPHLATTYAAVNSLITLGKPEALSSINREKLYTFLLRMKDASGGFRMHDGG
Tobacco      DFLSRCQDEDGGYGGGPGQMPHLATTYAAVNSLITLGSPKALSSINREKLYTFWLQMKDTSGGFRMHDGG

                     220       230       240       250       260       270       280
             ....|....|....|....|....|....|....|....|....|....|....|....|....|....|
PPI-BnFTb    EIDVRACYTAILIASILNIVDDELTRGLGDYILSCQTYEGGIGGEPGSEAHGGYTYCGLATMILINEVDR
era1         EIDVRACYTAISVASILNIMDDELTQGLGDYILSCQTYEGGIGGEPGSEAHGGYTYCGLAAMILINEVDR
Wiggum       EMDVRACYTAISVASILNIMDDELTQGLGDYILSCQTYEGGIGGEPGSEAHGGYTYCGLAAMILINEVDR
PPI-Soy-FTB  EIDVRACYTAISVASVLNILDDELIQNVGDYIISCQTYEGGIAGEPGSEAHGGYTFCGLATMILIGEVNH
DuP-Soy-FTB  EIDVRACYTAISVASVLNILDDELIQNVGDYIISCQTYEGGIAGEPGSEAHGGYTFCGLATMILIGEVNH
PPI-Corn-FTB EIDVRASYTAISVASLVNILDFKLAKGVGDYIARCQTYEGGIAGEPYAEAHGGYTFCGLAALILLNEAEK
DuP-Corn-FTB EIDVRASYTAISVASLVNILDFKLAKGVGDYIARCQTYEGGIAGEPYAEAHGGYTFCGLAALILLNEAEK
Pea FT-B     EIDVRACYTAISVASVLNILDDELIKNVGDFILSCQTYEGGLAGEPGSEAHGGYTFCGLAAMILIGEVNR
Tomato       EVDVRACYTAISVANILNIVDDELIHGVGNYILSCQTYEGGIAGEPGSEAHGGYTFCGLAAMILINEVDR
Tobacco      EVDVRACYTAISVASILQIVDDELINDVGNYILSCQTYEGGIAGEPGSEAHGGYTFCGLAAMILINEANR

                     290       300       310       320       330       340       350
             ....|....|....|....|....|....|....|....|....|....|....|....|....|....|
PPI-BnFTb    LNLDSLMNWVVHRQGVEMGFQGRTNKLVDGCYTFWQAAPCVLLQRFFSSQDMAPHGSSSHMSQGTDEDHE
era1         LNLDSLMNWAVHRQGVEMGFQGRTNKLVDGCYTFWQAAPCVLLQRLYSTNDHDVHG-SSHISEGTNEEH-
Wiggum       LNLDSLMNWAVHRQGVEMGFQGRTNKLVDGCYTFWQAAPCVLLQRLYSTNDHDVHG-SSHISEGTNEEH-
PPI-Soy-FTB  LDLPRLVDWVVFRQGKECGFQGRTNKLVDGCYSFWQGGAVALLQRLSSIINKQMEETSQIFAVSYVSEA-
DuP-Soy-FTB  LDLPRLVDWVVFRQGKECGFQGRTNKLVDGCYSFWQGGAVALLQRLSSIINKQMEETSQIFAVSYVSEA-
PPI-Corn-FTB VDLPSLIGWVAFRQGVECGFQGRTNKLVDGCYSFWQGAAIAFTQKLITIVDKQLRSSYSCKRPSGEDACS
DuP-Corn-FTB VDLPSLIGWVAFRQGVECGFQGRTNKLVDGCYSFWQGAAIAFTQKLITIVDKQLKSSYSCKRPSGEDACS
Pea FT-B     LDLPRLLDWVVFRQGKECGFQGRTNKLVDGCYSFWQGGAVALLQRLHSIIDEQMAEASQFVTVSDAPEE-
Tomato       LDLPGLIDWVVFRQGVEGGFQGRTNKLVDGCYSFWQGAVVFLIQRLNLIVHEQLGLSNDLSTESADDSSE
Tobacco      LDLPRLIDWVVFRQGVEGGFQGRTNKLVDGCYSFWQAAVAFLIQRLKSTVHEQLGLSNELSTESADDSSE

                     360       370       380       390       400       410       420
             ....|....|....|....|....|....|....|....|....|....|....|....|....|....|
PPI-BnFTb    EHGHDED-DPE--DSDEDD-S--DEDS--DEDSGNGHQVHHT-STYIDR--RIQPVFDSLGLQRYVLLCS
era1         -HAHDED-DLE--DSDDDDDS--DEDN--DEDSVNGHRIHHT-STYINR--RMQLVFDSLGLQRYVLLCS
Wiggum       -HAHDED-DLE--DSDDDDDS--DEDN--DEDSVNGHRIHHT-STYINR--RMQLVFDSLGLQRYVLLCS
PPI-Soy-FTB  -----KE-SLDGTSSHATCRG--EHEG---TSESSSSDFKNIAYKFINEWRAQEPLFHSIALQQYILLCA
DuP-Soy-FTB  -----KE-SLDGTSSHATCRG--EHEG---TSESSSSDFKNIAYKFINEWRAQEPLFHSIALQQYILLCA
PPI-Corn-FTB ------------TSSYGCTAN----------KSSSAVDYAKFGFDFIQQSNQIGPLFHNIALQQYILLCS
DuP-Corn-FTB ------------TSSYGCTAK----------KSSSAVDYAKFGFDFIQQSNQIGPLFHNIALQQYILLCS
Pea FT-B     -----KE-CLDGTSSHATSHI--RHEG---MNESCESDVKNIGYNFISEWRQSEPLFHSIALQQYILLCS
Tomato       SELSDKEEHLEGISSHVQDTFPLGQAGACQENASHSPKIADTGYEFINRPIAMRPLFDSMYLQQYVLLCS
Tobacco      SELSDEE-HLQGTSSHVQKTCPLGQEG--QENASDPTKIADTGYDFVNRTIAMRPVFDSFYLQQYVLLCS

                     430       440       450       460       470       480       490
             ....|....|....|....|....|....|....|....|....|....|....|....|....|....|
PPI-BnFTb    QVADGGFRDKLRKPRDFYHTCYCLSGLSVAQHAWSKDEDTPPLTRDILGGYAN-HLEPVHLLHNILVDRY
era1         KIPDGGFRDKPRKPRDFYHTCYCLSGLSVAQHAWLKDEDTPPLTRDIMGGYSN-LLEPVQLLHNIVMDQY
Wiggum       KIPDGGFRDKPRKPRDFYHTCYCLSGLSVAQHAWLKDEDTPPLTRDIMGGYSN-LLEPVQLLHNIVMDQY
PPI-Soy-FTB  QEQEGGLRDKPGKRRDHYHTCYCLSGLSLCQYSWSKHPDSPP----------------------------
DuP-Soy-FTB  QEQEGGLRDKPGKRRDHYHTCYCLSGLSLCQYSWSKHPDSPP----------------------------
PPI-Corn-FTB QVLEGGLRDKPGKNRDHYHSCYCLSGLAVSQYSAMTDTGSCPLPQHVLGPYSN-LLEPIH----------
DuP-Corn-FTB QVLEGGLRDKPGKNRDHYHSCYCLSGLAVSQYSAMTDTGSCPLPQHVLGPYSN-LLEPIH----------
Pea FT-B     QEQDGGLRDKPGKRRDHYHSCYCLSGLSLCQYSWSKRPDSPPLPKVVMGPYSSNLLEPIHPLFNVVLDRY
Tomato       QIEVGGFRDKPGKGRDYYHTCYCLSGLSIAQYSWTDEADSTPLPRDVFGPYSKCLLEQVHPLFNVVLDRY
Tobacco      QID-GGFRDKPGKGRDHYHTCYCLSGLSIAQYSWTNEADAPPLPRDVFGPYSQNLLEQIHPLYNVVLDRY

                     500       510
             ....|....|....|....|....|
PPI-BnFTb    YEASRF-------------------
era1         NEAIEFFFKA---------------
Wiggum       NEAIEFFFKA---------------
PPI-Soy-FTB  -------------------------
DuP-Soy-FTB  -------------------------
PPI-Corn-FTB -------------------------
DuP-Corn-FTB -------------------------
Pea FT-B     REAHEFFSQL---------------
Tomato       YEAREYSQACETVSPLSLAPTFSET
Tobacco      YEARSFFSCL---------------
```

Also included in the invention is the farnesyl transferase alpha consensus sequence of SEQ ID NO:87 and the farnesyl transferase beta consensus sequence of SEQ ID NO:88 To generate the consensus sequence, the farnesyl transferase alpha and farnesyl transferase beta sequences of the invention were aligned using the program BioEdit. The homology between the farnesyl transferase alpha (FTA) polypeptide sequences of the invention is shown graphically in the ClustalW analysis shown in Table 10E. The homology between the farnesyl transferase beta (FTB) polypeptide sequences of the invention is shown graphically in the ClustalW analysis shown in Table 10F.

TABLE 10E

ClustalW Amino Acid Analysis of FT Alphs

```
                       10        20        30        40        50        60        70
              ....|....|....|....|....|....|....|....|....|....|....|....|....|....|
BnA-12        --------------------------------------------------MDYFRAIYFSDERSARALRL
At-FT-A       --------MNFDETVPLSQRLEWSDVVPLTQDDGPNPVVPIAYKEEFRETMDYFRAIYFSDERSPRALRL
PPI-Soy-FTA   MESGSSEGEEVQQRVPLRERVEWSDVTPVPQNDGPNPVVPIQYTEEFSEVMDYFRAVYLTDERSPRALAL
Consensus     --------      VPL  R EWSDV P  Q DGPNPVVPI Y EEF E MDYFRAIYFSDERSPRALRL

                       80        90       100       110       120       130       140
              ....|....|....|....|....|....|....|....|....|....|....|....|....|....|
BnA-12        TEEALRLNSGNYTVWHFGRLVLEELNNDLYEELKFIESIAEDNSKNYQL----WHHRRWVAEKLGPDVAG
At-FT-A       TEETLLLNSGNYTVWHFRRLVLEALNHDLFEELEFIERIAEDNSKNYQL----WHHRRWVAEKLGPDVAG
PPI-Soy-FTA   TAEAVQFNSGNYTVWHFRRLLLESLKVDLNDELEFVERMAAGNSKNYQMXMFCRHPRRWVAEKLGPEARN
Consensus     TEEAL LNSGNYTVWHFRRLVLE LN DL EELEFIERIAEDNSKNYQL----WHHRRWVAEKLGPDVAG

                      150       160       170       180       190       200       210
              ....|....|....|....|....|....|....|....|....|....|....|....|....|....|
BnA-12        LEKEFTRRVLSLDAKHYHAWSHRQWALQALGGWENELNYCHELLEADVFNNSAWNQRYYVITRSPSLGGL
At-FT-A       RELEFTRRVLSLDAKHYHAWSHRQWTLRALGGWEDELDYCHELLEADVFNNSAWNQRYVVITQSPLLGGL
PPI-Soy-FTA   NELEFTKKILSVDAKHYHAWSHRQWALQTLGGWEDELNYCTELLKEDIFNNSAWNQRYFVITRSPFLGGL
Consensus      ELEFTRRVLSLDAKHYHAWSHRQWALQALGGWEDELNYCHELLEADVFNNSAWNQRYYVITRSP LGGL

                      220       230       240       250       260       270       280
              ....|....|....|....|....|....|....|....|....|....|....|....|....|....|
BnA-12        EAMRESEVSYTVKAILANPGNESSWRYLKALYKDDTESWISDPSVSSVCLKVLSRADCFHGFALSTLLDL
At-FT-A       EAMRESEVSYTIKAILTNPANESSWRYLKALYKDDKESWISDPSVSSVCLNVLSRTDCFHGFALSTLLDL
PPI-Soy-FTA   KAMRESEVLYTIEAITAYPENESSWRYLRGLYKGETTSWVNDPQVSSVCLKIL-RTKSNYVFALSTILDL
Consensus     EAMRESEVSYTIKAILANP NESSWRYLKALYKDDTESWISDPSVSSVCLKVLSRTDCFHGFALSTLLDL

                      290       300       310       320       330       340       350
              ....|....|....|....|....|....|....|....|....|....|....|....|....|....|
BnA-12        LCDGLRPTNEHRDSVKALAN--------------EEPETNLANLVCTILCRVDPIRANYWAWKL------
At-FT-A       LCDGLRPTNEHKDSVRALAN--------------EEPETNLANLVCTILGRVDPIRANYWAWRKSKITVA
PPI-Soy-FTA   ICFGYQPNEDIRDAIDALKTADMDKQDLDDDEKGEQQNLNIARNICSILKQVDPIRTNYWIWRKSRLP--
Consensus     LCDGLRPTNEHRDSV ALAN--------------EEPETNLANLVCTIL RVDPIRANYWAWRKS    --

              ..
BnA-12        -- (SEQ ID NO: 7)
At-FT-A       AI (SEQ ID NO: 2)
PPI-Soy-FTA   -- (SEQ ID NO: 33)
Consensus     -- (SEQ ID NO: 87)
```

TABLE 10F

ClustalW Amino Acid Analysis of FT Beta

```
                        10        20        30        40        50        60        70
               ....|....|....|....|....|....|....|....|....|....|....|....|....|....|
PPI-BnFTB      ----------------------------------------------------------------------
PPI-Soy-FTB    -------ATIPR----------------------NAQTLMLELQRDNHMQYVSKGLRHLSSAFSVLDANR
PPI-Corn-FTB   ADPDLPRLTVTQVEQMKVEARVGDIYRSLFGAAPNTKSIMLELWRDQHIEYLTPGLRHMGPAFHVLDANR
Consensus      ------- T   ----------------------N    MLEL RD H  Y   GLRH   AF VLDANR

                        80        90       100       110       120       130       140
               ....|....|....|....|....|....|....|....|....|....|....|....|....|....|
PPI-BnFTB      -WLCYWILHSIALLGESVDDDLENNAIDFLGRCQGSDGGYGGGPGQLPHLATSYAAVNTLVTLGGEKAFS
PPI-Soy-FTB    PWLCYWIFHSIALLGESVDDELEDNAIDFLNRCQDPNGGYAGGPGQMPHIATTYAAVNSLITLGGEKSLA
PPI-Corn-FTB   PWLCYWMVHPLALLDEALDDDLENDIIDFLARCQDKDGGYSGGPGQLPHLATTYAAVNTLVTIGSERALS
Consensus      PWLCYWI HSIALLGESVDDDLENNAIDFL RCQD DGGY GGPGQLPHLATTYAAVNTLVTLGGEKALS
```

TABLE 10F-continued

ClustalW Amino Acid Analysis of FT Beta

```
                        150       160       170       180       190       200       210
                ....|....|....|....|....|....|....|....|....|....|....|....|....|....|
PPI-BnFTB       SINREQMACFLRRMKDTNGGFRMHNMGEIDVRACYTAILIASILNIVDDELTRGLGDYILSCQTYEGGIG
PPI-Soy-FTB     SINRDKLYGFLRRMKQPNGGFRMHDEGEIDVRACYTAISVASVLNILDDELIQNVGDYIISCQTYEGGIA
PPI-Corn-FTB    SINRGNLYNFMLQMKDVSGAFRMHDGGEIDVRASYTAISVASLVNILDFKLAKGVGDYIARCQTYEGGIA
Consensus       SINR  LY FLRRMKD NGGFRMHD GEIDVRACYTAISVAS LNILDDEL   GVGDYI SCQTYEGGIA

                        220       230       240       250       260       270       280
                ....|....|....|....|....|....|....|....|....|....|....|....|....|....|
PPI-BnFTB       GEPGSEAHGGYTYCGLATMILINEVDRLNLDSLMNWVVHRQGVEMGFQGRTNKLVDGCYTFWQAAPCVLL
PPI-Soy-FTB     GEPGSEAHGGYTFCGLATMILIGEVNHLDLPRLVDWVVFRQGKECGFQGRTNKLVDGCYSFWQGGAVALL
PPI-Corn-FTB    GEPYAEAHGGYTFCGLAALILLNEAEKVDLPSLIGWVAFRQGVECGFQGRTNKLVDGCYSFWQGAAIAFT
Consensus       GEPGSEAHGGYTFCGLATMILINEV  LDLPSL  WVVFRQGVECGFQGRTNKLVDGCYSFWQGAA ALL

                        290       300       310       320       330       340       350
                ....|....|....|....|....|....|....|....|....|....|....|....|....|....|
PPI-BnFTB       QRFFSSQDMAPHGSSS--HMSQGTDEDHEEHGHDEDDPEDSDEDDSDEDSDEDSGNGHQVHHTSTYIDRR
PPI-Soy-FTB     QRLSSIINKQMEETSQIFAVSYVSEAKESLDGTSSHATCRGEHEGTSESSSSDFKN---IAYKFINEWRA
PPI-Corn-FTB    QKLITIVDKQLRSS-----YSCKRPSGEDACSTSSYG-CTANKS----SSAVDYAK---FGFDFIQQSNQ
Consensus       QRL SI DKQ   SS --  S      E  GTSS   C          ESS  D  N---     FI   R

                        360       370       380       390       400       410       420
                ....|....|....|....|....|....|....|....|....|....|....|....|....|....|
PPI-BnFTB       IQPVFDSLGLQRYVLLCSQVADGGFRDKLRKPRDFYHTCYCLSGLSVAQHAWSKDEDTPPLTRDILGGYA
PPI-Soy-FTB     QEPLFHSIALQQYILLCAQEQEGGLRDKPGKRRDHYHTCYCLSGLSLCQYSWSKHPDSPP----------
PPI-Corn-FTB    IGPLFHNIALQQYILLCSQVLEGGLRDKPGKNRDHYHSCYCLSGLAVSQYSAMTDTGSCPLPQHVLGPYS
Consensus       I PLFHSIALQQYILLCSQV EGGLRDKPGK RDHYHTCYCLSGLSV QYSWSKD DSPPL    LG Y

                        430       440
                ....|....|....|....|...
PPI-BnFTB       NHLEPVHLLHNILVDRYYEASRF (SEQ ID NO: 9)
PPI-Soy-FTB     ----------------------- (SEQ ID NO: 36)
PPI-Corn-FTB    NLLEPIH---------------- (SEQ ID NO: 39)
Consensus       N LEP H---------------- (SEQ ID NO: 88)
```

Also included in the invention is the farnesyl transferase alpha consensus sequence of SEQ ID NO:89 and the farnesyl transferase beta consensus sequence of SEQ ID NO:90. To generate the consensus sequence, the farnesyl transferase alpha and farnesyl transferase beta sequences of the invention were aligned using the program BioEdit. The homology between the farnesyl transferase alpha (FTA) nucleic acid sequences of the invention is shown graphically in the ClustalW analysis shown in Table 10G. The homology between the farnesyl transferase beta (FTB) nucleic acid sequences of the invention is shown graphically in the ClustalW analysis shown in Table 10H.

TABLE 10G

ClustalW Nucleic Acid Analysis of FT Alpha

```
                       10        20        30        40        50        60
              ....|....|....|....|....|....|....|....|....|....|....|....|
BnA-12        ------------------------------------------------------------   1
At-FT-A       -------------GAGTCGGGCAACATGAATTTCGACGAGACCGTGCCACTGAGCCAACG  47
PPI-Soy-FTA   ATGGAATCTGGGTCTAGCGAAGGAGAAGAGGTGCAGCAACGC-GTGCCGTTGAGGGAGAG  59
Consensus     -------------    CG  G A A GA  T C  C A  C-GTGCC  TGAG  A  G  23

                       70        80        90       100       110       120
              ....|....|....|....|....|....|....|....|....|....|....|....|
BnA-12        ------------------------------------------------------------   1
At-FT-A       ATTGGAGTGGTCAGACGTGGTCCCATTGACTCAGGACGATGGTCCGAATCCAGTGGTGCC 107
PPI-Soy-FTA   AGTGGAGTGGTCAGATGTTACTCCGGTTCCTCAAAACGACGGCCCTAACCCTGTCGTTCC 119
Consensus     A TGGAGTGGTCAGA GT    CC  T  CTCA  ACGA GG CC AA CC GT GT CC  64

                      130       140       150       160       170       180
              ....|....|....|....|....|....|....|....|....|....|....|....|
BnA-12        -------------------------------ATGGATTACTTCCGTGCGATTTACTTCTC  29
At-FT-A       AATTGCCTACAAGGAAGAGTTCCGCGAGACTATGGATTACTTCCGTGCGATTTACTTTTC 167
PPI-Soy-FTA   GATCCAGTACACTGAAGAGTTTTCCGAAGTTATGGATTACTTTCGCGCCGTTTACCTCAC 179
Consensus      AT     TACA  GAAGAGTT   CGA   TATGGATTACTTCCGTGCGATTTACTTCTC 111
```

TABLE 10G-continued

ClustalW Nucleic Acid Analysis of FT Alpha

```
                  190       200       210       220       230       240
              ....|....|....|....|....|....|....|....|....|....|....|....|

BnA-12        CGACGAGCGTTCTGCTCGCGCGCTGCGACTCACGGAAGAAGCTCTCCGCTTAAACTCGGG   89
At-FT-A       CGACGAGCGATCTCCTCGCGCACTACGACTCACGGAAGAAACCCTCCTCTTAAACTCCGG  227
PPI-Soy-FTA   CGATGAACGCTCCCCTCGCGCCCTCGCTCTCACAGCCGAAGCCGTTCAATTCAACTCCGG  239
Consensus     CGACGAGCG TCTCCTCGCGC CT CGACTCACGGAAGAAGCCCTCC CTTAAACTCCGG  167

                  250       260       270       280       290       300
              ....|....|....|....|....|....|....|....|....|....|....|....|

BnA-12        CAACTACACCGTGTGGCACTTCGGGCGCTTAGTACTCGAGGAGCTTAATAACGACTTGTA  149
At-FT-A       CAACTACACAGTGTGGCATTTCAGGCGCCTAGTACTCGAGGCCCTTAATCACGACTTGTT  287
PPI-Soy-FTA   CAACTACACTGTGTGGCATTTCCGACGGTTGTTACTTGAGTCGCTAAAAGTCGACTTGAA  299
Consensus     CAACTACAC GTGTGGCATTTC GGCGCTTAGTACTCGAGGCGCTTAAT ACGACTTGTA  224

                  310       320       330       340       350       360
              ....|....|....|....|....|....|....|....|....|....|....|....|

BnA-12        TGAAGAGCTCAAGTTCATCGAAAGCATTGCTGAGGATAACTCTAAGAACTACCAGTTGTG  209
At-FT-A       TGAAGAACTCGAGTTCATCGAACGCATTGCTGAGGATAACTCTAAGAACTACCAACTGTG  347
PPI-Soy-FTA   CGATGAACTGGAGTTTGTGGAGCGTATGGCCGCTGGAAATTCTAAAAATTATCAGATGTG  359
Consensus     TGAAGAACTCGAGTTCATCGAACGCATTGCTGAGGATAACTCTAAGAACTACCAG TGTG  283

                  370       380       390       400       410       420
              ....|....|....|....|....|....|....|....|....|....|....|....|

BnA-12        G------------CATCATCGACGATGGGTCGCAGAGAAACTGGGTCCTGATGTTGCAGG  257
At-FT-A       G------------CATCATCGGCGATGGGTTGCAGAGAAACTGGGTCCTGATGTTGCAGG  395
PPI-Soy-FTA   NATGTTCTGTAGGCATCCTAGACGATGGGTTGCCGAGAAGTTAGGTCCTGAAGCTAGAAA  419
Consensus     G------------CATCATCGACGATGGGTTGCAGAGAAACTGGGTCCTGATGTTGCAGG  331

                  430       440       450       460       470       480
              ....|....|....|....|....|....|....|....|....|....|....|....|

BnA-12        AAAGGAACTTGAGTTTACTCGGAGGGTACTATCACTTGATGCCAAGCATTATCATGCTTG  317
At-FT-A       GAGAGAACTTGAATTTACCCGTAGAGTACTTTCACTTGATGCCAAACATTATCATGCTTG  455
PPI-Soy-FTA   CAATGAGCTCGAGTTCACCAAAAAGATACTGTCCGTTGATGCCAAACATTATCATGCATG  479
Consensus      AA GAACTTGAGTTTACCCG AGGGTACT TCACTTGATGCCAAACATTATCATGCTTG  387

                  490       500       510       520       530       540
              ....|....|....|....|....|....|....|....|....|....|....|....|

BnA-12        GTCACATAGGCAGTGGGCGCTACAAGCATTAGGAGGATGGAAAATGAGCTTAACTACTG  377
At-FT-A       GTCACATAGGCAGTGGACACTACGGGCATTAGGAGGATGGAAGATGAGCTCGATTACTG  515
PPI-Soy-FTA   GTCTCATAGACAGTGGGCTCTTCAAACACTAGGAGGATGGAAGATGAACTTAATTATTG  539
Consensus     GTCACATAGGCAGTGGGC CTACAAGCATTAGGAGGATGGAAGATGAGCTTAATTACTG  446

                  550       560       570       580       590       600
              ....|....|....|....|....|....|....|....|....|....|....|....|

BnA-12        CCACGAGCTCCTTGAAGCTGACGTCTTTAACAACTCTGCATGGAATCAGAGGTATTACGT  437
At-FT-A       TCACGAGCTCCTTGAAGCTGACGTCTTTAACAATTCCGCCTGGAATCAGAGGTATTATGT  575
PPI-Soy-FTA   CACAGAACTACTTAAAGAAGACATTTTTAACAATTCTGCTTGGAATCAGAGATATTTTGT  599
Consensus     CCACGAGCTCCTTGAAGCTGACGTCTTTAACAATTCTGC TGGAATCAGAGGTATTATGT  505

                  610       620       630       640       650       660
              ....|....|....|....|....|....|....|....|....|....|....|....|

BnA-12        TATAACTAGATCACCTTCGTTGGGAGGCCTAGAAGCCATGAGAGAATCTGAAGTAAGCTA  497
At-FT-A       CATCACCCAATCTCCTTTGTTGGGAGGCCTAGAAGCCATGAGAGAATCTGAAGTAAGCTA  635
PPI-Soy-FTA   CATAACAAGGTCTCCTTTCTTGGGGGGCCTAAAAGCTATGAGAGAGTCTGAAGTGCTTTA  659
Consensus     CATAAC AGATCTCCTTTGTTGGGAGGCCTAGAAGCCATGAGAGAATCTGAAGTAAGCTA  564

                  670       680       690       700       710       720
              ....|....|....|....|....|....|....|....|....|....|....|....|

BnA-12        CACAGTCAAAGCCATTTTAGCAAATCCCGGGAACGAGAGCTCTTGGAGGTACCTGAAAGC  557
At-FT-A       CACAATCAAAGCCATTTTAACCAATCCTGCAAACGAGAGCTCATGGCGATACCTAAAAGC  695
PPI-Soy-FTA   CACCATCGAAGCCATTATAGCCTACCCTGAAAATGAAAGCTCGTGGAGATATCTACGAGG  719
Consensus     CACAATCAAAGCCATTTTAGCCAATCCTG AAACGAGAGCTC TGGAGATACCTAAAAGC  622

                  730       740       750       760       770       780
              ....|....|....|....|....|....|....|....|....|....|....|....|

BnA-12        CCTTTACAAAGACGACACAGAGTCTTGGATTAGTGATCCAAGTGTTTCCTCAGTCTGTTT  617
At-FT-A       GCTTTACAAAGACGACAAAGAATCCTGGATTAGTGATCCAAGTGTTTCCTCAGTCTGTTT  755
PPI-Soy-FTA   ACTTTATAAAGGTGAAACTACTTCATGGGTAAATGATCCTCAAGTTTCTTCAGTATGCTT  779
Consensus      CTTTACAAAGACGACACAGA TC TGGATTAGTGATCCAAGTGTTTCCTCAGTCTGTTT  679

                  790       800       810       820       830       840
              ....|....|....|....|....|....|....|....|....|....|....|....|

BnA-12        GAAAGTTCTCTCACGCGCGGACTGCTTCCATGGATTCGCTCTGAGCACCCTTTTGGATCT  677
At-FT-A       GAATGTTCTATCCCGCACAGATTGCTTCCATGGATTCGCTCTGAGCACCCTTTTGGATCT  815
PPI-Soy-FTA   AAAGATTTTGA---GAACTAAGAGCAACTACGTGTTTGCTCTTAGCACTATTTTAGATCT  836
Consensus     GAA GTTCT TC CGCAC GA TGCTTCCATGGATTCGCTCTGAGCACCCTTTTGGATCT  734
```

TABLE 10G-continued

ClustalW Nucleic Acid Analysis of FT Alpha

```
                    850       860       870       880       890       900
            ....|....|....|....|....|....|....|....|....|....|....|....|
BnA-12      TCTGTGCGATGGGTTGAGACCAACCAACGAGCATAGAGACTCGGTGAAAGCTCTAGCTAA  737
At-FT-A     TCTATGTGATGGACTGAGACCAACCAACGAGCATAAAGACTCAGTGAGAGCTCTAGCTAA  875
PPI-Soy-FTA TATATGCTTTGGTTATCAACCAAATGAAGACATTAGAGATGCCATTGACGCCTTAAAGAC  896
Consensus   TCTATGCGATGG TTGAGACCAACCAACGAGCATAGAGACTC GTGAAAGCTCTAGCTAA  792

                    910       920       930       940       950       960
            ....|....|....|....|....|....|....|....|....|....|....|....|
BnA-12      TGAAGAACCAGAGACTAACTTGGCCAATTTGGTGTGTACCATTCTGTGTCGTGTTGATCC  797
At-FT-A     TGAAGAACCAGAGACTAACTTGGCCAATTTGGTGTGTACTATTCTTGGTCGTGTAGATCC  935
PPI-Soy-FTA CGCAGA--TATGGATAAACAAGATTTAGATGATGATGAGAAAGGGGAACAACAAAATTTA  954
Consensus   TGAAGAACCAGAGACTAACTTGGCCAATTTGGTGTGTAC ATTCTG GTCGTGTAGATCC  850

                    970       980       990      1000      1010      1020
            ....|....|....|....|....|....|....|....|....|....|....|....|
BnA-12      AATA-AGAGCTAACTATTGGGC--ATGG--------------------------------  822
At-FT-A     TATA-AGAGCTAACTATTGGGC--ATGGAGGAACAGCAAGATTACAGTGGCAGCAATTTG  992
PPI-Soy-FTA AATATAGCACGAAATATTTGTTCTATCCTAAAACAAGTTGATCCAATTAGAACCAACTAT 1014
Consensus   AATA-AGAGCTAACTATTGGGC--ATGG   AA A    GAT    A T G A CAA T     889

                   1030      1040      1050      1060      1070      1080
            ....|....|....|....|....|....|....|....|....|....|....|....|
BnA-12      ------------------------------------------------------------  822
At-FT-A     AATATGTGACGCCCCAAAATCACACTTGAAAAAGACTTGATTATTAGTTTTTACGTAATT 1052
PPI-Soy-FTA TGGATTTGGCGCAAGAGCAGACTTCCT--------------------------------- 1041
Consensus      AT TG CGC   A  A     C T---------------------------------  900

                   1090      1100      1110      1120      1130      1140
            ....|....|....|....|....|....|....|....|....|....|....|....|
BnA-12      ------------------------------------------------------------  822
At-FT-A     AACTGCTTATTTATGAATCACATGTTCATGTTAACATGTATCAAAACAATCTTGATTTCT 1112
PPI-Soy-FTA ------------------------------------------------------------ 1041
Consensus   ------------------------------------------------------------  900

                   1150      1160      1170
            ....|....|....|....|....|....|.
BnA-12      -------------------------------  822 (SEQ ID NO: 6)
At-FT-A     CAAAAAAAAAAAAAAAAAAAAAAAAAAAAAA 1143 (SEQ ID NO: 1)
PPI-Soy-FTA ------------------------------- 1041 (SEQ ID NO: 31)
Consensus   -------------------------------  900 (SEQ ID NO: 89)
```

TABLE 10H

ClustalW Nucleic Acid Analysis of FT Beta

```
                      10        20        30        40        50        60
              ....|....|....|....|....|....|....|....|....|....|....|....|
PPI-BnFTb     ------------------------------------------------------------    1
era1          ------------------------------------------------------------    1
PPI-Soy-FTB   ------------------------------------------------------------    1
PPI-Corn-FTB  GGCGGATCCCGACCTACCGAGGCTCACGGTGACGCAGGTGGAGCAGATGAAGGTGGAGGC   60
Consensus     ------------------------------------------------------------    1

                      70        80        90       100       110       120
              ....|....|....|....|....|....|....|....|....|....|....|....|
PPI-BnFTb     ------------------------------------------------------------    1
era1          ------------------------------------------------------------    1
PPI-Soy-FTB   ----------------------------GCCACCATTCCTCGCAACGCCCAAACCCTCAT   32
PPI-Corn-FTB  CAGGGTTGGCGACATCTACCGCTCCCTCTTCGGGGCCGCGCCCAACACGAAATCCATCAT  120
Consensus     ----------------------------                                    1
```

TABLE 10H-continued

ClustalW Nucleic Acid Analysis of FT Beta

```
                        130       140       150       160       170       180
                ....|....|....|....|....|....|....|....|....|....|....|....|
PPI-BnFTb       ------------------------------------------------------------    1
eral            -ATGGAGATTCAGCGAGATAAGCAATTGGATTATCTGATGAAAGGCTTAAGGCAGCTTGG   59
PPI-Soy-FTB     GTTGGAGCTTCAACGCGATAATCACATGCAGTATGTCTCCAAAGGCCTTCGCCATCTCAG   92
PPI-Corn-FTB    GCTAGAGCTGTGGCGTGATCAGCATATCGAGTATCTGACGCCTGGCTGAGGCATATGGG   180
Consensus         T GAG T    CG GAT A CA  T  A TAT T       GG  T  G CA   T G   27

                        190       200       210       220       230       240
                ....|....|....|....|....|....|....|....|....|....|....|....|
PPI-BnFTb       ----------------------------------TGGCTTTGTTACTGGATTCTTCATTC   26
eral            TCCGCAGTTTTCTTCCTTAGATGCTAATCGACCTTGGCTTTGTTACTGGATTCTTCATTC  119
PPI-Soy-FTB     TTCCGCATTTTCCGTTTTGGACGCTAATCGACCCTGGCTCTGCTACTGGATCTTCCACTC  152
PPI-Corn-FTB    ACCAGCCTTTCATGTTCTAGATGCCAATCGCCCTTGGCTATGCTACTGGATGGTTCATCC  240
Consensus         C    TTT       T GA GC AATCG CC TGGCT TG TACTGGAT  TTCATTC   65

                        250       260       270       280       290       300
                ....|....|....|....|....|....|....|....|....|....|....|....|
PPI-BnFTb       AATTGCTTTGCTTGGGGAGTCTGTGGATGATGACTTAGAAAACAATGCAATCGATTTTCT   86
eral            AATAGCTTTGCTTGGGGAGACTGTGGATGATGAATTAGAAAGCAATGCCATTGACTTCCT  179
PPI-Soy-FTB     CATTGCTTTGTTGGGAGAATCCGTCGATGATGAACTCGAAGATAACGCTATCGATTTTCT  212
PPI-Corn-FTB    ACTTGCTTTGCTGGATGAAGCACTTGATGATGATCTTGAGAATGATATCATAGACTTCTT  300
Consensus       AATTGCTTTGCT GG GA  C GT GATGATGA  T GAAAA AATGC AT GA TT CT  111

                        310       320       330       340       350       360
                ....|....|....|....|....|....|....|....|....|....|....|....|
PPI-BnFTb       TGGACGTTGCCAGGGTTCTGATGGTGGATATGGTGGTGGTCCTGGCCAACTTCCACATCT  146
eral            TGGACGCTGCCAGGGCTCTGAAGGTGGATACGGTGGTGGTCCTGGCCAACTTCCACATCT  239
PPI-Soy-FTB     TAACCGTTGCCAGGATCCGAATGGTGGATATGCCGGGGGACCAGGCCAGATGCCTCATAT  272
PPI-Corn-FTB    AGCTCGATGTCAGGATAAAGATGGTGGATATAGTGGTGGACCTGGACAGTTGCCTCACCT  360
Consensus       TG  CG TGCCAGG T C GATGGTGGATATGGTGGTGG CCTGGCCA  T CC CATCT  160

                        370       380       390       400       410       420
                ....|....|....|....|....|....|....|....|....|....|....|....|
PPI-BnFTb       TGGAACAAGTTATGCTGCAGTGAATACACTTGTTACTTTAGGAGGTGAGAAAGCCTTCTC  206
eral            TGCAACTACTTATGCTGCAGTGAATGCACTTGTTACTTTAGGAGGTGACAAAGCCCTTTC  299
PPI-Soy-FTB     TGCCACAACTTATGCTGCTGTTAATTCACTTATTACTTTGGGTGGTGAGAAATCCCTGGC  332
PPI-Corn-FTB    AGCTACGACTTATGCTGCTGTAAATACACTTGTGACAATAGGGAGCGAAAGAGCATTGTC  420
Consensus       TGC AC ACTTATGCTGC GT AAT CACTTGTTACTTTAGG GGTGA AAAGCC T TC  211

                        430       440       450       460       470       480
                ....|....|....|....|....|....|....|....|....|....|....|....|
PPI-BnFTb       TTCAATTAACAGAGAACAAATGGCTTGTTTCTTAAGACCAATGAAGGATACAAATGGAGG  266
eral            TTCAATTAATAGAGAAAAAATGTCTTGTTTTTTAAGACGGATGAAGGATACAAGTGGAGG  359
PPI-Soy-FTB     ATCAATTAATAGAGATAAACTGTATGGGTTTCTGCGGCGGATGAAGCAACCAAATGGTGG  392
PPI-Corn-FTB    ATCAATCAATAGGGGCAACCTGTACAATTTTATGCTGCAGATGAAAGATGTATCAGGTGC  480
Consensus        TCAATTAATAGAGA AAA TGT T GTTTT T  G CGGATGAAGGAT CAA TGG GG  259

                        490       500       510       520       530       540
                ....|....|....|....|....|....|....|....|....|....|....|....|
PPI-BnFTb       TTTCAGGATGCATAATATGGGAGAAATAGATGTGCGAGGGTGCTACACTGCGATTTTGAT  326
eral            TTTCAGGATGCATGATATGGCAGAAATTGATGTTCGTGGATGCTACACTGCAATTTCGGT  419
PPI-Soy-FTB     ATTCAGGATGCATGATGAAGGTGAAATTGATGTTCGAGCTTGCTACACTGCCATTTCTGT  452
PPI-Corn-FTB    TTTCAGAATGCATGATGGTGGCGAAATTGATGTCCGTGCTTCCTACACCGCTATATCGGT  540
Consensus       TTTCAGGATGCATGAT   GG GAAATTGATGT CG GC TGCTACACTGC ATTTCGGT  311

                        550       560       570       580       590       600
                ....|....|....|....|....|....|....|....|....|....|....|....|
PPI-BnFTb       TGCAAGCATCCTGAACATTGTGGATGATGAACTCACCCGCGGCTTAGGAGATTACATTTT  386
eral            TGCAAGCATCCTAAATATTATGGATGATGAACTCACCCAGGGCCTAGGAGATTACATCTT  479
PPI-Soy-FTB     TGCAAGTGTTTTGAACATTTTGGATGATGAGCTGATCCAGAATGTTGGAGACTACATTAT  512
PPI-Corn-FTB    TGCCAGCCTTGTGAATATTCTTGATTTTAAACTGGCAAAAGGTGTAGGCGACTACATAGC  600
Consensus       TGCAAGC T  TGAA ATT TGGATGATGAACT ACCCA GG  TAGGAGA TACAT  T  359

                        610       620       630       640       650       660
                ....|....|....|....|....|....|....|....|....|....|....|....|
PPI-BnFTb       GAGTTGCCAAACTTATGAAGGTGGCATTGGAGGGGAACCTGGCTCCGAAGCTCATGGTGG  446
eral            GAGTTGCCAAACTTATGAAGGTGGCATTGGAGGGGAACCTGGCTCCGAAGCTCACGGTGG  539
PPI-Soy-FTB     AAGCTGTCAAACATATGAGGGTGGCATTGCTGGTGAGCCTGGTTCTGAGGCTCATGGTGG  572
PPI-Corn-FTB    AAGATGTCAAACTTATGAAGGTGGTATTGCTGGGGAGCCTTATGCTGAAGCACATGGTGG  660
Consensus        AG TG CAAACTTATGAAGGTGGCATTG  GGGGA CCTGG TC GAAGCTCATGGTGG  411
```

TABLE 10H-continued

ClustalW Nucleic Acid Analysis of FT Beta

```
                       670       680       690       700       710       720
               ....|....|....|....|....|....|....|....|....|....|....|....|
PPI-BnFTb      GTACACGTACTGTGGCTTGGCTACTATGATTTTAATCAATGAAGTCGACCGCTTGAATTT  506
eral           GTATACCTACTGTGGTTTGGCTGCTATGATTTTAATCAATGAGGTCGACCGTTTGAATTT  599
PPI-Soy-FTB    GTACACCTTTTGTGGATTAGCTACAATGATTCTGATTGGTGAGGTTAATCACTTGGATCT  632
PPI-Corn-FTB   GTATACATTCTGTGGATTGGCTGCTTTGATCCTGCTTAATGAGGCAGAGAAAGTTGACTT  720
Consensus      GTA AC T CTGTGG TTGGCT CTATGATT T AT AATGAGGT GA C  TTG ATTT  458

                       730       740       750       760       770       780
               ....|....|....|....|....|....|....|....|....|....|....|....|
PPI-BnFTb      GGATTCGTTAATGAATTGGGTTGTACATCGACAAGGAGTAGAAATGGGATTCCAAGGTAG  566
eral           GGATTCATTAATGAATTGGGCTGTACATCGACAAGGAGTAGAAATGGGATTTCAAGGTAG  659
PPI-Soy-FTB    GCCTCGATTAGTTGACTGGGTGGTATTCCGACAAGGTAAGGAATGTGGATTCCAGGGGAG  692
PPI-Corn-FTB   GCCTAGTTTGATTGGCTGGGTGGCTTTTCGTCAAGGAGTGGAATGCGGATTTCAAGGACG  780
Consensus      G  T    TTAAT  A TGGGT GTA  TCGACAAGGAGT GAA  GGATT CAAGG AG  501

                       790       800       810       820       830       840
               ....|....|....|....|....|....|....|....|....|....|....|....|
PPI-BnFTb      GACGAACAAATTGGTCGACGGTTGCTACACGTTTTGGCAGGCAGCCCCCTGTGTTCTACT  626
eral           GACGAACAAATTGGTCGATGGTTGCTACACATTTTGGCAGGCAGCCCCTTGTGTTCTACT  719
PPI-Soy-FTB    AACAAATAAACTGGTGGATGGATGCTATTCCTTTTGGCAGGGAGGTGCTGTTGCTCTATT  752
PPI-Corn-FTB   AACTAATAAATTGGTTGATGGTTGCTACTCCTTTTGGCAGGGAGCTGCCATTGCTTTCAC  840
Consensus       AC AA AAATTGGT GATGGTTGCTAC C TTTTGGCAGG AGC  C   TG TCTA T  547

                       850       860       870       880       890       900
               ....|....|....|....|....|....|....|....|....|....|....|....|
PPI-BnFTb      ACAGCGATTTTTTTCATCCCAGGAT-ATGGCACCTCATGGATCATCATCACATATGTCAC  685
eral           ACAAAGATTATATTCAACCAATGATCATGACGT-TCATGGATCATCA---CATATATCAG  775
PPI-Soy-FTB    GCAAAGATTATCTTCTATTATCAAC-AAACAGATGGAAGAGACATCA-C-----AGATTT  805
PPI-Corn-FTB   ACAAAAGTTAATTACCATTGTTGAT-AAGCAA----------------------------  871
Consensus      ACAAAGATTAT TTC A     GAT-A G      A G   CATCA- -              574

                       910       920       930       940       950       960
               ....|....|....|....|....|....|....|....|....|....|....|....|
PPI-BnFTb      AAGCGACAGATGAAGATCACGAGGAACATGGTCATGATGAAGATGATCCTGAAGACAGTG  745
eral           AAGCGACAAATGAAGAACAT------CATGCTCATGATGAAGATGACCTTGAAGACAGTG  829
PPI-Soy-FTB    TTGCGGTATCTTATGTATCTGAAGCAAAAGAAAGTTGGATGGAACCTCTAGTCATGCAA  865
PPI-Corn-FTB   TTGAGGT-CCTCGTATTCCTG---CAAAACGCCATCAGGAGAGGATGCCTG--CA-GCAC  924
Consensus        G G  A T A G  C TG    A A G  CAT A GA G     CCTG   A        598

                       970       980       990      1000      1010      1020
               ....|....|....|....|....|....|....|....|....|....|....|....|
PPI-BnFTb      ATCAAGATGAT---TCTGATCAGGATAGCGATGAAGATTCAGGCAATGGTCACCAAGTTC  802
eral           ATCATGATCATGATTCTGATGAGGACAACGATGAAGATTCAGTCAATGGTCACAGAATCC  889
PPI-Soy-FTB    CATGCCGTGCTGAGCATGAAGCACCAGTGAATCCAGTTCATCTGATTTAAAAATATTG  925
PPI-Corn-FTB   CAGTTCATA-TGGGTGCACCGCGAATAAGTCTTCCTCTGCTGTGGACTATGCGAAGTTTG  983
Consensus        G    ATG TG   T TGA G G A A  GAT      TTCAG G AT  T A AA  TT  629

                      1030      1040      1050      1060      1070      1080
               ....|....|....|....|....|....|....|....|....|....|....|....|
PPI-BnFTb      ATCATACGTCTACCTACATTGACAGGAGAATTCAACCTGTTTTTGATAGGCTCGGCTTGC  862
eral           ATCATACATCCACCTACATTAACAGGAGAATGCAACTGGTTTTTGATAGGCTCGGCTTGC  949
PPI-Soy-FTB    CCTATAAATTTATTAATGAGTGGAGAGCACAAGAACCACTTTTTCACAGTATTGCTTTAC  985
PPI-Corn-FTB   GATTTGATTTTATACAACAGAGCAACCAAATTGGCCACTCTTCCATAACATTGCGCTGC 1043
Consensus         ATA  T TA  A      CAG    AAT  AACC  TTTTT ATAGC T G CTTGC  663

                      1090      1100      1110      1120      1130      1140
               ....|....|....|....|....|....|....|....|....|....|....|....|
PPI-BnFTb      AAAGATATGTGCTCTTGTGCTCTCAGGTTGCTGATGGTGGATTCAGAGACAAGCTGAGGA  922
eral           AGAGATATGTACTCTTGTGCTCTAAGATCCCTGACGGTGGATTCAGAGACAAGCCGAGGA 1009
PPI-Soy-FTB    AGCAATATATTCTCTTATGTCACAGGAGCAAGAGGGTGGACTGAGAGACAAACCGGGTA 1045
PPI-Corn-FTB   AACAATACATCCTACTTTGTTCTCAGGTACTAGAGGGAGGCTTGAGGGATAAGCCTGGAA 1103
Consensus      A   ATAT T CTCTT TG TCTCAGGT C  GA GGTGGATT AGAGACAAGCCG G A  709

                      1150      1160      1170      1180      1190      1200
               ....|....|....|....|....|....|....|....|....|....|....|....|
PPI-BnFTb      AACCCGCGTGACTTCTACCACACATGTTACTGCCTAAGCGGTCTTTCCGTGGCTCAACACG  982
eral           AACCCGCGTGACTTCTACCACACATGTTACTGCCTGAGCGGCTTGTCTGTGGCTCAGCACG 1069
PPI-Soy-FTB    AACGTAGAGATCATTATCACACATGTTACTGTTTAAGTGGACTCTCATTGTGCCAGTATA 1105
PPI-Corn-FTB   AGAACAGAGATCACTATCATTCATGCTACTGCCTCAGTGGCCTCGCAGTTAGCCAGTACA 1163
Consensus      AAC C G GA    CTA CACACATGTTACTGCCT AG GG CT TC GTG   CAG AC   752
```

TABLE 10H-continued

ClustalW Nucleic Acid Analysis of FT Beta

```
                        1210      1220      1230      1240      1250      1260
               ....|....|....|....|....|....|....|....|....|....|....|....|
PPI-BnFTb      CTTGGTCAAAAGACGAGGACACTCCTCCTTTGACTCGTGACATTTTGGGTGGCTACGCAA 1042
era1           CTTGGTTAAAAGACGAGGACACTCCTCCTTTGACTCGCGACATTATGGGTGGCTACTCGA 1129
PPI-Soy-FTB    GTTGGTCAAAGCACCCAGATTCTCCACCAC------------------------------ 1135
PPI-Corn-FTB   GTGCCATGACTGATACTGGTTCGTGCCCATTACCTCAGCATGTGCTTGGACCGTACTCTA 1223
Consensus       TTGGT AAA GAC   GA  CTCC CC TT  CTC   A  T  T GG    TAC C A  786

                        1270      1280      1290      1300      1310      1320
               ....|....|....|....|....|....|....|....|....|....|....|....|
PPI-BnFTb      ACCACCTTGAACCTGTTCACCTCCTCCACAACATTGTCTTGGATCGGTATTATGAAGCTT 1102
era1           ATCTCCTTGAACCTGTTCAACTTCTTCACAACATTGTCATGGATCAGTATAATGAAGCTA 1189
PPI-Soy-FTB    ------------------------------------------------------------ 1135
PPI-Corn-FTB   ATTTGCTGGAGCCAATCCATCC-------------------------------------- 1245
Consensus      A    CT GA CC  T CA C                                         797

                        1330      1340      1350      1360      1370      1380
               ....|....|....|....|....|....|....|....|....|....|....|....|
PPI-BnFTb      CTAGATTT---------------------------------------------------- 1110
era1           TCGAGTTCTTCTTTAAAGCAGCATGACCCGTTGTTGCTAATGTATGGGAAACCCCAAACA 1249
PPI-Soy-FTB    ------------------------------------------------------------ 1135
PPI-Corn-FTB   ------------------------------------------------------------ 1245
Consensus              ----------------------------------------------------  797
                        1390      1400      1410      1420
               ....|....|....|....|....|....|....|....|.
PPI-BnFTb      ----------------------------------------- 1110 (SEQ ID NO: 8)
era1           TAAGAGTTTCCGTAGTGTTGTAACTTGTAAGATTTCAAAAG 1249 (SEQ ID NO: 73)
PPI-Soy-FTB    ----------------------------------------- 1135 (SEQ ID NO: 34)
PPI-Corn-FTB   ----------------------------------------- 1245 (SEQ ID NO: 37)
Consensus      -----------------------------------------  797 (SEQ ID NO: 90)
```

Example 5

Vector Constructs for Transformation

The FTA or FTB sequences have be used to produce constructs suitable for transformation into plants and under the control of appropriate regulatory sequences. The gene sequences were in either the sense orientation for over-expression or the antisense orientation for down-regulation. Portions of these sequences have been used to construct a double-stranded-RNA-inhibition (dsRNAi) construct. A sequence of preferably not less than 21 nt was cloned as an inverse repeat separated by a linker that when expressed results in down-regulation of the target gene. Double antisense (DA) vectors have been created in which a direct repeat of an antisense sequence is separated by a spacer sequence such as GUS. Promoters have been used for constitutive expression such as the 35S CaMV promoter, the MuA *Zea maize* promoter or inducible by specific environmental or cellular cues such as the ABA levels or drought conditions which induce expression of the RD29A promoter. Alternatively, tissue or organelle specific promoters such as the HIC or CUT1 promoter can be used. Such constructs have been transformed into *Arabidopsis thaliana, Brassica, Zea maize, Glycine max*. Other species can be transformed as desired. Each species to be transformed may make use of specific regulatory sequences as appropriate for those particular species. Transformed plants have be selected and their phenotypic properties analyzed. The transgenic plants were assessed for characteristics such as increased tolerance to drought, altered biomass accumulation, yield, nutritional requirements such as minerals or micro-nutrients, biotic stress such as fungal, bacterial, or other such pathogen infection or attack or any other such physical or biochemical characteristic.

Example 6

Plant Transformation

*Arabidopsis thaliana* transgenic plants were made by flower dipping method into an *Agrobacterium* culture. Wild type plants were grown under standard conditions until they began flowering. The plant was inverted for 2 min into a solution of *Agrobacterium* culture. Plants were then bagged for two days to maintain humidity and then uncovered to continue growth and seed development. Mature seed was bulk harvested.

Transformed T1 plants were selected by germination and growth on MS plates containing 50 μg/ml kanamycin. Green, kanamycin resistant seedlings were identified after 2 weeks growth and transplanted to soil. Plants were bagged to ensure self fertilization and the T2 seed of each plant harvested separately. During growth of T1 plants leaf samples were harvested, DNA extracted and Southern analysis performed.

T2 seeds were analyzed for $Kan^R$ segregation. From those lines that showed a 3:1 resistant phenotype surviving T2 plants were grown, bagged during seed set, and T3 seed harvested from each line. T3 seed was again used for $Kan^R$ segregation analysis and those lines showing 100% $Kan^R$ phenotype were selected as homozygous lines. Further analysis was done using T3 seed.

Transgenic *Brassica napus* plants were produced using *Agrobacterium* mediated transformation of cotyledon petiole tissue. Seeds were sterilized as follows. Seeds were wetted with 95% ethanol for a short period of time such as 15 seconds. Approximately 30 ml of sterilizing solution I was added (70% Javex, 100 μl Tween20) and left for approximately 15 minutes. Solution I was removed and replaced with 30 ml of solution II (0.25% mercuric chloride, 100 μl Tween20) and incubated for about 10 minutes. Seeds were rinsed with at least 500 ml double distilled sterile water and stored in a sterile dish. Seeds were germinated on plates of ½ MS medium, pH 5.8, supplemented with 1% sucrose and 0.7% agar. Fully expanded cotyledons were harvested and placed on Medium I (Murashige minimal organics (MMO), 3% sucrose, 4.5 mg/L benzyl adenine (BA), 0.7% phytoagar, pH5.8). An *Agrobacterium* culture containing the nucleic acid construct of interest was grown for 2 days in AB Minimal media. The cotyledon explants were dipped such that only the cut portion of the petiole is contacted by the *Agrobacterium* solution. The explants were then embedded in Medium I and maintained for 5 days at 24° C., with 16, 8 hr light dark cycles. Explants were transferred to Medium II (Medium 1,300 mg/L timentin,) for a further 7 days and then to Medium III (Medium II, 20 mg/L kanamycin). Any root or shoot tissue which had developed at this time was dissected away. Transfer explants to fresh plates of Medium III after 14-21 days. When regenerated shoot tissue developed the regenerated tissue was transferred to Medium IV (MMO, 3% sucrose, 1.0% phytoagar, 300 mg/L timentin, 20 mg/L 20 mg/L kanamycin). Once healthy shoot tissue developed shoot tissue dissected from any callus tissue was dipped in 10×IBA and transferred to Medium V (Murashige and Skooge (MS), 3% sucrose, 0.2 mg/L indole butyric acid (IBA), 0.7% agar, 300 mg/L timentin, 20 mg/L 20 mg/L kanamycin) for rooting. Healthy plantlets were transferred to soil.

Transgenic *Glycine max, Zea maize* and cotton can be produced using *Agrobacterium*-based methods which are known to one of skill in the art. Alternatively one can use a particle or non-particle biolistic bombardment transformation method. An example of non-particle biolistic transformation is given in U.S. Patent Application 20010026941. Viable plants are propagated and homozygous lines are generated. Plants are tested for the presence of drought tolerance, physiological and biochemical phenotypes as described elsewhere.

The following table identifies the constructs and the species which they have been transformed.

TABLE 11

| SEQ ID NO: | SEQ | Species Transformed | | | |
|---|---|---|---|---|---|
| SEQ ID NO: 4 | pBI121-35S-anti-AtFTA | *Arabidopsis thaliana* | | | |
| SEQ ID NO: 40 | pBI121-35S-AtFTA | *Arabidopsis thaliana* | *Brassica napus* | | |
| SEQ ID NO: 41 | pBI121-rd29A-anti-AtFTA | *Arabidopsis thaliana* | *Brassica napus* | | |
| SEQ ID NO: 42 | pBI121-35S-DA-AtFTA | *Arabidopsis thaliana* | *Brassica napus* | | |
| SEQ ID NO: 43 | pBI121-RD29A-DA-AtFTA | *Arabidopsis thaliana* | *Brassica napus* | | |
| SEQ ID NO: 44 | MuA-anti-GmFTA | | | | *Glycine max* |
| SEQ ID NO: 45 | RD29A-anti-GmFTA | | | | *Glycine max* |
| SEQ ID NO: 46 | MuA-HP-GmFTA-Nos-Term | | | | *Glycine max* |
| SEQ ID NO: 47 | RD29AP-HP-GmFTA-Nos-Term | | | | *Glycine max* |
| SEQ ID NO: 48 | pBI121-35S-Anti-AtFTB | *Arabidopsis thaliana* | *Brassica napus* | | |
| SEQ ID NO: 49 | pBI121-RD29AP-Anti-AtFTB | *Arabidopsis thaliana* | *Brassica napus* | | |
| SEQ ID NO: 50 | pBI121-35S-HP-AtFTB | *Arabidopsis thaliana* | *Brassica napus* | | |
| SEQ ID NO: 51 | pBI121-RD29AP-HP-AtFTB | *Arabidopsis thaliana* | *Brassica napus* | | |
| SEQ ID NO: 52 | pBI121-35S-AtFTB | *Arabidopsis thaliana* | | | |
| SEQ ID NO: 53 | MuA-anti-GmFTB-Nos-Term | | | | *Glycine max* |
| SEQ ID NO: 54 | RD29AP-anti-GmFTB-Nos-Term | | | | *Glycine max* |
| SEQ ID NO: 55 | MuA-HP-GmFTB-Nos-Term | | | | *Glycine max* |
| SEQ ID NO: 56 | RD29AP-HP-GmFTB-Nos-Term | | | | *Glycine max* |
| SEQ ID NO: 57 | MuA-anti-*Zea maize*FTB-Nos-Term | | | *Zea maize* | |
| SEQ ID NO: 58 | MuA-HP-*Zea maize*FTB-Nos-Term | | | *Zea maize* | |

Non-limiting examples of vector constructs suitable for plant transformation are given in SEQ ID NO: 4, 40-58.

SEQ ID NO: 4

*gtttacccgccaatatatcctgtc*aaacactgatagtttaaactgaaggc gggaaacgacaatctgatcatgagcggagaattaagggagtcacgttatg acccccgccgatgacgcgggacaagccgttttacgtttggaactgacaga accgcaacgttgaaggagccactcagccgcgggtttctggagtttaatga gctaagcacatacgtcagaaaccattattgcgcgttcaaaagtcgcctaa ggtcactatcagctagcaaatatttcttgtcaaaaatgctccactgacgt tccataaattcccctcggtatccaattagagtctcatattcactctcaat -continued ccaaataatctgcaccggatctggatcgtttcgcatgattgaacaagatg
gattgcacgcaggttctccggccgcttgggtggagaggctattcggctat
gactgggcacaacagacaatcggctgctctgatgccgccgtgttccggct
gtcagcgcaggggcgcccggttctttttgtcaagaccgacctgtccggtg
ccctgaatgaactgcaggacgaggcagcgcggctatcgtggctggccacg
acgggcgttccttgcgcagctgtgctcgacgttgtcactgaagcgggaag
ggactggctgctattgggcgaagtgccggggcaggatctcctgtcatctc
accttgctcctgccgagaaagtatccatcatggctgatgcaatgcggcgg
ctgcatacgcttgatccggctacctgcccattcgaccaccaagcgaaaca
tcgcatcgagcgagcacgtactcggatggaagccggtcttgtcgatcagg
atgatctggacgaagagcatcaggggctcgcgccagccgaactgttcgcc
aggctcaaggcgcgcatgcccgacggcgatgatctcgtcgtgacccatgg
cgatgcctgcttgccgaatatcatggtggaaaatggccgcttttctggat
tcatcgactgtggccggctgggtgtggcggaccgctatcaggacatagcg
ttggctacccgtgatattgctgaagagcttggcggcgaatgggctgaccg
cttcctcgtgctttacggtatcgccgctcccgattcgcagcgcatcgcct
tctatcgccttcttgacgagttcttctgagcgggactctggggttcgaaa
tgaccgaccaagcgacgcccaacctgccatcacgagatttcgattccacc
gccgccttctatgaaaggttgggcttcggaatcgttttccgggacgccgg
ctggatgatcctccagcgcggggatctcatgctggagttcttcgcccacg
ggatctctgcggaacaggcggtcgaaggtgccgatatcattacgacagca
acggccgacaagcacaacgccacgatcctgagcgacaatatgatcgggcc
cggcgtccacatcaacggcgtcggcggcgactgcccaggcaagaccgaga
tgcaccgcgatatcttgctgcgttcggatattttcgtggagttcccgcca
cagacccggatgatccccgatcgttcaaacatttggcaataaagtttctt
aagattgaatcctgttgccggtcttgcgatgattatcatataatttctgt
tgaattacgttaagcatgtaataattaacatgtaatgcatgacgttattt
atgagatgggtttttatgattagagtcccgcaattatacatttaatacgc
gatagaaaacaaaatatagcgcgcaaactaggataaattatcgcgcgcgg
tgtcatctatgttactagatcgggcctcctgtcaatgctggcggcggctc
tggtggtggttctggtggcggctctgagggtggtggctctgagggtggcg
gttctgagggtggcggctctgagggaggcggttccggtggtggctctggt
tccggtgattttgattatgaaaagatggcaaacgctaataagggggctat
gaccgaaaatgccgatgaaaacgcgctacagtctgacgctaaaggcaaac
ttgattctgtcgctactgattacggtgctgctatcgatggtttcattggt
gacgtttccggccttgctaatggtaatggtgctactggtgattttgctgg
ctctaattcccaaatggctcaagtcggtgacggtgataattcacctttaa
tgaataatttccgtcaatatttaccttccctccctcaatcggttgaatgt
cgcccttttgtctttggcccaatacgcaaaccgcctctccccgcgcgttg
gccgattcattaatgcagctggcacgacaggtttcccgactggaaagcgg -continued gcagtgagcgcaacgcaattaatgtgagttagctcactcattaggcaccc
caggctttacactttatgcttccggctcgtatgttgtgtggaattgtgag
cggataacaatttcacacaggaaacagctatgaccatgattacgccaagc
ttgcatgcctgcagcccacagatggttagagaggcttacgcagcaggtct
catcaagacgatctacccgagcaataatctccaggaaatcaaataccttc
ccaagaaggttaaagatgcagtcaaaagattcaggactaactgcatcaag
aacacagagaaagatatatttctcaagatcagaagtactattccagtatg
gacgattcaaggcttgcttcacaaaccaaggcaagtaatagagattggag
tctctaaaaaggtagttcccactgaatcaaaggccatggagtcaaagatt
caaatagaggacctaacagaactcgccgtaaagactggcgaacagttcat
acagagtctcttacgactcaatgacaagaagaaaatcttcgtcaacatgg
tggagcacgacacacttgtctactccaaaaatatcaaagatacagtctca
gaagaccaaagggcaattgagacttttcaacaaagggtaatatccggaaa
cctcctcggattccattgcccagctatctgtcactttattgtgaagatag
tggaaaaggaaggtggctcctacaaatgccatcattgcgataaaggaaag
gccatcgttgaagatgcctctgccgacagtggtcccaaagatggaccccc
acccacgaggagcatcgtggaaaaagaagacgttccaaccacgtcttcaa
agcaagtggattgatgtgatatctccactgacgtaagggatgacgcacaa
tcccactatccttcgcaagacccttcctctatataaggaagttcatttca
tttggagagaacacgggggactctagaggatcctcaaattgctgccactg
taatcttgctcttcctccatgcccaatagttagctcttataggatctaca
cgaccaagaatagtacacaccaaattggccaagttagtctctggttcttc
attagctagagctctcactgagtctttatgctcgttggttggtctcagtc
catcacatagaagatccaaaagggtgctcagagcgaatccatggaagcaa
tctgtgcgggatagaacattcaaacagactgaggaaacacttggatcact
aatccaggattctttgtcgtctttgtaaagcgcttttaggtatcgccatg
agctctcgtttgcaggattggttaaaatggctttgattgtgtagcttact
tcagattctctcatggcttctaggcctcccaacaaaggagattgggtgat
gacataatacctctgattccaggcggaattgttaaagacgtcagcttcaa
ggagctcgtgacagtaatcgagctcatcttcccatcctcctaatgcccgt
agtgtccactgcctatgtgaccaagcatgataatgtttggcatcaagtga
aagtactctacgggtaaattcaagttctctccctgcaacatcaggaccca
gtttctctgcaacccatcgccgatgatgccacagttggtagttcttagag
ttatcctcagcaatgcgttcgatgaactcgagttcttcaaacaagtcgtg
attaagggcctcgagtactaggcgcctgaaatgccacactgtgtagttgc
cggagtttaagaggagggtttcttccgtgagtcgtagtgcgcgaggagat
cgctcgtcggaaaagtaaatcgcacggaagtaatccatagtctcgcggaa
ctcttccttgtaggcaattggcaccactggattcggaccatcgtcctgag
tcaatgggaccacgtctgaccactccaatcgttggctcagtggcacggtc
tcgtcgaaattcatccccctcgaatttccccgatcgttcaaacatttggca -continued ataaagtttcttaagattgaatcctgttgccggtcttgcgatgattatca tataatttctgttgaattacgttaagcatgtaataattaacatgtaatgc atgacgttatttatgagatgggtttttatgattagagtcccgcaattata catttaatacgcgatagaaaacaaaatatagcgcgcaaactaggataaat tatcgcgcgcggtgtcatctatgttactagatcgggaattcactggccgt cgttttacaacgtcgtgactgggaaaaccctggcgttacccaacttaatc gccttgcagcacatccccctttcgccagctggcgtaatagcgaagaggcc cgcaccgatcgcccttcccaacagttgcgcagcctgaatggcgcccgctc ctttcgctttcttcccttcctttctcgccacgttcgccggctttccccgt caagctctaaatcgggggctccctttagggttccgatttagtgctttacg gcacctcgaccccaaaaaacttgatttgggtgatggttcacgtagtgggc catcgccctgatagacggtttttcgccctttgacgttggagtccacgttc tttaatagtggactcttgttccaaactggaacaacactcaaccctatctc gggctattcttttgatttataagggattttgccgatttcggaaccaccat caaacaggattttcgcctgctggggcaaaccagcgtggaccgcttgctgc aactctctcagggccaggcggtgaagggcaatcagctgttgcccgtctca ctggtgaaaagaaaaaccaccccagtacattaaaaacgtccgcaatgtgt

**tattaagttgtctaagcgtcaatttg*gtttacaccacaatatatc***

*ctgcca*

SEQ ID NO:4 is the nucleic acid sequence of pBI121-antisense-FTA vector construct used to transform *Arabidopsis* plants. Italicized sequences are the right and left border repeats (1-24, 5226-5230). Underlined sequence is the 35S promoter (2515-3318). Bold sequence is the anti-sense Farnesyl transferase alpha sequence (3334-4317).

SEQ ID NO: 40 gtttacccgccaatatatcctgtcaaacactgatagtttaaactgaaggc gggaaacgacaatctgatcatgagcggagaattaagggagtcacgttatg acccccgccgatgacgcgggacaagccgttttacgtttggaactgacaga accgcaacgttgaaggagccactcagccgcgggtttctggagtttaatga gctaagcacatacgtcagaaaccattattgcgcgttcaaaagtcgcctaa ggtcactatcagctagcaaatatttcttgtcaaaaatgctccactgacgt tccataaattcccctcggtatccaattagagtctcatattcactctcaat ccaaataatctgcaccggatctggatcgtttcgcatgattgaacaagatg gattgcacgcaggttctccggccgcttgggtggagaggctattcggctat gactgggcacaacagacaatcggctgctctgatgccgccgtgttccggct gtcagcgcaggggcgcccggttctttttgtcaagaccgacctgtccggtg ccctgaatgaactgcaggacgaggcagcgcggctatcgtggctggccacg acgggcgttccttgcgcagctgtgctcgacgttgtcactgaagcgggaag ggactggctgctattgggcgaagtgccggggcaggatctcctgtcatctc accttgctcctgccgagaaagtatccatcatggctgatgcaatgcggcgg ctgcatacgcttgatccggctacctgcccattcgaccaccaagcgaaaca -continued tcgcatcgagcgagcacgtactcggatggaagccggtcttgtcgatcagg atgatctggacgaagagcatcaggggctcgcgccagccgaactgttcgcc aggctcaaggcgcgcatgcccgacggcgatgatctcgtcgtgacccatgg cgatgcctgcttgccgaatatcatggtggaaaatggccgcttttctggat tcatcgactgtggccggctgggtgtggcggaccgctatcaggacatagcg ttggctacccgtgatattgctgaagagcttggcggcgaatgggctgaccg cttcctcgtgctttacggtatcgccgctcccgattcgcagcgcatcgcct tctatcgccttcttgacgagttcttctgagcgggactctggggttcgaaa tgaccgaccaagcgacgcccaacctgccatcacgagatttcgattccacc gccgccttctatgaaaggttgggcttcggaatcgttttccgggacgccgg ctggatgatcctccagcgcggggatctcatgctggagttcttcgcccacg ggatctctgcggaacaggcggtcgaaggtgccgatatcattacgacagca acggccgacaagcacaacgccacgatcctgagcgacaatatgatcgggcc cggcgtccacatcaacggcgtcggcggcgactgcccaggcaagaccgaga tgcaccgcgatatcttgctgcgttcggatattttcgtggagttcccgcca cagacccggatgatccccgatcgttcaaacatttggcaataaagtttctt aagattgaatcctgttgccggtcttgcgatgattatcatataatttctgt tgaattacgttaagcatgtaataattaacatgtaatgcatgacgttattt atgagatgggtttttatgattagagtcccgcaattatacatttaatacgc gatagaaaacaaaatatagcgcgcaaactaggataaattatcgcgcgcgg tgtcatctatgttactagatcgggcctcctgtcaatgctggcggcggctc tggtggtggttctggtggcggctctgagggtggtggctctgagggtggcg gttctgagggtggcggctctgagggaggcggttccggtggtggctctggt tccggtgattttgattatgaaaagatggcaaacgctaataagggggctat gaccgaaaatgccgatgaaaacgcgctacagtctgacgctaaaggcaaac ttgattctgtcgctactgattacggtgctgctatcgatggtttcattggt gacgtttccggccttgctaatggtaatggtgctactggtgattttgctgg ctctaattcccaaatggctcaagtcggtgacggtgataattcacctttaa tgaataatttccgtcaatatttaccttccctccctcaatcggttgaatgt cgcccttttgtctttggcccaatacgcaaaccgcctctccccgcgcgttg gccgattcattaatgcagctggcacgacaggtttcccgactggaaagcgg gcagtgagcgcaacgcaattaatgtgagttagctcactcattaggcaccc caggctttacactttatgcttccggctcgtatgttgtgtggaattgtgag cggataacaatttcacacaggaaacagctatgaccatgattacgccaagc ttgcatgcctgcagcccacagatggttagagaggcttacgcagcaggtct catcaagacgatctacccgagcaataatctccaggaaatcaaataccttc ccaagaaggttaaagatgcagtcaaaagattcaggactaactgcatcaag aacacagagaaagatatatttctcaagatcagaagtactattccagtatg gacgattcaaggcttgcttcacaaaccaaggcaagtaatagagattggag tctctaaaaaggtagttcccactgaatcaaaggccatggagtcaaagatt -continued caaatagaggacctaacagaactcgccgtaaagactggcgaacagttcat
acagagtctcttacgactcaatgacaagaagaaaatcttcgtcaacatgg
tggagcacgacacacttgtctactccaaaaatatcaaagatacagtctca
gaagaccaaagggcaattgagacttttcaacaaagggtaatatccggaaa
cctcctcggattccattgcccagctatctgtcactttattgtgaagatag
tggaaaaggaaggtggctcctacaaatgccatcattgcgataaaggaaag
gccatcgttgaagatgcctctgccgacagtggtcccaaagatggacccccc
acccacgaggagcatcgtggaaaaagaagacgttccaaccacgtcttcaa
agcaagtggattgatgtgatatctccactgacgtaagggatgacgcacaa
tcccactatccttcgcaagacccttcctctatataaggaagttcatttca
tttggagagaacacgggggactctagaggatccatgaatttcgacgagac
cgtgccactgagccaacgattggagtggtcagacgtggtcccattgactc
aggacgatggtccgaatccagtggtgccaattgcctacaaggaagagttc
cgcgagactatggattacttccgtgcgatttacttttccgacgagcgatc
tcctcgcgcactacgactcacggaagaaaccctcctcttaaactccggca
actacacagtgtggcatttcaggcgcctagtactcgaggcccttaatcac
gacttgtttgaagaactcgagttcatcgaacgcattgctgaggataactc
taagaactaccaactgtggcatcatcggcgatgggttgcagagaaactgg
gtcctgatgttgcagggagagaacttgaatttacccgtagagtactttca
cttgatgccaaacattatcatgcttggtcacataggcagtggacactacg
ggcattaggaggatgggaagatgagctcgattactgtcacgagctccttg
aagctgacgtctttaacaattccgcctggaatcagaggtattatgtcatc
acccaatctcctttgttgggaggcctagaagccatgagagaatctgaagt
aagctacacaatcaaagccattttaaccaatcctgcaaacgagagctcat
ggcgatacctaaaagctctttacaaagacgacaaagaatcctggattagt
gatccaagtgtttcctcagtctgtttgaatgttctatcccgcacagattg
cttccatggattcgctctgagcaccctttggatcttctatgtgatggac
tgagaccaaccaacgagcataaagactcagtgagagctctagctaatgaa
gaaccagagactaacttggccaatttggtgtgtactattcttggtcgtgt
agatcctgtaagagctaactattgggcatggaggaagagcaagattacag
tggcagcaatttgactcgaatttccccgatcgttcaaacatttggcaata
aagtttcttaagattgaatcctgttgccggtcttgcgatgattatcatat
aatttctgttgaattacgttaagcatgtaataattaacatgtaatgcatg
acgttatttatgagatgggtttttatgattagagtcccgcaattatacat
ttaatacgcgatagaaaacaaaatatagcgcgcaaactaggataaattat
cgcgcgcggtgtcatctatgttactagatcgggaattcactggccgtcgt
tttacaacgtcgtgactgggaaaaccctggcgttacccaacttaatcgcc
ttgcagcacatccccctttcgccagctggcgtaatagcgaagaggcccgc
accgatcgcccttcccaacagttgcgcagcctgaatggcgcccgctcctt
tcgctttcttcccttcctttctcgccacgttcgccggctttccccgtcaa -continued gctctaaatcgggggctccctttagggttccgatttagtgctttacggca
cctcgaccccaaaaaacttgatttgggtgatggttcacgtagtgggccat
cgccctgatagacggtttttcgccctttgacgttggagtccacgttcttt
aatagtggactcttgttccaaactggaacaacactcaaccctatctcggg
ctattcttttgatttataagggattttgccgatttcggaaccaccatcaa
acaggattttcgcctgctggggcaaaccagcgtggaccgcttgctgcaac
tctctcagggccaggcggtgaagggcaatcagctgttgcccgtctcactg
gtgaaaagaaaaaccaccccagtacattaaaaacgtccgcaatgtgttat
taagttgtctaagcgtcaattt*gtttacaccacaatatatcctgcca*
(Underlined Seq: 35S promoter; Bold: AtFTA)

SEQ ID NO: 41

*gtttacccgccaatatatcctgtc*aaacactgatagtttaaactgaaggc
gggaaacgacaatctgatcatgagcggagaattaagggagtcacgttatg
acccccgccgatgacgcgggacaagccgttttacgtttggaactgacaga
accgcaacgttgaaggagccactcagccgcgggtttctggagtttaatga
gctaagcacatacgtcagaaaccattattgcgcgttcaaaagtcgcctaa
ggtcactatcagctagcaaatatttcttgtcaaaaatgctccactgacgt
tccataaattcccctcggtatccaattagagtctcatattcactctcaat
ccaaataatctgcaccggatctggatcgtttcgcatgattgaacaagatg
gattgcacgcaggttctccggccgcttgggtggagaggctattcggctat
gactgggcacaacagacaatcggctgctctgatgccgccgtgttccggct
gtcagcgcaggggcgcccggttctttttgtcaagaccgacctgtccggtg
ccctgaatgaactgcaggacgaggcagcgcggctatcgtggctggccacg
acgggcgttccttgcgcagctgtgctcgacgttgtcactgaagcgggaag
ggactggctgctattgggcgaagtgccggggcaggatctcctgtcatctc
accttgctcctgccgagaaagtatccatcatggctgatgcaatgcggcgg
ctgcatacgcttgatccggctacctgcccattcgaccaccaagcgaaaca
tcgcatcgagcgagcacgtactcggatggaagccggtcttgtcgatcagg
atgatctggacgaagagcatcaggggctcgcgccagccgaactgttcgcc
aggctcaaggcgcgcatgcccgacggcgatgatctcgtcgtgacccatgg
cgatgcctgcttgccgaatatcatggtggaaaatggccgcttttctggat
tcatcgactgtggccggctgggtgtggcggaccgctatcaggacatagcg
ttggctacccgtgatattgctgaagagcttggcggcgaatgggctgaccg
cttcctcgtgctttacggtatcgccgctcccgattcgcagcgcatcgcct
tctatcgccttcttgacgagttcttctgagcgggactctggggttcgaaa
tgaccgaccaagcgacgcccaacctgccatcacgagatttcgattccacc
gccgccttctatgaaaggttgggcttcggaatcgttttccgggacgccgg
ctggatgatcctccagcgcggggatctcatgctggagttcttcgcccacg
ggatctctgcggaacaggcggtcgaaggtgccgatatcattacgacagca
acggccgacaagcacaacgccacgatcctgagcgacaatatgatcgggcc
cggcgtccacatcaacggcgtcggcggcgactgcccaggcaagaccgaga -continued tgcaccgcgatatcttgctgcgttcggatattttcgtggagttcccgcca
cagacccggatgatccccgatcgttcaaacatttggcaataaagtttctt
aagattgaatcctgttgccggtcttgcgatgattatcatataatttctgt
tgaattacgttaagcatgtaataattaacatgtaatgcatgacgttattt
atgagatgggtttttatgattagagtcccgcaattatacatttaatacgc
gatagaaaacaaaatatagcgcgcaaactaggataaattatcgcgcgcgg
tgtcatctatgttactagatcgggcctcctgtcaatgctggcggcggctc
tggtggtggttctggtggcggctctgagggtggtggctctgagggtggcg
gttctgagggtggcggctctgagggaggcggttccggtggtggctctggt
tccggtgattttgattatgaaaagatggcaaacgctaataagggggctat
gaccgaaaatgccgatgaaaacgcgctacagtctgacgctaaaggcaaac
ttgattctgtcgctactgattacggtgctgctatcgatggtttcattggt
gacgtttccggccttgctaatggtaatggtgctactggtgattttgctgg
ctctaattcccaaatggctcaagtcggtgacggtgataattcacctttaa
tgaataatttccgtcaatatttaccttccctccctcaatcggttgaatgt
cgcccttttgtctttggcccaatacgcaaaccgcctctccccgcgcgttg
gccgattcattaatgcagctggcacgacaggtttcccgactggaaagcgg
gcagtgagcgcaacgcaattaatgtgagttagctcactcattaggcaccc
caggctttacactttatgcttccggctcgtatgttgtgtggaattgtgag
cggataacaatttcacacaggaaacagctatgaccatgattacgccaagc
ttgcatgcctgcagggagccatagatgcaattcaatcaaactgaaatttc
tgcaagaatctcaaacacggagatctcaaagtttgaaagaaaatttattt
cttcgactcaaaacaaacttacgaaatttaggtagaacttatatacatta
tattgtaatttttttgtaacaaaatgtttttattattattatagaattta
ctggttaaattaaaaatgaatagaaaaggtgaattaagaggagagaggag
gtaaacatttttcttctatttttttcatattttcaggataaattattgtaaa
agtttacaagatttccatttgactagtgtaaatgaggaatattctctagt
aagatcattatttcatctacttcttttatcttctaccagtagaggaataa
acaatatttagctcctttgtaaatacaaattaattttccttcttgacatc
attcaattttaattttacgtataaaataaaagatcatacctattagaacg
attaaggagaaatacaattcgaatgagaaggatgtgccgtttgttataat
aaacagccacacgacgtaaacgtaaaatgaccacatgatgggccaataga
catggaccgactactaataatagtaagttacattttaggatggaataaat
atcataccgacatcagttttgaaagaaaagggaaaaaaagaaaaaataaa
taaaagatatactaccgacatgagttccaaaaagcaaaaaaaaagatcaa
gccgacacagacacgcgtagagagcaaaatgactttgacgtcacaccacg
aaaacagacgcttcatacgtgtccctttatctctctcagtctctctataa
acttagtgagaccctcctctgttttactcacaaatatgcaaactagaaaa
caatcatcaggaataaagggtttgattacttctattggaaagactctaga
ggatcctcaaattgctgccactgtaatcttgctcttcctccatgcccaat
agttagctcttataggatctacacgaccaagaatagtacacaccaaattg
gccaagttagtctctggttcttcattagctagagctctcactgagtcttt
atgctcgttggttggtctcagtccatcacatagaagatccaaaagggtgc
tcagagcgaatccatggaagcaatctgtgcgggatagaacattcaaacag
actgaggaaacacttggatcactaatccaggattctttgtcgtctttgta
aagcgcttttaggtatcgccatgagctctcgtttgcaggattggttaaaa
tggctttgattgtgtagcttacttcagattctctcatggcttctaggcct
cccaacaaaggagattgggtgatgacataatacctctgattccaggcgga
attgttaaagacgtcagcttcaaggagctcgtgacagtaatcgagctcat
cttcccatcctcctaatgcccgtagtgtccactgcctatgtgaccaagca
tgataatgtttggcatcaagtgaaagtactctacgggtaaattcaagttc
tctccctgcaacatcaggacccagtttctctgcaacccatcgccgatgat
gccacagttggtagttcttagagttatcctcagcaatgcgttcgatgaac
tcgagttcttcaaacaagtcgtgattaagggcctcgagtactaggcgcct
gaaatgccacactgtgtagttgccggagtttaagaggagggtttcttccg
tgagtcgtagtgcgcgaggagatcgctcgtcggaaaagtaaatcgcacgg
aagtaatccatagtctcgcggaactcttccttgtaggcaattggcaccac
tggattcggaccatcgtcctgagtcaatgggaccacgtctgaccactcca
atcgttggctcagtggcacggtctcgtcgaaattcatcccctcgaatttc
cccgatcgttcaaacatttggcaataaagtttcttaagattgaatcctgt
tgccggtcttgcgatgattatcatataatttctgttgaattacgttaagc
atgtaataattaacatgtaatgcatgacgttatttatgagatgggttttt
atgattagagtcccgcaattatacatttaatacgcgatagaaaacaaaat
atagcgcgcaaactaggataaattatcgcgcgcggtgtcatctatgttac
tagatcgggaattcactggccgtcgttttacaacgtcgtgactgggaaaa
ccctggcgttacccaacttaatcgccttgcagcacatccccctttcgcca
gctggcgtaatagcgaagaggcccgcaccgatcgcccttcccaacagttg
cgcagcctgaatggcgcccgctcctttcgctttcttcccttcctttctcg
ccacgttcgccggctttccccgtcaagctctaaatcgggggctccctttta
gggttccgatttagtgctttacggcacctcgaccccaaaaaacttgattt
gggtgatggttcacgtagtgggccatcgccctgatagacggtttttcgcc
ctttgacgttggagtccacgttctttaatagtggactcttgttccaaact
ggaacaacactcaaccctatctcgggctattcttttgatttataagggat
tttgccgatttcggaaccaccatcaaacaggattttcgcctgctggggca
aaccagcgtggaccgcttgctgcaactctctcagggccaggcggtgaagg
gcaatcagctgttgcccgtctcactggtgaaaagaaaaaccaccccagta
cattaaaaacgtccgcaatgtgttattaagttgtctaagcgtcaattt*gt*
*ttacaccacaatatatcctgcca*

(Underlined Seq: RD29A promoter; Bold: Anti-sense-AtFTA)

-continued

SEQ ID NO: 42

*gtttacccgccaatatatcctgtc*aaacactgatagtttaaactgaaggc
gggaaacgacaatctgatcatgagcggagaattaagggagtcacgttatg
acccccgccgatgacgcgggacaagccgttttacgtttggaactgacaga
accgcaacgttgaaggagccactcagccgcgggtttctggagtttaatga
gctaagcacatacgtcagaaaccattattgcgcgttcaaaagtcgcctaa
ggtcactatcagctagcaaatatttcttgtcaaaaatgctccactgacgt
tccataaattcccctcggtatccaattagagtctcatattcactctcaat
ccaaataatctgcaccggatctggatcgtttcgcatgattgaacaagatg
gattgcacgcaggttctccggccgcttgggtggagaggctattcggctat
gactgggcacaacagacaatcggctgctctgatgccgccgtgttccggct
gtcagcgcaggggcgcccggttctttttgtcaagaccgacctgtccggtg
ccctgaatgaactgcaggacgaggcagcgcggctatcgtggctggccacg
acgggcgttccttgcgcagctgtgctcgacgttgtcactgaagcgggaag
ggactggctgctattgggcgaagtgccggggcaggatctcctgtcatctc
accttgctcctgccgagaaagtatccatcatggctgatgcaatgcggcgg
ctgcatacgcttgatccggctacctgcccattcgaccaccaagcgaaaca
tcgcatcgagcgagcacgtactcggatggaagccggtcttgtcgatcagg
atgatctggacgaagagcatcaggggctcgcgccagccgaactgttcgcc
aggctcaaggcgcgcatgcccgacggcgatgatctcgtcgtgacccatgg
cgatgcctgcttgccgaatatcatggtggaaaatggccgcttttctggat
tcatcgactgtggccggctgggtgtggcggaccgctatcaggacatagcg
ttggctacccgtgatattgctgaagagcttggcggcgaatgggctgaccg
cttcctcgtgctttacggtatcgccgctcccgattcgcagcgcatcgcct
tctatcgccttcttgacgagttcttctgagcgggactctggggttcgaaa
tgaccgaccaagcgacgcccaacctgccatcacgagatttcgattccacc
gccgccttctatgaaaggttgggcttcggaatcgttttccgggacgccgg
ctggatgatcctccagcgcggggatctcatgctggagttcttcgcccacg
ggatctctgcggaacaggcggtcgaaggtgccgatatcattacgacagca
acggccgacaagcacaacgccacgatcctgagcgacaatatgatcgggcc
cggcgtccacatcaacggcgtcggcggcgactgcccaggcaagaccgaga
tgcaccgcgatatcttgctgcgttcggatattttcgtggagttcccgcca
cagacccggatgatccccgatcgttcaaacatttggcaataaagtttctt
aagattgaatcctgttgccggtcttgcgatgattatcatataatttctgt
tgaattacgttaagcatgtaataattaacatgtaatgcatgacgttattt
atgagatgggtttttatgattagagtcccgcaattatacatttaatacgc
gatagaaaacaaaatatagcgcgcaaactaggataaattatcgcgcgcgg
tgtcatctatgttactagatcgggcctcctgtcaatgctggcggcggctc
tggtggtggttctggtggcggctctgagggtggtggctctgagggtggcg
gttctgagggtggcggctctgagggaggcggttccggtggtggctctggt -continued tccggtgattttgattatgaaaagatggcaaacgctaataaggggggctat
gaccgaaaatgccgatgaaaacgcgctacagtctgacgctaaaggcaaac
ttgattctgtcgctactgattacggtgctgctatcgatggtttcattggt
gacgtttccggccttgctaatggtaatggtgctactggtgattttgctgg
ctctaattcccaaatggctcaagtcggtgacggtgataattcacctttaa
tgaataatttccgtcaatatttaccttccctccctcaatcggttgaatgt
cgccctttttgtctttggcccaatacgcaaaccgcctctccccgcgcgttg
gccgattcattaatgcagctggcacgacaggtttcccgactggaaagcgg
gcagtgagcgcaacgcaattaatgtgagttagctcactcattaggcaccc
caggctttacactttatgcttccggctcgtatgttgtgtggaattgtgag
cggataacaatttcacacaggaaacagctatgaccatgattacgccaagc
ttgcatgcctgcagcccacagatggttagagaggcttacgcagcaggtct
catcaagacgatctacccgagcaataatctccaggaaatcaaataccttc
ccaagaaggttaaagatgcagtcaaaagattcaggactaactgcatcaag
aacacagagaaagatatatttctcaagatcagaagtactattccagtatg
gacgattcaaggcttgcttcacaaaccaaggcaagtaatagagattggag
tctctaaaaaggtagttcccactgaatcaaaggccatggagtcaaagatt
caaatagaggacctaacagaactcgccgtaaagactggcgaacagttcat
acagagtctcttacgactcaatgacaagaagaaaatcttcgtcaacatgg
tggagcacgacacacttgtctactccaaaaatatcaaagatacagtctca
gaagaccaaagggcaattgagacttttcaacaaagggtaatatccggaaa
cctcctcggattccattgcccagctatctgtcactttattgtgaagatag
tggaaaaggaaggtggctcctacaaatgccatcattgcgataaaggaaag
gccatcgttgaagatgcctctgccgacagtggtcccaaagatggaccccc
acccacgaggagcatcgtggaaaaagaagacgttccaaccacgtcttcaa
agcaagtggattgatgtgatatctccactgacgtaagggatgacgcacaa
tcccactatccttcgcaagacccttcctctatataaggaagttcatttca
tttggagagaacacggggactctagaggatcctcGCTCTTCCTCCATGC
CCAATAGTTAGCTCTTACAGGATCTACACGACCAAGAATAGTACACACCA
AATTGGCCAAGTTAGTCTCTGGTTCTTCATTAGCTAGAGCTCTCACTGAG
TCTTTATGCTCGTTGGTTGGTCTCAGTCCATCACATAGAAGATCCAAAAG
GGTGCTCAGAGCGAATCCATGGAAGCAATCTGTGCGGGATAGAACATTCA
AACAGACTGAGGAAACACTTGGATCACTAATCCAGGATTCTTTGTCGTCT
TTGTAAAGAGCTTTTAGGTATCGCCATGAGCTCTCGTTTGCAGGATTGGT
TAAAATGGCTTTGATTGTGTAGCTTACTTCAGATTCTCTCATGGCTTCTA
GGCCTCCCAACAAAGGAGATTGGGTGATGACATAATACCTCTGATTCCAG
GCGGAATTGTTAAAGACGTCAGCTTCAAGGAGCTCGTGACAGTAATCGAG
CTCATCTTCCCATCCTCCTAATGCCCGgaggatccccATCTACCCGCTTC
GCGTCGGCATCCGGTCAGTGGCAGTGAAGGGCGAACAGTTCCTGATTAAC
CACAAACCGTTCTACTTTACTGGCTTTGGTCGTCATGAAGATGCGGACTT -continued GCGTGGCAAAGGATTCGATAACGTGCTGATGGTGCACGACCACGCATTAA
TGGACTGGATTGGGGCCAACTCCTACCGTACCTCGCATTACCCTTACGCT

GAAGAGATGCTCGACTGGGCAGATGAACATGGCATCGTGGTGATTGATGA

AACTGCTGCTGTCGGCTTTTCGCTCTCTTTAGGCATTGGTTTCGAAGCGG

GCAACAAGCCGAAAGAACTGTACAGCGAAGAGGCAGTCAACGGGGAAACT

CAGCAAGCGCACTTACAGGCGATTAAAGAGCTGATAGCGCGTGACAAAAA

CCACCCAAGCGTGGTGATGTGGAGTATTGCCAACGAACCGGATACCCGTC

CGCAAGGTGCACGGGAATATTTCGCGCCACTGGCGGAAGCAACGCGTAAA

CTCGACCCGACGCGTCCGATCACCTGCGTCAATGTAATGTTCTGCGACGC

TCACACCGATACCATCAGCGATCTCTTTGATGTGCTGTGCCTGAACCGTT

ATTACGGATGGTATGTCCAAAGCGGCGATTTGGAAACGGCAGAGAAGGTA

CTGGAAAAAGAACTTCTGGCCTGGCAGGAGAAACTGTACACCGACATGTG

GAGTGAAGAGTATCAGTGTGCATGGCTGGATATGTATCACCGCGTCTTTG

ATCGCGTCAGCGCCGTCGTCGGTGAACAGGTATGGAATTTCGCCGATTTT

GCGACCTCGCAAGGCATATTGCGCGTTGGCGGTAACAAGAAAGGGATCTT

CACTCGCGACCGCAAACCGAAGTCGGCGGCTTTTCTGCTGCAAAAACGCT

GGACTGGCATGAACTTCGGTGAAAAACCGCAGCAGGGAGGCAAACAATGA

ATCAACAACTCTCCTGGCGCACCATCGTCGGCTACAGCCTCGGGAATTGC

TACCGAGCTCGCTCTTCCTCCATGCCCAATAGTTAGCTCTTACAGGATCT

ACACGACCAAGAATAGTACACACCAAATTGGCCAAGTTAGTCTCTGGTTC

TTCATTAGCTAGAGCTCTCACTGAGTCTTTATGCTCGTTGGTTGGTCTCA

GTCCATCACATAGAAGATCCAAAAGGGTGCTCAGAGCGAATCCATGGAAG

CAATCTGTGCGGGATAGAACATTCAAACAGACTGAGGAAACACTTGGATC

ACTAATCCAGGATTCTTTGTCGTCTTTGTAAAGAGCTTTTAGGTATCGCC

ATGAGCTCTCGTTTGCAGGATTGGTTAAAATGGCTTTGATTGTGTAGCTT

ACTTCAGATTCTCTCATGGCTTCTAGGCCTCCCAACAAAGGAGATTGGGT

GATGACATAATACCTCTGATTCCAGGCGGAATTGTTAAAGACGTCAGCTT

CAAGGAGCTCGTGACAGTAATCGAGCTCATCTTCCCATCCTCCTAATGCC

CGctcgaatttccccgatcgttcaaacatttggcaataaagtttcttaag attgaatcctgttgccggtcttgcgatgattatcatataatttctgttga attacgttaagcatgtaataattaacatgtaatgcatgacgttatttatg agatgggtttttatgattagagtcccgcaattatacatttaatacgcgat agaaaacaaaatatagcgcgcaaactaggataaattatcgcgcgcggtgt catctatgttactagatcgggaattcactggccgtcgttttacaacgtcg tgactgggaaaaccctggcgttacccaacttaatcgccttgcagcacatc ccccttcgccagctggcgtaatagcgaagaggcccgcaccgatcgccct tcccaacagttgcgcagcctgaatggcgcccgctcctttcgctttcttcc cttcctttctcgccacgttcgccggctttccccgtcaagctctaaatcgg gggctccctttagggttccgatttagtgctttacggcacctcgaccccaa aaaacttgatttgggtgatggttcacgtagtgggccatcgccctgataga cggtttttcgccctttgacgttggagtccacgttctttaatagtggactc -continued ttgttccaaactggaacaacactcaaccctatctcgggctattcttttga tttataagggattttgccgatttcggaaccaccatcaaacaggattttcg cctgctggggcaaaccagcgtggaccgcttgctgcaactctctcagggcc aggcggtgaagggcaatcagctgttgcccgtctcactggtgaaaagaaaa accaccccagtacattaaaaacgtccgcaatgtgttattaagttgtctaa gcgtcaattt*gtttacaccacaatatatcctgcca*

(Underlined Seq: 35S promoter; Bold: AtFTA anti-sense sequence separated by GUS Seq.)

SEQ ID NO: 43

*gtttacccgccaatatatcctgtc*aaacactgatagtttaaactgaaggc gggaaacgacaatctgatcatgagcggagaattaagggagtcacgttatg acccccgccgatgacgcgggacaagccgttttacgtttggaactgacaga accgcaacgttgaaggagccactcagccgcgggtttctggagtttaatga gctaagcacatacgtcagaaaccattattgcgcgttcaaaagtcgcctaa ggtcactatcagctagcaaatatttcttgtcaaaaatgctccactgacgt tccataaattcccctcggtatccaattagagtctcatattcactctcaat ccaaataatctgcaccggatctggatcgtttcgcatgattgaacaagatg gattgcacgcaggttctccggccgcttgggtggagaggctattcggctat gactgggcacaacagacaatcggctgctctgatgccgccgtgttccggct gtcagcgcaggggcgcccggttctttttgtcaagaccgacctgtccggtg ccctgaatgaactgcaggacgaggcagcgcggctatcgtggctggccacg acgggcgttccttgcgcagctgtgctcgacgttgtcactgaagcgggaag ggactggctgctattgggcgaagtgccggggcaggatctcctgtcatctc accttgctcctgccgagaaagtatccatcatggctgatgcaatgcggcgg ctgcatacgcttgatccggctacctgcccattcgaccaccaagcgaaaca tcgcatcgagcgagcacgtactcggatggaagccggtcttgtcgatcagg atgatctggacgaagagcatcaggggctcgcgccagccgaactgttcgcc aggctcaaggcgcgcatgcccgacggcgatgatctcgtcgtgacccatgg cgatgcctgcttgccgaatatcatggtggaaaatggccgcttttctggat tcatcgactgtggccggctgggtgtggcggaccgctatcaggacatagcg ttggctacccgtgatattgctgaagagcttggcggcgaatgggctgaccg cttcctcgtgctttacggtatcgccgctcccgattcgcagcgcatcgcct tctatcgccttcttgacgagttcttctgagcgggactctggggttcgaaa tgaccgaccaagcgacgcccaacctgccatcacgagatttcgattccacc gccgccttctatgaaaggttgggcttcggaatcgttttccgggacgccgg ctggatgatcctccagcgcggggatctcatgctggagttcttcgcccacg ggatctctgcggaacaggcggtcgaaggtgccgatatcattacgacagca acggccgacaagcacaacgccacgatcctgagcgacaatatgatcgggcc cggcgtccacatcaacggcgtcggcggcgactgcccaggcaagaccgaga tgcaccgcgatatcttgctgcgttcggatattttcgtggagttcccgcca cagacccggatgatccccgatcgttcaaacatttggcaataaagtttctt aagattgaatcctgttgccggtcttgcgatgattatcatataatttctgt -continued tgaattacgttaagcatgtaataattaacatgtaatgcatgacgttattt
atgagatgggtttttatgattagagtcccgcaattatacatttaatacgc
gatagaaaacaaaatatagcgcgcaaactaggataaattatcgcgcgcgg
tgtcatctatgttactagatcgggcctcctgtcaatgctggcggcggctc
tggtggtggttctggtggcggctctgagggtggtggctctgagggtggcg
gttctgagggtggcggctctgagggaggcggttccggtggtggctctggt
tccggtgattttgattatgaaaagatggcaaacgctaataagggggctat
gaccgaaaatgccgatgaaaacgcgctacagtctgacgctaaaggcaaac
ttgattctgtcgctactgattacggtgctgctatcgatggtttcattggt
gacgtttccggccttgctaatggtaatggtgctactggtgattttgctgg
ctctaattcccaaatggctcaagtcggtgacggtgataattcacctttaa
tgaataatttccgtcaatatttaccttccctccctcaatcggttgaatgt
cgcccttttgtctttggcccaatacgcaaaccgcctctccccgcgcgttg
gccgattcattaatgcagctggcacgacaggtttcccgactggaaagcgg
gcagtgagcgcaacgcaattaatgtgagttagctcactcattaggcaccc
caggctttacactttatgcttccggctcgtatgttgtgtggaattgtgag
cggataacaatttcacacaggaaacagctatgaccatgattacgccaagc
ttgcatgcctgcagggagccatagatgcaattcaatcaaactgaaatttc
tgcaagaatctcaaacacggagatctcaaagtttgaaagaaaatttattt
cttcgactcaaaacaaacttacgaaatttaggtagaacttatatacatta
tattgtaatttttttgtaacaaaatgtttttattattattatagaattta
ctggttaaattaaaaatgaatagaaaaggtgaattaagaggagagaggag
gtaaacattttcttctatttttttcatatttcaggataaattattgtaaa
agtttacaagatttccatttgactagtgtaaatgaggaatattctctagt
aagatcattatttcatctacttcttttatcttctaccagtagaggaataa
acaatatttagctcctttgtaaatacaaattaattttccttcttgacatc
attcaattttaattttacgtataaaataaaagatcatacctattagaacg
attaaggagaaatacaattcgaatgagaaggatgtgccgtttgttataat
aaacagccacacgacgtaaacgtaaaatgaccacatgatgggccaataga
catggaccgactactaataatagtaagttacattttaggatggaataaat
atcataccgacatcagttttgaaagaaaagggaaaaaaagaaaaaataaa
taaaagatatactaccgacatgagttccaaaaagcaaaaaaaaagatcaa
gccgacacagacacgcgtagagagcaaaatgactttgacgtcacaccacg
aaaacagacgcttcatacgtgtccctttatctctctcagtctctctataa
acttagtgagaccctcctctgttttactcacaaatatgcaaactagaaaa
caatcatcaggaataaagggtttgattacttctattggaaaggactctag
aggatcctcGCTCTTCCTCCATGCCCAATAGTTAGCTCTTACAGGATCTA
CACGACCAAGAATAGTACACACCAAATTGGCCAAGTTAGTCTCTGGTTCT
TCATTAGCTAGAGCTCTCACTGAGTCTTTATGCTCGTTGGTTGGTCTCAG
TCCATCACATAGAAGATCCAAAAGGGTGCTCAGAGCGAATCCATGGAAGC
AATCTGTGCGGGATAGAACATTCAAACAGACTGAGGAAACACTTGGATCA
CTAATCCAGGATTCTTTGTCGTCTTTGTAAAGAGCTTTTAGGTATCGCCA
TGAGCTCTCGTTTGCAGGATTGGTTAAAATGGCTTTGATTGTGTAGCTTA
CTTCAGATTCTCTCATGGCTTCTAGGCCTCCCAACAAAGGAGATTGGGTG
ATGACATAATACCTCTGATTCCAGGCGGAATTGTTAAAGACGTCAGCTTC
AAGGAGCTCGTGACAGTAATCGAGCTCATCTTCCCATCCTCCTAATGCCC
GgaggatccccATCTACCCGCTTCGCGTCGGCATCCGGTCAGTGGCAGTG
AAGGGCGAACAGTTCCTGATTAACCACAAACCGTTCTACTTTACTGGCTT
TGGTCGTCATGAAGATGCGGACTTGCGTGGCAAAGGATTCGATAACGTGC
TGATGGTGCACGACCACGCATTAATGGACTGGATTGGGGCCAACTCCTAC
CGTACCTCGCATTACCCTTACGCTGAAGAGATGCTCGACTGGGCAGATGA
ACATGGCATCGTGGTGATTGATGAAACTGCTGCTGTCGGCTTTTCGCTCT
CTTTAGGCATTGGTTTCGAAGCGGGCAACAAGCCGAAAGAACTGTACAGC
GAAGAGGCAGTCAACGGGGAAACTCAGCAAGCGCACTTACAGGCGATTAA
AGAGCTGATAGCGCGTGACAAAAACCACCCAAGCGTGGTGATGTGGAGTA
TTGCCAACGAACCGGATACCCGTCCGCAAGGTGCACGGGAATATTTCGCG
CCACTGGCGGAAGCAACGCGTAAACTCGACCCGACGCGTCCGATCACCTG
CGTCAATGTAATGTTCTGCGACGCTCACACCGATACCATCAGCGATCTCT
TTGATGTGCTGTGCCTGAACCGTTATTACGGATGGTATGTCCAAAGCGGC
GATTTGGAAACGGCAGAGAAGGTACTGGAAAAAGAACTTCTGGCCTGGCA
GGAGAAACTGTACACCGACATGTGGAGTGAAGAGTATCAGTGTGCATGGC
TGGATATGTATCACCGCGTCTTTGATCGCGTCAGCGCCGTCGTCGGTGAA
CAGGTATGGAATTTCGCCGATTTTGCGACCTCGCAAGGCATATTGCGCGT
TGGCGGTAACAAGAAAGGGATCTTCACTCGCGACCGCAAACCGAAGTCGG
CGGCTTTTCTGCTGCAAAAACGCTGGACTGGCATGAACTTCGGTGAAAAA
CCGCAGCAGGGAGGCAAACAATGAATCAACAACTCTCCTGGCGCACCATC
GTCGGCTACAGCCTCGGGAATTGCTACCGAGCTCGCTCTTCCTCCATGCC
CAATAGTTAGCTCTTACAGGATCTACACGACCAAGAATAGTACACACCAA
ATTGGCCAAGTTAGTCTCTGGTTCTTCATTAGCTAGAGCTCTCACTGAGT
CTTTATGCTCGTTGGTTGGTCTCAGTCCATCACATAGAAGATCCAAAAGG
GTGCTCAGAGCGAATCCATGGAAGCAATCTGTGCGGGATAGAACATTCAA
ACAGACTGAGGAAACACTTGGATCACTAATCCAGGATTCTTTGTCGTCTT
TGTAAAGAGCTTTTAGGTATCGCCATGAGCTCTCGTTTGCAGGATTGGTT
AAAATGGCTTTGATTGTGTAGCTTACTTCAGATTCTCTCATGGCTTCTAG
GCCTCCCAACAAAGGAGATTGGGTGATGACATAATACCTCTGATTCCAGG
CGGAATTGTTAAAGACGTCAGCTTCAAGGAGCTCGTGACAGTAATCGAGC
TCATCTTCCCATCCTCCTAATGCCCGctcgaatttccccgatcgttcaaa
catttggcaataaagtttcttaagattgaatcctgttgccggtcttgcga
tgattatcatataatttctgttgaattacgttaagcatgtaataattaac
atgtaatgcatgacgttatttatgagatgggtttttatgattagagtccc -continued gcaattatacatttaatacgcgatagaaaacaaaatatagcgcgcaaact
aggataaattatcgcgcgcggtgtcatctatgttactagatcgggaattc
actggccgtcgttttacaacgtcgtgactgggaaaaccctggcgttaccc
aacttaatcgccttgcagcacatccccctttcgccagctggcgtaatagc
gaagaggcccgcaccgatcgcccttcccaacagttgcgcagcctgaatgg
cgcccgctcctttcgctttcttcccttcctttctcgccacgttcgccggc
tttccccgtcaagctctaaatcgggggctccctttagggttccgatttag
tgctttacggcacctcgaccccaaaaaacttgatttgggtgatggttcac
gtagtgggccatcgccctgatagacggtttttcgccctttgacgttggag
tccacgttctttaatagtggactcttgttccaaactggaacaacactcaa
ccctatctcgggctattcttttgatttataagggattttgccgatttcgg
aaccaccatcaaacaggattttcgcctgctggggcaaaccagcgtggacc
gcttgctgcaactctctcagggccaggcggtgaagggcaatcagctgttg
cccgtctcactggtgaaaagaaaaaccaccccagtacattaaaaacgtcc
gcaatgtgttattaagttgtctaagcgtcaattt*gtttacaccacaatat*
*atcctgcca*

(Underlined Seq: RD29A promoter; Bold: AtFTA anti-sense sequence, separated by GUS Seq.)

SEQ ID NO: 44

GAATTCAAATTTTTCGCCAGTTCTAAATATCCGGAAACCTCTTGGGATGC
CATTGCCCATCTATCTGTAATTTATTGACGAAATAGACGAAAAGGAAGGT
GGCTCCTATAAAGCACATCATTGCGATAACAGAAAGGCCATTGTTGAAGA
TACCTCTGCTGACATTGGTCCCCAAGTGGAAGCACCACCCCATGAGGAGC
ACCGTGGAGTAAGAAGACGTTCGAGCCACGTCGAAAAAGCAAGTGTGTTG
ATGTAGTATCTCCATTGACGTAAGGGATGACGCACAATCCAACTATCCAT
CGCAAGACCATTGCTCTATATAAGAAAGTTAATATCATTTCGAGTGGCCA
CGCTGAGCTCAGGAAGTCTGCTCTTGCGCCAAATCCAATAGTTGGTTCTA
ATTGGATCAACTTGTTTTAGGATAGAACAAATATTTCGTGCTATATTTAA
ATTTTGTTGTTCCCCTTTCTCATCATCATCTAAATCTTGTTTATCCATAT
CTGCGGTCTTTAAGGCGTCAATGGCATCTCTAATGTCTTCATTTGGTTGA
TAACCAAAGCATATAAGATCTAAAATAGTGCTAAGAGCAAACACGTAGTT
GCTCTTAGTTCTCAAAATCTTTAAGCATACTGAAGAAACTTGAGGATCAT
TTACCCATGAAGTAGTTTCACCTTTATAAAGTCCTCGTAGATATCTCCAC
GAGCTTTCATTTTCAGGGTAGGCTATAATGGCTTCGATGGTGTAAAGCAC
TTCAGACTCTCTCATAGCTTTTAGGCCCCCCAAGAAAGGAGACCTTGTTA
TGACAAAATATCTCTGATTCCAAGCAGAATTGTTAAAAATGTCTTCTTTA
AGTAGTTCTGTGCAATAATTAAGTTCATCTTCCCATCCTCCTAGTGTTTG
AAGAGCCCACTGTCTATGAGACCATGCATGATAATGTTTGGCATCAACGG
ACAGTATCTTTTTGGTGAACTCGAGCTgagctcgaatttccccgatcgtt
caaacatttggcaataaagtttcttaagattgaatcctgttgccggtctt
gcgatgattatcatataatttctgttgaattacgttaagcatgtaataat -continued taacatgtaatgcatgacgttatttatgagatgggtttttatgattagag
tcccgcaattatacatttaatacgcgatagaaaacaaaatatagcgcgca
aactaggataaattatcgcgcgcggtgtcatctatgttactagatcggga
attc (Underlined MuA Promoter; Bold: *Glycine max* anti-FTA; lower case: NOS terminater Seq.)

SEQ ID NO: 45

GGAGCCATAGATGCAATTCAATCAAACTGAAATTTCTGCAAGAATCTCAA
ACACGGAGATCTCAAAGTTTGAAAGAAAATTTATTTCTTCGACTCAAAAC
AAACTTACGAAATTTAGGTAGAACTTATATACATTATATTGTAATTTTTT
GTAACAAAATGTTTTTATTATTATTATAGAATTTTACTGGTTAAATTAAA
AATGAATAGAAAAGGTGAATTAAGAGGAGAGAGGAGGTAAACATTTTCTT
CTATTTTTTCATATTTTCAGGATAAATTATTGTAAAAGTTTACAAGATTT
CCATTTGACTAGTGTAAATGAGGAATATTCTCTAGTAAGATCATTATTTC
ATCTACTTCTTTTATCTTCTACCAGTAGAGGAATAAACAATATTTAGCTC
CTTTGTAAATACAAATTAATTTTCCTTCTTGACATCATTCAATTTTAATT
TTACGTATAAAATAAAAGATCATACCTATTAGAACGATTAAGGAGAAATA
CAATTCGAATGAGAAGGATGTGCCGTTTGTTATAATAAACAGCCACACGA
CGTAAACGTAAAATGACCACATGATGGGCCAATAGACATGGACCGACTAC
TAATAATAGTAAGTTACATTTTAGGATGGAATAAATATCATACCGACATC
AGTTTTGAAAGAAAAGGGAAAAAAAGAAAAAATAAATAAAAGATATACTA
CCGACATGAGTTCCAAAAAGCAAAAAAAAAGATCAAGCCGACACAGACAC
GCGTAGAGAGCAAAATGACTTTGACGTCACACCACGAAAACAGACGCTTC
ATACGTGTCCCTTTATCTCTCTCAGTCTCTCTATAAACTTAGTGAGACCC
TCCTCTGTTTTACTCACAAATATGCAAACTAGAAAACAATCATCAGGAAT
AAAGGGTTTGATTACTTCTATTGGAAAGAGGAAGTCTGCTCTTGCGCCAA
ATCCAATAGTTGGTTCTAATTGGATCAACTTGTTTTAGGATAGAACAAAT
ATTTCGTGCTATATTTAAATTTTGTTGTTCCCCTTTCTCATCATCATCTA
AATCTTGTTTATCCATATCTGCGGTCTTTAAGGCGTCAATGGCATCTCTA
ATGTCTTCATTTGGTTGATAACCAAAGCATATAAGATCTAAAATAGTGCT
AAGAGCAAACACGTAGTTGCTCTTAGTTCTCAAAATCTTTAAGCATACTG
AAGAAACTTGAGGATCATTTACCCATGAAGTAGTTTCACCTTTATAAAGT
CCTCGTAGATATCTCCACGAGCTTTCATTTTCAGGGTAGGCTATAATGGC
TTCGATGGTGTAAAGCACTTCAGACTCTCTCATAGCTTTTAGGCCCCCCA
AGAAAGGAGACCTTGTTATGACAAATATCTCTGATTCCAAGCAGAATTGT
TAAAAATGTCTTCTTTAAGTAGTTCTGTGCAATAATTAAGTTCATCTTCC
CATCCTCCTAGTGTTTGAAGAGCCCACTGTCTATGAGACCATGCATGATA
ATGTTTGGCATCAACGGACAGTATCTTTTTGGTGAACTCGAGCTgagctc
gaatttccccgatcgttcaaacatttggcaataaagtttcttaagattga
atcctgttgccggtcttgcgatgattatcatataatttctgttgaattac
gttaagcatgtaataattaacatgtaatgcatgacgttatttatgagatg
ggtttttatgattagagtcccgcaattatacatttaatacgcgatagaaa -continued acaaaatatagcgcgcaaactaggataaattatcgcgcgcggtgtcatct atgttactagatcgggaattc
(Underlined RD29A Promoter; Bold: *Glycine max* anti-*Glycine max* FTA; lower case: NOS terminater Seq.)

SEQ ID NO: 46

GAATTCAAATTTTTCGCCAGTTCTAAATATCCGGAAACCTCTTGGGATGC

CATTGCCCATCTATCTGTAATTTATTGACGAAATAGACGAAAAGGAAGGT

GGCTCCTATAAAGCACATCATTGCGATAACAGAAAGGCCATTGTTGAAGA

TACCTCTGCTGACATTGGTCCCCAAGTGGAAGCACCACCCCATGAGGAGC

ACCGTGGAGTAAGAAGACGTTCGAGCCACGTCGAAAAAGCAAGTGTGTTG

ATGTAGTATCTCCATTGACGTAAGGGATGACGCACAATCCAACTATCCAT

CGCAAGACCATTGCTCTATATAAGAAAGTTAATATCATTTCGAGTGGCCA

CGCTGAGCTCAGGAAGTCTGCTCTTGCGCCAAATCCAATAGTTGGTTCTA

ATTGGATCAACTTGTTTTAGGATAGAACAAATATTTCGTGCTATATTTAA

ATTTTGTTGTTCCCCTTTCTCATCATCATCTAAATCTTGTTTATCCATAT

CTGCGGTCTTTAAGGCGTCAATGGCATCTCTAATGTCTTCATTTGGTTGA

TAACCAAAGCATATAAGATCTAAAATAGTGCTAAGAGCAAACACGTAGTT

GCTCTTAGTTCTCAAAATCTTTAAGCATACTGAAGAAACTTGAGGATCAT

TTACCCATGAAGTAGTTTCACCTTTATAAAGTCCTCGTAGATATCTCCAC

GAGCTTTCATTTTCAGGGTAGGCTATAATGGCTTCGATGGTGTAAAGCAC

TTCAGACTCTCTCATAGCTTTTAGGCCCCCCAAGAAAGGAGACCTTGTTA

TGACAAAATATCTCTGATTCCAAGCAGAATTGTTAAAAATGTCTTCTTTA

AGTAGTTCTGTGCAATAATTAAGTTCATCTTCCCATCCTCCTAGTGTTTG

AAGAGCCCACTGTCTATGAGACCATGCATGATAATGTTTGGCATCAACGG

ACAGTATCTTTTTGGTGAACTCGAGCT*TAAAGGTGAAACTACTTCATGGG*

*TAAATGATCCTCAAGTTTCTTCAGTATGCTTAAAGATTTTGAGAACTAAG*

*AGCAACTACGTGTTTGCTCTTAGCACTATTTTAGATCTTATATGCTTTGG*

*TTATCAACCAAATGAAGACATTAGAGATGCCATTGACGCCTTAAAGACCG*

*CAGATATGGATAAACAAGATTTAGATGATGATGAGAAAGGGGAACAACAA*

*AATTTAAATATACCACGAAATATTTGTTCTATCCTAAAACAAGTTGATCC*

*AATTAGAACCAACTATTGGATTTGGCGCAAGAGCAGACTTCCT*gagctcg aatttccccgatcgttcaaacatttggcaataaagtttcttaagattgaa tcctgttgccggtcttgcgatgattatcatataatttctgttgaattacg ttaagcatgtaataattaacatgtaatgcatgacgttatttatgagatgg gtttttatgattagagtcccgcaattatacatttaatacgcgatagaaaa caaaatatagcgcgcaaactaggataaattatcgcgcgcggtgtcatcta tgttactagatcgggaattc
(Underlined: *Glycine max* FTA Anti-Sense section; Bold: MuA Promoter; Italics: *Glycine max* FTA Sense section; lower case: NOS terminater Seq.)

SEQ ID NO: 47 ggagccatagatgcaattcaatcaaactgaaatttctgcaagaatctcaa acacggagatctcaaagtttgaaagaaaatttatttcttcgactcaaaac

-continued aaacttacgaaatttaggtagaacttatatacattatattgtaattttt gtaacaaaatgtttttattattattatagaattttactggttaaattaaa aatgaatagaaaaggtgaattaagaggagagaggaggtaaacattttctt ctatttttcatattttcaggataaattattgtaaaagtttacaagattt ccatttgactagtgtaaatgaggaatattctctagtaagatcattatttc atctacttcttttatcttctaccagtagaggaataaacaatatttagctc ctttgtaaatacaaattaattttccttcttgacatcattcaattttaatt ttacgtataaaataaaagatcatacctattagaacgattaaggagaaata caattcgaatgagaaggatgtgccgtttgttataataaacagccacacga cgtaaacgtaaaatgaccacatgatgggccaatagacatggaccgactac taataatagtaagttacattttaggatggaataaatatcataccgacatc agttttgaaagaaaagggaaaaaaagaaaaaataaataaaagatatacta ccgacatgagttccaaaaagcaaaaaaaaagatcaagccgacacagacac gcgtagagagcaaaatgactttgacgtcacaccacgaaaacagacgcttc atacgtgtccctttatctctctcagtctctctataaacttagtgagaccc tcctctgttttactcacaaatatgcaaactagaaaacaatcatcaggaat aaagggtttgattacttctattggaaagAGGAAGTCTGCTCTTGCGCCAA

ATCCAATAGTTGGTTCTAATTGGATCAACTTGTTTTAGGATAGAACAAAT

ATTTCGTGCTATATTTAAATTTTGTTGTTCCCCTTTCTCATCATCATCTA

AATCTTGTTTATCCATATCTGCGGTCTTTAAGGCGTCAATGGCATCTCTA

ATGTCTTCATTTGGTTGATAACCAAAGCATATAAGATCTAAAATAGTGCT

AAGAGCAAACACGTAGTTGCTCTTAGTTCTCAAAATCTTTAAGCATACTG

AAGAAACTTGAGGATCATTTACCCATGAAGTAGTTTCACCTTTATAAAGT

CCTCGTAGATATCTCCACGAGCTTTCATTTTCAGGGTAGGCTATAATGGC

TTCGATGGTGTAAAGCACTTCAGACTCTCTCATAGCTTTTAGGCCCCCCA

AGAAAGGAGACCTTGTTATGACAAAATATCTCTGATTCCAAGCAGAATTG

TTAAAAATGTCTTCTTTAAGTAGTTCTGTGCAATAATTAAGTTCATCTTC

CCATCCTCCTAGTGTTTGAAGAGCCCACTGTCTATGAGACCATGCATGAT

AATGTTTGGCATCAACGGACAGTATCTTTTTGGTGAACTCGAGCTTAAAG

GTGAAACTACTTCATGGGTAAATGATCCTCAAGTTTCTTCAGTATGCTTA

AAGATTTTGAGAACTAAGAGCAACTACGTGTTTGCTCTTAGCACTATTTT

AGATCTTATATGCTTTGGTTATCAACCAAATGAAGACATTAGAGATGCCA

TTGACGCCTTAAAGACCGCAGATATGGATAAACAAGATTTAGATGATGAT

GAGAAAGGGGAACAACAAAATTTAAATATAGCACGAAATATTTGTTCTAT

CCTAAAACAAGTTGATCCAATTAGAACCAACTATTGGATTTGGCGCAAGA

GCAGACTTCCTgagctcgaatttccccgatcgttcaaacatttggcaata aagtttcttaagattgaatcctgttgccggtcttgcgatgattatcatat aatttctgttgaattacgttaagcatgtaataattaacatgtaatgcatg acgttatttatgagatgggtttttatgattagagtcccgcaattatacat ttaatacgcgatagaaaacaaaatatagcgcgcaaactaggataaattat -continued cgcgcgcggtgtcatctatgttactagatcgggaattc
(Bold lower case: RD29A Promoter; Underline, Upper case: Antisense GmFTA; Upper case: Sense GmFTA; lower case: NOS terminater)

SEQ ID NO: 48

*gtttacccgccaatatatcctgtc*aaacactgatagtttaaactgaaggc gggaaacgacaatctgatcatgagcggagaattaagggagtcacgttatg acccccgccgatgacgcgggacaagccgttttacgtttggaactgacaga accgcaacgttgaaggagccactcagccgcgggtttctggagtttaatga gctaagcacatacgtcagaaaccattattgcgcgttcaaaagtcgcctaa ggtcactatcagctagcaaatatttcttgtcaaaaatgctccactgacgt tccataaattcccctcggtatccaattagagtctcatattcactctcaat ccaaataatctgcaccggatctggatcgtttcgcatgattgaacaagatg gattgcacgcaggttctccggccgcttgggtggagaggctattcggctat gactgggcacaacagacaatcggctgctctgatgccgccgtgttccggct gtcagcgcaggggcgcccggttctttttgtcaagaccgacctgtccggtg ccctgaatgaactgcaggacgaggcagcgcggctatcgtggctggccacg acgggcgttccttgcgcagctgtgctcgacgttgtcactgaagcgggaag ggactggctgctattgggcgaagtgccggggcaggatctcctgtcatctc accttgctcctgccgagaaagtatccatcatggctgatgcaatgcggcgg ctgcatacgcttgatccggctacctgcccattcgaccaccaagcgaaaca tcgcatcgagcgagcacgtactcggatggaagccggtcttgtcgatcagg atgatctggacgaagagcatcaggggctcgcgccagccgaactgttcgcc aggctcaaggcgcgcatgcccgacggcgatgatctcgtcgtgacccatgg cgatgcctgcttgccgaatatcatggtggaaaatggccgcttttctggat tcatcgactgtggccggctgggtgtggcggaccgctatcaggacatagcg ttggctacccgtgatattgctgaagagcttggcggcgaatgggctgaccg cttcctcgtgctttacggtatcgccgctcccgattcgcagcgcatcgcct tctatcgccttcttgacgagttcttctgagcgggactctggggttcgaaa tgaccgaccaagcgacgcccaacctgccatcacgagatttcgattccacc gccgccttctatgaaaggttgggcttcggaatcgttttccgggacgccgg ctggatgatcctccagcgcggggatctcatgctggagttcttcgcccacg ggatctctgcggaacaggcggtcgaaggtgccgatatcattacgacagca acggccgacaagcacaacgccacgatcctgagcgacaatatgatcgggcc cggcgtccacatcaacggcgtcggcggcgactgcccaggcaagaccgaga tgcaccgcgatatcttgctgcgttcggatattttcgtggagttcccgcca cagacccggatgatccccgatcgttcaaacatttggcaataaagtttctt aagattgaatcctgttgccggtcttgcgatgattatcatataatttctgt tgaattacgttaagcatgtaataattaacatgtaatgcatgacgttattt atgagatgggtttttatgattagagtcccgcaattatacatttaatacgc gatagaaaacaaaatatagcgcgcaaactaggataaattatcgcgcgcgg tgtcatctatgttactagatcgggcctcctgtcaatgctggcggcggctc -continued tggtggtggttctggtggcggctctgagggtggtggctctgagggtggcg gttctgagggtggcggctctgagggaggcggttccggtggtggctctggt tccggtgattttgattatgaaaagatggcaaacgctaataagggggctat gaccgaaaatgccgatgaaaacgcgctacagtctgacgctaaaggcaaac ttgattctgtcgctactgattacggtgctgctatcgatggtttcattggt gacgtttccggccttgctaatggtaatggtgctactggtgattttgctgg ctctaattcccaaatggctcaagtcggtgacggtgataattcacctttaa tgaataatttccgtcaatatttaccttccctccctcaatcggttgaatgt cgcccttttgtctttggcccaatacgcaaaccgcctctccccgcgcgttg gccgattcattaatgcagctggcacgacaggtttcccgactggaaagcgg gcagtgagcgcaacgcaattaatgtgagttagctcactcattaggcaccc caggctttacactttatgcttccggctcgtatgttgtgtggaattgtgag cggataacaatttcacacaggaaacagctatgaccatgattacgccaagc ttgcatgcctgcagcccacagatggttagagaggcttacgcagcaggtct catcaagacgatctacccgagcaataatctccaggaaatcaaataccttc ccaagaaggttaaagatgcagtcaaaagattcaggactaactgcatcaag aacacagagaaagatatatttctcaagatcagaagtactattccagtatg gacgattcaaggcttgcttcacaaaccaaggcaagtaatagagattggag tctctaaaaaggtagttcccactgaatcaaaggccatggagtcaaagatt caaatagaggacctaacagaactcgccgtaaagactggcgaacagttcat acagagtctcttacgactcaatgacaagaagaaaatcttcgtcaacatgg tggagcacgacacacttgtctactccaaaaatatcaaagatacagtctca gaagaccaaagggcaattgagacttttcaacaaagggtaatatccggaaa cctcctcggattccattgcccagctatctgtcactttattgtgaagatag tggaaaaggaaggtggctcctacaaatgccatcattgcgataaaggaaag gccatcgttgaagatgcctctgccgacagtggtcccaaagatggaccccc acccacgaggagcatcgtggaaaaagaagacgttccaaccacgtcttcaa agcaagtggattgatgtgatatctccactgacgtaagggatgacgcacaa tcccactatccttcgcaagacccttcctctatataaggaagttcatttca tttggagagaacacgggggactctagaggatccgtccggaattcccgggt cgacccacgcgtccgggagattcagcgagataagcaattggattatctga tgaaaggcttaaggcagcttggtccgcagttttcttccttagatgctaat cgaccttggctttgttactggattcttcattcaatagctttgcttgggga gactgtggatgatgaattagaaagcaatgccattgacttccttggacgct gccagggctctgaaggtggatacggtggtggtcctggccaacttccacat cttgcaactacttatgctgcagtgaatgcacttgttactttaggaggtga caaagccctttcttcaattaatagagaaaaaatgtcttgtttttttaagac ggatgaaggatacaagtggaggtttcaggatgcatgatatgggagaaatg gatgttcgtgcatgctacactgcaatttcggttgcaagcatcctaaatat tatggatgatgaactcacccagggcctaggagattacatcttgagttgcc

-continued aaacttatgaaggtggcattggaggggaacctggctccgaagctcacggt
gggtatacctactgtggtttggctgctatgattttaatcaatgaggtcga
ccgtttgaatttggattcattaatgaattgggctgtacatcgacaaggag
tagaaatgggatttcaaggtaggacgaacaaattggtcgatggttgctac
acattttggcaggcagccccttgtgttctactacaaagattatattcaac
caatgatcatgacgttcatggatcatcacatatatcagaagggacaaatg
aagaacatcatgctcatgatgaagatgaccttgaagacagtgatgatgat
gatgattctgatgaggacaacgatgaagattcagtgaatggtcacagaat
ccatcatacatccacctacattaacaggagaatgcaactggtttttgata
gcctcggcttgcagagatatgtactcttgtgctctaagatccctgacggt
ggattcagagacaagccgaggaaaccccgtgacttctaccacacatgtta
ctgcctgagcggcttgtctgtggctcagcacgcttggttaaaagacgagg
acactcctcctttgactcgcgacattatgggtggctactcgaatctcctt
gaacctgttcaacttcttcacaacattgtcatggatcagtataatgaagc
tatcgagttcttctttaaagcagcatgactcgaatttccccgatcgttca
aacatttggcaataaagtttcttaagattgaatcctgttgccggtcttgc
gatgattatcatataatttctgttgaattacgttaagcatgtaataatta
acatgtaatgcatgacgttatttatgagatgggtttttatgattagagtc
ccgcaattatacatttaatacgcgatagaaaacaaaatatagcgcgcaaa
ctaggataaattatcgcgcgcggtgtcatctatgttactagatcgggaat
tcactggccgtcgttttacaacgtcgtgactgggaaaaccctggcgttac
ccaacttaatcgccttgcagcacatccccctttcgccagctggcgtaata
gcgaagaggcccgcaccgatcgcccttcccaacagttgcgcagcctgaat
ggcgcccgctcctttcgctttcttcccttcctttctcgccacgttcgccg
gctttccccgtcaagctctaaatcgggggctccctttagggttccgattt
agtgctttacggcacctcgaccccaaaaaacttgatttgggtgatggttc
acgtagtgggccatcgccctgatagacggtttttcgccctttgacgttgg
agtccacgttctttaatagtggactcttgttccaaactggaacaacactc
aaccctatctcgggctattcttttgatttataagggattttgccgatttc
ggaaccaccatcaaacaggattttcgcctgctggggcaaaccagcgtgga
ccgcttgctgcaactctctcagggccaggcggtgaagggcaatcagctgt
tgcccgtctcactggtgaaaagaaaaaccaccccagtacattaaaaacgt
ccgcaatgtgttattaagttgtctaagcgtcaattt*gtttacaccacaat*
*atatcctgcca*
(Underline: 35S promoter; Bold: anti-AtFTB)

SEQ ID NO: 49
*gtttacccgccaatatatcctgtc*aaacactgatagtttaaactgaaggc
gggaaacgacaatctgatcatgagcggagaattaagggagtcacgttatg
acccccgccgatgacgcgggacaagccgttttacgtttggaactgacaga
accgcaacgttgaaggagccactcagccgcgggtttctggagtttaatga
gctaagcacatacgtcagaaaccattattgcgcgttcaaaagtcgcctaa -continued ggtcactatcagctagcaaatatttcttgtcaaaaatgctccactgacgt
tccataaattcccctcggtatccaattagagtctcatattcactctcaat
ccaaataatctgcaccggatctggatcgtttcgcatgattgaacaagatg
gattgcacgcaggttctccggccgcttgggtggagaggctattcggctat
gactgggcacaacagacaatcggctgctctgatgccgccgtgttccggct
gtcagcgcaggggcgcccggttctttttgtcaagaccgacctgtccggtg
ccctgaatgaactgcaggacgaggcagcgcggctatcgtggctggccacg
acgggcgttccttgcgcagctgtgctcgacgttgtcactgaagcgggaag
ggactggctgctattgggcgaagtgccggggcaggatctcctgtcatctc
accttgctcctgccgagaaagtatccatcatggctgatgcaatgcggcgg
ctgcatacgcttgatccggctacctgcccattcgaccaccaagcgaaaca
tcgcatcgagcgagcacgtactcggatggaagccggtcttgtcgatcagg
atgatctggacgaagagcatcaggggctcgcgccagccgaactgttcgcc
aggctcaaggcgcgcatgcccgacggcgatgatctcgtcgtgacccatgg
cgatgcctgcttgccgaatatcatggtggaaaatggccgcttttctggat
tcatcgactgtggccggctgggtgtggcggaccgctatcaggacatagcg
ttggctacccgtgatattgctgaagagcttggcggcgaatgggctgaccg
cttcctcgtgctttacggtatcgccgctcccgattcgcagcgcatcgcct
tctatcgccttcttgacgagttcttctgagcgggactctggggttcgaaa
tgaccgaccaagcgacgcccaacctgccatcacgagatttcgattccacc
gccgccttctatgaaaggttgggcttcggaatcgttttccgggacgccgg
ctggatgatcctccagcgcggggatctcatgctggagttcttcgcccacg
ggatctctgcggaacaggcggtcgaaggtgccgatatcattacgacagca
acggccgacaagcacaacgccacgatcctgagcgacaatatgatcgggcc
cggcgtccacatcaacggcgtcggcggcgactgcccaggcaagaccgaga
tgcaccgcgatatcttgctgcgttcggatattttcgtggagttcccgcca
cagacccggatgatccccgatcgttcaaacatttggcaataaagtttctt
aagattgaatcctgttgccggtcttgcgatgattatcatataatttctgt
tgaattacgttaagcatgtaataattaacatgtaatgcatgacgttattt
atgagatgggtttttatgattagagtcccgcaattatacatttaatacgc
gatagaaaacaaaatatagcgcgcaaactaggataaattatcgcgcgcgg
tgtcatctatgttactagatcgggcctcctgtcaatgctggcggcggctc
tggtggtggttctggtggcggctctgagggtggtggctctgagggtggcg
gttctgagggtggcggctctgagggaggcggttccggtggtggctctggt
tccggtgattttgattatgaaaagatggcaaacgctaataaggggctat
gaccgaaaatgccgatgaaaacgcgctacagtctgacgctaaaggcaaac
ttgattctgtcgctactgattacggtgctgctatcgatggtttcattggt
gacgtttccggccttgctaatggtaatggtgctactggtgattttgctgg
ctctaattcccaaatggctcaagtcggtgacggtgataattcacctttaa
tgaataatttccgtcaatatttaccttccctccctcaatcggttgaatgt -continued cgccccttttgtctttggcccaatacgcaaaccgcctctccccgcgcgttg
gccgattcattaatgcagctggcacgacaggtttcccgactggaaagcgg
gcagtgagcgcaacgcaattaatgtgagttagctcactcattaggcaccc
caggctttacactttatgcttccggctcgtatgttgtgtggaattgtgag
cggataacaatttcacacaggaaacagctatgaccatgattacgccaagc
ttgcatgcctgcagggagccatagatgcaattcaatcaaactgaaatttc
tgcaagaatctcaaacacggagatctcaaagtttgaaagaaaatttattt
cttcgactcaaaacaaacttacgaaatttaggtagaacttatatacatta
tattgtaatttttgtaacaaaatgtttttattattattatagaattta
ctggttaaattaaaaatgaatagaaaaggtgaattaagaggagagaggag
gtaaacattttcttctatttttcatattttcaggataaattattgtaaa
agtttacaagatttccatttgactagtgtaaatgaggaatattctctagt
aagatcattatttcatctacttcttttatcttctaccagtagaggaataa
acaatatttagctcctttgtaaatacaaattaattttccttcttgacatc
attcaattttaattttacgtataaaataaaagatcatacctattagaacg
attaaggagaaatacaattcgaatgagaaggatgtgccgtttgttataat
aaacagccacacgacgtaaacgtaaaatgaccacatgatgggccaataga
catggaccgactactaataatagtaagttacattttaggatggaataaat
atcataccgacatcagttttgaaagaaaagggaaaaaaagaaaaaataaa
taaaagatatactaccgacatgagttccaaaaagcaaaaaaaaagatcaa
gccgacacagacacgcgtagagagcaaaatgactttgacgtcacaccacg
aaaacagacgcttcatacgtgtccctttatctctctcagtctctctataa
acttagtgagaccctcctctgttttactcacaaatatgcaaactagaaaa
caatcatcaggaataaagggtttgattacttctattggaaaggactctag
aggatccgtccggaattcccgggtcgacccacgcgtccgggagattcagc
gagataagcaattggattatctgatgaaaggcttaaggcagcttggtccg
cagttttcttccttagatgctaatcgaccttggctttgttactggattct
tcattcaatagctttgcttggggagactgtggatgatgaattagaaagca
atgccattgacttccttggacgctgccagggctctgaaggtggatacggt
ggtggtcctggccaacttccacatcttgcaactacttatgctgcagtgaa
tgcacttgttactttaggaggtgacaaagccctttcttcaattaatagag
aaaaaatgtcttgtttttaagacggatgaaggatacaagtggaggtttc
aggatgcatgatatgggagaaatggatgttcgtgcatgctacactgcaat
ttcggttgcaagcatcctaaatattatggatgatgaactcacccagggcc
taggagattacatcttgagttgccaaacttatgaaggtggcattggaggg
gaacctggctccgaagctcacggtgggtatacctactgtggtttggctgc
tatgattttaatcaatgaggtcgaccgtttgaatttggattcattaatga
attgggctgtacatcgacaaggagtagaaatgggatttcaaggtaggacg
aacaaattggtcgatggttgctacacattttggcaggcagccccttgtgt
tctactacaaagattatattcaaccaatgatcatgacgttcatggatcat
cacatatatcagaagggacaaatgaagaacatcatgctcatgatgaagat
gaccttgaagacagtgatgatgatgatgattctgatgaggacaacgatga
agattcagtgaatggtcacagaatccatcatacatccacctacattaaca
ggagaatgcaactggtttttgatagcctcggcttgcagagatatgtactc
ttgtgctctaagatccctgacggtggattcagagacaagccgaggaaacc
ccgtgacttctaccacacatgttactgcctgagcggcttgtctgtggctc
agcacgcttggttaaaagacgaggacactcctcctttgactcgcgacatt
atgggtggctactcgaatctccttgaacctgttcaacttcttcacaacat
tgtcatggatcagtataatgaagctatcgagttcttctttaaagcagcat
gactcgaatttccccgatcgttcaaacatttggcaataaagtttcttaag
attgaatcctgttgccggtcttgcgatgattatcatataatttctgttga
attacgttaagcatgtaataattaacatgtaatgcatgacgttatttatg
agatgggtttttatgattagagtcccgcaattatacatttaatacgcgat
agaaaacaaaatatagcgcgcaaactaggataaattatcgcgcgcggtgt
catctatgttactagatcgggaattcactggccgtcgttttacaacgtcg
tgactgggaaaaccctggcgttacccaacttaatcgccttgcagcacatc
ccccttttcgccagctggcgtaatagcgaagaggcccgcaccgatcgccct
tcccaacagttgcgcagcctgaatggcgcccgctcctttcgctttcttcc
cttcctttctcgccacgttcgccggctttccccgtcaagctctaaatcgg
gggctccctttagggttccgatttagtgctttacggcacctcgaccccaa
aaaacttgatttgggtgatggttcacgtagtgggccatcgccctgataga
cggtttttcgccctttgacgttggagtccacgttctttaatagtggactc
ttgttccaaactggaacaacactcaaccctatctcgggctattcttttga
tttataagggatttgccgatttcggaaccaccatcaaacaggattttcg
cctgctggggcaaaccagcgtggaccgcttgctgcaactctctcagggcc
aggcggtgaagggcaatcagctgttgcccgtctcactggtgaaaagaaaa
accaccccagtacattaaaaacgtccgcaatgtgttattaagttgtctaa
gcgtcaattt*gtttacaccacaatatatcctgcca*
(Underline: RD29A Promoter; Bold: anti-AtFTB)

SEQ ID NO: 50

*gtttacccgccaatatatcctgtc*aaacactgatagtttaaactgaaggc
gggaaacgacaatctgatcatgagcggagaattaagggagtcacgttatg
acccccgccgatgacgcgggacaagccgttttacgtttggaactgacaga
accgcaacgttgaaggagccactcagccgcgggtttctggagtttaatga
gctaagcacatacgtcagaaaccattattgcgcgttcaaaagtcgcctaa
ggtcactatcagctagcaaatatttcttgtcaaaaatgctccactgacgt
tccataaattcccctcggtatccaattagagtctcatattcactctcaat
ccaaataatctgcaccggatctggatcgtttcgcatgattgaacaagatg
gattgcacgcaggttctccggccgcttgggtggagaggctattcggctat
gactgggcacaacagacaatcggctgctctgatgccgccgtgttccggct
gtcagcgcaggggcgcccggttctttttgtcaagaccgacctgtccggtg -continued ccctgaatgaactgcaggacgaggcagcgcggctatcgtggctggccacg
acgggcgttccttgcgcagctgtgctcgacgttgtcactgaagcgggaag
ggactggctgctattgggcgaagtgccggggcaggatctcctgtcatctc
accttgctcctgccgagaaagtatccatcatggctgatgcaatgcggcgg
ctgcatacgcttgatccggctacctgcccattcgaccaccaagcgaaaca
tcgcatcgagcgagcacgtactcggatggaagccggtcttgtcgatcagg
atgatctggacgaagagcatcaggggctcgcgccagccgaactgttcgcc
aggctcaaggcgcgcatgcccgacggcgatgatctcgtcgtgacccatgg
cgatgcctgcttgccgaatatcatggtggaaaatggccgcttttctggat
tcatcgactgtggccggctgggtgtggcggaccgctatcaggacatagcg
ttggctacccgtgatattgctgaagagcttggcggcgaatgggctgaccg
cttcctcgtgctttacggtatcgccgctcccgattcgcagcgcatcgcct
tctatcgccttcttgacgagttcttctgagcgggactctggggttcgaaa
tgaccgaccaagcgacgcccaacctgccatcacgagatttcgattccacc
gccgccttctatgaaaggttgggcttcggaatcgttttccgggacgccgg
ctggatgatcctccagcgcggggatctcatgctggagttcttcgcccacg
ggatctctgcggaacaggcggtcgaaggtgccgatatcattacgacagca
acggccgacaagcacaacgccacgatcctgagcgacaatatgatcgggcc
cggcgtccacatcaacggcgtcggcggcgactgcccaggcaagaccgaga
tgcaccgcgatatcttgctgcgttcggatattttcgtggagttcccgcca
cagacccggatgatccccgatcgttcaaacatttggcaataaagtttctt
aagattgaatcctgttgccggtcttgcgatgattatcatataatttctgt
tgaattacgttaagcatgtaataattaacatgtaatgcatgacgttattt
atgagatgggtttttatgattagagtcccgcaattatacatttaatacgc
gatagaaaacaaaatatagcgcgcaaactaggataaattatcgcgcgcgg
tgtcatctatgttactagatcgggcctcctgtcaatgctggcggcggctc
tggtggtggttctggtggcggctctgagggtggtggctctgagggtggcg
gttctgagggtggcggctctgagggaggcggttccggtggtggctctggt
tccggtgattttgattatgaaaagatggcaaacgctaataaggggctat
gaccgaaaatgccgatgaaaacgcgctacagtctgacgctaaaggcaaac
ttgattctgtcgctactgattacggtgctgctatcgatggtttcattggt
gacgtttccggccttgctaatggtaatggtgctactggtgattttgctgg
ctctaattcccaaatggctcaagtcggtgacggtgataattcacctttaa
tgaataatttccgtcaatatttaccttccctccctcaatcggttgaatgt
cgcccttttgtctttggcccaatacgcaaaccgcctctccccgcgcgttg
gccgattcattaatgcagctggcacgacaggtttcccgactggaaagcgg
gcagtgagcgcaacgcaattaatgtgagttagctcactcattaggcaccc
caggctttacactttatgcttccggctcgtatgttgtgtggaattgtgag
cggataacaatttcacacaggaaacagctatgaccatgattacgccaagc
ttgcatgcctgcagcccacagatggttagagaggcttacgcagcaggtct -continued catcaagacgatctacccgagcaataatctccaggaaatcaaataccttc
ccaagaaggttaaagatgcagtcaaaagattcaggactaactgcatcaag
aacacagagaaagatatatttctcaagatcagaagtactattccagtatg
gacgattcaaggcttgcttcacaaaccaaggcaagtaatagagattggag
tctctaaaaaggtagttcccactgaatcaaaggccatggagtcaaagatt
caaatagaggacctaacagaactcgccgtaaagactggcgaacagttcat
acagagtctcttacgactcaatgacaagaagaaaatcttcgtcaacatgg
tggagcacgacacacttgtctactccaaaaatatcaaagatacagtctca
gaagaccaaagggcaattgagacttttcaacaaagggtaatatccggaaa
cctcctcggattccattgcccagctatctgtcactttattgtgaagatag
tggaaaaggaaggtggctcctacaaatgccatcattgcgataaaggaaag
gccatcgttgaagatgcctctgccgacagtggtcccaaagatggaccccc
acccacgaggagcatcgtggaaaaagaagacgttccaaccacgtcttcaa
agcaagtggattgatgtgatatctccactgacgtaagggatgacgcacaa
tcccactatccttcgcaagacccttcctctatataaggaagttcatttca
tttggagagaacacggggggactctagaggatcctcCTCCTAGGCCCTGGG
TGAGTTCATCATCCATAATATTTAGGATGCTTGCAACCGAAATTGCAGTG
TAGCATGCACGAACATCCATTTCTCCCATATCATGCATCCTGAAACCTCC
ACTTGTATCCTTCATCCGTCTTAAAAAACAAGACATTTTTTCTCTATTAA
TTGAAGAAAGGGCTTTGTCACCTCCTAAAGTAACAAGTGCATTCACTGCA
GCATAAGTAGTTGCAAGATGTGGAAGTTGGCCAGGACCACCACCGTATCC
ACCTTCAGAGCCCTGGCAGCGTCCAAGGAAGTCAATGGCATTGCTTTCTA
ATTCATCATCCACAGTCTCCCCAAGCAAAGCTATTGAATGAAGAATCCAG
TAACAAAGCCAAGGTCGATTAGCATCTAAGGAAGAAAACTGCGGACCAAG
CTGCCTTAAGCCTTTCATCAGATAATCCAATTGCTTATCTCGCTGAATCT
CCCGGACGCGTGGGTCGACCCGGGAATTCCGGACgaggatccccATCTAC
CCGCTTCGCGTCGGCATCCGGTCAGTGGCAGTGAAGGGCGAACAGTTCCT
GATTAACCACAAACCGTTCTACTTTACTGGCTTTGGTCGTCATGAAGATG
CGGACTTGCGTGGCAAAGGATTCGATAACGTGCTGATGGTGCACGACCAC
GCATTAATGGACTGGATTGGGGCCAACTCCTACCGTACCTCGCATTACCC
TTACGCTGAAGAGATGCTCGACTGGGCAGATGAACATGGCATCGTGGTGA
TTGATGAAACTGCTGCTGTCGGCTTTTCGCTCTCTTTAGGCATTGGTTTC
GAAGCGGGCAACAAGCCGAAAGAACTGTACAGCGAAGAGGCAGTCAACGG
GGAAACTCAGCAAGCGCACTTACAGGCGATTAAAGAGCTGATAGCGCGTG
ACAAAAACCACCCAAGCGTGGTGATGTGGAGTATTGCCAACGAACCGGAT
ACCCGTCCGCAAGGTGCACGGGAATATTTCGCGCCACTGGCGGAAGCAAC
GCGTAAACTCGACCCGACGCGTCCGATCACCTGCGTCAATGTAATGTTCT
GCGACGCTCACACCGATACCATCAGCGATCTCTTTGATGTGCTGTGCCTG
AACCGTTATTACGGATGGTATGTCCAAAGCGGCGATTTGGAAACGGCAGA
GAAGGTACTGGAAAAAGAACTTCTGGCCTGGCAGGAGAAACTGTACACCG -continued ACATGTGGAGTGAAGAGTATCAGTGTGCATGGCTGGATATGTATCACCGC
GTCTTTGATCGCGTCAGCGCCGTCGTCGGTGAACAGGTATGGAATTTCGC
CGATTTTGCGACCTCGCAAGGCATATTGCGCGTTGGCGGTAACAAGAAAG
GGATCTTCACTCGCGACCGCAAACCGAAGTCGGCGGCTTTTCTGCTGCAA
AAACGCTGGACTGGCATGAACTTCGGTGAAAAACCGCAGCAGGGAGGCAA
ACAATGAATCAACAACTCTCCTGGCGCACCATCGTCGGCTACAGCCTCGG
GAATTGCTACCGAGCTCgtccggaattcccgggtcgacccacgcgtccgg
gagattcagcgagataagcaattggattatctgatgaaaggcttaaggca
gcttggtccgcagttttcttccttagatgctaatcgaccttggctttgtt
actggattcttcattcaatagctttgcttggggagactgtggatgatgaa
ttagaaagcaatgccattgacttccttggacgctgccagggctctgaagg
tggatacggtggtggtcctggccaacttccacatcttgcaactacttatg
ctgcagtgaatgcacttgttactttaggaggtgacaaagccctttcttca
attaatagagaaaaaatgtcttgtttttaagacggatgaaggatacaag
tggaggtttcaggatgcatgatatgggagaaatggatgttcgtgcatgct
acactgcaatttcggttgcaagcatcctaaatattatggatgatgaactc
acccagggcctaggagctcgaatttccccgatcgttcaaacatttggcaa
taaagtttcttaagattgaatcctgttgccggtcttgcgatgattatcat
ataatttctgttgaattacgttaagcatgtaataattaacatgtaatgca
tgacgttatttatgagatgggtttttatgattagagtcccgcaattatac
atttaatacgcgatagaaaacaaaatatagcgcgcaaactaggataaatt
atcgcgcgcggtgtcatctatgttactagatcgggaattcactggccgtc
gttttacaacgtcgtgactgggaaaaccctggcgttacccaacttaatcg
ccttgcagcacatccccctttcgccagctggcgtaatagcgaagaggccc
gcaccgatcgcccttcccaacagttgcgcagcctgaatggcgcccgctcc
tttcgctttcttcccttcctttctcgccacgttcgccggctttccccgtc
aagctctaaatcgggggctccctttagggttccgatttagtgctttacgg
cacctcgaccccaaaaaacttgatttgggtgatggttcacgtagtgggcc
atcgccctgatagacggtttttcgccctttgacgttggagtccacgttct
ttaatagtggactcttgttccaaactggaacaacactcaaccctatctcg
ggctattcttttgatttataagggattttgccgatttcggaaccaccatc
aaacaggattttcgcctgctggggcaaaccagcgtggaccgcttgctgca
actctctcagggccaggcggtgaagggcaatcagctgttgcccgtctcac
tggtgaaaagaaaaaccaccccagtacattaaaaacgtccgcaatgtgtt
attaagttgtctaagcgtcaattt*gtttacaccacaatatatcctgcca*

(Underline: 35S promoter; Bold uppercase: antisense AtFTB; Lower case Bold: sense AtFTB)

SEQ ID NO: 51

*gtttacccgccaatatatcctgtc*caaacactgatagtttaaactgaaggc
gggaaacgacaatctgatcatgagcggagaattaagggagtcacgttatg
acccccgccgatgacgcgggacaagccgttttacgtttggaactgacaga -continued accgcaacgttgaaggagccactcagccgcgggtttctggagtttaatga
gctaagcacatacgtcagaaaccattattgcgcgttcaaaagtcgcctaa
ggtcactatcagctagcaaatatttcttgtcaaaaatgctccactgacgt
tccataaattcccctcggtatccaattagagtctcatattcactctcaat
ccaaataatctgcaccggatctggatcgtttcgcatgattgaacaagatg
gattgcacgcaggttctccggccgcttgggtggagaggctattcggctat
gactgggcacaacagacaatcggctgctctgatgccgccgtgttccggct
gtcagcgcaggggcgcccggttctttttgtcaagaccgacctgtccggtg
ccctgaatgaactgcaggacgaggcagcgcggctatcgtggctggccacg
acgggcgttccttgcgcagctgtgctcgacgttgtcactgaagcgggaag
ggactggctgctattgggcgaagtgccggggcaggatctcctgtcatctc
accttgctcctgccgagaaagtatccatcatggctgatgcaatgcggcgg
ctgcatacgcttgatccggctacctgcccattcgaccaccaagcgaaaca
tcgcatcgagcgagcacgtactcggatggaagccggtcttgtcgatcagg
atgatctggacgaagagcatcaggggctcgcgccagccgaactgttcgcc
aggctcaaggcgcgcatgcccgacggcgatgatctcgtcgtgacccatgg
cgatgcctgcttgccgaatatcatggtggaaaatggccgcttttctggat
tcatcgactgtggccggctgggtgtggcggaccgctatcaggacatagcg
ttggctacccgtgatattgctgaagagcttggcggcgaatgggctgaccg
cttcctcgtgctttacggtatcgccgctcccgattcgcagcgcatcgcct
tctatcgccttcttgacgagttcttctgagcgggactctggggttcgaaa
tgaccgaccaagcgacgcccaacctgccatcacgagatttcgattccacc
gccgccttctatgaaaggttgggcttcggaatcgttttccgggacgccgg
ctggatgatcctccagcgcggggatctcatgctggagttcttcgcccacg
ggatctctgcggaacaggggtcgaaggtgccgatatcattacgacagcaa
cggccgacaagcacaacgccacgatcctgagcgacaatatgatcgggccc
ggcgtccacatcaacggcgtcggcggcgactgcccaggcaagaccgagat
gcaccgcgatatcttgctgcgttcggatattttcgtggagttcccgccac
agacccggatgatccccgatcgttcaaacatttggcaataaagtttctta
agattgaatcctgttgccggtcttgcgatgattatcatataatttctgtt
gaattacgttaagcatgtaataattaacatgtaatgcatgacgttattta
tgagatgggtttttatgattagagtcccgcaattatacatttaatacgcg
atagaaaacaaaatatagcgcgcaaactaggataaattatcgcgcgcggt
gtcatctatgttactagatcgggcctcctgtcaatgctggcggcggctct
ggtggtggttctggtggcggctctgagggtggtggctctgagggtggcgg
ttctgagggtggcggctctgagggaggcggttccggtggtggctctggtt
ccggtgattttgattatgaaaagatggcaaacgctaataagggggctatg
accgaaaatgccgatgaaaacgcgctacagtctgacgctaaaggcaaact
tgattctgtcgctactgattacggtgctgctatcgatggtttcattggtg
acgtttccggccttgctaatggtaatggtgctactggtgattttgctggc -continued tctaattcccaaatggctcaagtcggtgacggtgataattcacctttaat
gaataatttccgtcaatatttaccttccctccctcaatcggttgaatgtc
gcccttttgtctttggcccaatacgcaaaccgcctctccccgcgcgttgg
ccgattcattaatgcagctggcacgacaggtttcccgactggaaagcggg
cagtgagcgcaacgcaattaatgtgagttagctcactcattaggcacccc
aggctttacactttatgcttccggctcgtatgttgtgtggaattgtgagc
ggataacaatttcacacaggaaacagctatgaccatgattacgccaagct
tgcatgcctgcagggagccatagatgcaattcaatcaaactgaaatttct
gcaagaatctcaaacacggagatctcaaagtttgaaagaaaatttatttc
ttcgactcaaaacaaacttacgaaatttaggtagaacttatatacattat
attgtaatttttgtaacaaaatgtttttattattattatagaatttttac
tggttaaattaaaaatgaatagaaaaggtgaattaagaggagagaggagg
taaacatttttcttctatttttttcatattttcaggataaattattgtaaaa
gtttacaagatttccatttgactagtgtaaatgaggaatattctctagta
agatcattatttcatctacttcttttatcttctaccagtagaggaataaa
caatatttagctcctttgtaaatacaaattaattttccttcttgacatca
ttcaattttaattttacgtataaaataaaagatcatacctattagaacga
ttaaggagaaatacaattcgaatgagaaggatgtgccgtttgttataata
aacagccacacgacgtaaacgtaaaatgaccacatgatgggccaatagac
atggaccgactactaataatagtaagttacattttaggatggaataaata
tcataccgacatcagttttgaaagaaaagggaaaaaaagaaaaaataaat
aaaagatatactaccgacatgagttccaaaaagcaaaaaaaaagatcaag
ccgacacagacacgcgtagagagcaaaatgactttgacgtcacaccacga
aaacagacgcttcatacgtgtccctttatctctctcagtctctctataaa
cttagtgagaccctcctctgttttactcacaaatatgcaaactagaaaac
aatcatcaggaataaagggtttgattacttctattggaaaggactctaga
ggatcctcCTCCTAGGCCCTGGGTGAGTTCATCATCCATAATATTTAGGA
TGCTTGCAACCGAAATTGCAGTGTAGCATGCACGAACATCCATTTCTCCC
ATATCATGCATCCTGAAACCTCCACTTGTATCCTTCATCCGTCTTAAAAA
ACAAGACATTTTTTCTCTATTAATTGAAGAAAGGGCTTTGTCACCTCCTA
AAGTAACAAGTGCATTCACTGCAGCATAAGTAGTTGCAAGATGTGGAAGT
TGGCCAGGACCACCACCGTATCCACCTTCAGAGCCCTGGCAGCGTCAAGG
AAGTCAATGGCATTGCTTTCTAATTCATCATCCACAGTCTCCCCAAGCAA
AGCTATTGAATGAAGAATCCAGTAACAAAGCCAAGGTCGATTAGCATCTA
AGGAAGAAAACTGCGGACCAAGCTGCCTTAAGCCTTTCATCAGATAATCC
AATTGCTTATCTCGCTGAATCTCCCGGACGCGTGGGTCGACCCGGGAATT
CCGGACgaggatccccATCTACCCGCTTCGCGTCGGCATCCGGTCAGTGG
CAGTGAAGGGCGAACAGTTCCTGATTAACCACAAACCGTTCTACTTTACT
GGCTTTGGTCGTCATGAAGATGCGGACTTGCGTGGCAAAGGATTCGATAA
CGTGCTGATGGTGCACGACCACGCATTAATGGACTGGATTGGGGCCAACT -continued CCTACCGTACCTCGCATTACCCTTACGCTGAAGAGATGCTCGACTGGGCA
GATGAACATGGCATCGTGGTGATTGATGAAACTGCTGCTGTCGGCTTTTC
GCTCTCTTTAGGCATTGGTTTCGAAGCGGGCAACAAGCCGAAAGAACTGT
ACAGCGAAGAGGCAGTCAACGGGGAAACTCAGCAAGCGCACTTACAGGCG
ATTAAAGAGCTGATAGCGCGTGACAAAAACCACCCAAGCGTGGTGATGTG
GAGTATTGCCAACGAACCGGATACCCGTCCGCAAGGTGCACGGGAATATT
TCGCGCCACTGGCGGAAGCAACGCGTAAACTCGACCCGACGCGTCCGATC
ACCTGCGTCAATGTAATGTTCTGCGACGCTCACACCGATACCATCAGCGA
TCTCTTTGATGTGCTGTGCCTGAACCGTTATTACGGATGGTATGTCCAAA
GCGGCGATTTGGAAACGGCAGAGAAGGTACTGGAAAAAGAACTTCTGGCC
TGGCAGGAGAAACTGTACACCGACATGTGGAGTGAAGAGTATCAGTGTGC
ATGGCTGGATATGTATCACCGCGTCTTTGATCGCGTCAGCGCCGTCGTCG
GTGAACAGGTATGGAATTTCGCCGATTTTGCGACCTCGCAAGGCATATTG
CGCGTTGGCGGTAACAAGAAAGGGATCTTCACTCGCGACCGCAAACCGAA
GTCGGCGGCTTTTCTGCTGCAAAAACGCTGGACTGGCATGAACTTCGGTG
AAAAACCGCAGCAGGGAGGCAAACAATGAATCAACAACTCTCCTGGCGCA
CCATCGTCGGCTACAGCCTCGGGAATTGCTACCGAGCTCgtccggaattc
ccgggtcgacccacgcgtccgggagattcagcgagataagcaattggatt
atctgatgaaaggcttaaggcagcttggtccgcagttttcttccttagat
gctaatcgaccttggctttgttactggattcttcattcaatagctttgct
tggggagactgtggatgatgaattagaaagcaatgccattgacttccttg
gacgctgccagggctctgaaggtggatacggtggtggtcctggccaactt
ccacatcttgcaactacttatgctgcagtgaatgcacttgttactttagg
aggtgacaaagccctttcttcaattaatagagaaaaaatgtcttgttttt
taagacggatgaaggatacaagtggaggtttcaggatgcatgatatggga
gaaatggatgttcgtgcatgctacactgcaatttcggttgcaagcatcct
aaatattatggatgatgaactcacccagggcctaggagctcgaatttccc
cgatcgttcaaacatttggcaataaagtttcttaagattgaatcctgttg
ccggtcttgcgatgattatcatataatttctgttgaattacgttaagcat
gtaataattaacatgtaatgcatgacgttatttatgagatgggtttttat
gattagagtcccgcaattatacatttaatacgcgatagaaaacaaaatat
agcgcgcaaactaggataaattatcgcgcgcggtgtcatctatgttacta
gatcgggaattcactggccgtcgttttacaacgtcgtgactgggaaaacc
ctggcgttacccaacttaatcgccttgcagcacatccccctttcgccagc
tggcgtaatagcgaagaggcccgcaccgatcgcccttcccaacagttgcg
cagcctgaatggcgcccgctcctttcgctttcttcccttcctttctcgcc
acgttcgccggctttccccgtcaagctctaaatcgggggctccctttagg
gttccgatttagtgctttacggcacctcgaccccaaaaaacttgatttgg
gtgatggttcacgtagtgggccatcgccctgatagacggtttttcgccct
ttgacgttggagtccacgttctttaatagtggactcttgttccaaactgg -continued aacaacactcaaccctatctcgggctattcttttgatttataagggatttt gccgatttcggaaccaccatcaaacaggattttcgcctgctggggcaaaccagcgtggaccgcttgctgcaactctctcagggccaggcggtgaagggcaatcagctgttgcccgtctcactggtgaaaagaaaaaccaccccagtacattaaaaacgtccgcaatgtgttattaagttgtctaagcgtcaattt*gtttacaccacaatatatcctgcca*

(Underline: RD29A promoter; Bold uppercase: antisense AtFTB; Lower case Bold: sense AtFTB)

SEQ ID NO: 52

*gtttacccgccaatatatcctgtc*caaacactgatagtttaaactgaaggcgggaaacgacaatctgatcatgagcggagaattaagggagtcacgttatgacccccgccgatgacgcgggacaagccgttttacgtttggaactgacagaaccgcaacgttgaaggagccactcagccgcgggtttctggagtttaatgagctaagcacatacgtcagaaaccattattgcgcgttcaaaagtcgcctaaggtcactatcagctagcaaatatttcttgtcaaaaatgctccactgacgttccataaattcccctcggtatccaattagagtctcatattcactctcaatccaaataatctgcaccggatctggatcgtttcgcatgattgaacaagatggattgcacgcaggttctccggccgcttgggtggagaggctattcggctatgactgggcacaacagacaatcggctgctctgatgccgccgtgttccggctgtcagcgcaggggcgcccggttctttttgtcaagaccgacctgtccggtgccctgaatgaactgcaggacgaggcagcgcggctatcgtggctggccacgacgggcgttccttgcgcagctgtgctcgacgttgtcactgaagcgggaagggactggctgctattgggcgaagtgccggggcaggatctcctgtcatctcaccttgctcctgccgagaaagtatccatcatggctgatgcaatgcggcggctgcatacgcttgatccggctacctgcccattcgaccaccaagcgaaacatcgcatcgagcgagcacgtactcggatggaagccggtcttgtcgatcaggatgatctggacgaagagcatcaggggctcgcgccagccgaactgttcgccaggctcaaggcgcgcatgcccgacggcgatgatctcgtcgtgacccatggcgatgcctgcttgccgaatatcatggtggaaaatggccgcttttctggattcatcgactgtggccggctgggtgtggcggaccgctatcaggacatagcgttggctacccgtgatattgctgaagagcttggcggcgaatgggctgaccgcttcctcgtgctttacggtatcgccgctcccgattcgcagcgcatcgccttctatcgccttcttgacgagttcttctgagcgggactctggggttcgaaatgaccgaccaagcgacgcccaacctgccatcacgagatttcgattccaccgccgccttctatgaaaggttgggcttcggaatcgttttccgggacgccggctggatgatcctccagcgcggggatctcatgctggagttcttcgcccacgggatctctgcggaacaggcggtcgaaggtgccgatatcattacgacagcaacggccgacaagcacaacgccacgatcctgagcgacaatatgatcgggcccggcgtccacatcaacggcgtcggcggcgactgcccaggcaagaccgagatgcaccgcgatatcttgctgcgttcggatattttcgtggagttcccgccacagacccggatgatccccgatcgttcaaacatttggcaataaagtttcttaagattgaatcctgttgccggtcttgcgatgattatcatataatttctgt -continued tgaattacgttaagcatgtaataattaacatgtaatgcatgacgttatttatgagatgggtttttatgattagagtcccgcaattatacatttaatacgcgatagaaaacaaaatatagcgcgcaaactaggataaattatcgcgcgcggtgtcatctatgttactagatcgggcctcctgtcaatgctggcggcggctctggtggtggttctggtggcggctctgagggtggtggctctgagggtggcggttctgagggtggcggctctgagggaggcggttccggtggtggctctggttccggtgattttgattatgaaaagatggcaaacgctaataagggggctatgaccgaaaatgccgatgaaaacgcgctacagtctgacgctaaaggcaaacttgattctgtcgctactgattacggtgctgctatcgatggtttcattggtgacgtttccggccttgctaatggtaatggtgctactggtgattttgctggctctaattcccaaatggctcaagtcggtgacggtgataattcacctttaatgaataatttccgtcaatatttaccttccctccctcaatcggttgaatgtcgcccttttgtctttggcccaatacgcaaaccgcctctccccgcgcgttggccgattcattaatgcagctggcacgacaggtttcccgactggaaagcgggcagtgagcgcaacgcaattaatgtgagttagctcactcattaggcaccccaggctttacactttatgcttccggctcgtatgttgtgtggaattgtgagcggataacaatttcacacaggaaacagctatgaccatgattacgccaagcttgcatgcctgcagcccacagatggttagagaggcttacgcagcaggtctcatcaagacgatctacccgagcaataatctccaggaaatcaaataccttcccaagaaggttaaagatgcagtcaaaagattcaggactaactgcatcaagaacacagagaaagatatatttctcaagatcagaagtactattccagtatggacgattcaaggcttgcttcacaaaccaaggcaagtaatagagattggagtctctaaaaaggtagttcccactgaatcaaaggccatggagtcaaagattcaaatagaggacctaacagaactcgccgtaaagactggcgaacagttcatacagagtctcttacgactcaatgacaagaagaaaatcttcgtcaacatggtggagcacgacacacttgtctactccaaaaatatcaaagatacagtctcagaagaccaaagggcaattgagacttttcaacaaagggtaatatccggaaacctcctcggattccattgcccagctatctgtcactttattgtgaagatagtggaaaaggaaggtggctcctacaaatgccatcattgcgataaaggaaaggccatcgttgaagatgcctctgccgacagtggtcccaaagatggacccccacccacgaggagcatcgtggaaaaagaagacgttccaaccacgtcttcaaagcaagtggattgatgtgatatctccactgacgtaagggatgacgcacaatcccactatccttcgcaagacccttcctctatataaggaagttcatttcatttggagagaacacggggactctagaggatccatgccagtagtaacccgcttgattcgtttgaagtgtgtagggctcagacttgaccggagtggactcaatcggcgaatctgtcacggaggacacggggaatcaacgcggcggagagtgatggaagagctttcaagcctaaccgtgagtcagcgcgagcaatttctggtggagaacgatgtgttcgggatctataattacttcgacgccagcgacgtttctactcaaaaatacatgatggagattcagcgagataagcaattggattatctgatgaaaggcttaaggcagcttggtccgcagttttcttccttagatgc

-continued taatcgaccttggctttgttactggattcttcattcaatagctttgcttg
gggagactgtggatgatgaattagaaagcaatgccattgacttccttgga
cgctgccagggctctgaaggtggatacggtggtggtcctggccaacttcc
acatcttgcaactacttatgctgcagtgaatgcacttgttactttaggag
gtgacaaagccctttcttcaattaatagagaaaaaatgtcttgtttttta
agacggatgaaggatacaagtggaggtttcaggatgcatgatatgggaga
aatggatgttcgtgcatgctacactgcaatttcggttgcaagcatcctaa
atattatggatgatgaactcacccagggcctaggagattacatcttgagt
tgccaaacttatgaaggtggcattggaggggaacctggctccgaagctca
cggtgggtatacctactgtggtttggctgctatgattttaatcaatgagg
tcgaccgtttgaatttggattcattaatgaattgggctgtacatcgacaa
ggagtagaaatgggatttcaaggtaggacgaacaaattggtcgatggttg
ctacacattttggcaggcagccccttgtgttctactacaaagattatatt
caaccaatgatcatgacgttcatggatcatcacatatatcagaagggaca
aatgaagaacatcatgctcatgatgaagatgaccttgaagacagtgatga
tgatgatgattctgatgaggacaacgatgaagattcagtgaatggtcaca
gaatccatcatacatccacctacattaacaggagaatgcaactggttttt
gatagcctcggcttgcagagatatgtactcttgtgctctaagatccctga
cggtggattcagagacaagccgaggaaaccccgtgacttctaccacacat
gttactgcctgagcggcttgtctgtggctcagcacgcttggttaaaagac
gaggacactcctcctttgactcgcgacattatgggtggctactcgaatct
ccttgaacctgttcaacttcttcacaacattgtcatggatcagtataatg
aagctatcgagttcttctttaaagcagcatgactcgaatttccccgatcg
ttcaaacatttggcaataaagtttcttaagattgaatcctgttgccggtc
ttgcgatgattatcatataatttctgttgaattacgttaagcatgtaata
attaacatgtaatgcatgacgttatttatgagatgggtttttatgattag
agtcccgcaattatacatttaatacgcgatagaaaacaaaatatagcgcg
caaactaggataaattatcgcgcgcggtgtcatctatgttactagatcgg
gaattcactggccgtcgttttacaacgtcgtgactgggaaaaccctggcg
ttacccaacttaatcgccttgcagcacatccccctttcgccagctggcgt
aatagcgaagaggcccgcaccgatcgcccttcccaacagttgcgcagcct
gaatggcgcccgctcctttcgctttcttcccttcctttctcgccacgttc
gccggctttccccgtcaagctctaaatcgggggctccctttagggttccg
atttagtgctttacggcacctcgaccccaaaaaacttgatttgggtgatg
gttcacgtagtgggccatcgccctgatagacggtttttcgccctttgacg
ttggagtccacgttctttaatagtggactcttgttccaaactggaacaac
actcaaccctatctcgggctattcttttgatttataagggattttgccga
tttcggaaccaccatcaaacaggattttcgcctgctggggcaaaccagcg
tggaccgcttgctgcaactctctcagggccaggcggtgaagggcaatcag
ctgttgcccgtctcactggtgaaaagaaaaaccaccccagtacattaaaa
acgtccgcaatgtgttattaagttgtctaagcgtcaatttgtttacacca
caatatatcctgcca
(Underlined: 35S promoter; Bold: Sense AtFTB)

SEQ ID NO: 53

GAATTCAAATTTTTCGCCAGTTCTAAATATCCGGAAACCTCTTGGGATGC
CATTGCCCATCTATCTGTAATTTATTGACGAAATAGACGAAAAGGAAGGT
GGCTCCTATAAAGCACATCATTGCGATAACAGAAAGGCCATTGTTGAAGA
TACCTCTGCTGACATTGGTCCCCAAGTGGAAGCACCACCCCATGAGGAGC
ACCGTGGAGTAAGAAGACGTTCGAGCCACGTCGAAAAAGCAAGTGTGTTG
ATGTAGTATCTCCATTGACGTAAGGGATGACGCACAATCCAACTATCCAT
CGCAAGACCATTGCTCTATATAAGAAAGTTAATATCATTTCGAGTGGCCA
CGCTGAGCTCGTGGTGGAGAATCTGGGTGCTTTGACCAACTATACTGGCA
CAATGAGAGTCCACTTAAACAGTAACATGTGTGATAATGATCTCTACGTT
TACCCGGTTTGTCTCTCAGTCCACCCTCTTGCTCCTGTGCACATAAGAGA
ATATATTGCTGTAAAGCAATACTGTGAAAAAGTGGTTCTTGTGCTCTCCA
CTCATTAATAAATTTATAGGCAATATTTTTAAAATCAGATGAACTGGATT
CACTGGTGCCTTCATGCTCACCACGGCATGTTGCATGACTAGAGGTTCCA
TCCAAACTTTCTTTTGCTTCAGATACATAAGATACCGCAAAAATCTGTGA
TGTCTCTTCCATCTGTTTGTTGATAATAGAAGATAATCTTTGCAATAGAG
CAACAGCACCTCCCTGCCAAAAGGAATAGCATCCATCCACCAGTTTATTT
GTTCTCCCCTGGAATCCACATTCCTTACCTTGTCGGAATACCACCCAGTC
AACTAATCGAGGCAGATCCAAGTGATTAACCTCACCAATCAGAATCATTG
TAGCTAATCCACAAAAGGTGTACCCACCATGAGCCTCAGAACCAGGCTCA
CCAGCAATGCCACCCTCATATGTTTGACAGCTTATAATGTAGTCTCCAAC
ATTCTGGATCAGCTCATCATCCAAAATGTTCAAAACACTTGCAACAGAAA
TGGCAGTGTAGCAAGCTCGAACATCAATTTCACCTTCATCATGCATCCTG
AATCCACCATTTGGTTGCTTCATCCGCCGCAGAAACCCATACAGTTTATC
TCTATTAATTGATGCCAGGGATTTCTCACCACCCAAAGTAATAAGTGAAT
TAACAGCAGCATAAGTTGTGGCAATATGAGGCATCTGGCCTGGTCCCCCG
GCATATCCACCATTCGGATCCTGGCAACGGTTAAGAAAATCGATAGCGTT
ATCTTCGAGTTCATCATCGACGGATTCTCCCAACAAAGCAATGGAGTGGA
AGATCCAGTAGCAGAGCCAGGGTCGATTAGCGTCCAAAACGGAAAATGCG
GAACTGAGATGGCGAAGGCCTTTGGAGACATACTGCATGTGATTATCGCG
TTGAAGCTCCAACATGAGGGTTTGGGCGTTGCGAGGAATGGTGGCgagct
cgaatttccccgatcgttcaaacatttggcaataaagtttcttaagattg
aatcctgttgccggtcttgcgatgattatcatataatttctgttgaatta
cgttaagcatgtaataattaacatgtaatgcatgacgttatttatgagat
gggtttttatgattagagtcccgcaattatacatttaatacgcgatagaa
aacaaaatatagcgcgcaaactaggataaattatcgcgcgcggtgtcatc
tatgttactagatcgggaattc
(Upper Case: MuA Promoter; Underlined: Antisense GmFTB; Lower case: NOS terminater)

-continued

SEQ ID NO: 54

GGAGCCATAGATGCAATTCAATCAAACTGAAATTTCTGCAAGAATCTCAA
ACACGGAGATCTCAAAGTTTGAAAGAAAATTTATTTCTTCGACTCAAAAC
AAACTTACGAAATTTAGGTAGAACTTATATACATTATATTGTAATTTTTT
GTAACAAAATGTTTTTATTATTATTATAGAATTTTACTGGTTAAATTAAA
AATGAATAGAAAAGGTGAATTAAGAGGAGAGAGGAGGTAAACATTTTCTT
CTATTTTTTCATATTTTCAGGATAAATTATTGTAAAAGTTTACAAGATTT
CCATTTGACTAGTGTAAATGAGGAATATTCTCTAGTAAGATCATTATTTC
ATCTACTTCTTTTATCTTCTACCAGTAGAGGAATAAACAATATTTAGCTC
CTTTGTAAATACAAATTAATTTTCCTTCTTGACATCATTCAATTTTAATT
TTACGTATAAAATAAAAGATCATACCTATTAGAACGATTAAGGAGAAATA
CAATTCGAATGAGAAGGATGTGCCGTTTGTTATAATAAACAGCCACACGA
CGTAAACGTAAAATGACCACATGATGGGCCAATAGACATGGACCGACTAC
TAATAATAGTAAGTTACATTTTAGGATGGAATAAATATCATACCGACATC
AGTTTTGAAAGAAAAGGGAAAAAAAGAAAAAATAAATAAAAGATATACTA
CCGACATGAGTTCCAAAAAGCAAAAAAAAAGATCAAGCCGACACAGACAC
GCGTAGAGAGCAAAATGACTTTGACGTCACACCACGAAAACAGACGCTTC
ATACGTGTCCCTTTATCTCTCTCAGTCTCTCTATAAACTTAGTGAGACCC
TCCTCTGTTTTACTCACAAATATGCAAACTAGAAAACAATCATCAGGAAT
AAAGGGTTTGATTACTTCTATTGGAAAGGTGGTGGAGAATCTGGGTGCTT
TGACCAACTATACTGGCACAATGAGAGTCCACTTAAACAGTAACATGTGT
GATAATGATCTCTACGTTTACCCGGTTTGTCTCTCAGTCCACCCTCTTGC
TCCTGTGCACATAAGAGAATATATTGCTGTAAAGCAATACTGTGAAAAAG
TGGTTCTTGTGCTCTCCACTCATTAATAAATTTATAGGCAATATTTTTAA
AATCAGATGAACTGGATTCACTGGTGCCTTCATGCTCACCACGGCATGTT
GCATGACTAGAGGTTCCATCCAAACTTTCTTTTGCTTCAGATACATAAGA
TACCGCAAAAATCTGTGATGTCTCTTCCATCTGTTTGTTGATAATAGAAG
ATAATCTTTGCAATAGAGCAACAGCACCTCCCTGCCAAAAGGAATAGCAT
CCATCCACCAGTTTATTTGTTCTCCCCTGGAATCCACATTCCTTACCTTG
TCGGAATACCACCCAGTCAACTAATCGAGGCAGATCCAAGTGATTAACCT
CACCAATCAGAATCATTGTAGCTAATCCACAAAAGGTGTACCCACCATGA
GCCTCAGAACCAGGCTCACCAGCAATGCCACCCTCATATGTTTGACAGCT
TATAATGTAGTCTCCAACATTCTGGATCAGCTCATCATCCAAAATGTTCA
AAACACTTGCAACAGAAATGGCAGTGTAGCAAGCTCGAACATCAATTTCA
CCTTCATCATGCATCCTGAATCCACCATTTGGTTGCTTCATCCGCCGCAG
AAACCCATACAGTTTATCTCTATTAATTGATGCCAGGGATTTCTCACCAC
CCAAAGTAATAAGTGAATTAACAGCAGCATAAGTTGTGGCAATATGAGGC
ATCTGGCCTGGTCCCCCGGCATATCCACCATTCGGATCCTGGCAACGGTT
AAGAAAATCGATAGCGTTATCTTCGAGTTCATCATCGACGGATTCTCCCA
ACAAAGCAATGGAGTGGAAGATCCAGTAGCAGAGCCAGGGTCGATTAGCG
TCCAAAACGGAAAATGCGGAACTGAGATGGCGAAGGCCTTTGGAGACATA
CTGCATGTGATTATCGCGTTGAAGCTCCAACATGAGGGTTTGGGCGTTGC
GAGGAATGGTGGCgagctcgaatttccccgatcgttcaaacatttggcaa
taaagtttcttaagattgaatcctgttgccggtcttgcgatgattatcat
ataatttctgttgaattacgttaagcatgtaataattaacatgtaatgca
tgacgttatttatgagatgggtttttatgattagagtcccgcaattatac
atttaatacgcgatagaaaacaaaatatagcgcgcaaactaggataaatt
atcgcgcgcggtgtcatctatgttactagatcgggaattc (Upper Case: RD29A Promoter; Underlined: Antisense GmFTB; Lower case: NOS) terminater

SEQ ID NO: 55

GAATTCAAATTTTTCGCCAGTTCTAAATATCCGGAAACCTCTTGGGATGC
CATTGCCCATCTATCTGTAATTTATTGACGAAATAGACGAAAAGGAAGGT
GGCTCCTATAAAGCACATCATTGCGATAACAGAAAGGCCATTGTTGAAGA
TACCTCTGCTGACATTGGTCCCCAAGTGGAAGCACCACCCCATGAGGAGC
ACCGTGGAGTAAGAAGACGTTCGAGCCACGTCGAAAAAGCAAGTGTGTTG
ATGTAGTATCTCCATTGACGTAAGGGATGACGCACAATCCAACTATCCAT
CGCAAGACCATTGCTCTATATAAGAAAGTTAATATCATTTCGAGTGGCCA
CGCTGAGCTCGTGGTGGAGAATCTGGGTGCTTTGACCAACTATACTGGCA
CAATGAGAGTCCACTTAAACAGTAACATGTGTGATAATGATCTCTACGTT
TACCCGGTTTGTCTCTCAGTCCACCCTCTTGCTCCTGTGCACATAAGAGA
ATATATTGCTGTAAAGCAATACTGTGAAAAAGTGGTTCTTGTGCTCTCCA
CTCATTAATAAATTTATAGGCAATATTTTTAAAATCAGATGAACTGGATT
CACTGGTGCCTTCATGCTCACCACGGCATGTTGCATGACTAGAGGTTCCA
TCCAAACTTTCTTTTGCTTCAGATACATAAGATACCGCAAAAATCTGTGA
TGTCTCTTCCATCTGTTTGTTGATAATAGAAGATAATCTTTGCAATAGAG
CAACAGCACCTCCCTGCCAAAAGGAATAGCATCCATCCACCAGTTTATTT
GTTCTCCCCTGGAATCCACATTCCTTACCTTGTCGGAATACCACCCAGTC
AACTAATCGAGGCAGATCCAAGTGATTAACCTCACCAATCAGAATCATTG
TAGCTAATCCACAAAAGGTGTACCCACCATGAGCCTCAGAACCAGGCTCA
CCAGCAATGCCACCCTCATATGTTTGACAGCTTATAATGTAGTCTCCAAC
ATTCTGGATCAGCTCATCATCCAAAATGTTCAAAACACTTGCAACAGAAA
TGGCAGTGTAGCAAGCTCGAACATCAATTTCACCTTCATCATGCATCCTG
AATCCACCATTTGGTTGCTTCATCCGCCGCAGAAACCCATACAGTTTATC
TCTATTAATTGATGCCAGGGATTTCTCACCACCCAAAGTAATAAGTGAAT
TAACAGCAGCATAAGTTGTGGCAATATGAGGCATCTGGCCTGGTCCCCCG
GCATATCCACCATTCGGATCCTGGCAACGGTTAAGAAAATCGATAGCGTT
ATCTTCGAGTTCATCATCGACGGATTCTCCCAACAAAGCAATGGAGTGGA
AGATCCAGTAGCAGAGCCAGGGTCGATTAGCGTCCAAAACGGAAAATGCG
GAACTGAGATGGCGAAGGCCTTTGGAGACATACTGCATGTGATTATCGCG
TTGAAGCTCCAACATGAGGGTTTGGGCGTTGCGAGGAATGGTGGCGGTGA
GGTTAATCACTTGGATCTGCCTCGATTAGTTGACTGGGTGGTATTCCGAC

-continued

AAGGTAAGGAATGTGGATTCCAGGGGAGAACAAATAAACTGGTGGATGGA
TGCTATTCCTTTTGGCAGGGAGGTGCTGTTGCTCTATTGCAAAGATTATC
TTCTATTATCAACAAACAGATGGAAGAGACATCACAGATTTTTGCGGTAT
CTTATGTATCTGAAGCAAAAGAAAGTTTGGATGGAACCTCTAGTCATGCA
ACATGCCGTGGTGAGCATGAAGGCACCAGTGAATCCAGTTCATCTGATTT
TAAAAATATTGCCTATAAATTTATTAATGAGTGGAGAGCACAAGAACCAC
TTTTTCACAGTATTGCTTTACAGCAATATATTCTCTTATGTGCACAGGAG
CAAGAGGGTGGACTGAGAGACAAACCGGGTAAACGTAGAGATCATTATCA
CACATGTTACTGTTTAAGTGGACTCTCATTGTGCCAGTATAGTTGGTCAA
AGCACCCAGATTCTCCACCACgagctcgaatttccccgatcgttcaaaca
tttggcaataaagtttcttaagattgaatcctgttgccggtcttgcgatg
attatcatataatttctgttgaattacgttaagcatgtaataattaacat
gtaatgcatgacgttatttatgagatgggtttttatgattagagtcccgc
aattatacatttaatacgcgatagaaaacaaaatatagcgcgcaaactag
gataaattatcgcgcgcggtgtcatctatgttactagatcgggaattc
(Upper Case: MuA Promoter; Underlined: Antisense GmFTB; Bold: Sense GmFTB; Lower case: NOS terminater)

SEQ ID NO: 56

GGAGCCATAGATGCAATTCAATCAAACTGAAATTTCTGCAAGAATCTCAA
ACACGGAGATCTCAAAGTTTGAAAGAAAATTTATTTCTTCGACTCAAAAC
AAACTTACGAAATTTAGGTAGAACTTATATACATTATATTGTAATTTTTT
GTAACAAAATGTTTTTATTATTATTATAGAATTTTACTGGTTAAATTAAA
AATGAATAGAAAAGGTGAATTAAGAGGAGAGAGGAGGTAAACATTTTCTT
CTATTTTTTCATATTTTCAGGATAAATTATTGTAAAAGTTTACAAGATTT
CCATTTGACTAGTGTAAATGAGGAATATTCTCTAGTAAGATCATTATTTC
ATCTACTTCTTTTATCTTCTACCAGTAGAGGAATAAACAATATTTAGCTC
CTTTGTAAATACAAATTAATTTTCCTTCTTGACATCATTCAATTTTAATT
TTACGTATAAAATAAAAGATCATACCTATTAGAACGATTAAGGAGAAATA
CAATTCGAATGAGAAGGATGTGCCGTTTGTTATAATAAACAGCCACACGA
CGTAAACGTAAAATGACCACATGATGGGCCAATAGACATGGACCGACTAC
TAATAATAGTAAGTTACATTTTAGGATGGAATAAATATCATACCGACATC
AGTTTTGAAAAGAAGGGAAAAAAAGAAAAAAATAAATAAAAGATATACTA
CCGACATGAGTTCCAAAAAGCAAAAAAAAAGATCAAGCCGACACAGACAC
GCGTAGAGAGCAAAATGACTTTGACGTCACACCACGAAAACAGACGCTTC
ATACGTGTCCCTTTATCTCTCTCAGTCTCTCTATAAACTTAGTGAGACCC
TCCTCTGTTTTACTCACAAATATGCAAACTAGAAAACAATCATCAGGAAT
AAAGGGTTTGATTACTTCTATTGGAAAGGTGGTGGAGAATCTGGGTGCTT
TGACCAACTATACTGGCACAATGAGAGTCCACTTAAACAGTAACATGTGT
GATAATGATCTCTACGTTTACCCGGTTTGTCTCTCAGTCCACCCTCTTGC
TCCTGTGCACATAAGAGAATATATTGCTGTAAAGCAATACTGTGAAAAAG
TGGTTCTTGTGCTCTCCACTCATTAATAAATTTATAGGCAATATTTTTAA
AATCAGATGAACTGGATTCACTGGTGCCTTCATGCTCACCACGGCATGTT
GCATGACTAGAGGTTCCATCCAAACTTTCTTTTGCTTCAGATACATAAGA
TACCGCAAAAATCTGTGATGTCTCTTCCATCTGTTTGTTGATAATAGAAG
ATAATCTTTGCAATAGAGCAACAGCACCTCCCTGCCAAAAGGAATAGCAT
CCATCCACCAGTTTATTTGTTCTCCCCTGGAATCCACATTCCTTACCTTG
TCGGAATACCACCCAGTCAACTAATCGAGGCAGATCCAAGTGATTAACCT
CACCAATCAGAATCATTGTAGCTAATCCACAAAAGGTGTACCCACCATGA
GCCTCAGAACCAGGCTCACCAGCAATGCCACCCTCATATGTTTGACAGCT
TATAATGTAGTCTCCAACATTCTGGATCAGCTCATCATCCAAAATGTTCA
AAACACTTGCAACAGAAATGGCAGTGTAGCAAGCTCGAACATCAATTTCA
CCTTCATCATGCATCCTGAATCCACCATTTGGTTGCTTCATCCGCCGCAG
AAACCCATACAGTTTATCTCTATTAATTGATGCCAGGGATTTCTCACCAC
CCAAAGTAATAAGTGAATTAACAGCAGCATAAGTTGTGGCAATATGAGGC
ATCTGGCCTGGTCCCCCGGCATATCCACCATTCGGATCCTGGCAACGGTT
AAGAAAATCGATAGCGTTATCTTCGAGTTCATCATCGACGGATTCTCCCA
ACAAAGCAATGGAGTGGAAGATCCAGTAGCAGAGCCAGGGTCGATTAGCG
TCCAAAACGGAAAATGCGGAACTGAGATGGCGAAGGCCTTTGGAGACATA
CTGCATGTGATTATCGCGTTGAAGCTCCAACATGAGGGTTTGGGCGTTGC
GAGGAATGGTGGCGGTGAGGTTAATCACTTGGATCTGCCTCGATTAGTTG
ACTGGGTGGTATTCCGACAAGGTAAGGAATGTGGATTCCAGGGGAGAACA
AATAAACTGGTGGATGGATGCTATTCCTTTTGGCAGGGAGGTGCTGTTGC
TCTATTGCAAAGATTATCTTCTATTATCAACAAACAGATGGAAGAGACAT
CACAGATTTTTGCGGTATCTTATGTATCTGAAGCAAAAGAAAGTTTGGAT
GGAACCTCTAGTCATGCAACATGCCGTGGTGAGCATGAAGGCACCAGTGA
ATCCAGTTCATCTGATTTTAAAAATATTGCCTATAAATTTATTAATGAGT
GGAGAGCACAAGAACCACTTTTTCACAGTATTGCTTTACAGCAATATATT
CTCTTATGTGCACAGGAGCAAGAGGGTGGACTGAGAGACAAACCGGGTAA
ACGTAGAGATCATTATCACACATGTTACTGTTTAAGTGGACTCTCATTGT
GCCAGTATAGTTGGTCAAAGCACCCAGATTCTCCACCACgagctcgaatt
tccccgatcgttcaaacatttggcaataaagtttcttaagattgaatcct
gttgccggtcttgcgatgattatcatataatttctgttgaattacgttaa
gcatgtaataattaacatgtaatgcatgacgttatttatgagatgggttt
ttatgattagagtcccgcaattatacatttaatacgcgatagaaaacaaa
atatagcgcgcaaactaggataaattatcgcgcgcggtgtcatctatgtt
actagatcgggaattc
(Upper Case: RD29A Promoter; Underlined: Antisense GmFTB; Bold: Sense GmFTB; Lower case: NOS terminater)

SEQ ID NO: 57

GAATTCAAATTTTTCGCCAGTTCTAAATATCCGGAAACCTCTTGGGATGC
CATTGCCCATCTATCTGTAATTTATTGACGAAATAGACGAAAAGGAAGGT
GGCTCCTATAAAGCACATCATTGCGATAACAGAAAGGCCATTGTTGAAGA

-continued

TACCTCTGCTGACATTGGTCCCCAAGTGGAAGCACCACCCCATGAGGAGC
ACCGTGGAGTAAGAAGACGTTCGAGCCACGTCGAAAAAGCAAGTGTGTTG
ATGTAGTATCTCCATTGACGTAAGGGATGACGCACAATCCAACTATCCAT
CGCAAGACCATTGCTCTATATAAGAAAGTTAATATCATTTCGAGTGGCCA
CGCTGAGCTCGGATGGATTGGCTCCAGCAAATTAGAGTACGGTCCAAGCA
CATGCTGAGGTAATGGGCACGAACCAGTATCAGTCATGGCACTGTACTGG
CTAACTGCGAGGCCACTGAGGCAGTAGCATGAATGATAGTGATCTCTGTT
CTTTCCAGGCTTATCCCTCAAGCCTCCCTCTAGTACCTGAGAACAAAGTA
GGATGTATTGTTGCAGGGCAATGTTATGGAAGAGTGGGCCAATTTGGTTG
CTCTGTTGTATAAAATCAAATCCAAACTTCGCATAGTCCACAGCAGAGGA
AGACTTATTCGCGGTGCACCCATATGAACTGGTGCTGCAGGCATCCTCTC
CTGATGGCCTTTTGCAGGAATACGAGGACCTCAATTGCTTATCAACAATC
GTAATTAACTTTTGTGTGAAAGCAATGGCAGCTCCCTGCCAAAAGGAGTA
GCAACCATCAACCAATTTATTAGTTCGTCCTTGAAATCCGCATTCCACTC
CTTGACGAAAAGCCACCCAGCCAATCAAACTAGGCAAGTCAACTTTCTCT
GCCTCATTAAGCAGGATCAAAGCAGCCAATCCACAGAATGTATACCCACC
ATGTGCTTCAGCATAAGGCTCCCCAGCAATACCACCTTCATAAGTTTGAC
ATCTTGCTATGTAGTCGCCTACACCTTTTGCCAGTTTAAAATCAAGAATA
TTCACAAGGCTGGCAACCGATATAGCGGTGTAGGAAGCACGGACATCAAT
TTCGCCACCATCATGCATTCTGAAAGCACCTGATACATCTTTCATCTGCA
GCATAAAATTGTACAGGTTGCCCCTATTGATTGATGACAATGCTCTTTCG
CTCCCTATTGTCACAAGTGTATTTACAGCAGCATAAGTCGTAGCTAGGTG
AGGCAACTGTCCAGGTCCACCACTATATCCACCATCTTTATCCTGACATC
GAGCTAAGAAGTCTATGATATCATTCTCAAGATCATCATCAAGTGCTTCA
TCCAGCAAAGCAAGTGGATGAACCATCCAGTAGCATAGCCAAGGGCGATT
GGCATCTAGAACATGAAAGGCTGGTCCCATATGCCTCAGCCCAGGCGTCA
GATACTCGATATGCTGATCACGCCACAGCTCTAGCATGATGGATTTCGTG
TTGGGCGCGGCCCCGAAGAGGGAGCGGTAGATGTCGCCAACCCTGGCCTC
CACCTTCATCTGCTCCACCTGCGTCACCGTGAGCCTCGGTAGGTCGGGAT
CCGCCgagctcgaatttccccgatcgttcaaacatttggcaataaagttt
cttaagattgaatcctgttgccggtcttgcgatgattatcatataatttc
tgttgaattacgttaagcatgtaataattaacatgtaatgcatgacgtta
tttatgagatgggtttttatgattagagtcccgcaattatacatttaata
cgcgatagaaaacaaaatatagcgcgcaaactaggataaattatcgcgcg
cggtgtcatctatgttactagatcgggaattc (Upper Case: MuA Promoter; Underlined: Antisense *Zea maize*-FTB; Lower case: NOS terminater)

SEQ ID NO: 58

GAATTCAAATTTTTCGCCAGTTCTAAATATCCGGAAACCTCTTGGGATGC
CATTGCCCATCTATCTGTAATTTATTGACGAAATAGACGAAAAGGAAGGT
GGCTCCTATAAAGCACATCATTGCGATAACAGAAAGGCCATTGTTGAAGA

-continued

TACCTCTGCTGACATTGGTCCCCAAGTGGAAGCACCACCCCATGAGGAGC
ACCGTGGAGTAAGAAGACGTTCGAGCCACGTCGAAAAAGCAAGTGTGTTG
ATGTAGTATCTCCATTGACGTAAGGGATGACGCACAATCCAACTATCCAT
CGCAAGACCATTGCTCTATATAAGAAAGTTAATATCATTTCGAGTGGCCA
CGCTGAGCTCGGATGGATTGGCTCCAGCAAATTAGAGTACGGTCCAAGCA
CATGCTGAGGTAATGGGCACGAACCAGTATCAGTCATGGCACTGTACTGG
CTAACTGCGAGGCCACTGAGGCAGTAGCATGAATGATAGTGATCTCTGTT
CTTTCCAGGCTTATCCCTCAAGCCTCCCTCTAGTACCTGAGAACAAAGTA
GGATGTATTGTTGCAGGGCAATGTTATGGAAGAGTGGGCCAATTTGGTTG
CTCTGTTGTATAAAATCAAATCCAAACTTCGCATAGTCCACAGCAGAGGA
AGACTTATTCGCGGTGCACCCATATGAACTGGTGCTGCAGGCATCCTCTC
CTGATGGCCTTTTGCAGGAATACGAGGACCTCAATTGCTTATCAACAATC
GTAATTAACTTTTGTGTGAAAGCAATGGCAGCTCCCTGCCAAAAGGAGTA
GCAACCATCAACCAATTTATTAGTTCGTCCTTGAAATCCGCATTCCACTC
CTTGACGAAAAGCCACCCAGCCAATCAAACTAGGCAAGTCAACTTTCTCT
GCCTCATTAAGCAGGATCAAAGCAGCCAATCCACAGAATGTATACCCACC
ATGTGCTTCAGCATAAGGCTCCCCAGCAATACCACCTTCATAAGTTTGAC
ATCTTGCTATGTAGTCGCCTACACCTTTTGCCAGTTTAAAATCAAGAATA
TTCACAAGGCTGGCAACCGATATAGCGGTGTAGGAAGCACGGACATCAAT
TTCGCCACCATCATGCATTCTGAAAGCACCTGATACATCTTTCATCTGCA
GCATAAAATTGTACAGGTTGCCCCTATTGATTGATGACAATGCTCTTTCG
CTCCCTATTGTCACAAGTGTATTTACAGCAGCATAAGTCGTAGCTAGGTG
AGGCAACTGTCCAGGTCCACCACTATATCCACCATCTTTATCCTGACATC
GAGCTAAGAAGTCTATGATATCATTCTCAAGATCATCATCAAGTGCTTCA
TCCAGCAAAGCAAGTGGATGAACCATCCAGTAGCATAGCCAAGGGCGATT
GGCATCTAGAACATGAAAGGCTGGTCCCATATGCCTCAGCCCAGGCGTCA
GATACTCGATATGCTGATCACGCCACAGCTCTAGCATGATGGATTTCGTG
TTGGGCGCGGCCCCGAAGAGGGAGCGGTAGATGTCGCCAACCCTGGCCTC
CACCTTCATCTGCTCCACCTGCGTCACCGTGAGCCTCGGTAGGTCGGGAT
CCGCCggatccGCTGGGGAGCCTTATGCTGAAGCACATGGTGGGTATACA
TTCTGTGGATTGGCTGCTTTGATCCTGCTTAATGAGGCAGAGAAAGTTGA
CTTGCCTAGTTTGATTGGCTGGGTGGCTTTTCGTCAAGGAGTGGAATGCG
GATTTCAAGGACGAACTAATAAATTGGTTGATGGTTGCTACTCCTTTTGG
CAGGGAGCTGCCATTGCTTTCACACAAAAGTTAATTACGATTGTTGATAA
GCAATTGAGGTCCTCGTATTCCTGCAAAAGGCCATCAGGAGAGGATGCCT
GCAGCACCAGTTCATATGGGTGCACCGCGAATAAGTCTTCCTCTGCTGTG
GACTATGCGAAGTTTGGATTTGATTTTATACAACAGAGCAACCAAATTGG
CCCACTCTTCCATAACATTGCCCTGCAACAATACATCCTACTTTGTTCTC
AGGTACTAGAGGGAGGCTTGAGGGATAAGCCTGGAAAGAACAGAGATCAC
TATCATTCATGCTACTGCCTCAGTGGCCTCGCAGTTAGCCAGTACAGTGC

-continued

CATGACTGATACTGGTTCGTGCCCATTACCTCAGCATGTGCTTGGACCGT

ACTCTAATTTGCTGGAGCCAATCCATCCaagcttgaatttccccgatcgt tcaaacatttggcaataaagtttcttaagattgaatcctgttgccggtct tgcgatgattatcatataatttctgttgaattacgttaagcatgtaataa ttaacatgtaatgcatgacgttatttatgagatgggtttttatgattaga gtcccgcaattatacatttaatacgcgatagaaaacaaaatatagcgcgc aaactaggataaattatcgcgcgcggtgtcatctatgttactagatcgga agctt (Upper Case: MuA Promoter; Underlined: Antisense *Zea maize*-FTB; Bold: Sense *Zea maize*-FTB; Lower case: NOS terminater)

Example 7

PCR Analysis of Putative Transgenic Plants

To verify that the putative transgenic plants carried the gene of interest PCR analysis was performed. Genomic DNA was isolated and PCR run according to standard protocols and conditions which are known to one of skill in the art. A typical reaction was performed in a volume of 25 μl and primer pairs used were dependent on the gene and promoter combination of the particular construct (Table 12).

Figure 15:
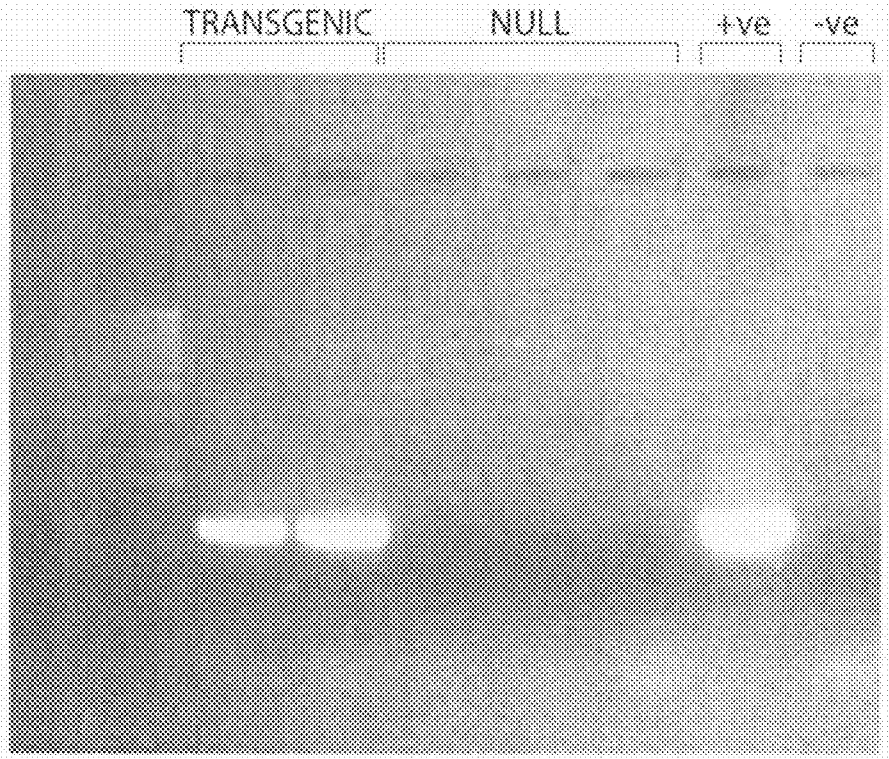
FIG. 15 is a representative illustration of gel electrophoresis analysis of PCR products in an assay to detect transgenic lines of *Brassica napus.*

Putative transgenic *Brassica napus* plants were screened using the primer combinations detailed in the table below. A representative gel showing PCR analysis results is shown in FIG. 15 which represents transgenic plants carrying the pRD29A-anti-FTA construct. Transformants were confirmed in an analogous manner for each species and construct transformation done.

TABLE 12

| Construct Name | Primer Name | Primer Sequence (5'-3') |
|---|---|---|
| 35S-antiFTA | SEQ ID NO: 10 | GCCGACAGTGGTCCCAAAGATGG |
| | SEQ ID NO: 11 | AAAGGATCCTCAAATTGCTGCCAC TGTAAT |
| rd29A-antiFTA | SEQ ID NO: 12 | AAACCCGGGATGAATTTCGACGAG AACGTG |
| | SEQ ID NO: 13 | GCAAGACCGGCAACAGGA |
| rd29B-antiFTA | SEQ ID NO: 14 | TTTAAGCTTGACAGAAACAGTCAG CGAGAC |
| | SEQ ID NO: 11 | AAACCCGGGATGAATTTCGACGAG AACGTG |
| 35S-DA-FTA | SEQ ID NO: 15 | GCTCTTCCTCCATGCCCA |
| | SEQ ID NO: 13 | GCAAGACCGGCAACAGGA |
| rd29A-DA-FTA | SEQ ID NO: 16 | TTTAAGCTTGGAGCCATAGATGCA ATTCAA |
| | SEQ ID NO: 17 | CGGGCATTAGGAGGATGGGAA |
| 35S-HP-FTB | SEQ ID NO: 10 | GCCGACAGTGGTCCCAAAGATGG |
| | SEQ ID NO: 18 | GTCCGGAATTCCCGGGTC |
| rd29A-HP-FTB | SEQ ID NO: 16 | TTTAAGCTTGGAGCCATAGATGCA ATTCAA |
| | SEQ ID NO: 18 | GTCCGGAATTCCCGGGTC |

Example 8

Southern Analysis

Figure 2:
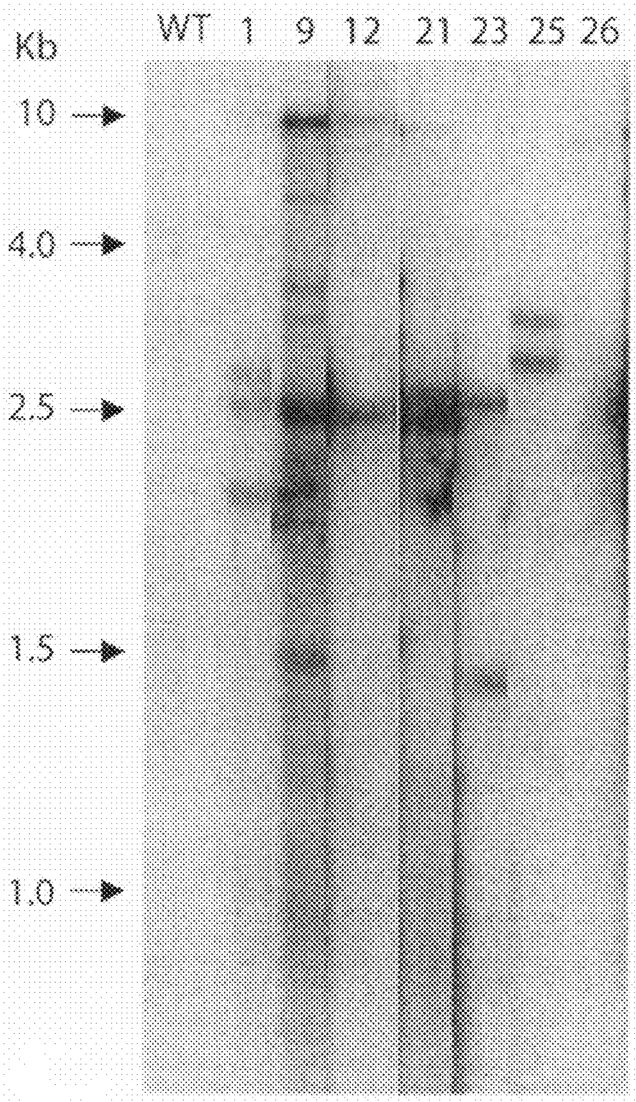
FIG. 2 is an illustration of genomic Southern hybridization analysis of anti-FTA transgenic *Arabidopsis thaliana.*

Genomic Southern analysis of anti-FTA transgenic *Arabidopsis thaliana*. The numbers indicate the line numbers. Five micrograms of genomic DNA of T1 plants was digested with HindIII (a unique site in the T-DNA plasmid) and separated in a 0.8% agarose gel. The NPTII coding region was used as the probe for radio-labeling. FIG. 2 shows a typical result from Southern analysis indicating the presence of the transgene.

Example 9

Northern Blots of Antisense FTA Lines

Figure 3A:
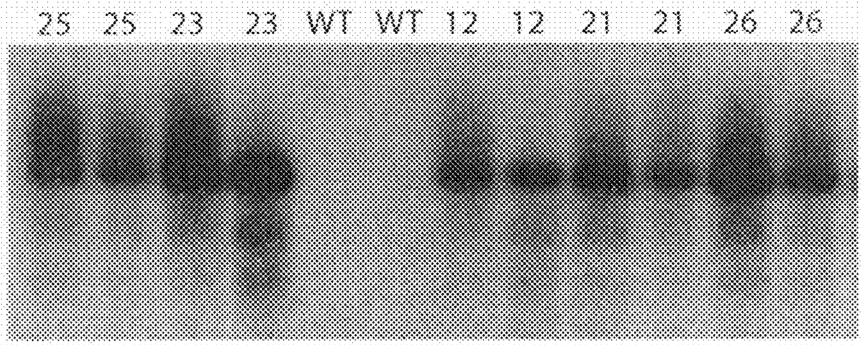
FIG. 3 is an illustration of Northern analysis of five 35S-anti-FTA *Arabidopsis thaliana* lines (T3 plants).
Figure 3B:
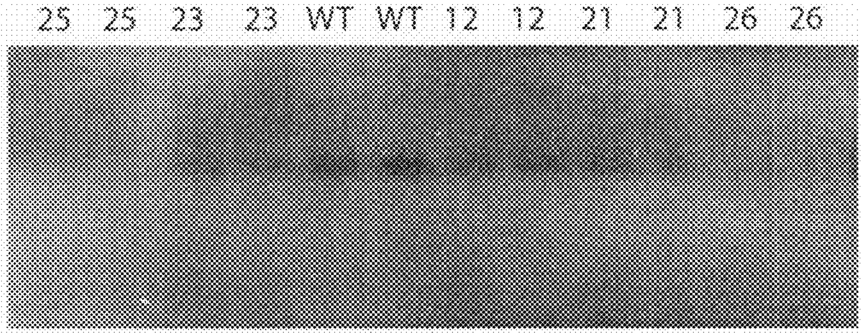
Figure 3C:
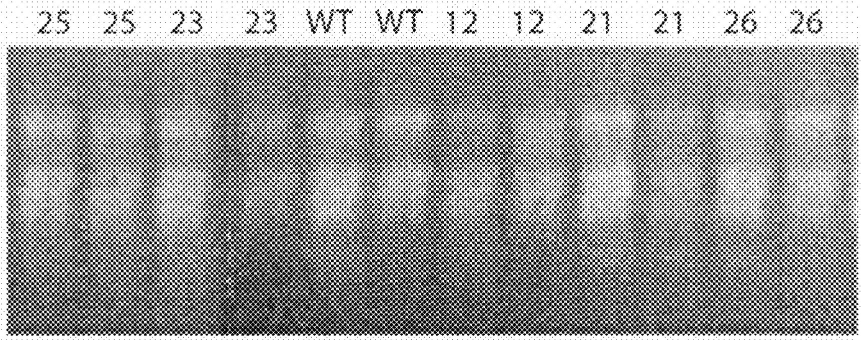

RNA was isolated from developing leaf tissue of five 35S-anti-FTA *Arabidopsis thaliana* lines (T3 plants). The blot was first probed with $P^{32}$ labeled, single-stranded sense transcript of FTA (FIG. 3 panel A) which detects antisense transcript, then stripped and re-probed with the single-stranded anti-sense transcript of FTA (FIG. 3 panel B) that detects the sense transcript. FIG. 3 panel C shows the ethidium bromide stained gel for the blot. Approximately 5 μg of total RNA was loaded into each lane. FIG. 3 indicates the accumulation of the transgene anti-sense transcript and a reduction in the sense transcript in transgenic plants.

Example 10

Western Blot Antisense FTA Lines with Anti-FT-α Antibodies

Figure 4:
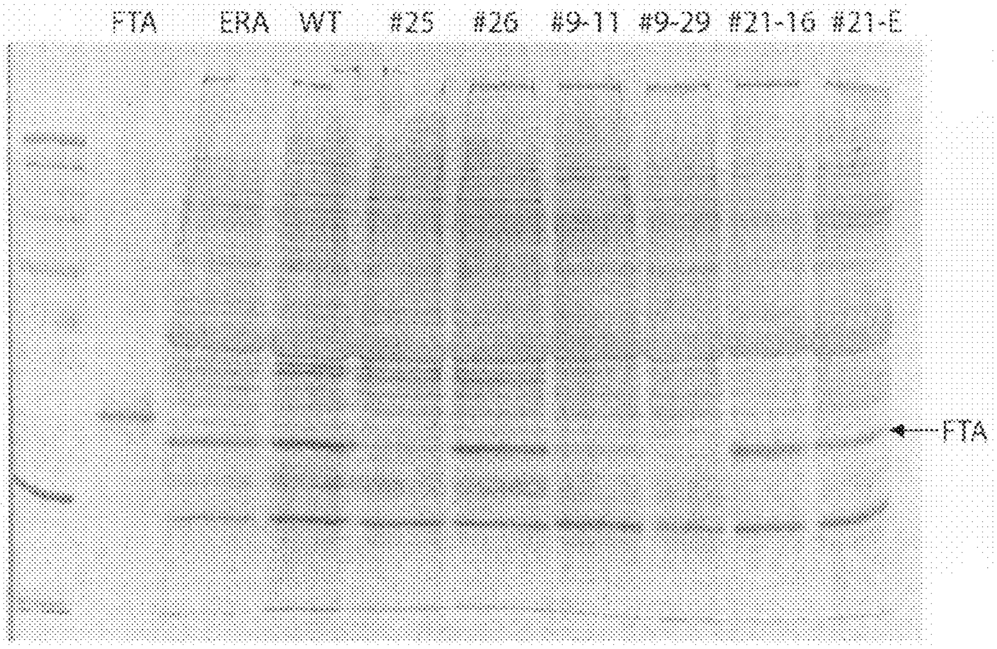
FIG. 4 shows a Western expression analysis using anti-FTA antibodies to detect the FTA polypeptides.

The antibodies produced according to the methods of Example 19 were used to analyze protein extracts from transgenic plants on western blots. Lane 1 of FIG. 4 is a molecular weight standard, lane 2 purified FTA protein, lanes 3-10 are protein extracts from the ERA1 mutant, wild type, and 4 lines of transgenic *Arabidopsis thaliana*. FIG. 4 illustrates the reduction of detectable FTA protein in transgenic lines.

Example 11

ABA Sensitivity of Transgenic Seedlings

Figure 5:
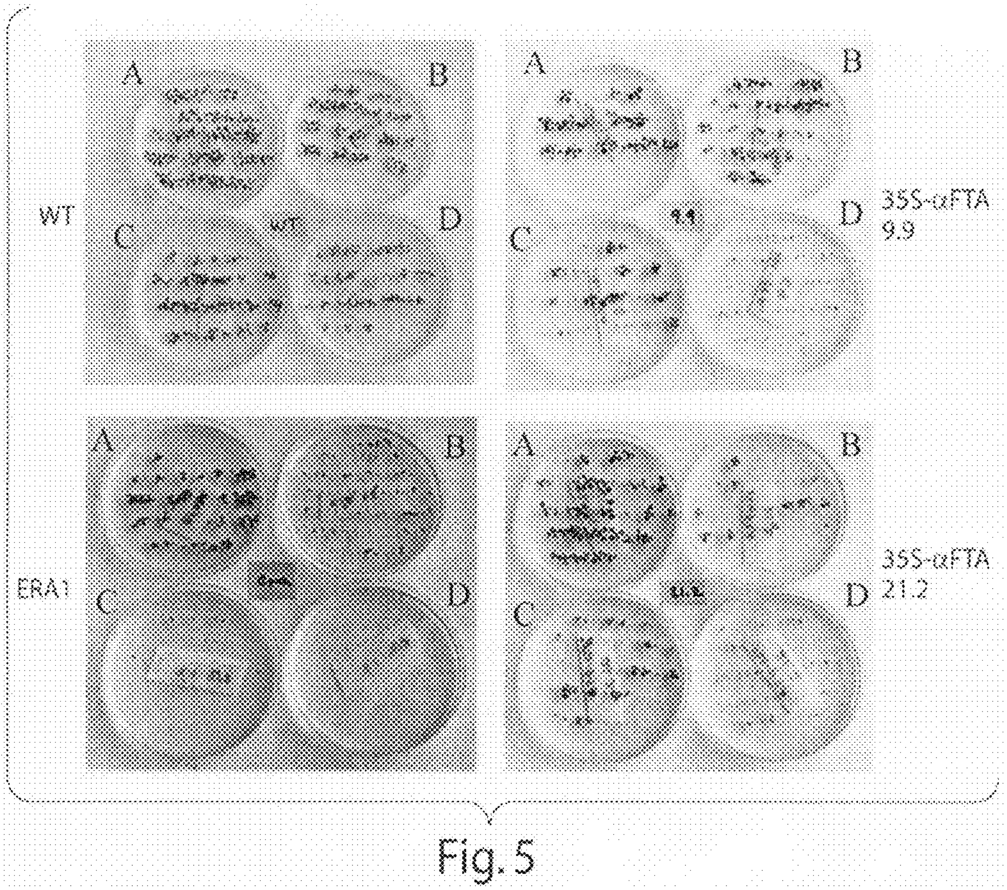
FIG. 5 is a set of photographs showing ABA effects on seedling growth and development. FTA Antisense transgenic seedlings exhibit enhanced ABA sensitivity.

Seeds of wild type Columbia, era 1-2 and T3 homozygous seeds of two antisense, drought tolerant lines of 35S-antisense-FTA were plated on minimum medium (½ MS) supplemented with no ABA (A), 0.3 μM (B), 0.5 μM (C) or 1.0 μM ABA (D). Plates were chilled for 3 days in 4° C. in the dark, and incubated for 11 days at 22° C. with 24 hour continuous light. era1 and transgenic lines were more inhibited in germination than wild type plants. Results are shown in FIG. 5.

Figure 6A:
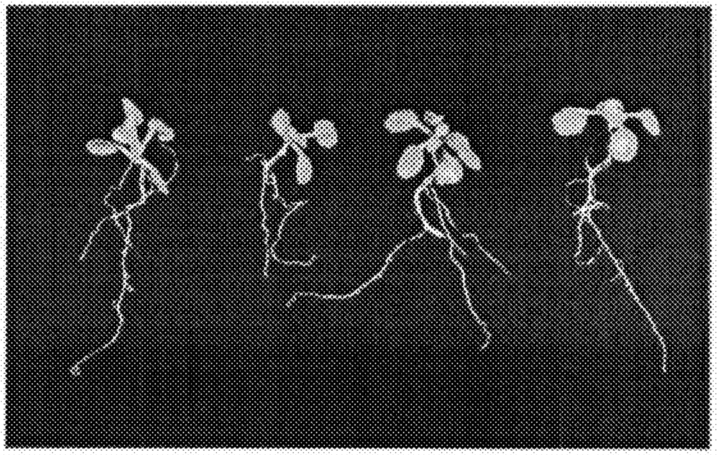
FIG. 6 shows the effect of ABA on seedling growth and development.
Figure 6B:

Twelve day old seedling phenotypes of wild type Columbia, era1-2 and two drought tolerant 35S-antisense-FTA lines (9.9 & 21.2) in minimum medium without (A) or with (B) 1 μM ABA. FIG. 6 shows the reduced root growth and development of era1 and transgenic lines relative to wild type plants. The 35S-antisense-FTA lines show reduced root growth, similar to the era1 mutant, in response to ABA.

A transgenic *Brassica napus* line carrying the 35S-antisense-FTA construct was assessed for ABA sensitivity. At about 10 μm an effect was observed showing reduced seedling development and vigor at the cotyledon and first leaf stage, thereby indicating an increased sensitivity to ABA ABA sensitivity is assessed in all transgenic plants engineered to have reduced or increased FTA or FTB expression or activity by the methods above. The ABA concentration used varies depending upon the species under examination.

Example 12

Drought Experiment

To assess the response of plants under water stress or drought one can expose plants to various situations. For example, the plant can be removed from soil or media and placed on paper towel for a period of time, such as 4 hours, then returned to a plate to continue growth and development. Survival and vigor can be assessed.

Figure 7:
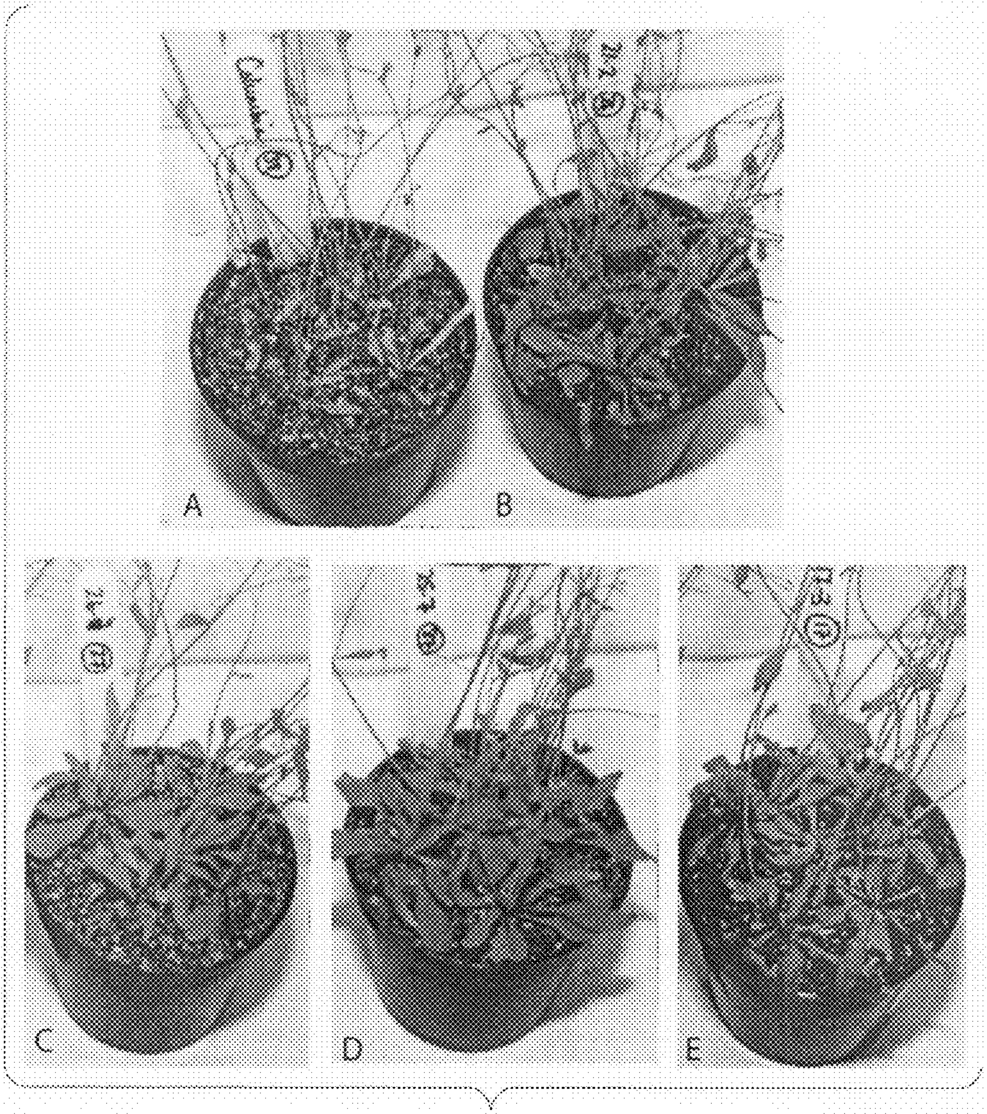
FIG. 7 shows photographs of wild type Columbia (A) and four antisense FTA transgenic lines (B, C, D, E) of *Arabidopsis thaliana* after 8 days without watering.

Alternatively one can impose a water stress in such a way as to more closely resemble a field situation by withholding water for a period of time, such as up to 6 days. Plants were grown five plants per four inch pot, in a replicated water-stress experiment. All pots were filled with equal amounts of homogeneous premixed and wetted soil. Growth conditions were 16 hour daylight (150-200 $\mu mol/m^2/s$) at 22° C. and 70% relative humidity. On the day that the first flower opened drought treatment was initiated first by equalizing the soil water content in each pot on a weight basis and then cessation of watering. At the end of the water stress treatment plants were typically either harvested for biomass data or re-watered to complete the life cycle and determination of biomass and yield data. Physiological parameters have been assessed under stressed and optimal conditions, for example, shoot and root biomass accumulation, soil water content, water loss alone or as a function of parameters such as biomass, seed yield, and leaf number and leaf area. FIG. 7 shows photographs of wild type Columbia (A) and four 35S-antisense-FTA transgenic *Arabidopsis thaliana* lines (B, C, D, E) after 8 days of water stress treatment. The control plant is visibly stressed and less healthy. This experiment has been conducted on transgenic lines containing vectors described by SEQ ID NO: 4, 40-58.

Drought or water stress tolerance is assessed in all transgenic plants engineered to have reduced or increased FTA or FTB expression or activity by the described methods.

Example 13

Figure 10:
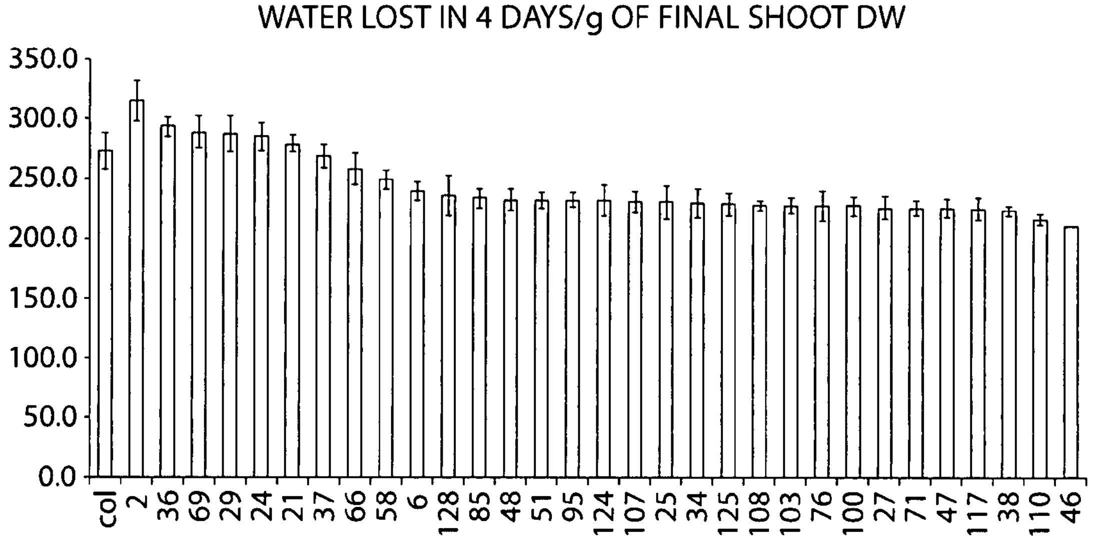
FIG. 10 is an illustration of transgenic performance during water stress.

Analysis of Water Loss in *Arabidopsis thaliana* pRD29A-DA-FTA Lines During Drought Stress Plants were grown 5 plants per 4 inch pot and 6 pots per line. When the plants had grown to the first flower stage drought treatment was initiated as described in Example 12. Pots were weighed daily and at the end of the 7 day drought treatment all plants were harvested for shoot fresh weight and dry weight determinations. FIG. 10 shows the water loss on a per shoot dry weight basis at 4 days of water stress treatment. Of the 31 lines examined in this experiment 25 showed lower water loss relative to the Columbia wild type, 22 of which were statistically significant. All lines had been assessed for ABA sensitivity as described in Example 6, increased ABA sensitivity ($ABA^S$) also correlated with a decreased water loss during drought treatment. Those lines determined to have wild type ABA sensitivity ($ABA^{WT}$) were the same 6 lines (lines 2, 36, 69, 29, 24, 21) that did not show a reduced water loss compared to wild type.

The above experiment was repeated using two $ABA^S$ lines, one $ABA^{WT}$ line and a Columbia control. Plants were harvested after 2, 4 and 6 days of water stress treatment for shoot dry weight determinations. $ABA^S$ transgenics had greater leaf and shoot biomass, greater soil water contents and lower water loss per shoot dry weight when compared to the $ABA^{WT}$ or Columbia controls. Results were consistent at all three harvest stages.

The data shown in this example was obtained using transgenic plants carrying the pRD29A-DA-FTA construct. The experiment has also been conducted on lines carrying variations of this construct such as 35S-DA-FTA, pRD29A-antisense-FTA or 35S-antisense-FTA, with similar water stress tolerant trends observed. Soil water loss is assessed in all transgenic plants engineered to have reduced or increased FTA or FTB expression or activity by the described methods.

Example 14

Figure 11:
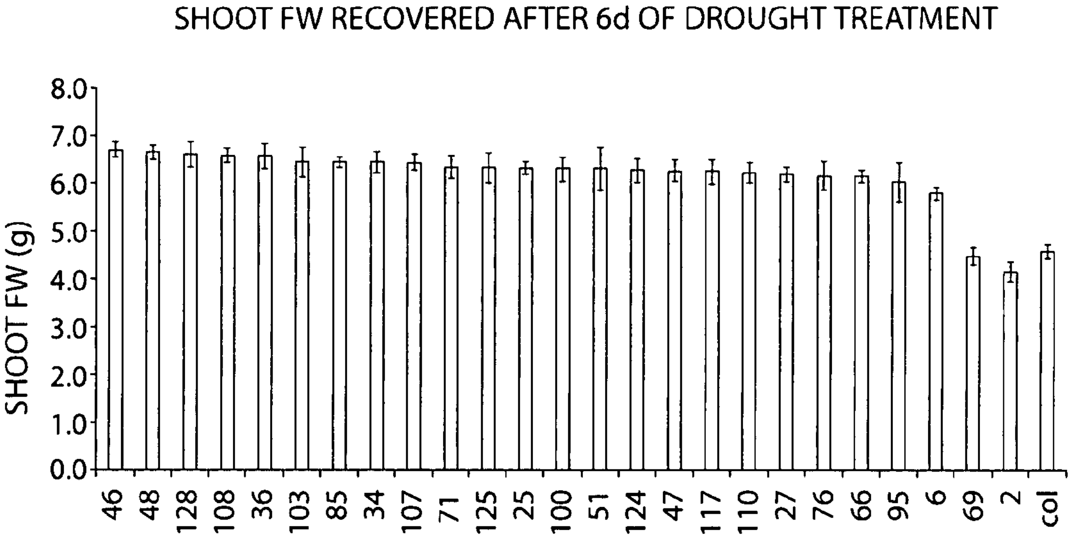
FIG. 11 is an illustration of shoot fresh weight, or biomass accumulation, after 6 days of water stress treatment and 6 days recovery time.

Analysis of Shoot Fresh Weight in *Arabidopsis thaliana* pRD29A-DA-FTA Lines During Drought Stress Plants were grown 5 plants per 4 inch pot and 8 pots per line. When the plants had grown to the first flower stage drought treatment was initiated as described in Example 12. Plants were re-watered after 6 days drought treatment and allowed to recover for an additional 6 days. Plants were harvested and shoot fresh weights determined. FIG. 11 shows the shoot fresh weights. This experiment consisted of 25 transgenic lines, 2 of which are $ABA^{WT}$ (line 2 and 69) and a Columbia wild type control. All 23 $ABA^S$ transgenic lines had statistically significant greater shoot fresh weights, on average 44% greater.

The data shown in this example was obtained using transgenic plants carrying the pRD29A-DA-FTA construct. The experiment has been conducted on lines carrying variations of this construct such as 35S-DA-FTA, pRD29A-antisense-FTA or 35S-antisense-FTA, with similar trends observed.

Example 15

Analysis of Seed Yield in *Arabidopsis thaliana* pRD29A-DA-FTA Lines During Drought Stress and Under Optimal Conditions Plants were grown 1 plant per 4 inch pot. When the plants had grown to the first flower stage drought treatment was initiated as described in Example 12. Plants were re-watered after 6 days drought treatment and allowed to grow to maturity. The optimal group was not exposed to the drought treatment.

Figure 12:
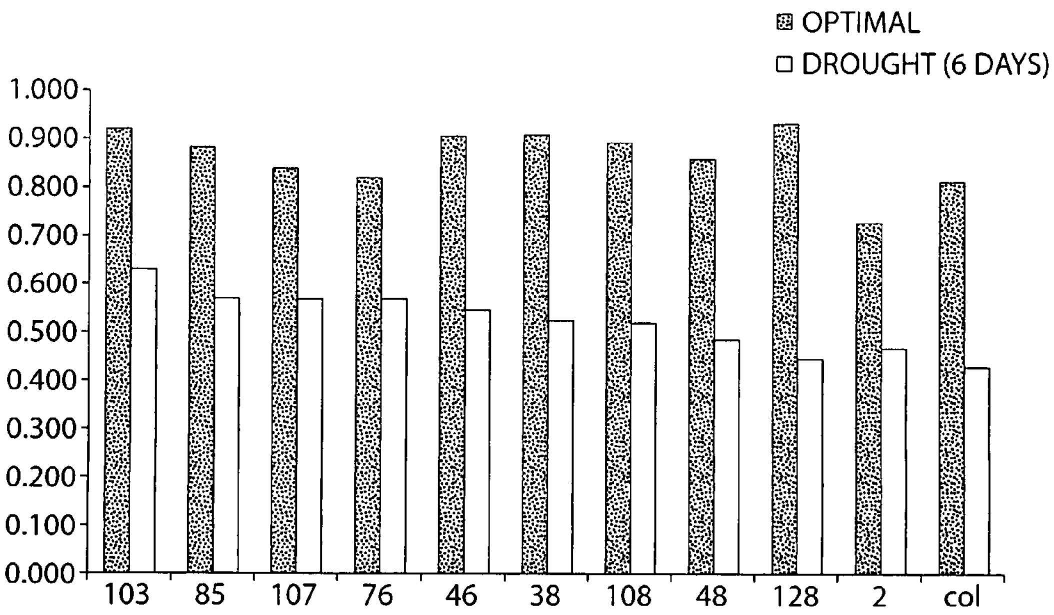
FIG. 12 is an illustration of seed yield (grams) obtained under optimal conditions or following a 6 day water stress treatment.

Yield analysis indicates that although drought treatment results in decreased yields, the transgenics do not suffer as severely as controls and maintain a productivity advantage (FIG. 12) as shown previously in Experiment 14. Comparison of the yields produced by the $ABA^S$ transgenics versus the control plants show that a 15% greater yield was obtained under optimal conditions and a 20% increase under drought conditions. In the drought treatment group 8 of 9 transgenic lines showed greater yield than controls. Expression of yield of each line obtained under drought treatment as a percentage of its performance under optimum conditions indicates that 8 of 9 $ABA^S$ lines outperformed the control line while 4 of 9 out performed the $ABA^{WT}$ controls.

The data shown in this example was obtained using transgenic plants carrying the pRD29A-DA-FTA construct. The experiment has been conducted on lines carrying variations of this construct such as 35S-DA-FTA, pRD29A-antisense-FTA or 35S-antisense-FTA, with similar trends observed.

Example 16

Figure 13:
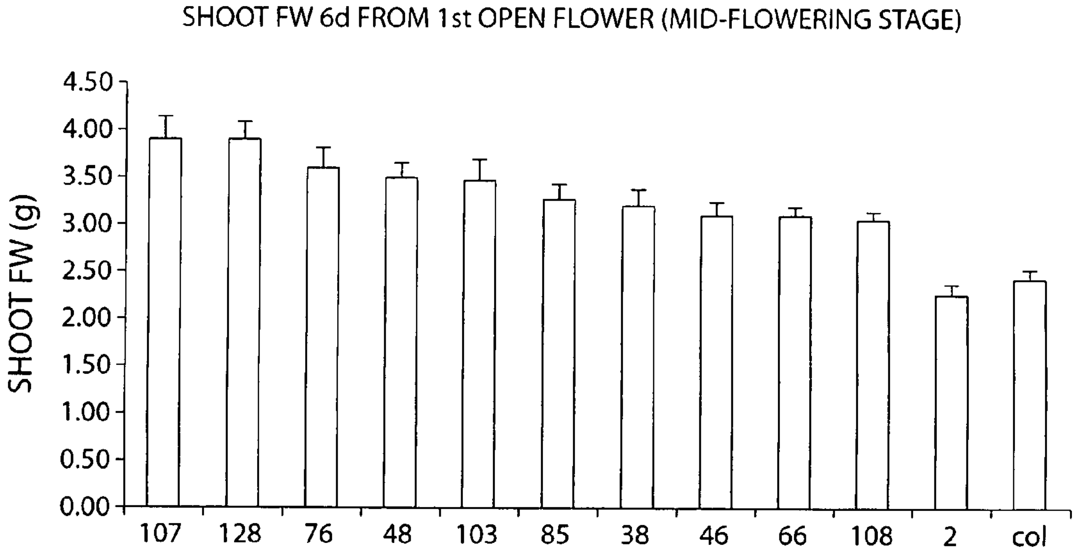
FIG. 13 is an illustration of vegetative growth under optimal conditions, shown is shoot fresh weight 6 days after the first flower opened.

Analysis of Vegetative Growth in *Arabidopsis thaliana* pRD29A-DA-FTA Lines Under Optimum Growth Conditions Plants were grown 1 plant per 3 inch pot and 8 pots per line. Plants were harvested at three stages and fresh weights determined. Vegetative stage was defined as 14 day old seedlings, bolting stage as the appearance of first flower (19-21 day seedlings) and mid-flowering as 6 days from first flower. At each of the above stages respectively 7, 8 and 10 of the 10 $ABA^{S}$ transgenic lines tested showed statistically greater shoot fresh weight biomass than the control plants (FIG. 13). One Columbia line and an $ABA^{WT}$ (line 2) line were used as the control group. Additionally, there was a statistically significant trend for the transgenic lines to have an increased number of rosette leaves.

The data shown in this example was obtained using transgenic plants carrying the pRD29A-DA-FTA construct. The experiment has been conducted on lines carrying variations of this construct such as 35S-DA-FTA, pRD29A-antisense-FTA or 35S-antisense-FTA, with similar trends observed.

Example 17

Figure 14:
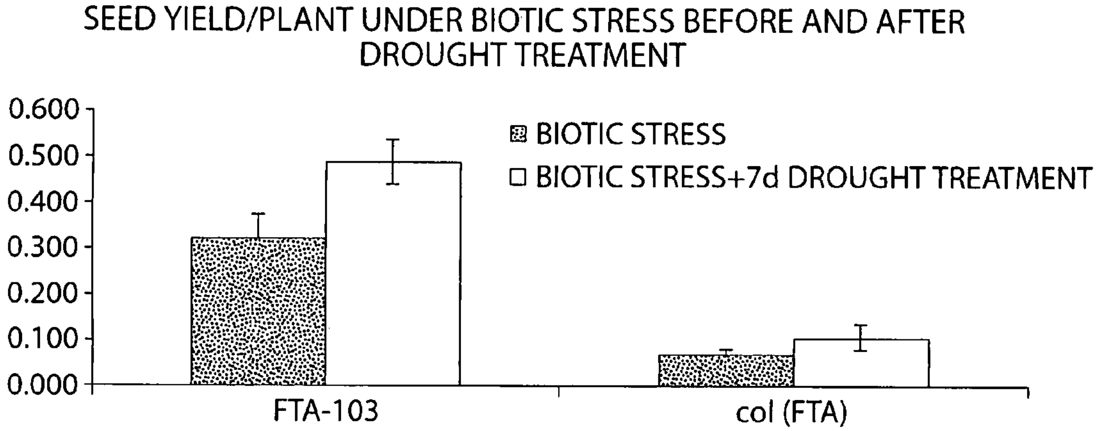
FIG. 14 is an illustration of the effect of a biotic stress coupled with drought stress treatment on seed yield.

Analysis of *Arabidopsis thaliana* pRD29A-DA-FTA Lines Under Drought Treatment and Biotic Stress Plants were grown 1 plant per 4 inch pot and 8 pots. When the plants had grown to the first flower stage drought treatment was initiated as described in Example 12. Plants were re-watered after 7 days drought treatment and allowed to grow to maturity. One Columbian control line (col) and one transgenic line were evaluated. Analysis of seed yield indicated less than normal yields, approximately 12% of expected optimal yield. It was determined that the soil used contained a fungal contaminant that was responsible for the reduced yields as the biotic stress could be negated by sterilization of the soil prior to use. This biotic stress was less severe in the transgenic line compared to the control which had a yield 22% of the transgenic line. In the drought treatment groups of plants the biotic stress was reduced however, transgenics outperformed controls by nearly 4.5 fold (FIG. 14).

The data shown in this example was obtained using transgenic plants carrying the pRD29A-DA-FTA construct. The experiment has been conducted on lines carrying variations of this construct such as 35S-DA-FTA, pRD29A-antisense-FTA or 35S-antisense-FTA, with similar trends observed.

Example 18

Analysis of *Arabidopsis thaliana* pRD29A-DA-FTA Lines for Stomatal Number

The number of stomata on both the upper and lower surface of the leaf was assessed on two transgenic lines and a wild type Columbia control. Nail polish imprints were made of both upper and lower leaf surfaces of the fifth leaf, plants were at the early flowering stage. No differences in stoma density were observed.

The data shown in this example was obtained using transgenic plants carrying the pRD29A-DA-FTA construct. The experiment has been conducted on lines carrying variations of this construct such as 35S-DA-FTA, pRD29A-antisense-FTA or 35S-antisense-FTA, with similar trends observed.

Example 19

Production of Polyclonal Antibodies Against FT-A and FT-B

The isolated *Arabidopsis thaliana* FT sequences were cloned into the *E. coli* expression vector derived from pET11D. To generate the Histidine tagged FT-B construct the *Arabidopsis thaliana* FT-B clone and pET vector were digested with BamHI and ligated together. Restriction digests were performed to verify the orientation of the insert. To produce the FT-A construct the *Arabidopsis thaliana* FT-A clone and pET vector were digested with BamHI and EcoRI and subsequently ligated together. The resultant plasmids directed the expression of fusion proteins containing 6 consecutive histidine residues at the N-termini of AtFTA and AtFTB. The fusion proteins were expressed in the bacterial host BL21(DE3) and purified using Hi-Trap chelating chromatography as described by the manufacturer (Pharmacia). The soluble fraction of the crude bacterial extract containing the His-FT fusion proteins were loaded to a Hi-Trap column (1.5 cm×2.0 cm), and the proteins eluted with a 200 ml linear gradient of 0.0 to 0.3 M imidazole in column buffer (25 mM Tris-HCl, pH 7.5, 1 mM DTT). Fractions containing purified His-FT proteins were pooled, desalted and concentrated with a Centriprep-30 concentrator (Amicon). All purification steps were carried out at 4° C. To generate an antibody, the purified fusion protein was further separated by SDS/PAGE and the Coomassie stained band corresponding to the fusion protein was excised. Protein was eluted from the gel slice by electro-elution and then emulsified in Ribi adjuvant (Ribi Immunochem) to a final volume of 1 ml. His-AtFTA or His-AtFTB (250 μg) were injected into a 3 kg New Zealand rabbit on day 1 and booster injections given on day 21 and day 35 with 200 μg of the protein. High-titer antisera were obtained one week after the final injection. These antibodies were used in the western analysis of example 10, FIG. 4.

Example 20

Screening for Related Genes

The transgenic plants of the invention can be used to identify genes which interact with the genes of the present invention. One can make use of the transgenic plants of the invention to screen for related genes, for example, suppressors, enhancers or modulators of gene expression or activity can be identified through genetic screening protocols. By way of example, a mutant library can be generated using the transgenic plants of the invention as the genetic background. Various methods are available and would be known to one of skill in the art. For example, chemical mutagens such as EMS can be used to induce point mutations in the genome, fast neutron irradiation of seeds can result in deletion mutations, T-DNA libraries can be produced that inactivate genes through insertional effects or activation tagging methods can be used to produce libraries with up-regulated genes. Analysis of these types of libraries can identify genes which rescue or modulate the phenotypes observed in the transgenic plants of the present invention.

What is claimed is:

1. A method of producing a drought tolerant plant comprising:

a) providing a nucleic acid construct comprising a promoter operably linked to a farnesyltransferase alpha nucleic acid that inhibits farnesyltransferase alpha activity;

b) inserting said nucleic acid construct into a vector;

c) transforming a plant, tissue culture, or a plant with the vector to obtain a plant, tissue culture or a plant with decreased farnesyltransferase alpha activity;

d) growing said plant or regenerating a plant form said tissue culture or plant cells, wherein a drought tolerant plant is produced.

2. The method of claim 1, wherein said promoter is a constitutive promoter, an ABA inducible promoter, a tissue specific promoters or a guard cell specific promoter.

3. A drought tolerant transgenic plant produced by the method claim 1 or 2.

4. A transgenic seed produced by the transgenic plant of claim 3, wherein said seed produces a drought tolerant plant.

* * * * *